(12) United States Patent  
Asahara et al.

(10) Patent No.: US 12,253,515 B2  
(45) Date of Patent: *Mar. 18, 2025

(54) METHOD FOR INHIBITING THE EXPRESSION OF CANCER-PROMOTING FACTORS

(71) Applicants: National University Corporation Tokyo Medical and Dental University, Tokyo (JP); Nippon Zoki Pharmaceutical Co., Ltd., Osaka (JP)

(72) Inventors: Hiroshi Asahara, Tokyo (JP); Tomoki Chiba, Tokyo (JP); Kentaro Abe, Osaka (JP)

(73) Assignees: National University Corporation Tokyo Medical and Dental University, Tokyo (JP); Nippon Zoki Pharmaceutical Co., Ltd., Osaka (JP)

( * ) Notice: Subject to any disclaimer, the term of this patent is extended or adjusted under 35 U.S.C. 154(b) by 609 days.

This patent is subject to a terminal disclaimer.

(21) Appl. No.: 16/762,227

(22) PCT Filed: Nov. 9, 2018

(86) PCT No.: PCT/JP2018/041758  
§ 371 (c)(1),  
(2) Date: May 7, 2020

(87) PCT Pub. No.: WO2019/093502  
PCT Pub. Date: May 16, 2019

(65) Prior Publication Data  
US 2020/0355672 A1 Nov. 12, 2020

(30) Foreign Application Priority Data  
Nov. 9, 2017 (JP) ................. 2017-216747

(51) Int. Cl.  
*C12N 15/10* (2006.01)  
*C12N 15/113* (2010.01)  
(Continued)

(52) U.S. Cl.  
CPC ...... *G01N 33/5011* (2013.01); *C12N 2310/11* (2013.01); *C12N 2310/14* (2013.01);  
(Continued)

(58) Field of Classification Search  
CPC ............ C12N 2310/11; C12N 2310/14; C12N 2310/141; C12N 15/113; G01N 33/574  
See application file for complete search history.

(56) References Cited

U.S. PATENT DOCUMENTS

2006/0173006 A1   8/2006   Sun et al.  
2009/0149403 A1*  6/2009   MacLachlan ...... A61K 31/7088  
                                              435/375

(Continued)

FOREIGN PATENT DOCUMENTS

CA    2455447 A1 *  2/2003  ............. C07H 21/04  
CN   101389957 A    3/2009  
(Continued)

OTHER PUBLICATIONS

Sun et al. (Journal of Experimental & Clinical Cancer Research, 2018, 37:298), plus Supplementary Information.*

(Continued)

*Primary Examiner* — Terra C Gibbs  
(74) *Attorney, Agent, or Firm* — McNeill PLLC

(57) ABSTRACT

Provided are an expression inhibitor of a cancer promoting factor based on the discovery of a new factor influencing the expression amount/level of a cancer promoting factor, and a development tool therefor. Provided are also a diagnostic agent and a diagnosis method for cancer. More specifically provided are: an expression inhibitor of a cancer promoting (Continued)

factor containing at least one kind of inhibitor selected from the group consisting of RBMS expression inhibitor and RBMS function inhibitor; a screening method using as an indicator the expression or the function of RBMS; an expression cassette useful for the method; as well as a diagnostic agent containing a product detection agent for RBMS gene expression and cancer detection method using as an indicator RBMS gene expression amount/level.

4 Claims, 26 Drawing Sheets

Specification includes a Sequence Listing.

(51) Int. Cl.
*C12N 15/63* (2006.01)
*G01N 33/50* (2006.01)

(52) U.S. Cl.
CPC . *C12N 2310/141* (2013.01); *C12Y 113/12007* (2013.01); *G01N 2500/10* (2013.01)

(56) References Cited

U.S. PATENT DOCUMENTS

| | | | |
|---|---|---|---|
| 2009/0181384 | A1 | 7/2009 | Nekarda et al. |
| 2010/0099746 | A1 | 4/2010 | Yamada et al. |
| 2010/0280101 | A1 | 11/2010 | Kohno et al. |
| 2011/0039729 | A1 | 2/2011 | DeLisa et al. |
| 2011/0053804 | A1 | 3/2011 | Massague et al. |
| 2011/0091419 | A1* | 4/2011 | Oft .................. C07K 16/3069 424/85.2 |
| 2013/0274128 | A1 | 10/2013 | Reiter |
| 2016/0068916 | A1 | 3/2016 | Nekarda et al. |
| 2019/0242875 | A1 | 8/2019 | Asahara et al. |
| 2020/0140955 | A1 | 5/2020 | Nekarda et al. |
| 2020/0386741 | A1 | 12/2020 | Asahara et al. |

FOREIGN PATENT DOCUMENTS

| | | |
|---|---|---|
| JP | 2009159869 A | 7/2009 |
| JP | 2014518610 A | 8/2014 |
| JP | 2014236717 A | 12/2014 |
| JP | 2015522260 A | 8/2015 |
| JP | 2016512032 A | 4/2016 |
| WO | 2003074654 A2 | 9/2003 |
| WO | 2007118149 A2 | 10/2007 |
| WO | 2008044787 A1 | 4/2008 |
| WO | 2011123388 A1 | 10/2011 |
| WO | 2012046063 A2 | 4/2012 |
| WO | 2012122499 A2 | 9/2012 |
| WO | 2013188846 A1 | 12/2013 |
| WO | 2014159791 A1 | 10/2014 |
| WO | 2016106404 A2 | 6/2016 |
| WO | 2016161361 A1 | 10/2016 |
| WO | 2017195809 A1 | 11/2017 |

OTHER PUBLICATIONS

David Bartel (Cell, 2009, 136:215-233).*
Valle Oseguera and Spencer (PLOS One, 2014 vol. 9:e88708, pp. 1-8).*
Monti et al. (Cancer Research, 2003 vol. 63:7451-7461).*
Flieger et al. (Clin Exp Immunol., 2001 vol. 123: 9-14).*
Extended European Search Report issued in EP Patent Application No. 18876883.2, dated Jul. 30, 2021, 11 pages.
Yu et al., "RBMS1 Suppresses Colon Cancer Metastasis through Targeted Stabilization of Its mRNA Regulon," Cancer Discovery 10(9):1410-1423 (2020).
Chang et al., "The IL-6/JAK/Stat3 Feed-Forward Loop Drives Tumorigenesis and Metastasis," Neoplasia 15 (7):848-862 (2013).
Elinav et al., "Inflammation-induced cancer: crosstalk between tumours, immune cells and microorganisms," Nat Rev Cancer 13(11):759-771 (2013).
Gao et al., "Mutations in the EGFR kinase domain mediate STAT3 activation via IL-6 production in human lung adenocarcinomas," J Clin Invest 117(12):3846-3856 (2007).
Grivennikov et al., "Autocrine IL-6 Signaling: A Key Event in Tumorigenesis?" Cancer Cell 13(1):7-9 (2008).
Hartman et al., "Growth of Triple-Negative Breast Cancer Cells Relies upon Coordinate Autocrine Expression of the Proinflammatory Cytokines IL-6 and IL-8," Cancer Res 73(11):3470-3480 (2013).
He et al., "Identification of Liver Cancer Progenitors Whose Malignant Progression Depends on Autocrine IL-6 Signaling," Cell 155(2):384-396 (2013).
Jayasena et al., "Rbms3 functions in craniofacial development by posttranscriptionally modulating TGF-βsignaling," J. Cell Bio. 199(3):453-466 (2012).
Journal of Japan Society of Immunology & Allergology in Otolaryngology, 2016, vol. 34, No. 1, pp. 13-18 (English Abstract).
Kulbe et al., "The Inflammatory Cycokine Tumor Necrosis Factor-α Generates an Autocrine Tumor-Promoting Network In Epithelial Ovarian Cancer Cells," Cancer Res 67(2):585-592 (2007).
Lecture abstracts of BMB2015, (Collaborative conference of the 38th annual conference of the Molecular Biology Society of Japan and the 88th conference of the Japanese Biochemical Society), 2015, p. 1P0844.
Lee et al., "Identification of Novel Alternatively Spliced Transcripts of RBMS3 in Skeletal Muscle with Correlations to Insulin Action in vivo," J. Exp. Biomed. Sci. 15:301-307 (2009).
Leppek et al., "An optimized streptavidin-binding RNA aptamer for purification of ribonucleoprotein complexes identifies novel AREbinding proteins," Nucleic Acids Research, 42 (2):1-15 (2014).
Penkov et al., "Cloning of a human gene closely related to the genes coding for the c-myc single-strand binding proteins," Gene 243:27-36 (2000).
Rodriguez-Barrueco et al., "Inhibition of the autocrine IL-6-JAK2-STAT3-calprotectin axis as targeted therapy for HR-/HER2+ breast cancers," Genes Dev 29(15):1631-1648 (2015).
Sansone et al., "IL-6 triggers malignant features in mammospheres from human ductal breast carcinoma and normal mammary gland," J Clin Invest 117(12):3988-4002 (2007).
Yeh et al., "Autocrine IL-6-induced Stat3 activation contributes to the pathogenesis of lung adenocarcinoma and malignant pleural effusion," Oncogene 25(31):4300-4309 (2006).
Zhou et al., "Autocrine HBEGF expression promotes breast cancer intravasation, metastasis and macrophage-independent invasion in vivo," Oncogene 33(29)3784-3793 (2014).
International Search Report issued in PCT/JP2018/041758, mailed Feb. 12, 2019, 5 pages.
Alten et al., "Tocilizumab: A novel humanized anti-interleukin 6 (IL-6) receptor antibody for the treatment of patients with non-RA systemic, inflammatory rheumatic diseases," Annals of Medicine 45(4):357-363 (2013).
Asahara et al., "Inflammatory Signal Regulation at RNA Level", BMB2015 (Joint Meeting of the 38th Annual Meeting of the Molecular Biology Society of Japan and the 88th Annual Meeting of the Japanese Biochemical Society) Koen Yoshishu, Nov. 16, 2015.
Becher et al., "Cytokine networks in neuroinflammation," Nature Reviews Immunology 17(1):49-59 (2017).
Beneviste et al., "Involvement of the Janus Kinase/Signal Transducer and Activator of Transcription Signaling Pathway in Multiple Sclerosis and the Animal Model of Experimental Autoimmune Encephalomyelitis," Journal of Interferon & Cytokine Research 34(8):577-588 (2014).
Calich et al., "Osteoarthritis: can anti-cytokine therapy play a role in treatment?" Clin Rheumatol 29(5):451-455 (2010).
Cavaillon et al., "Cytokine Cascade in Sepsis," Scand J Infect Dis 35(9):535-544 (2003).
Clarke et al., "Single dose oral etoricoxib for acute postoperative pain in adults (Review)," Cochrane Database of Systemic Reviews, Cochrane Library, CD004309, 36 pages (2014).

(56) References Cited

OTHER PUBLICATIONS

Cua et al., "Central Nervous System Expression of IL-10 Inhibits Autoimmune Encephalomyelitis," Journal of Immunology 166:603-608 (2001).
Eisen, "Manifold beneficial effects of acetyl salicylic acid and nonsteroidal anti-inflammatory drugs on sepsis," Intensive Care Med 38:1249-1257 (2012).
Filion et al., "Monocyte-derived cytokines in multiple sclerosis," Clin. Exp. Immunol. 131:324-334 (2003).
Firestein et al., "Evolving concepts of rheumatoid arthritis," Nature 423(6937):356-361 (2003).
Galli et al., "The development of allergic inflammation," Nature, Macmillan Journals LTD 454(7203):445-454 (2008).
Hermouet et al., "Pathogenesis of Myeloproliferative Neoplasms: Role and Mechanisms of Chronic Inflammation," Mediators of Inflammation, vol. 2015, Article ID 145293, 16 pages.
Hreggvidsdottir et al., "Inflammatory pathways in spondyloarthritis," Molecular Immunology 57(1):28-37 (2014).
Ito et al., "Development of a Post-transcriptional Regulator Screening System by Using RNA Binding Protein Gene Library", BMB2015 (Joint Meeting of the 38th Annual Meeting of the Molecular Biology Society of Japan and the 88th Annual Meeting of the Japanese Biochemical Society) Koen Yoshishu, Nov. 16, 2015.
Jones et al., "Comparison of U2OS and Huh-7 cells for identifying host factors that affect hepatitis C virus RNA replication," Journal of General Virology, vol. 91, pp. 2238-2248 (2010).
Kalden, "Emerging role of anti-tumor necrosis factor therapy in rheumatic diseases," Arthritis Research, vol. 4(Suppl 2):S34-S40 (2002).
Kanaoka et al., "SCR: Novel Human Suppressors of cdc2/cdc13 Mutants of Schizosaccharomyces pombe Harbour Motifs for RNA Binding Proteins," Nucleic Acids Research 22(13):2687-2693 (1994).
Kang et al., "Therapeutic uses of anti-interleukin-6 receptor antibody," International Immunology 27(1):21-29 (2014).
Katsikis et al., "Immunoregulatory Role of Interleukin 10 in Rheumatoid Arthritis," J. Exp. Med. 179(5):1517-1527 (1994).
Kwilasz et al, "The therapeutic potential of interleukin-10 in neuroimmune disease," Neuropharmacology 95:55-69 (2015).
Latifi et al., "Interleukin-10 Controls the Onset of Irreversible Septic Shock," Infection and Immunity 70(8):4441-4446 (2002).
Maroon et al., "Natural anti-inflammatory agents for pain relief," Surgical Neurology International 1:80, 10 pages (2010).
Masuda et al., "Arid5a Controls IL-6 mRNA Stability, Which Contributes to Elevation of IL-6 Level In Vivo," PNAS 110(23):9409-9414, epub doi: 10.1073/pnas.1307419110 (6 pages) (2013).
McInnes et al., "Cytokines in the pathogenesis of rheumatoid arthritis," Nature Reviews Immunology 7(6):429-442 (2007).
Mendez-Samperio et al., "Regulation of Interleukin-8 by Interleukin-10 and Transforming Growth Factor B in Human Monocytes Infected with Mycobacterium bovis," Clinical and Diagnostic Laboratory Immunology 9(4):802-807 (2002).
Nathan et al., "Nonresolving Inflammation," Cell 140:871-882 (2010).
Nathan, "Points of control in inflammation," Nature 420(6917):846-852 (2002).
Niki, et al., "MSSP promotes ras/myc cooperative cell transforming activity by binding to c-Myc," Genes to Cells 5:127-141 (2000).
Rizzi et al., "Spontaneous remission of 'methotrexate-associated lymphoproliferative disorders' after discontinuation of immunosuppressive treatment for autoimmune disease. Review of the literature," Med Oncol 26(1):1-9 (2008).
Sinatra, "Role of COX-2 Inhibitors in the Evolution of Acute Pain Management," Journal of Pain and Symptom Management, 24(1S):S18-S27 (2002).
Steinhauser et al., "IL-10 is a Major Mediator of Sepsis-Induced Impairment in Lung Antibacterial Host Defense," Journal of Immunoloy 162(1):392-399 (1999).
Tanaka et al., "Interleukin-6; Pathogenesis and Treatment of Autoimmune Inflammatory Diseases," Inflammation and Regeneration 33(1):54-65 (2013).
Van De Ven et al., "Causes and prevention of chronic postsurgical pain," Current Opinion in Critical Care 18 (4):366-371 (2012).
Zhang et al., "Cytokines, Inflammation, and Pain," International Anesthesiology Clinics, 27-37 (2007).
Zhang, et al., "Low expression of RBMS3 and SFRP1 are associated with poor prognosis in patients with gastric cancer," Am J Cancer Res 6(11):2679-2689 (2016).
Zhao et al., "Tristetraprolin Regulates Interleukin-6 Expression Through p38 MAPK-Dependent Affinity Changes with mRNA 3' Untranslated Region," Journal of Interferon & Cytokine Research 31(8):629-637, 2011.
File History of U.S. Appl. No. 16/913,376, filed Jun. 26, 2020.
File History of U.S. Appl. No. 16/300,442, filed Nov. 9, 2018.
Ivashchenko et al., Binding sites of miR-1273 family on the mRNA of target genes, Bio Med Research International, vol. 2014, Article ID 620530, 11 pages. (Year: 2014).
Wu et al., "Down regulation of RNA binding motif, single-stranded interacting protein 3, along with up regulation of nuclear HIF1A correlates with poor prognosis in patients with gastric cancer," Oncotarget 8(1):1262-1277 (2017).
Mannino et al., "The paradoxical role of IL-10 in immunity and cancer," Cancer Letters 367:103-107 (2015).
Office Action issued in Canadian Application No. 3,082,006, mailed Oct. 28, 2024, 7 pages.

\* cited by examiner

[Fig1A]
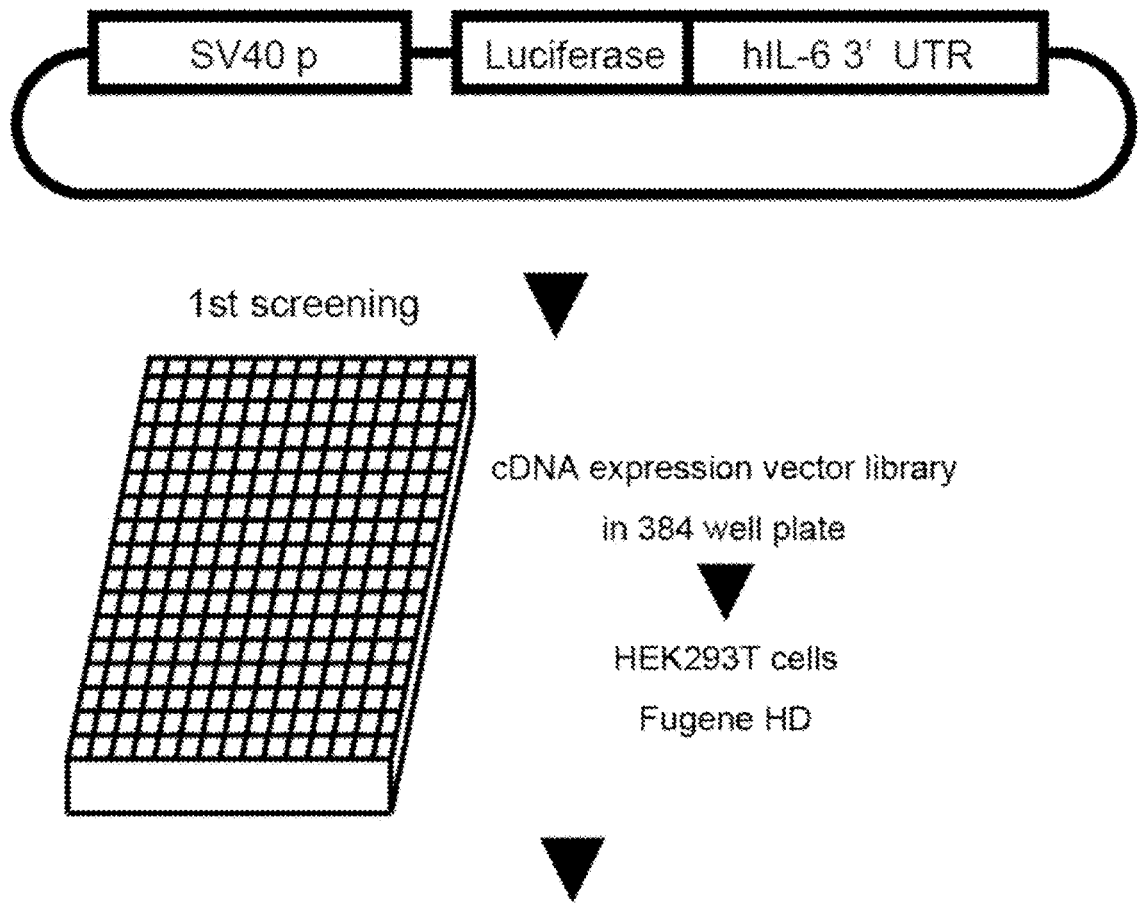
[Fig1B]
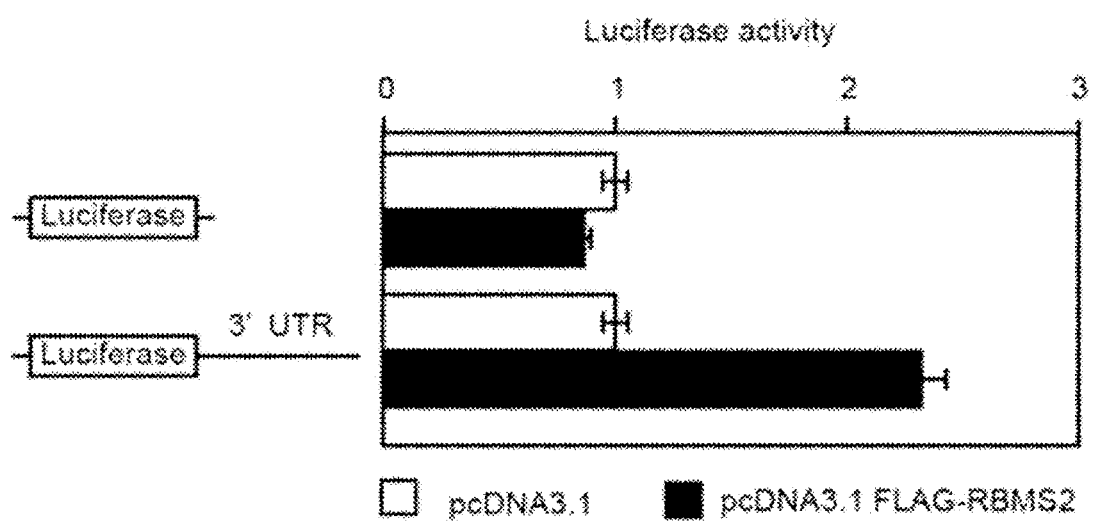

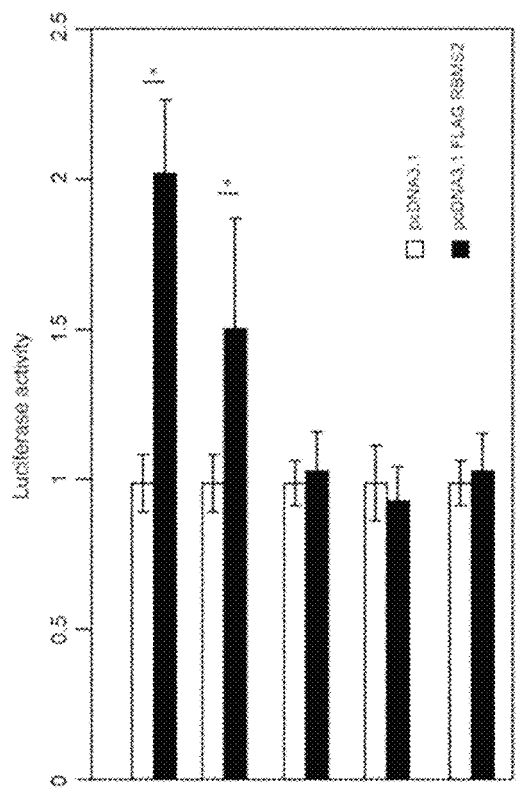
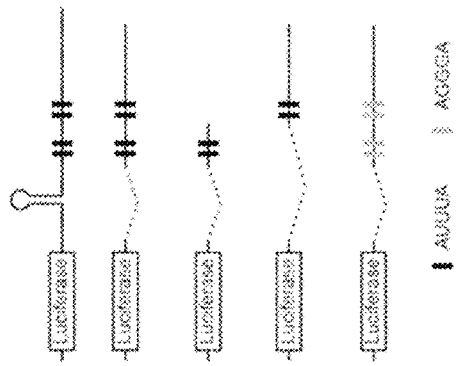
[Fig2]

[Fig3A]
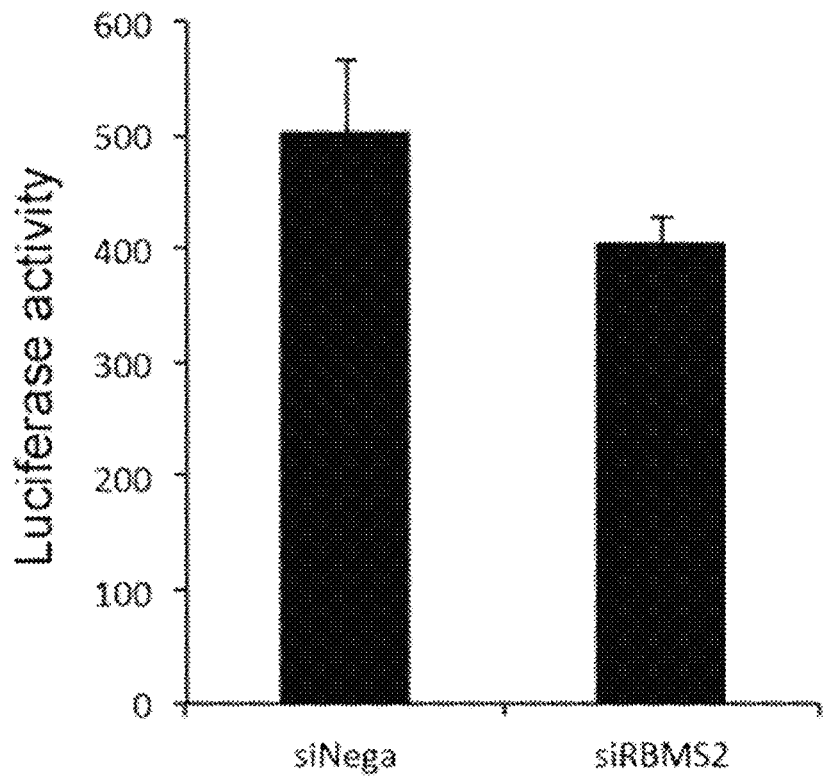
[Fig3B]
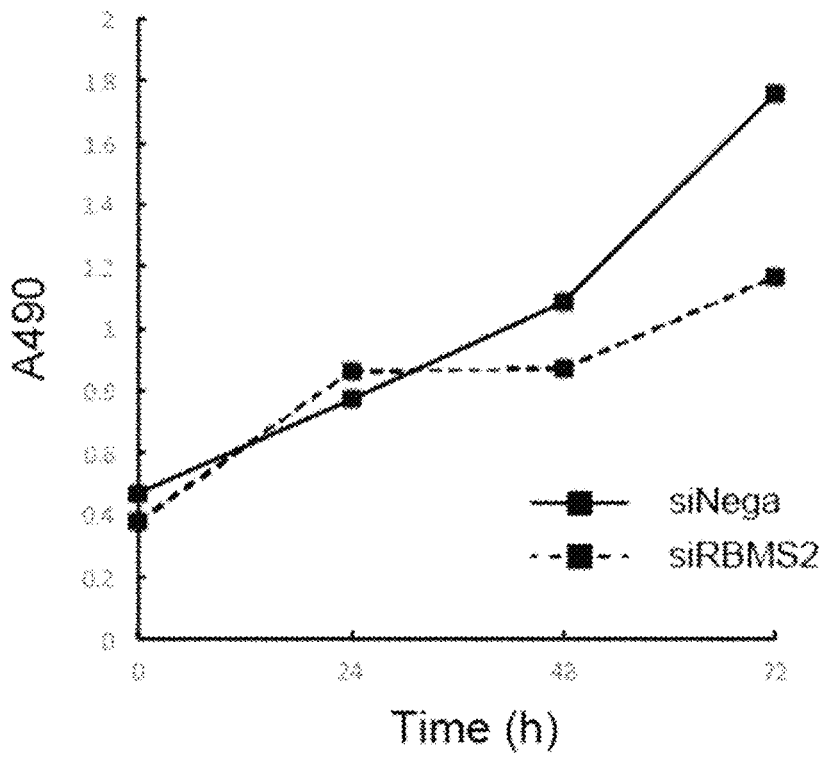

[Fig3C]
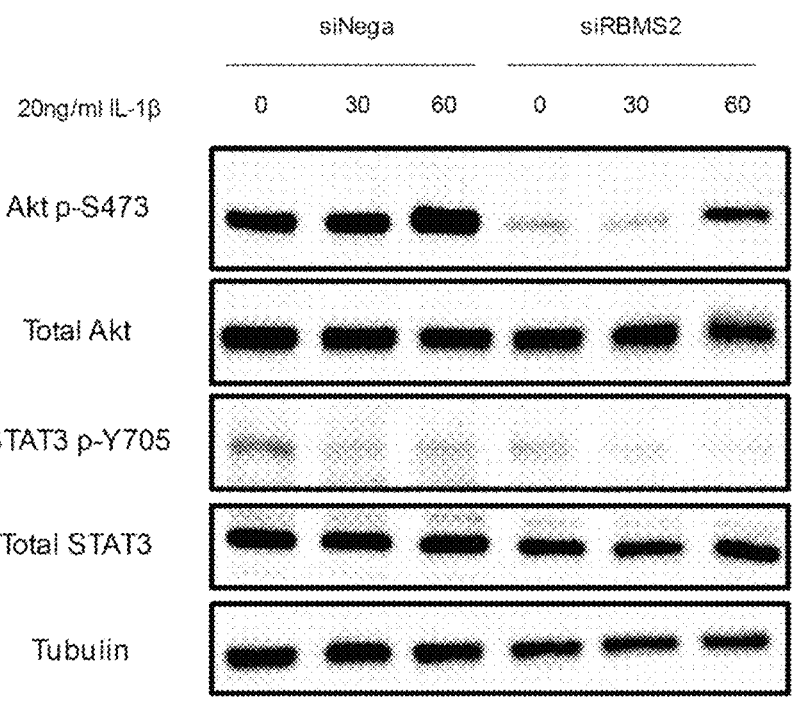
[Fig4]
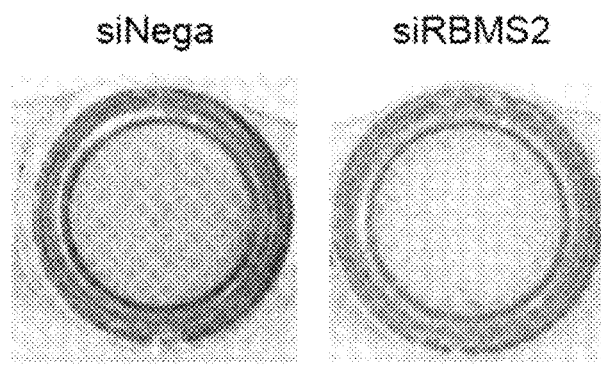
[Fig5]
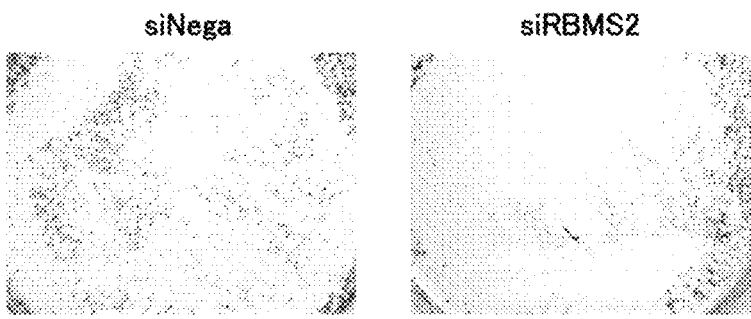

[Fig6]
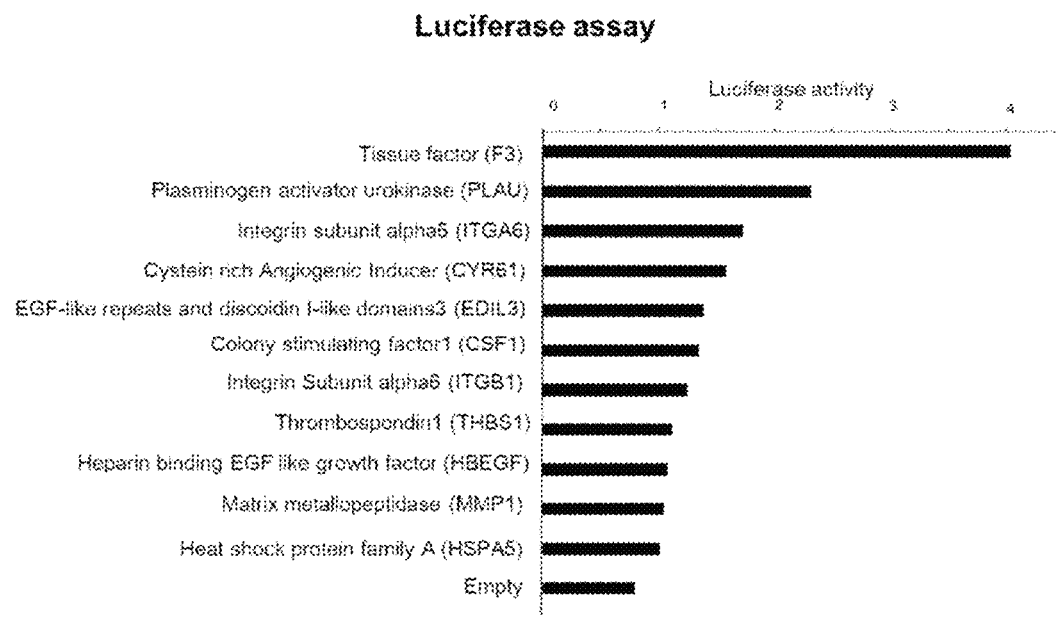
[Fig7]
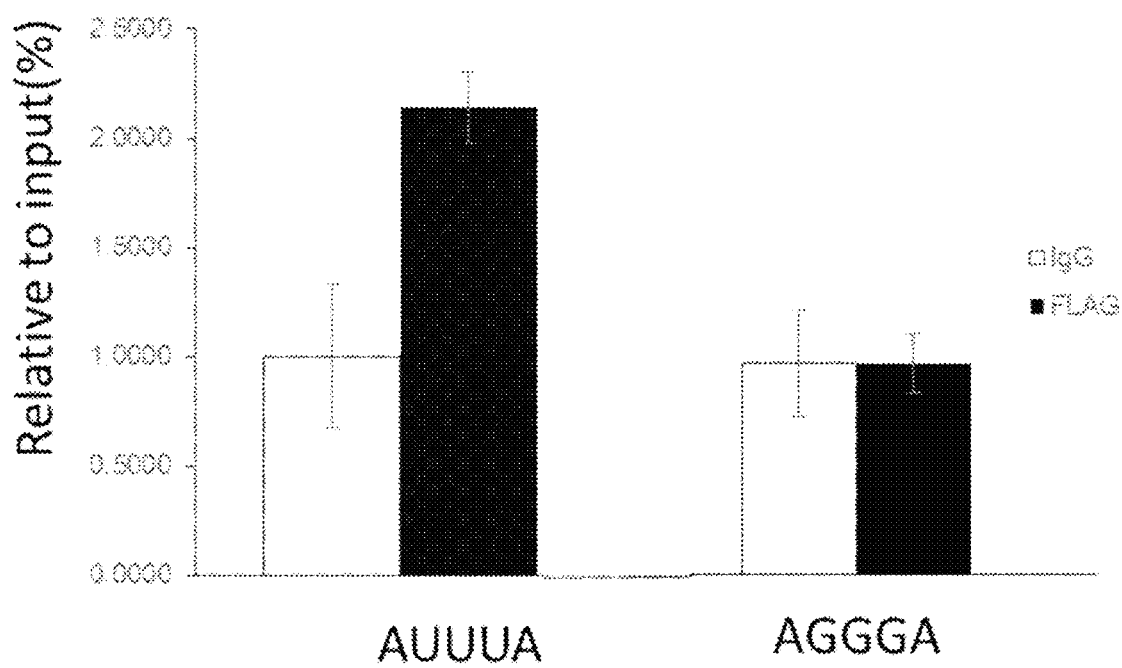

[Fig8]

```
hRBMS1    PSTTSSNNNS  SSSSNSGWDQ  LSKTNLYIRG  LPPHTTDQDL  78
hRBMS2    PS--NSTPNS  SSCSN-GNDQ  LSKTNLYIRG  LQPGTTDQDL  72
hRBMS3    PSTNSSSNNS  SN--NSSGEQ  LSKTNLYIRG  LPPGTTDQDL  77
Consensus PSTXSSXNNS  SSXSNSGXDQ  LSKTNLYIRG  LPPGTTDQDL
Conservation hRBMS1    VKLCQPYGKI  VSTKAILDKT  TNKCKGYGFV  DFDSPAAAQK  118
hRBMS2    VKLCQPYGKI  VSTKAILDKT  TNKCKGYGFV  DFDSPSAAQK  112
hRBMS3    VKLCQPYGKI  VSTKAILDKN  TNQCKGYGFV  DFDSPAAAQK  117
Consensus VKLCQPYGKI  VSTKAILDKT  TNKCKGYGFV  DFDSPAAAQK
Conservation hRBMS1    AVSALKASGV  QAQMAKQQEQ  DPTNLYISNL  PLSMDEQELE  158
hRBMS2    AVTALKASGV  QAQMAKQQEQ  DPTNLYISNL  PLSMDEQELE  152
hRBMS3    AVASKKANGV  QAQMAKQQEQ  DPTNLYISNL  PLSMDEQELE  157
Consensus AVXALKASGV  QAQMAKQQEQ  DPTNLYISNL  PLSMDEQELE
Conservation hRBMS1    NMLKPFGQVI  STRILRDSSG  TSRGVGFARM  ESTEKCEAVI  198
hRBMS2    GMLKPFGQVI  STRILRDTSG  TSRGVGFARM  ESTEKCEAVI  192
hRBMS3    NMLKPFGHVI  STRILRDANG  VSRGVGFARM  ESTEKCEVVI  197
Consensus NMLKPFGQVI  STRILRDXSG  TSRGVGFARM  ESTEKCEAVI
Conservation hRBMS1    GHENGKLLKT  PPGVSAPTEP  LLCKEADGGQ  KKRQNPNKYI  238
hRBMS2    THENGKLLKT  PPGVPAPSDP  LLCKEADGGP  KKRQNQGKYV  232
hRBMS3    QHENGKLLKT  PPGVPAPSEP  LLCKEADGGQ  KKRQNQSKYT  237
```

[Fig9]
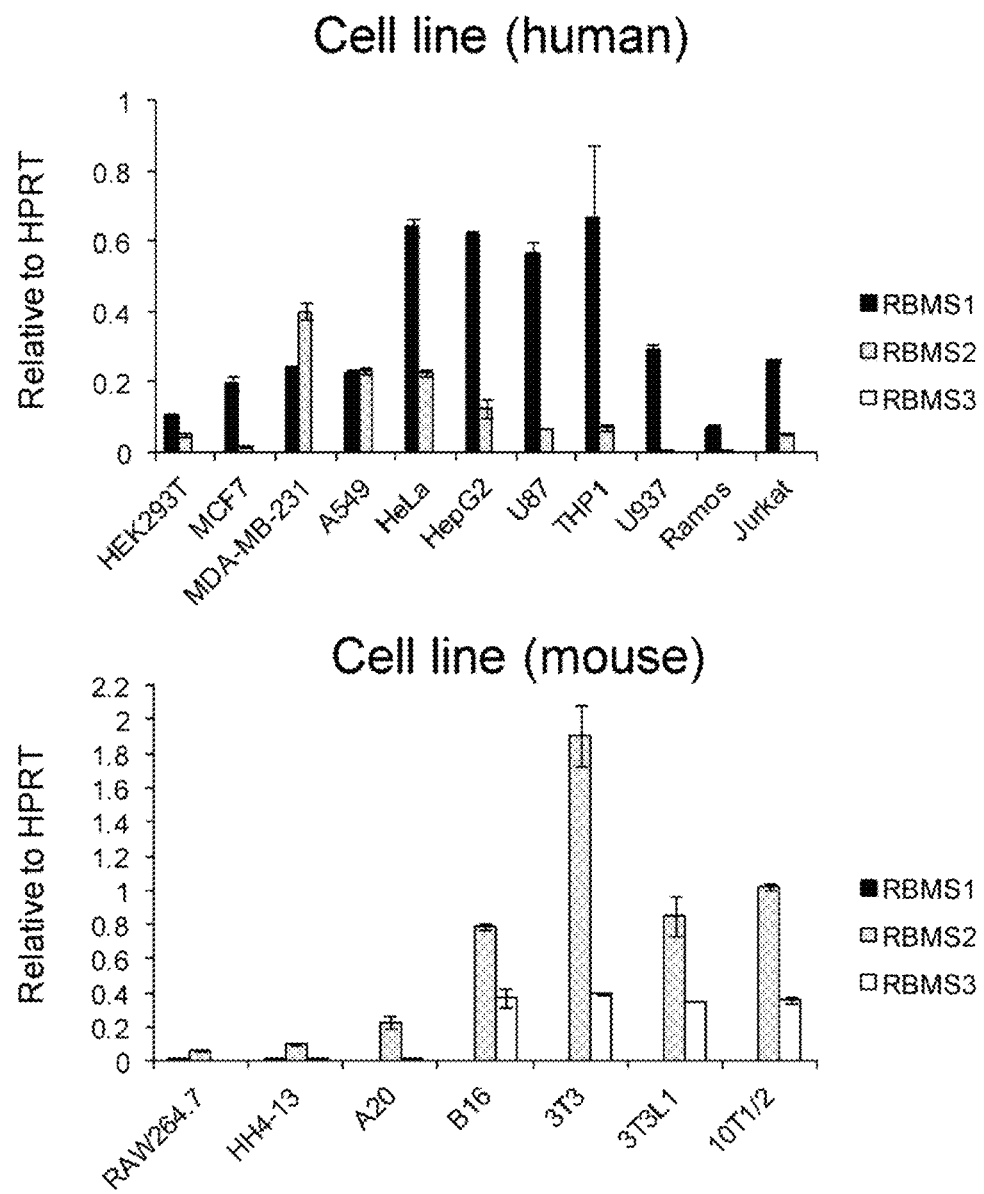

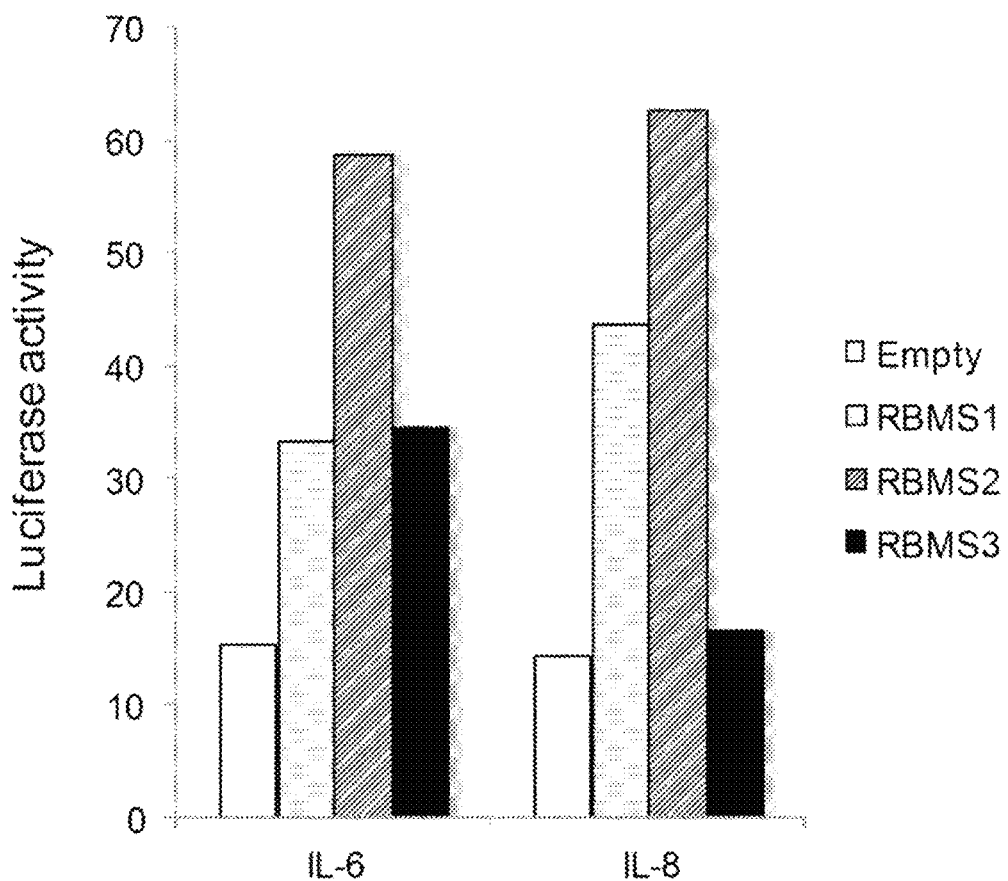
[Fig10]

[Fig11]
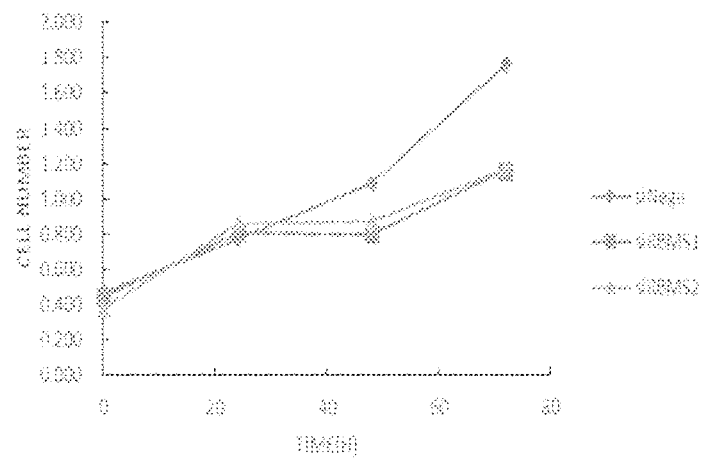
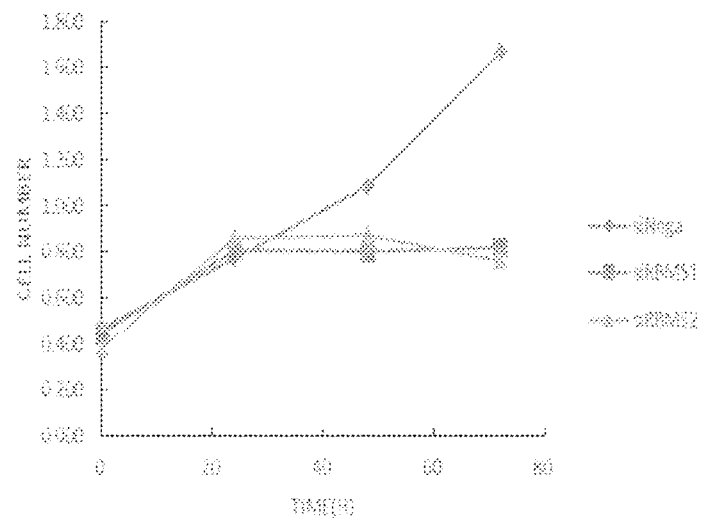

[Fig12]
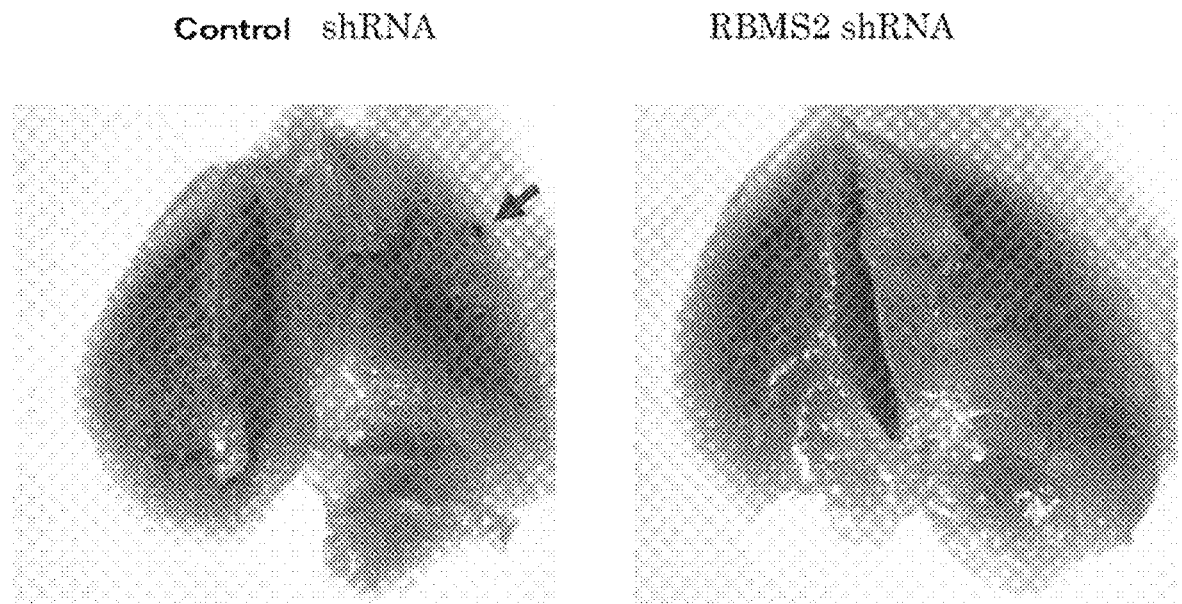
[Fig13]
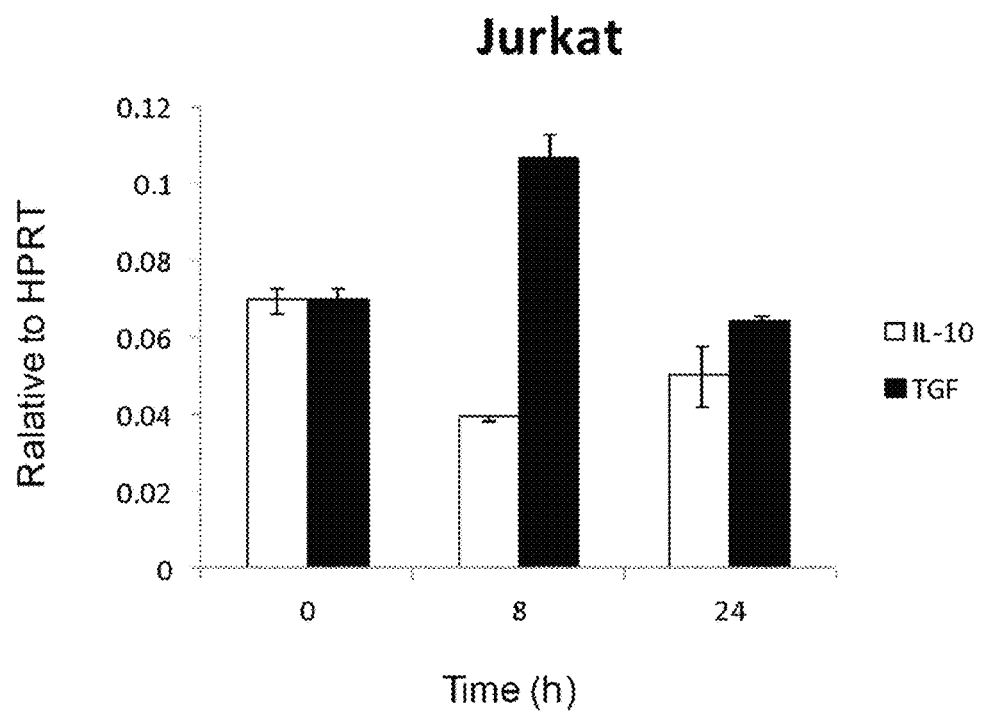

[Fig14]
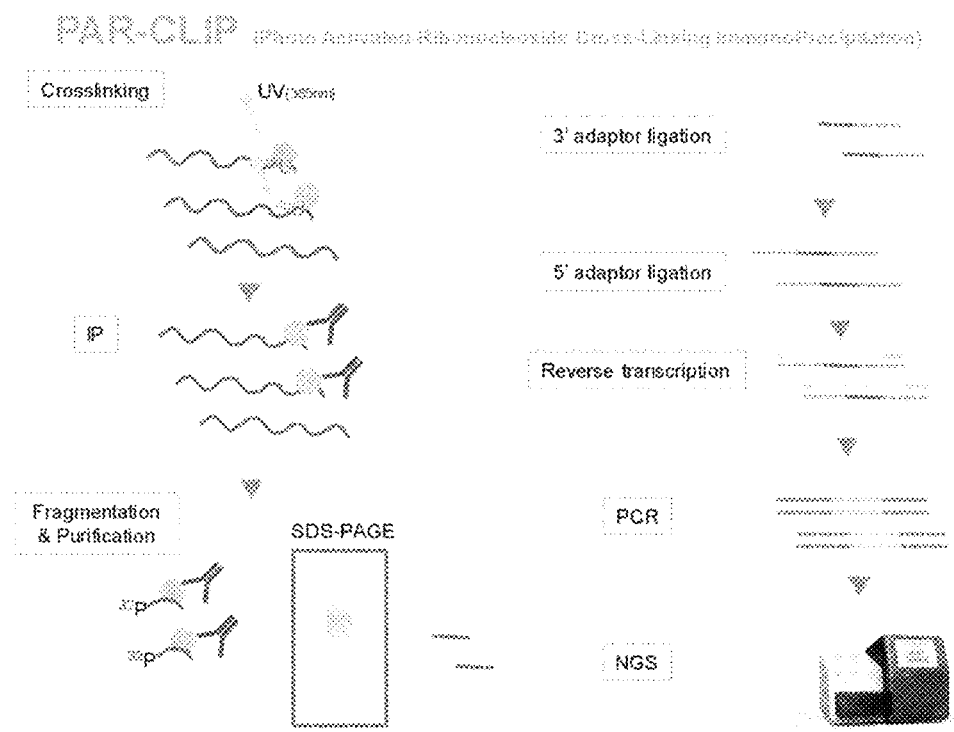
[Fig15]
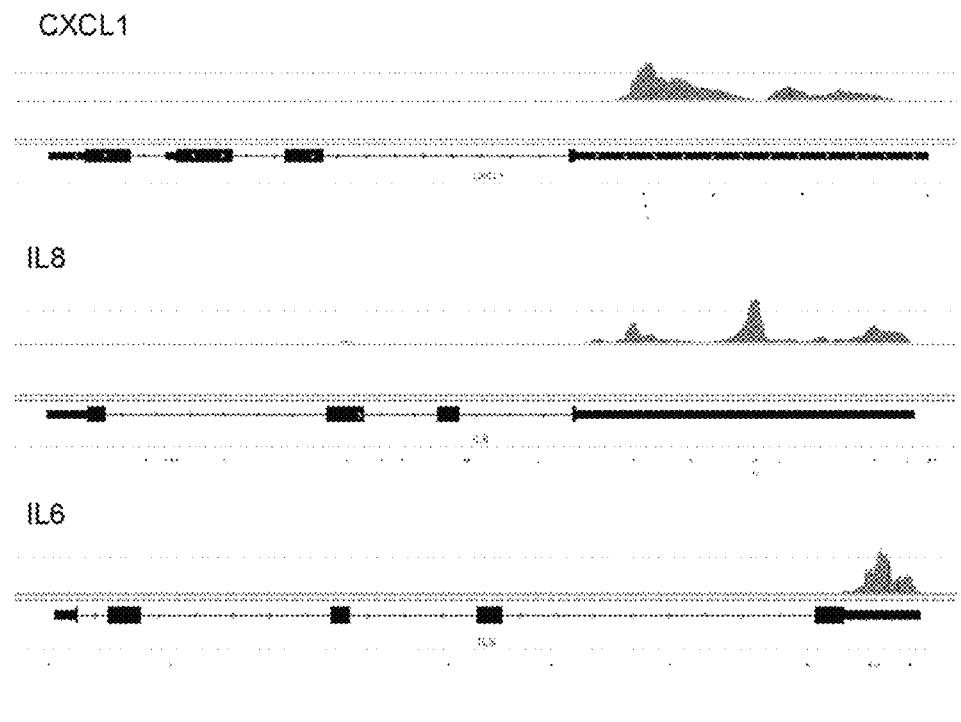

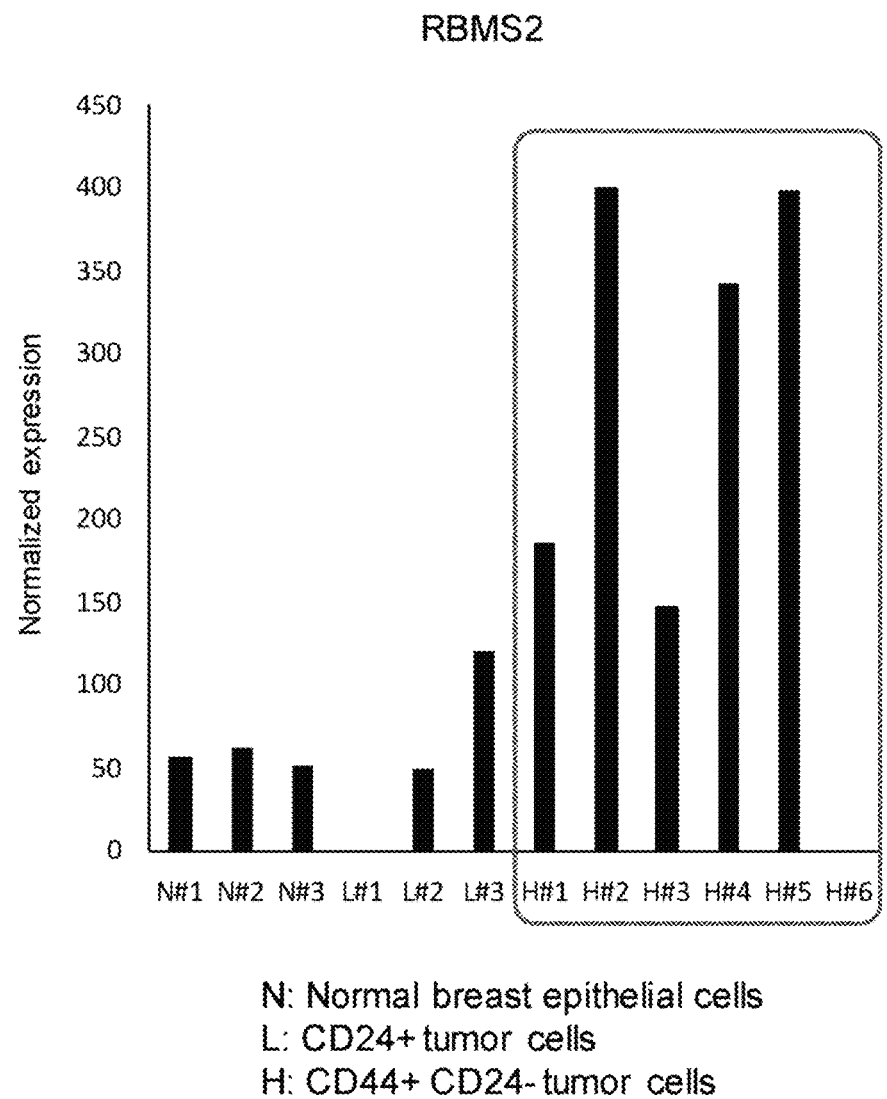
[Fig16A]
N: Normal breast epithelial cells
L: CD24+ tumor cells
H: CD44+ CD24- tumor cells

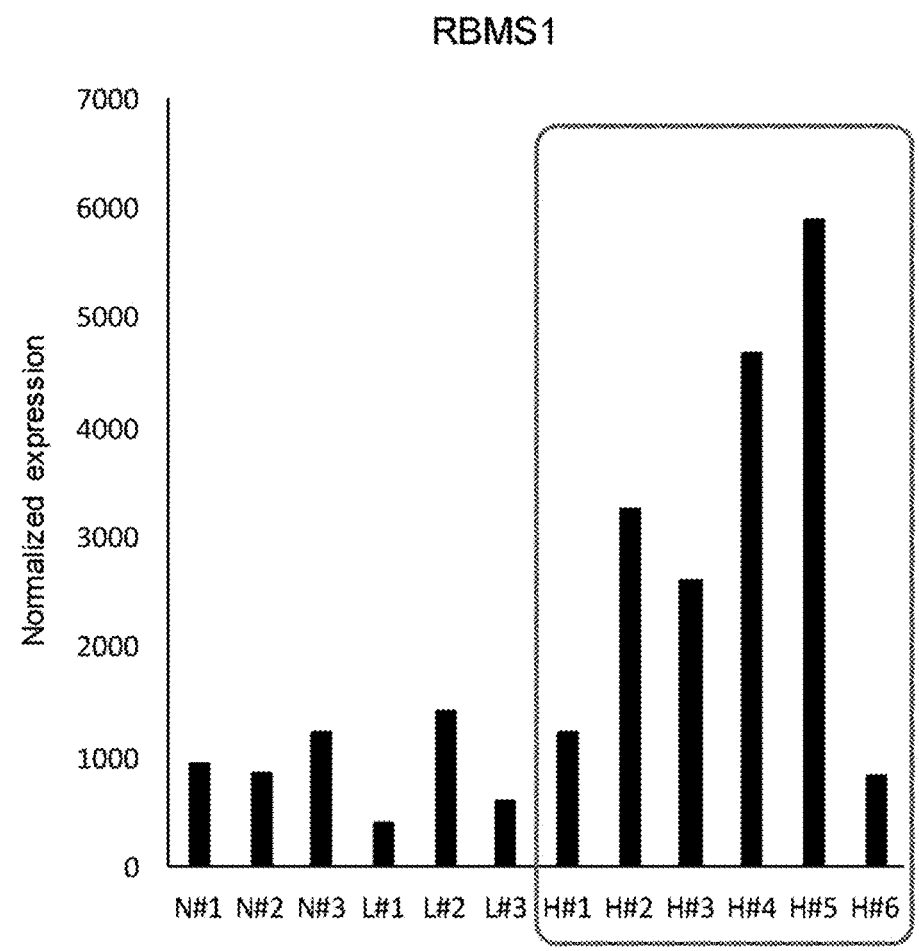
[Fig16B]

[Fig17A]
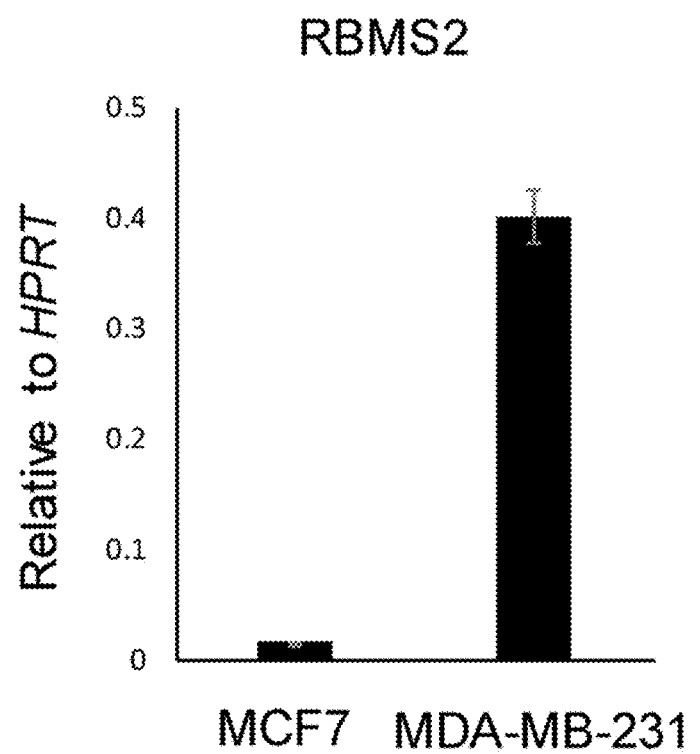

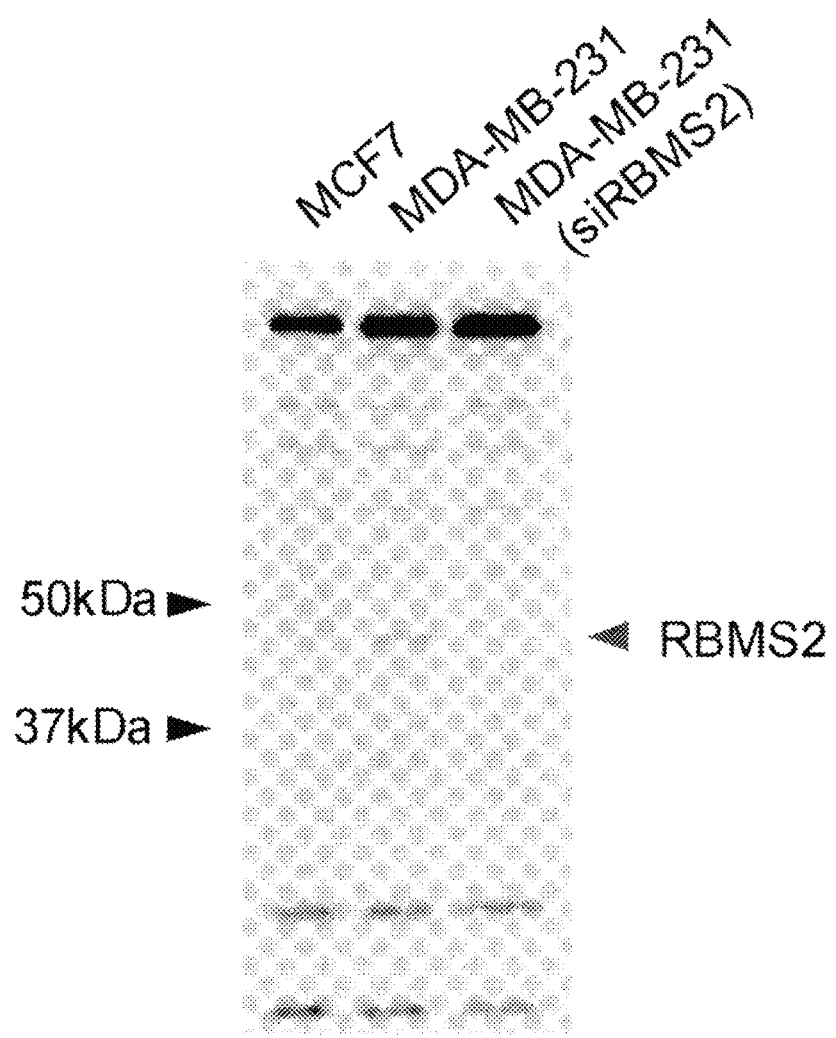
[Fig17B]

[Fig17C]
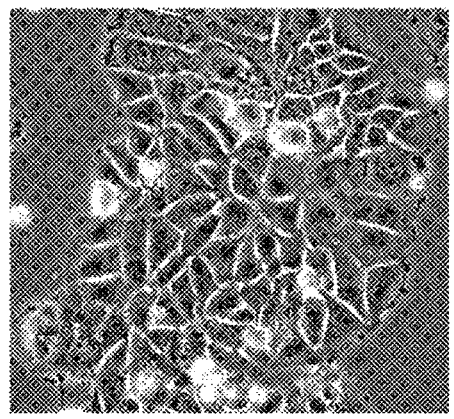
Control
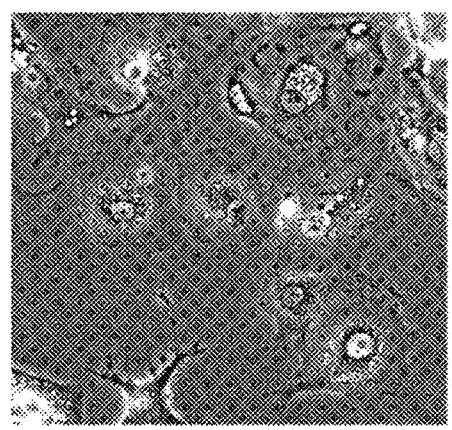
KRAS^G13D
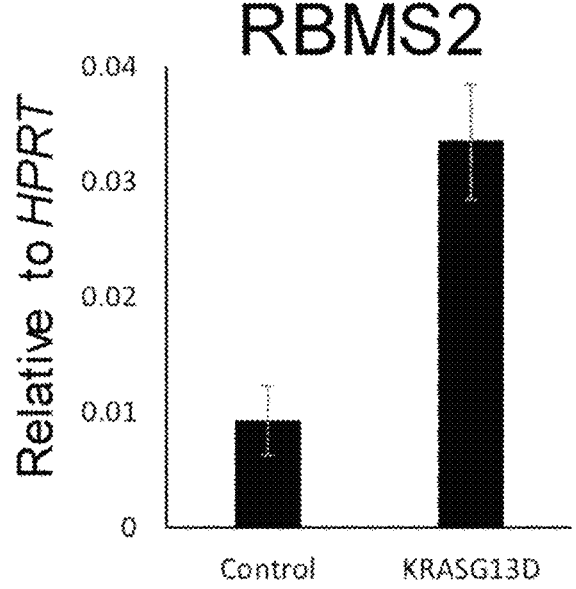
RBMS2
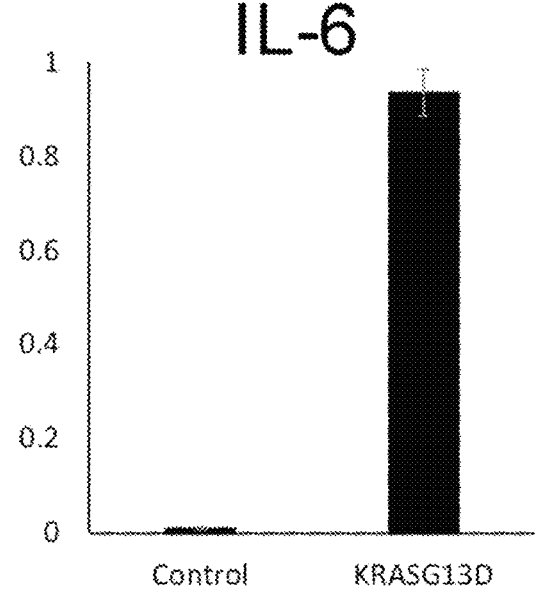
IL-6

[Fig17D]
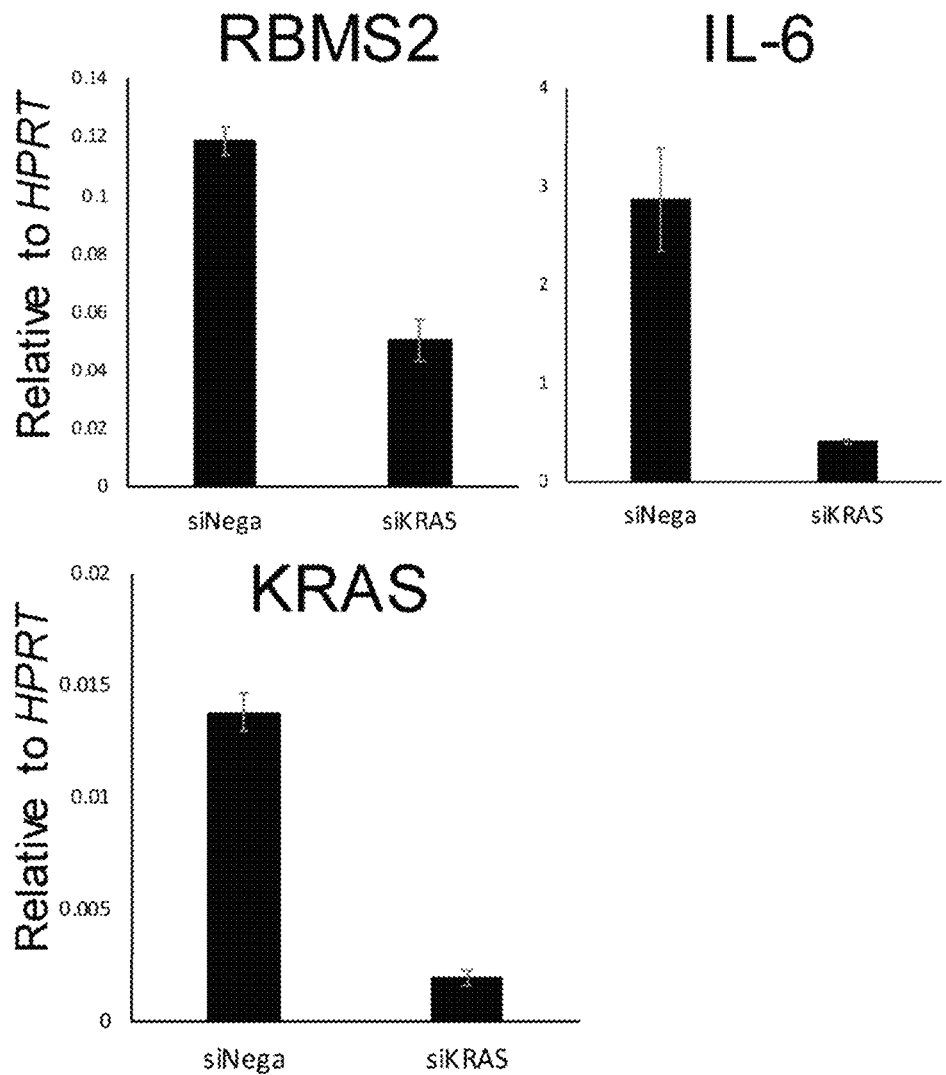
[Fig17E]
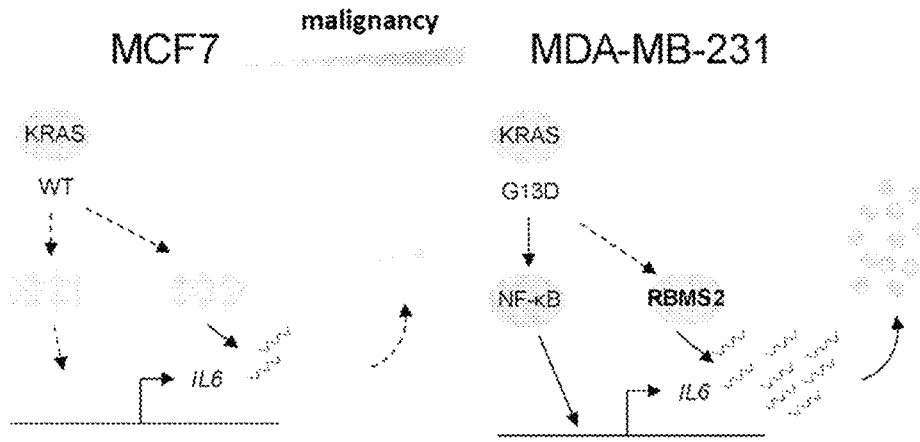

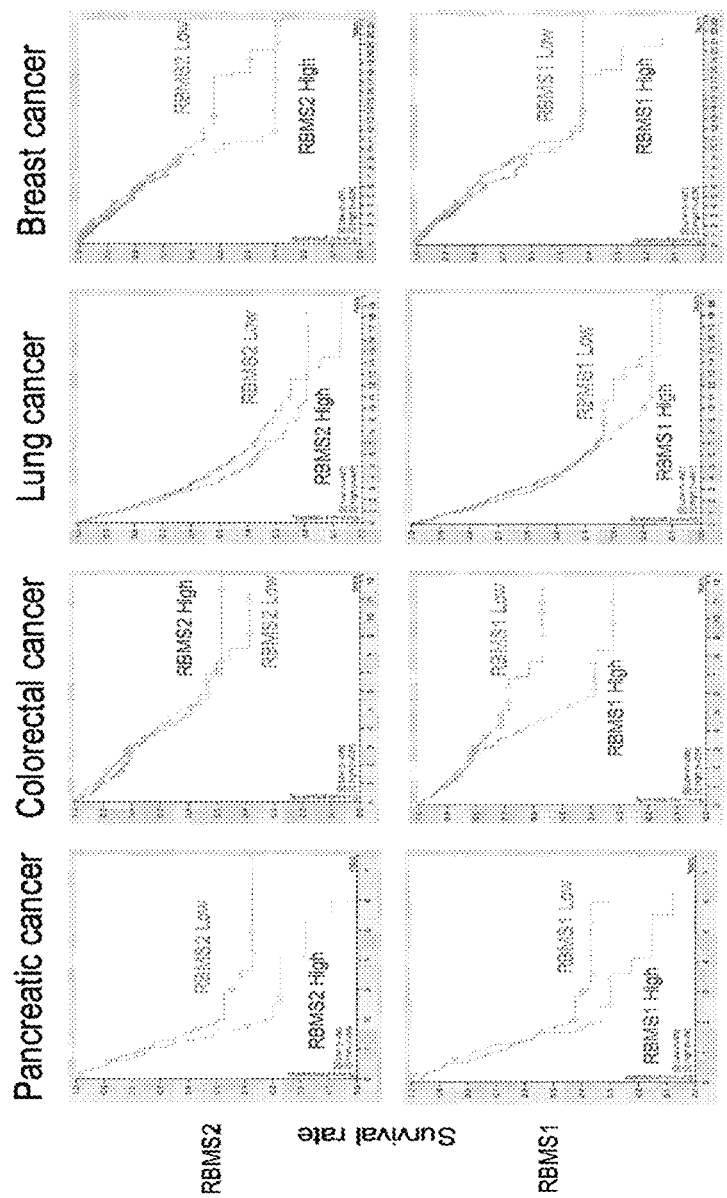
[Fig18]

[Fig19]
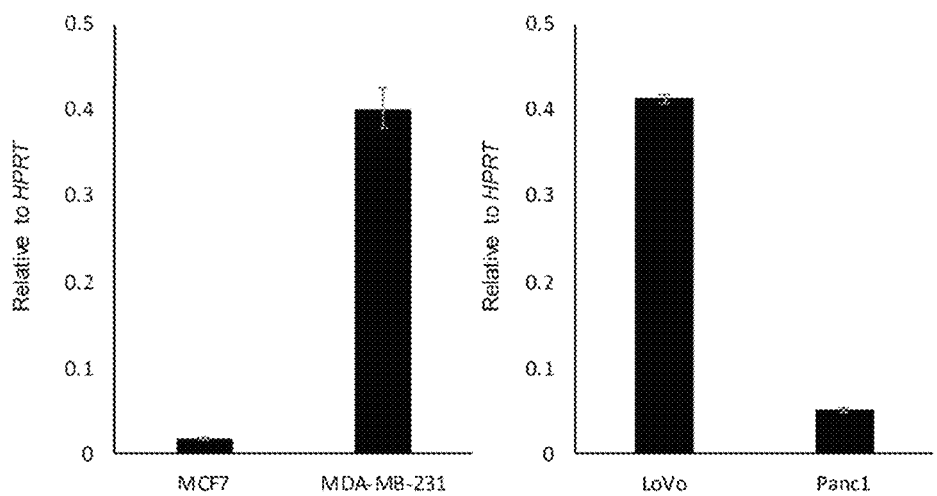
[Fig20A]
RBMS2
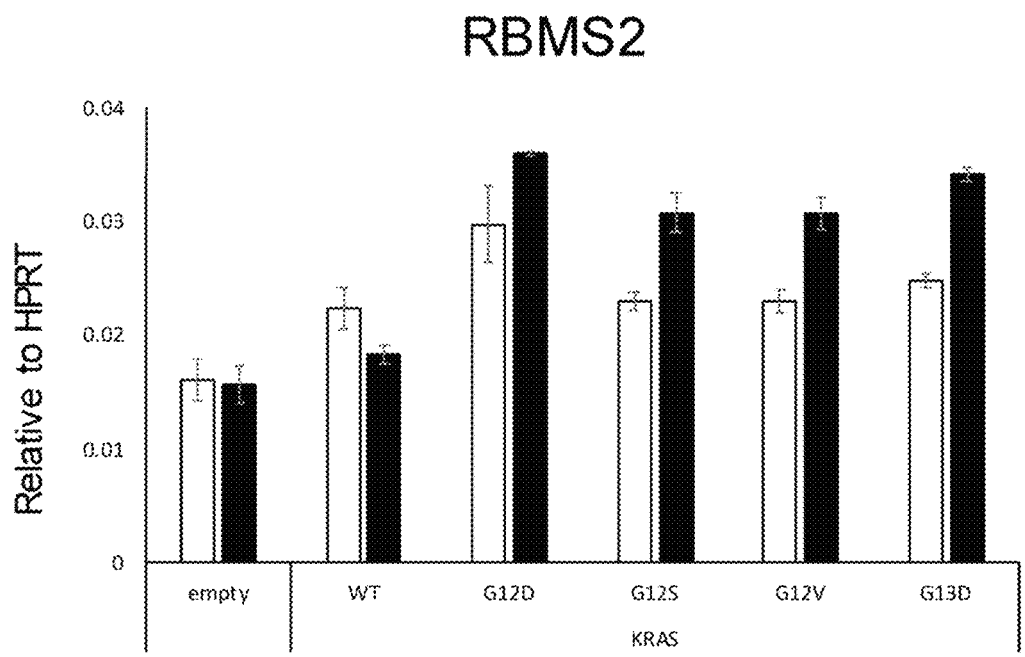

[Fig20B]
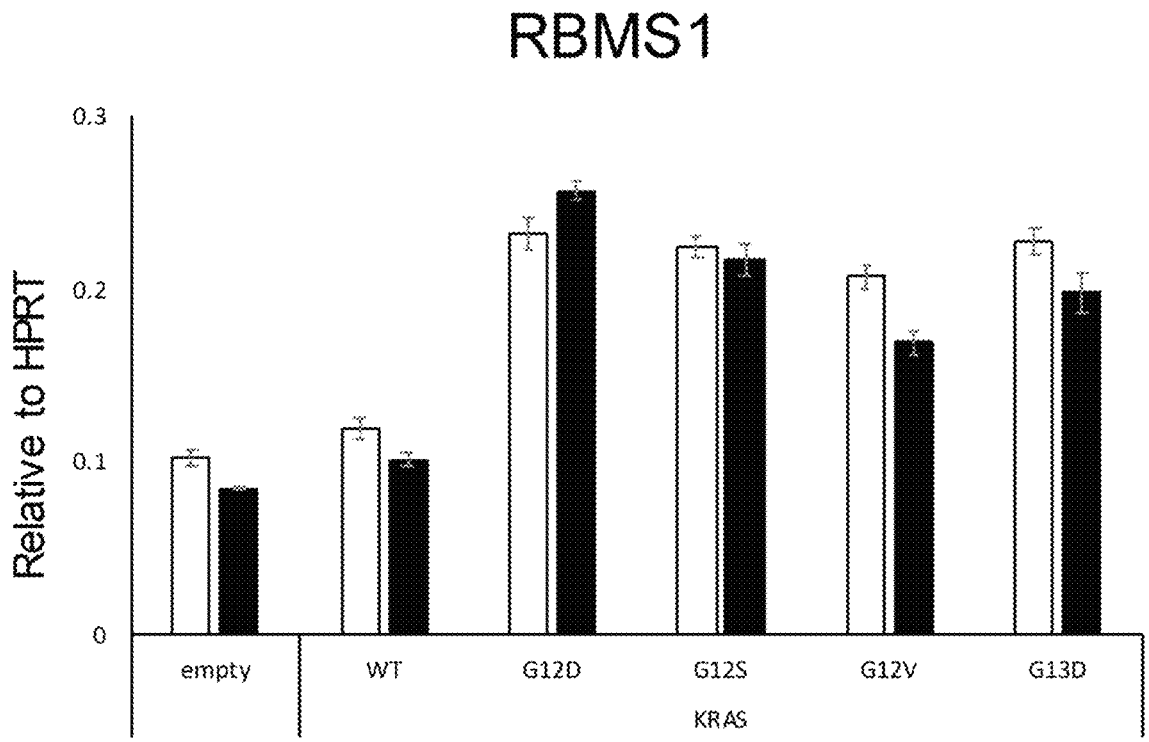
[Fig20C]
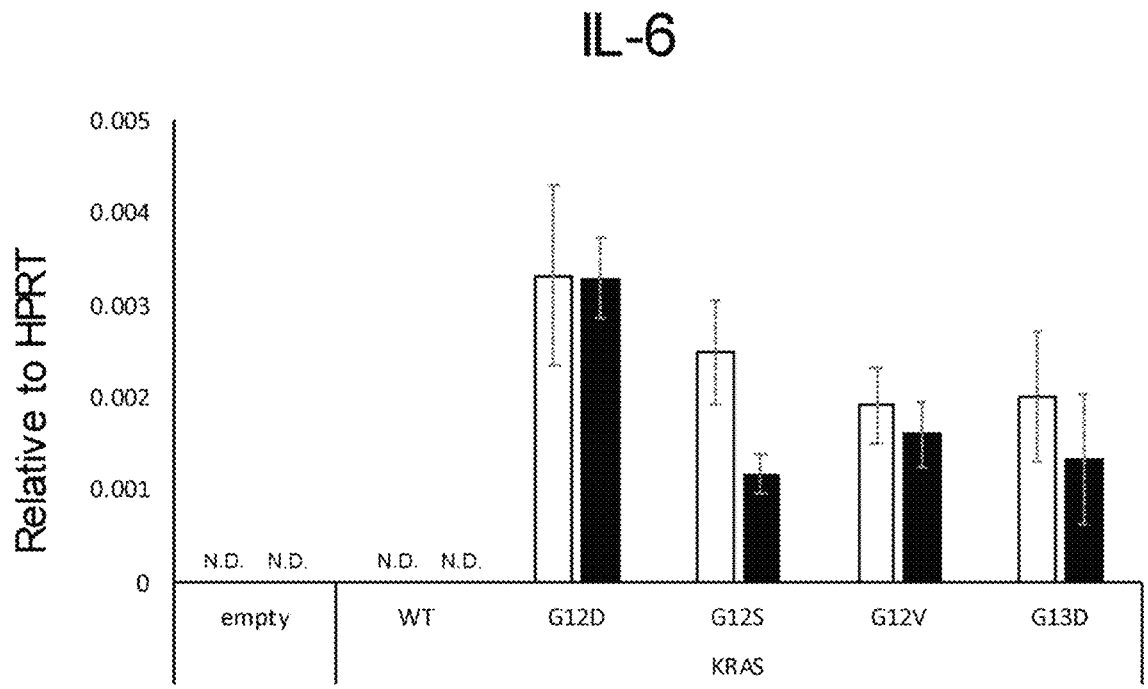
N.D.; not detected

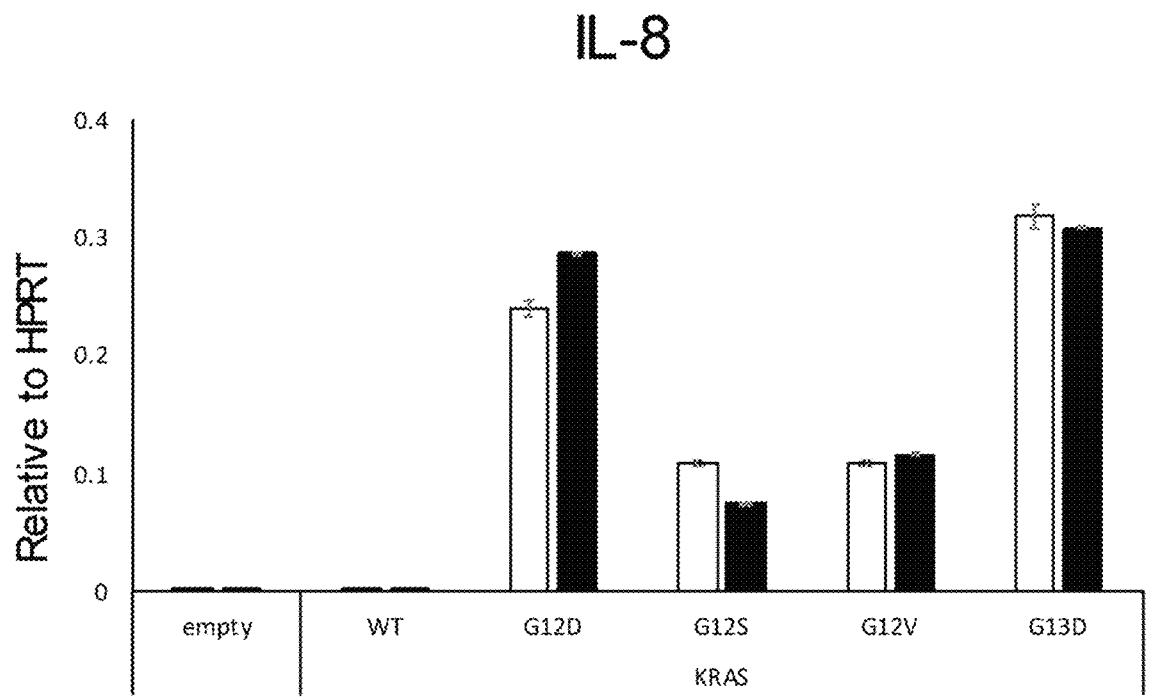
[Fig20D]

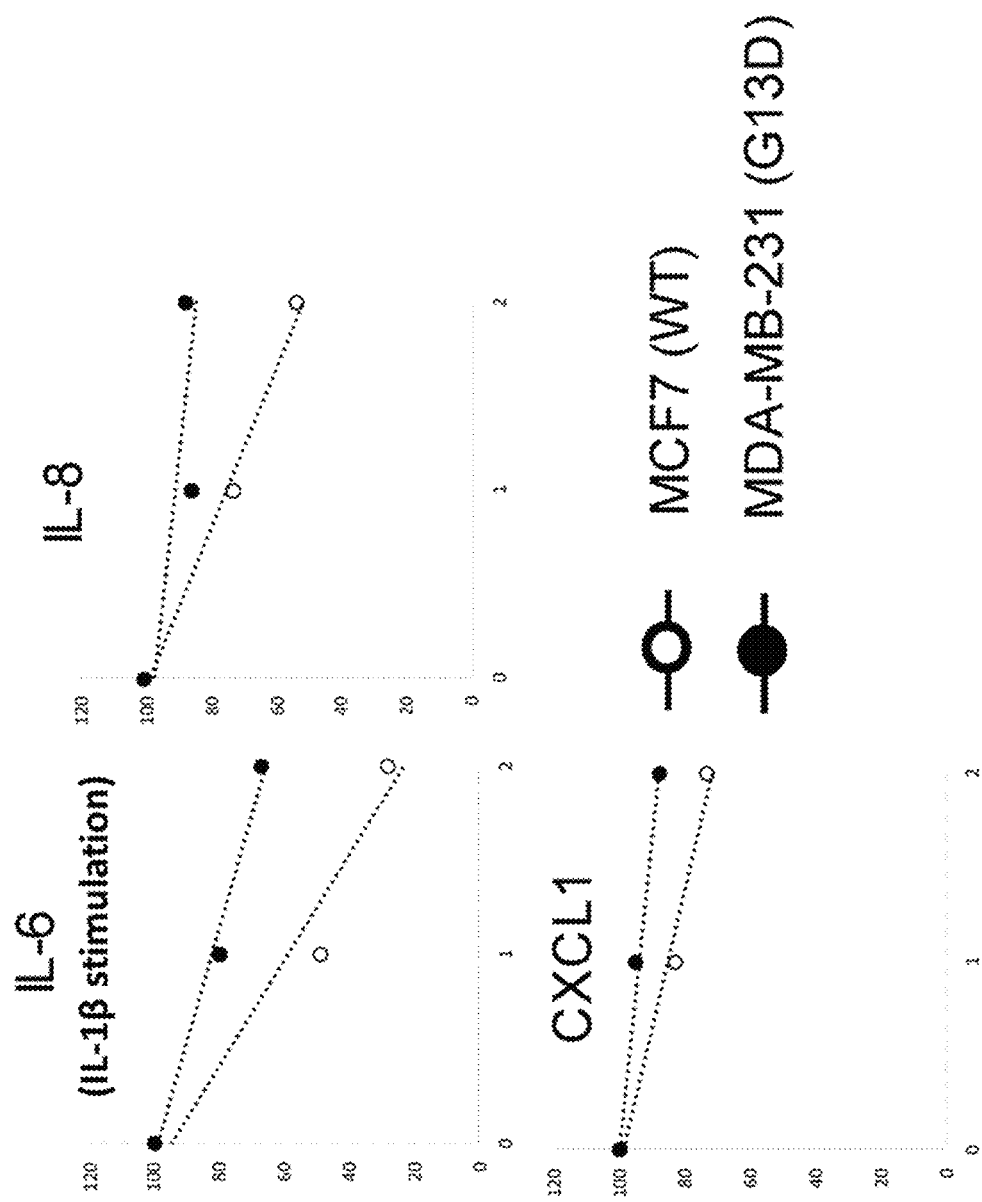
[Fig21A]

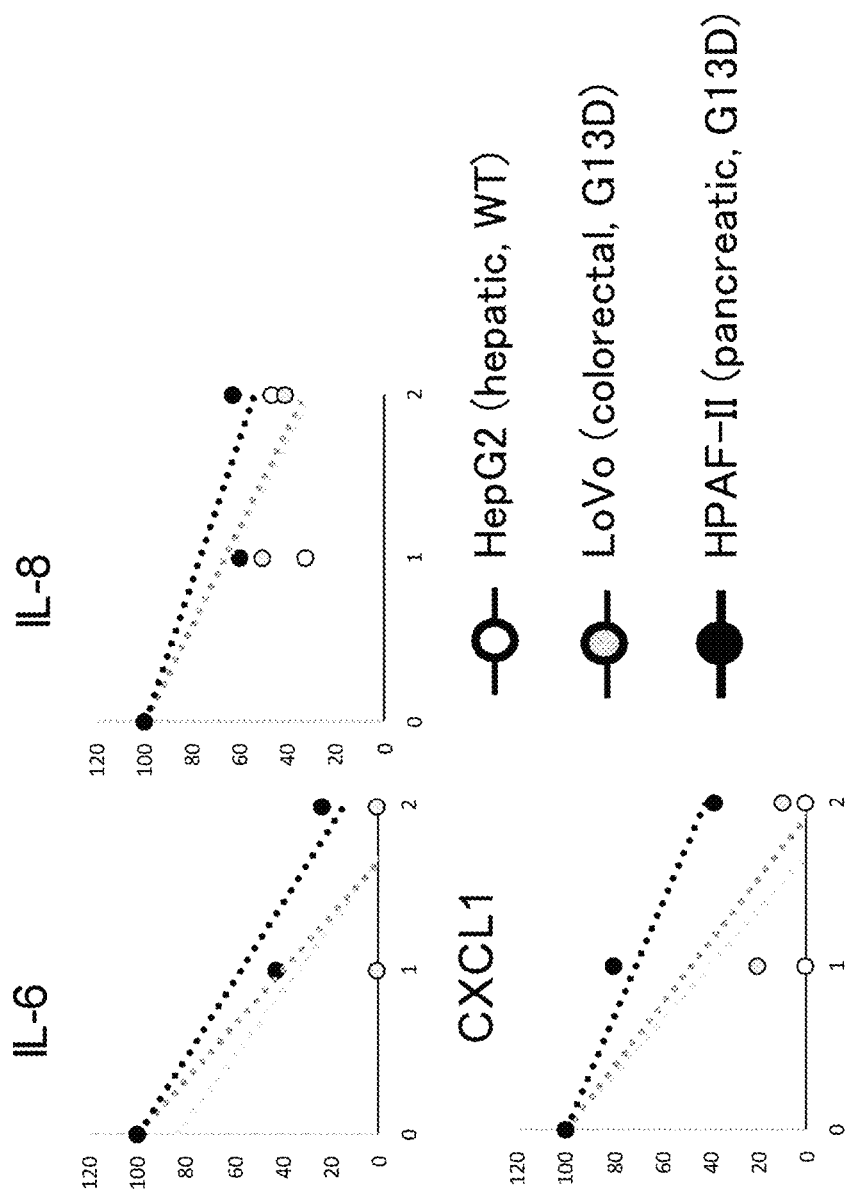
[Fig21B]

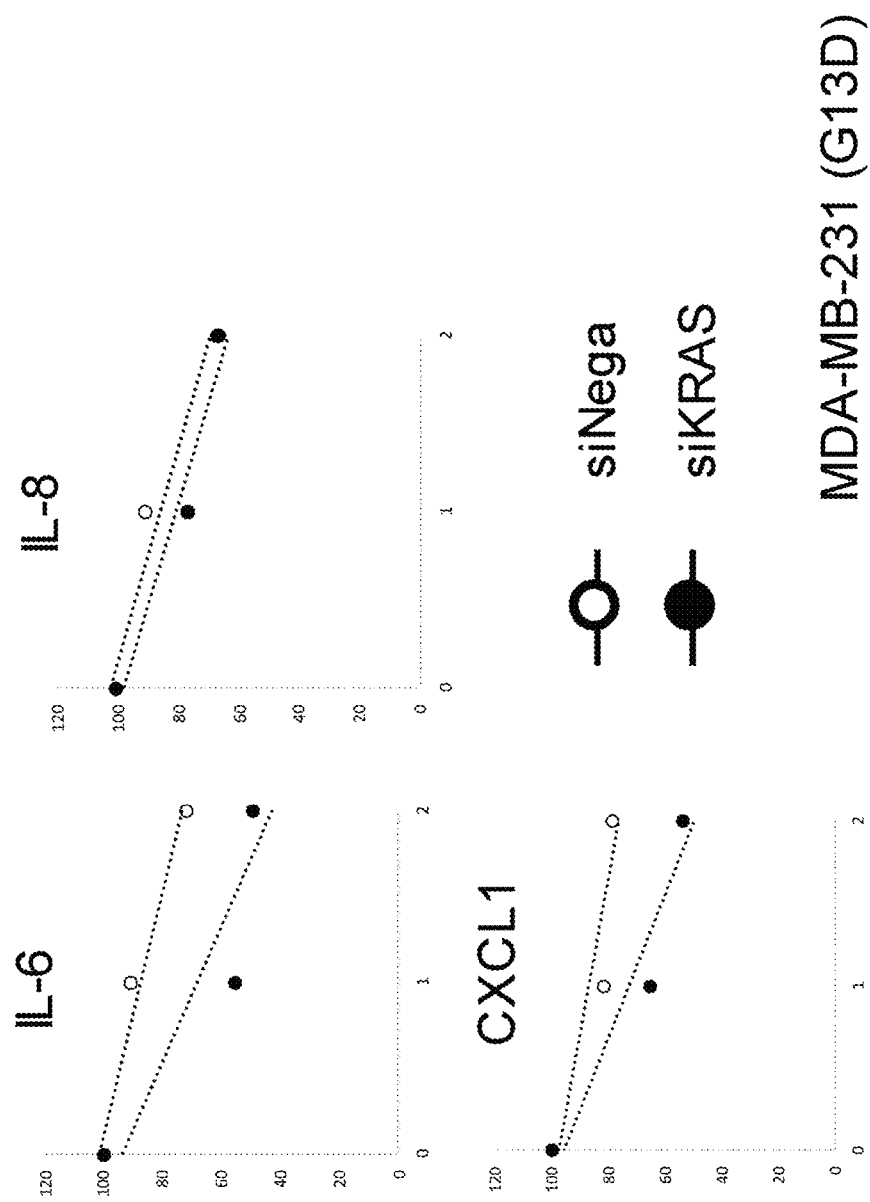
[Fig21C]

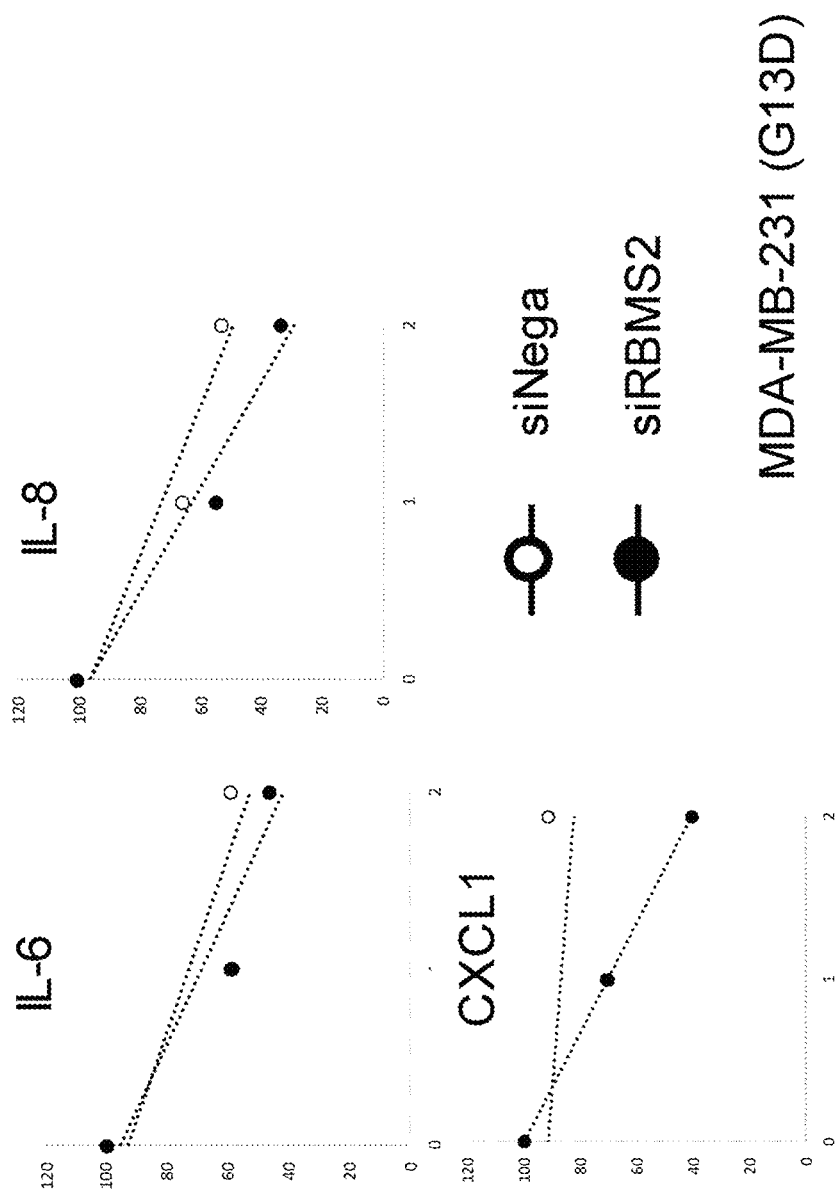
[Fig21D]

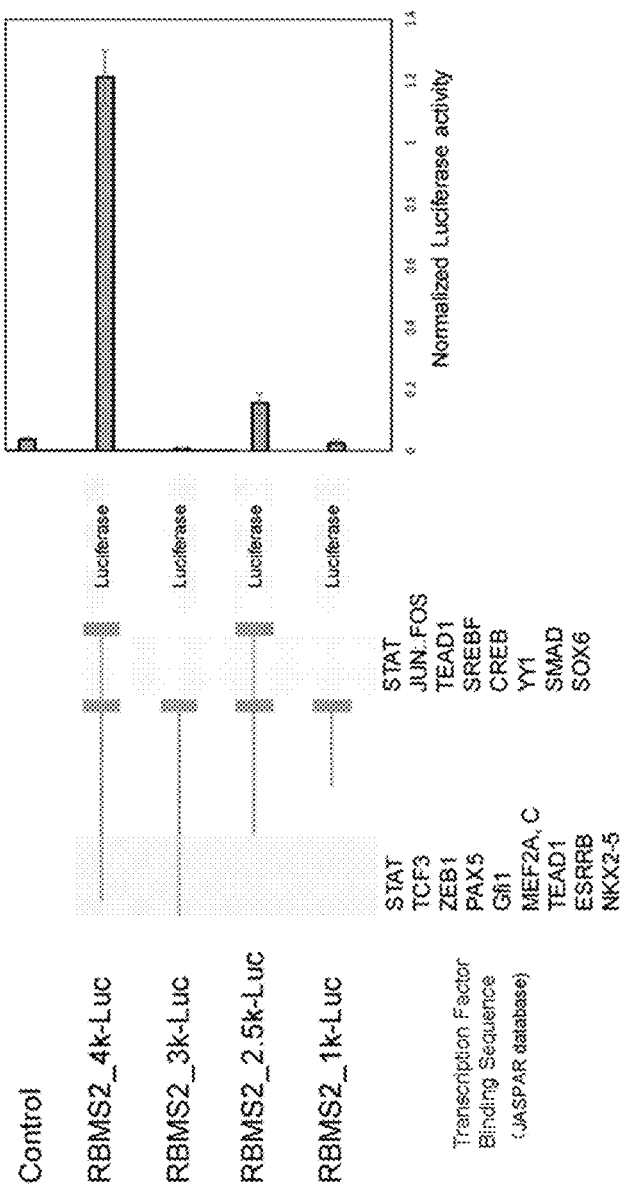
[Fig22]

SEQUENCE LISTING

```
<160> NUMBER OF SEQ ID NOS: 77

<210> SEQ ID NO 1
<211> LENGTH: 8504
<212> TYPE: DNA
<213> ORGANISM: Homo sapiens

<400> SEQUENCE: 1
gagctcattc tctgcccgca gcccccttc atctctctcc tcctgctcct tttctcctcc      60
tttctcctcc cctcccttt tttcctccct ccctctcccc ctttccctcg ctccctcct     120 ccctccctcc ccgtctttct tacccctcc ctttctctct ctctctctct ctcgctcgtt    180
ccctaacatt aaagagaaaa tgctgctatc cgtgacttcc aggcccggga tttcgacttt    240
```

-continued

| | |
|---|---|
| tggctacaat agaaacaaca agaagccata tgtgtcattg gctcagcaga tggcaccacc | 300 |
| tagcccaagc aacagtacac ctaacagcag tagtggaagc aatggaaatg accagctgag | 360 |
| caaaaccaac ctatacatcc gaggattgca accaggcact actgaccaag atcttgtcaa | 420 |
| gctgtgtcag ccatatggca agattgtttc cactaaggcc atactggaca agaccacaaa | 480 |
| caaatgtaaa ggctatggct tgtagattt tgacagccct tcagcagcac agaaagctgt | 540 |
| aacagcactg aaggccagcg tgtacaggc acagatggca agcaacagg aacaggaccc | 600 |
| cacaaattta tacatctcaa acctcccact gtcaatggat gagcaggaac tggaggggat | 660 |
| gctgaagccc tttggccagg ttatctccac ccgtatcctt cgagatacca gtgggaccag | 720 |
| cagaggtgtt ggctttgcaa ggatggagtc cacagagaag tgtgaagcca tcatcccca | 780 |
| ctttaatgga aaatatatta agacacccc tggagtacca gccccatccg atcccttgct | 840 |
| ttgcaaattt gctgatggcg ggccaaagaa acgacagaac caaggaaaat tgtgcaaaa | 900 |
| tggacgggc tggccaagga atgcagacat gggcgtcatg gccttgacct atgaccccac | 960 |
| cacagctctt cagaatgggt tttacccagc ccctataaac atcacccca acaggatgct | 1020 |
| tgctcagtct gcactctccc catacctttc ctctcctgtg tcttcgtatc agagagtgac | 1080 |
| tcagacatct ccctctacaag tacctaaccc atcctggatg caccaccatt catacctcat | 1140 |
| gcagccttca ggttcagttc tgacaccagg gatggaccat cccatttctc tccagcctgc | 1200 |
| ctccatgatg ggaccccctta cccagcaact gggccatctc tccctcagca gcacaggcac | 1260 |
| gtatatgccg acggctgcag ctatgcaagg agcttacatc tcccagtaca ccctgtgcc | 1320 |
| ttcttccagt gtttcagtcg aggagagcag cggccaacag aaccaagtgg cagtggacgc | 1380 |
| accctcagag catggggtct attctttcca gttcaacaag taacagtggg attcccctcc | 1440 |
| ccatctttac tgaatagaaa tgaattcttg gagatactca tgctcccaga ttccagaggg | 1500 |
| ttaaccagga atggagacca tccgtcggcc ctgctaagga ctaacactta gccatcgttt | 1560 |
| ttcacaggcc tgggcctgga aaagaaatc tctacgttcc tgccctttac tattgctgat | 1620 |
| ggagcctggg ggaaccatca cttttttttgt gtgctacatt caaggagatc aaaaaaactt | 1680 |
| ttcttctttt gcaaagaaag cttttgtttt ttaactgcaa cgtacttttc ccctaccttg | 1740 |
| aagagacatg gtggtcgcag cttctcatct atatgaaaaa gttttcgatg tattggaatt | 1800 |
| atttgggaat gcttttaaaa caatttgtaa ttatttcttt acaaaccaaa acagaacaga | 1860 |
| aaggtgtggt gctggaacat cgatgaagga gcctacttta ctgagcttag ttatggactt | 1920 |
| ttttgatgca tgtgtgtatg tgtttttaaaa agtatgcagg ctctaaaaat gttattttgt | 1980 |
| aaagctctca gctcatgcac cccatctcct cttcacccat attatgcctt ctttctcttg | 2040 |
| tccagattct tcttttttctc ttttctaaac agctgagcct gcctactttg ccctttttaca | 2100 |
| gcttttaatt ttatggattt taaaaatga aatttcatgt ggaatttggg gttgggggc | 2160 |
| aggctgggca aggaacaagg cagaacacta agtaggccat ggaagtggct gttctttccc | 2220 |
| ccaccctgcc acaccctggg agaaaaaact agactttggc ttcagaaagc acagatgtga | 2280 |
| cccaggctta ctaaagagac aactccacag ccctgggaac acaccttga gccaaacttg | 2340 |
| gttgaagact aggtcttccc tggcaagttc cggaagaatg gacttactga cttttatcaa | 2400 |
| ctcttctcac tgccaaggcc aacagcatct gaggtatagc ttttttgggag tacctgctt | 2460 |
| cttgcctcct ggaggatatt ttctgtcctg ggcttcatgg cccctctctt ccctgttaca | 2520 |
| cattgctgtg ctcagagcct ttgcagctgc gacctagttg aatccacata ggctccttcc | 2580 |
| acacggtgga agatctgctg cttcactcac agaccaggag ttctcaatca gaggtggttt | 2640 |

-continued

```
tgtccctcag gcctttggca acatctagag acagttttga ttgccacgcc tggaggtggg    2700
atgtgtgtgc tactggcatc tagtggctgc taaacatcct acactgcata ggatagtccc    2760
cactaccccc agccaagaat tatctgactc caggggtcaa tattgccaag actgggaaac    2820
actgatatag acagtgttgt ccctgcctcc tgggttaggg taaattttca ccccaaccct    2880
ggacaaacag tgccttttga cactcatgca actgttgggg aaggactgga ctgggatcct    2940
tgaattctcc ccagactttg acttttgata actctgcata tagcaagagt gattcttgaa    3000
agagctgtgg ctccatgctg aatgcacaca tgtactcaga gggattcagg tgggcattgt    3060
tctggtgtgt gctgtgcaat ggtgggaaag gacaaagctc tctaaactgt ccagagcaac    3120
ctgccctgcc ccggtgtgct tggaccccttt gcccagggaa ccaggacatc agaaataatg    3180
ttccttctgt ggaaggacaa cggggagcta gggtagcaaa agcaataaa ttccaactct     3240 ttatgaggtc aggagtcctt taaaaaagcc tatgtcttgg tctttaactg tccccttctg    3300
caagatgtga ctctatacac atggagacag attgaagaaa gacttcaccc atcttctagg    3360
aaataaaatc ctgctcttgt cttctcccag tcactccctt atgcactgaa aggagaattt    3420
gactcccttg cacttcaagg ccaggtgcct ctccactaga cagtcagaca aaggcaaata    3480
atggaggata gagagacagg tgttcattag gctggccata gggagaggaa ggggtgaca    3540 gcagggggaaa agaaactgta gtatcagttg tcacaagtag agctcggccc agctttccct    3600
cccttcccag ccaccctaga attgagagtc ccagtgcccc tagtgtcgac tttctatgta    3660
catcctaggg gtgagggagt gcggggcaat gggtaggata taaagcgtaa aggacaaatt    3720
gccgcagtct tctaattgat gcttccaaac tcaggaaggg cttatccagt gtaaaatagc    3780
cccaagccca gcaaccttct agagggctct ggctgggcag atagcttttg tttttgagtc    3840
tccagccctc agtcaaggaa aatataccat agctgctttc ttgtcagtgg cctttgagag    3900
aaagagaaaa caaatctaga attcgttca tctgatagac cggggagct ttgctatggt    3960 aggaggttta ggaagggcct ttcacgcata gaaaccattg ttgatattgc cactcccctc    4020
tcctctgcct cacagaactc ctgattctgt cttctttctc tctctatata tatattttaa    4080
aatgttaaaa tggctctaat ttttttgtttt gaattttgaa tttacctttt ggagttcttc    4140
tcatgtgaat ctacttgtta gattgtatta atgagtgttt ctggtttggg catgggaagt    4200
gatgggggcc tgaagttatt ttgcagtggc taatggcact gaggaatttc ttttttggtg    4260
catttggttt acactcattt cctctcctaa ttgttagttc atttgtaaca gtgggtgagt    4320
gtttggagga aaggagggag aagaaaggag ggatactgtt tctcccatga aatagtctaa    4380
ttggttgggt tgatggcaga aggaaacata ggggagcctt ccagctcaca gccaagggtt    4440
gggctcttaa acactatgcc tagtgttttc tgaatgctgt cttcatggag cccagctctt    4500
actctctttg tactttacat ctcaccccca ctcattacag atgctcataa cattcttaaa    4560 atatttagt acttggcatt tttctgtttt cagtcagcta aaacacacta gagtccttc     4620 ctcagatggc ataatccttt ataggctctg agcctgccta gccatctcct atcggtgtta    4680
ttactcctca tctcaggctc tgagatgata ctcagaccct aaactgattg gacttttgg     4740 aggagggtgc cagtagagag gtcaggaaga tgtggagatg atgatggaga gagatgtttt    4800 tatttattt tatttttca gacagagtct tgctctgtcg cccaggctgg agtgcaatgg    4860
cacgatctcg gctcactgca acctccgcct cccaggttca gcaattctc ctgcctcagc     4920 ctcccatgta gctgggatta caggcaccca ccaccatgcc cggctaattt ttttattttt    4980
```

```
agtagagatg gggtttcacc atgttggcca ggctggtctc gaactcctga cctcaggtga      5040
tctgcccgcc ttagcctccc aaagtgctgg gattacaggc gtgagccacc gcgcccggcc      5100
tttattttat tttttagaga tggtcttgct gtgtcaccca ggctggagtg cagtgatgca      5160
gtcgtagtct actacagtct tgaattcctg ggcccaaggg ttcttcccac ctaagcctcc      5220
caagtagctg gaagtacagg cacatactac caagcccagt tcgttatttt aagttttttgt     5280 agagacaggg gtcttactat gttgcccaga ctggtcttga actcctgtca agtgagcctc      5340
ccacctcagc ctcccaaagt gctatgatta caggtgtgag cctccatgct tggatgagat      5400
gttgttttta atgttttttgg ttttttggtt ttgttgtttt gttttttga dacagggtct      5460 cactctgtgg cccaggctgg agtgcagtgg caccataatg gctcactgca gcctcgacct      5520
cccaaggctc aggtgatcct cttgcctcag ccaccccttc ccggccacc aagtagctgg       5580 gactatgggc ttgtgccacc atgcctggct aatttttttta ttttttagtag atgggggtt    5640 ttaccacgtt ggccaggcta gtgtccaact cctgacctcc aaacagctaa ttttttgtatt    5700 tttaatagag acaggttttc gccatgttgc ccagcctcgt ctcgaactcc tgggctcaaa      5760
tgatccaccc acctcggcct cccaaagtgc tgggattata ggcatgagcc accacacctg      5820
gccttttcag ttttttttatt tttattttt ctttgagacg gagtctcgct ctgtcgccca      5880
ggctggagtg cagtggcgtg atcttggctc actgaaacct ccatctcctg ggttcaagca      5940
gttctcctgc ctcagcctcc tgagtagctg ggattacagg tgcctgccac catgcctggc      6000
taatttttgt atttttagta gagacagggt tttgccacat tgcccaggct ggtgttgaac      6060
tcctgggctc aaatgatcca cctgccttgg cctcccaaag tgctgggatt acaggcgtga      6120
gccactgcac ccggcccttt gtagtgtttt taactaaaga atttgtagag ttgcccaggc      6180
caggaagcct ggtggctcta aagggtaata gaccttgtca gtaacagata aggagtggta      6240
agaggacatt actcatattg aagatgaaga ccagactttg ctgcttcaca ggccatgcgc      6300
tgggttgggc cacttcagct ccactccatt cgttttcctt tcctaacttg acaatcagct      6360
cactcaccct cccttagtgc ctccagtgcc tactcctgtc actccaatgt caacccattg      6420
ggagttgagg cctgtcactc caatgtcaac ccgtgggctg ttactttgcg tcatatgatg      6480
ctgtgagagg ccttgctgga atgtcctagg aatccctagt agcagtggct attagtcttc      6540
tagaaaagaa ctattgctgc tgccttgtgc acatgcccca ccttctgggc aagtggcagc      6600
attgcgctca tgaggggctt tgcattctta gccaagggca ataaactggg tgggtgatct      6660
ggcccaaact tgcccctagg ctctgctagc cctgaatcag caggcttcag agacgagggt      6720
gggtgttata aaagccagtc tgtaaagggt aaattccaaa tcttgtgcct tgttataccà      6780 atccttcctg attcccgttt aaaccaacta ctctatttct gtgctgccta cattttcaat      6840
cctcccacgc attagcaaat tcctgaaatt tcctcatttg gtaggccttc cataggagtc      6900
agctatggac ttccatagga gttggcagct aaaaccagac tgtgagcttc tgtctccgtt      6960 ctgattttttg ctgcacctcc caggggacag tccccacatg attacaaaag ccaggtgccc    7020
tcatcacccg ttacccctga cctgtccact tgttttgaat aaaccttcat tctccaagca     7080
gatccccaaa cttccttgtc cttgttacac gtctacctca caacctcaca attcaacaac     7140
aggtaaatac ctggattcac tgatttcttt actgtccttc tctgagggtt gggaaggtgg     7200
gggctagaaa aggctcataa ttttttaaact cttgggaatt aaacttggga atttctattc    7260
ctacagtgtt ttctctggga ttttttagctc actgatcgcc ctagaatagt gtgaactctc    7320
cagataggtc ctgctgtgat aggccagggg agtaggctgt gcagtgacgg cttagggtaa     7380
```

```
taagtaatgg ttggaggaca ccagcatagg agcagagttt agaacttaag aggacaagaa    7440
agctgctcag tggctggcgt atagctgtga aggtaaccaa acaccaaaga gggagtctgt    7500
catttttata aggctggaag cgaatgttcc ttttctacct taacatacag tttaggggt     7560 tgcaccaaga caaagtttcc aggctggagg gtaatacata tccagcgcga gtgaagtccc    7620
cactccaaca tatacccttt tgggtgggt  aaacacctct tgcatgtgg  acagaaaatg    7680 tttatactta aacagacata ttttgcatat ttttatctgg agacttcttc tagttttata    7740
ctcttcccac atctatgcca atgccaccat tctaaaactt acactccttt tctaccctg     7800 gtcttttcct tgtccttccc tacaacttgg tagaggtcca ttttgtctta cttcacactt    7860
tttttttttt aaataaaaca caaaagtcta cgtcttggtg tcttatccgt gagtgggaag    7920
tggtaagctg gtgatggtcc catatttgct atgacaggaa cacagaggtg gcagcttagg    7980
aagctggggc cacatctcac aaggcaggac ctggatgcac tgaatccccc tttgctccag    8040
caactcagcc agacatttag gcaggagcac taatgaccct ttccatccac acagagggta    8100
tggaacagga gcccctgttg ttcccttgcc tgtggtctct taagccagtc ataccctatcc   8160 caacgccgtc tcccctcag  gtgtgtagaa gggaagatga atacacagag tcttttgaat    8220
ctctatcaaa tgtggttttt tttattcaac aactgacaag cacttttcta cagctgcact    8280
tgtggaacat cacatggcaa aaacaggagt ttttcgcta  gacttttttt ttctttttaa    8340
ccttattaaa aatgagattg gtcctaaaaa tatagaaaga aataaattta aattcacaaa    8400
aaactgtaca ttatcaaaaa gtcactaaaa caccacattt ggttatataa aaagtccctt    8460
ttgctgtaaa aggaacacag aaacttaaaa aaaaaaaaaa aaaa                     8504
```

<210> SEQ ID NO 2
<211> LENGTH: 5207
<212> TYPE: DNA
<213> ORGANISM: Mus musculus

<400> SEQUENCE: 2

```
ctttctcctc cccctccctt ctcccttccc tccctctttc cctccctttcc tctctccctc     60 tcctttcccc ctcccctcct ccctcccctct ttctccctcc cttcccttca ctctcttctt   120
tctctctctc agctccgtaa cagtaaagaa aaaatgctgc tatcagtgac ttccaggcct   180
gggatttcga cttttggcta taacaagaac aacaagaagc tatatgtggc tcagcaaatg   240
gcacctccaa gtccaaggaa tagcacccccc aacagcagcg gcggaggcgg cggcgggagt   300
ggtgggaacg accagctgag caaaaccaac ctgtatatcc gaggactgca gccaggcacc   360
actgaccagg accttgtcaa gctctgtcag ccgtatggca agattgtctc cactaaggcc   420
atcctggaca agaccacaaa caagtgcaaa ggctatggct tgtgtgactt cgacagtccg   480
tcatcagcac agaaagctgt aactgcactg aaagccagtg gtgtgcaggc acaaatggca   540
aagcaacaga agcaagaccc tacaaactta tacatctcaa acctccctct gtcaatggac   600
gagcaggaac tggaggggat gctgaagccc tttggccagg tcatctctac tcggatcctt   660
cgagacacta gtggggccag cagagggtc  ggctttgcaa ggatggagtc aacagagaag   720
tgtgaagcca tcatcaccca ctttaatgga agtatataa  agacaccccc tggagtagca   780
gcaccttctg acccctttgct ttgcaaattt gctgacggtg gccaaagaa  acgacagagc   840 caaggaagat acgtgcaaaa tggacgggcc tggccaagga acggagacat gggcggtatg   900
gccttgacct atgaccccac tgctgccctt cagaatgggt tctacgcagc tccttacagt   960
```

```
atcgcccaca gcaggatgct tgctcaatct gcgctagccc cgtatcttcc atctcctgtg    1020
tcttcctatc agggctcagt tctgacacca gggatggacc accccctctc tctccagcct    1080
gcctccatga tgggacctct tacccagcaa ctgggtcacc tgtcactcaa cagtctgggc    1140
acgttcatgc cggcagctgc tgctatgcat ggggcttaca tctcccagta cccagctgtg    1200
ccttcttcca gtgtttctgc tgaggagagc aatggccagc agaatcaact ggcagtggag    1260 ccccccctcag accacggggt ctatcctttc cagttcagca ataatgagg tccagacctg    1320 gggagagaag cctatgcagt cctccttggg ctccttcctg tggctgatgg aacctgagga    1380
atcacgttgg tttttttttt tgaatgtgct acattcaaga tcaaaaagac ttttttttct    1440
tttgcaaaag aagtttcttg ctttgtattt aattgcagcg aacctttctc ctaccccaaa    1500
gacaccagtt gaggtgcttc tcatcttcga gaggtttggg tatgttgggc ttttaaaatg    1560
gtttaagaac aatcgcagtg ctgtgaagtc agtgaagggg cgctgcttgc caggttcagt    1620
tagggactat tttcaatgtg tgttttagat atgcaggctt aaaactttg ttttgcaaag    1680 ctctcaacac acactttgca cacccacc cacctccctc ccacgcactg tttaaggcag    1740
ggtctcacag tgcagtcctg gctggctgac aatgtagacc aggctggctt tgaactcagc    1800
gatccttccc actctgtctg agtgcaccgc catgcctagc tagttgtttt ttttttttg    1860 gttttttttt tttcaagaca gggtttctct gtgtagccct ggctgtcctg gcgctcactt    1920
tgtagaccaa gctagcctcg aacttagaaa tccacctgcc tctgcctccc aagtgctggg    1980
attaaaggcg tgcgccacca ccgcccggct agttgttttt taaaacttct ccacaatggt    2040 cttttttct tttccattta gcttagcctg cctactttgc cttttacaa tttttaattt    2100 tatgaatttg atttaaattt catgtggaat tgggggaagg gagagcaacg cacaggtaga    2160
gaagtgtggc agtagaggtt gctttccctc tgccctcctg gcctaggagg ggttagactt    2220
tgacttcagg aagcagacat gtgacaacca tgcagccttt ggaaaccacc ttcaaccaac    2280
tctggtggca agtgccactg agaagtggca tccagcttca gcatcctgga tacctgctct    2340
gcctcctgga gggtcttggg tcttcatcct gccccaggtc tcacagcccc tgcccctgct    2400
gagcaagttc tgccttccac tttaccagga ggttgttttg tccccgagag ctgctgtct    2460 tgtccatcat catccttgat taccaagcct ggggagtatc atgtgtgctg gtcctgaaca    2520
cctgacagaa cctggcccca ctcctccacc ccttattccc tggcagttat ttggtgtaga    2580
ctaaacccca gtccagcctt ggacatggag cctgttagtt catgtacttg gccagcagtg    2640
acatctgtga ctttgcctcc tggaggatct tttctgcctg ggttctcaca gcctctcatc    2700
ccagctgcac atggctgtac tcaagtggta cttggctgaa tcacttaatt cagcaggagc    2760
catcttattt agcagggctc acccttggtt gtatgtacat gccaagtgca cacagtttga    2820
agggatgaaa gcaagaactg ttgtgtatac tgtgcatgct tgagaatgga ctgagctttc    2880
tctatgcagc atacccagcc cagccctggt gtttggaccc cttccccagg gaaccagacc    2940
accagaaata attttccttc ttgtggaagg acgacggggt gctaggatag aaaaaggcaa    3000
gactcacagc tccctggcca ctcaaaggtc aggagggact tgtaaacatg cctgccgtta    3060
actattccct tctgcaagac tttcagcaca aaatgtgact tgttacatca catcccttca    3120
cgtcataagt acacctccag tagacaaagc aatggagatg gggaagtgtg tccagaggtc    3180
agtgtgaaag aggaagggca gggcatggtg atggtgagaa actggctcag cagctgtgca    3240
cactacagaa ttgggaatcc tggcctgact gtgctgctgt gcgttctaga ctgaggaagg    3300
ggctgaggac aatggacagc ataaagtaca aaatgaccag ttttctcatt ggtgcttcca    3360
```

```
acatcaggaa ggtcataccc agttatcgac ctctagccct ctagcactca gtgacagact   3420
cagagctctg tcctgtggaa accctgctga cagtcttgct gccactgctg ctccttcact   3480
gcctattaaa aattgttcct ttttctgtag ttctaaagca atttgaataa ctgacagttt   3540
taaaatttga aattaccttt ttaggttttt cttttgagta tactggttag ggttctagtg   3600
tttctggttg aacaggtgtg agcatgggaa atgagggcaa cctgtaattt tgtttttata   3660
gtggttaatg gcactcactg tgtaatttct gcttagtgat ttccatccac tcttttcctc   3720
attagctcat tactcagaaa ggtagcgact gaagacagga agtagtatgc aagccatgag   3780
ggatgagttg taagcctcct ctccatcatc ctgcccaagg ctcctaacag tctcctgagt   3840
cctgtttgca tggaggccag atagatggct ctgcactcta tatctcacct gtactcattt   3900
tagtacattg tggttttgct tccaatcaat cagagtggac tagagctcac acctgacctc   3960
gtgtgactct tcactaggct ccaggcctat cccatctcat tgggtcagac tgtagatgga   4020
ctggactttt ggagacaggt cctgctatta cttaggaata tgtgggaaca atgataggga   4080
ccaagcttgt gaagcaaaac ggctttggaa agggcaagtg ctcaataata aaaaatgggg   4140
tggaagtgaa gcgttatttg ctgagggttt cggaaggact agtttgtttt tgtccctggc   4200
ccttccggtc aagtgggcac ctcccatttt gtcgccaaga gcaatacagt tgagtaggtg   4260
gtagacccaa actcacccag ccatttctag acctgaattc agaggataag gtgagtctag   4320
aggtatatac aaccaatgct tgttagacca attcttacca attcggagca agccggtggc   4380
tctacttctg ggtaacctgc ctcttaaaag tgcctttgat cccagtagta gattcagggt   4440
ctacaggagc cttccctcag cagctaaaac caatttgtct cctctactct ttgctgcacc   4500
tcccggaggt ggtctccatg tggcagtgat gccctcatca cccttgtgac caccgctctg   4560
aatgttcaaa ataagcattt cctgtccaag caaatcccta aactccctcg tcctcattac   4620
tcaactacct cagtctgaca actcaaggca cacaagcacc tacttgcctc ccaccatcct   4680
ttactgccct tgtctttgtg gggttggaac aaatgcaaac tcctcagttc cacaacccaa   4740
aactgctctt tctggatcgt cttctccagt gacgttggct ccctacaaga gcgaactctc   4800
catatgggtc agtccctgta ggacaagcca gggactatgc tgtgcagtca aatgccaggt   4860
ttggagcata gcttaagacc gcagagagta aggacttgag tggtggtggt gtgcagtttg   4920
agagagctgg aatggacgtc tctgctcctg ccctctgggc gggtcgggtg atgacttcta   4980
gatgcactcc ttaccctgga gggaagttaa tttatactta agatgcattt tgtacatttc   5040 cccctttaccc agaaacctgt agtttcatac tcccatgtct atgccaacac tacctatcgc   5100
tcactctccg tggctgactt ctggttccat ttccttcctg tgacttggaa gagctttact   5160
tttgctcacg tgaaccttc tttttaaat aaaacacaaa agcctcc               5207
```

<210> SEQ ID NO 3
<211> LENGTH: 407
<212> TYPE: PRT
<213> ORGANISM: Homo sapiens

<400> SEQUENCE: 3

Met Leu Leu Ser Val Thr Ser Arg Pro Gly Ile Ser Thr Phe Gly Tyr
1               5                   10                  15

Asn Arg Asn Asn Lys Lys Pro Tyr Val Ser Leu Ala Gln Gln Met Ala
            20                  25                  30

Pro Pro Ser Pro Ser Asn Ser Thr Pro Asn Ser Ser Ser Gly Ser Asn
        35                  40                  45

```
Gly Asn Asp Gln Leu Ser Lys Thr Asn Leu Tyr Ile Arg Gly Leu Gln
         50                  55                  60

Pro Gly Thr Thr Asp Gln Asp Leu Val Lys Leu Cys Gln Pro Tyr Gly
 65                  70                  75                  80

Lys Ile Val Ser Thr Lys Ala Ile Leu Asp Lys Thr Thr Asn Lys Cys
                     85                  90                  95

Lys Gly Tyr Gly Phe Val Asp Phe Asp Ser Pro Ser Ala Ala Gln Lys
                100                 105                 110

Ala Val Thr Ala Leu Lys Ala Ser Gly Val Gln Ala Gln Met Ala Lys
            115                 120                 125

Gln Gln Glu Gln Asp Pro Thr Asn Leu Tyr Ile Ser Asn Leu Pro Leu
    130                 135                 140

Ser Met Asp Glu Gln Glu Leu Glu Gly Met Leu Lys Pro Phe Gly Gln
145                 150                 155                 160

Val Ile Ser Thr Arg Ile Leu Arg Asp Thr Ser Gly Thr Ser Arg Gly
                165                 170                 175

Val Gly Phe Ala Arg Met Glu Ser Thr Glu Lys Cys Glu Ala Ile Ile
            180                 185                 190

Thr His Phe Asn Gly Lys Tyr Ile Lys Thr Pro Pro Gly Val Pro Ala
    195                 200                 205

Pro Ser Asp Pro Leu Leu Cys Lys Phe Ala Asp Gly Gly Pro Lys Lys
210                 215                 220

Arg Gln Asn Gln Gly Lys Phe Val Gln Asn Gly Arg Ala Trp Pro Arg
225                 230                 235                 240

Asn Ala Asp Met Gly Val Met Ala Leu Thr Tyr Asp Pro Thr Thr Ala
                245                 250                 255

Leu Gln Asn Gly Phe Tyr Pro Ala Pro Tyr Asn Ile Thr Pro Asn Arg
            260                 265                 270

Met Leu Ala Gln Ser Ala Leu Ser Pro Tyr Leu Ser Ser Pro Val Ser
    275                 280                 285

Ser Tyr Gln Arg Val Thr Gln Thr Ser Pro Leu Gln Val Pro Asn Pro
290                 295                 300

Ser Trp Met His His Ser Tyr Leu Met Gln Pro Ser Gly Ser Val
305                 310                 315                 320

Leu Thr Pro Gly Met Asp His Pro Ile Ser Leu Gln Pro Ala Ser Met
                325                 330                 335

Met Gly Pro Leu Thr Gln Gln Leu Gly His Leu Ser Leu Ser Ser Thr
            340                 345                 350

Gly Thr Tyr Met Pro Thr Ala Ala Met Gln Gly Ala Tyr Ile Ser
    355                 360                 365

Gln Tyr Thr Pro Val Pro Ser Ser Ser Val Ser Val Glu Glu Ser Ser
    370                 375                 380

Gly Gln Gln Asn Gln Val Ala Val Asp Ala Pro Ser Glu His Gly Val
385                 390                 395                 400

Tyr Ser Phe Gln Phe Asn Lys
                405

<210> SEQ ID NO 4
<211> LENGTH: 383
<212> TYPE: PRT
<213> ORGANISM: Mus musculus

<400> SEQUENCE: 4

Met Leu Leu Ser Val Thr Ser Arg Pro Gly Ile Ser Thr Phe Gly Tyr
```

```
1               5                   10                  15
Asn Lys Asn Asn Lys Lys Leu Tyr Val Ala Gln Gln Met Ala Pro Pro
            20                  25                  30

Ser Pro Arg Asn Ser Thr Pro Asn Ser Ser Gly Gly Gly Gly Gly Gly
            35                  40                  45

Ser Gly Gly Asn Asp Gln Leu Ser Lys Thr Asn Leu Tyr Ile Arg Gly
            50                  55                  60

Leu Gln Pro Gly Thr Thr Asp Gln Asp Leu Val Lys Leu Cys Gln Pro
65                  70                  75                  80

Tyr Gly Lys Ile Val Ser Thr Lys Ala Ile Leu Asp Lys Thr Thr Asn
                85                  90                  95

Lys Cys Lys Gly Tyr Gly Phe Val Asp Phe Asp Ser Pro Ser Ser Ala
                100                 105                 110

Gln Lys Ala Val Thr Ala Leu Lys Ala Ser Gly Val Gln Ala Gln Met
                115                 120                 125

Ala Lys Gln Gln Glu Gln Asp Pro Thr Asn Leu Tyr Ile Ser Asn Leu
130                 135                 140

Pro Leu Ser Met Asp Glu Gln Glu Leu Glu Gly Met Leu Lys Pro Phe
145                 150                 155                 160

Gly Gln Val Ile Ser Thr Arg Ile Leu Arg Asp Thr Ser Gly Ala Ser
                165                 170                 175

Arg Gly Val Gly Phe Ala Arg Met Glu Ser Thr Glu Lys Cys Glu Ala
                180                 185                 190

Ile Ile Thr His Phe Asn Gly Lys Tyr Ile Lys Thr Pro Pro Gly Val
                195                 200                 205

Ala Ala Pro Ser Asp Pro Leu Leu Cys Lys Phe Ala Asp Gly Gly Pro
210                 215                 220

Lys Lys Arg Gln Ser Gln Gly Arg Tyr Val Gln Asn Gly Arg Ala Trp
225                 230                 235                 240

Pro Arg Asn Gly Asp Met Gly Gly Met Ala Leu Thr Tyr Asp Pro Thr
                245                 250                 255

Ala Ala Leu Gln Asn Gly Phe Tyr Ala Ala Pro Tyr Ser Ile Ala His
                260                 265                 270

Ser Arg Met Leu Ala Gln Ser Ala Leu Ala Pro Tyr Leu Pro Ser Pro
                275                 280                 285

Val Ser Ser Tyr Gln Gly Ser Val Leu Thr Pro Gly Met Asp His Pro
                290                 295                 300

Leu Ser Leu Gln Pro Ala Ser Met Met Gly Pro Leu Thr Gln Gln Leu
305                 310                 315                 320

Gly His Leu Ser Leu Asn Ser Leu Gly Thr Phe Met Pro Ala Ala Ala
                325                 330                 335

Ala Met His Gly Ala Tyr Ile Ser Gln Tyr Pro Ala Val Pro Ser Ser
                340                 345                 350

Ser Val Ser Ala Glu Glu Ser Asn Gly Gln Gln Asn Gln Leu Ala Val
                355                 360                 365

Glu Pro Pro Ser Asp His Gly Val Tyr Pro Phe Gln Phe Ser Lys
                370                 375                 380

<210> SEQ ID NO 5
<211> LENGTH: 355
<212> TYPE: PRT
<213> ORGANISM: Mus musculus

<400> SEQUENCE: 5
```

```
Met Ala Pro Pro Ser Pro Arg Asn Ser Thr Pro Asn Ser Ser Gly Gly
1               5                   10                  15
Gly Gly Gly Gly Ser Gly Gly Asn Asp Gln Leu Ser Lys Thr Asn Leu
            20                  25                  30
Tyr Ile Arg Gly Leu Gln Pro Gly Thr Thr Asp Gln Asp Leu Val Lys
        35                  40                  45
Leu Cys Gln Pro Tyr Gly Lys Ile Val Ser Thr Lys Ala Ile Leu Asp
    50                  55                  60
Lys Thr Thr Asn Lys Cys Lys Gly Tyr Gly Phe Val Asp Phe Asp Ser
65                  70                  75                  80
Pro Ser Ser Ala Gln Lys Ala Val Thr Ala Leu Lys Ala Ser Gly Val
                85                  90                  95
Gln Ala Gln Met Ala Lys Gln Gln Glu Gln Asp Pro Thr Asn Leu Tyr
            100                 105                 110
Ile Ser Asn Leu Pro Leu Ser Met Asp Glu Gln Glu Leu Glu Gly Met
        115                 120                 125
Leu Lys Pro Phe Gly Gln Val Ile Ser Thr Arg Ile Leu Arg Asp Thr
    130                 135                 140
Ser Gly Ala Ser Arg Gly Val Gly Phe Ala Arg Met Glu Ser Thr Glu
145                 150                 155                 160
Lys Cys Glu Ala Ile Ile Thr His Phe Asn Gly Lys Tyr Ile Lys Thr
                165                 170                 175
Pro Pro Gly Val Ala Ala Pro Ser Asp Pro Leu Leu Cys Lys Phe Ala
            180                 185                 190
Asp Gly Gly Pro Lys Lys Arg Gln Ser Gln Gly Arg Tyr Val Gln Asn
        195                 200                 205
Gly Arg Ala Trp Pro Arg Asn Gly Asp Met Gly Gly Met Ala Leu Thr
    210                 215                 220
Tyr Asp Pro Thr Ala Ala Leu Gln Asn Gly Phe Tyr Ala Ala Pro Tyr
225                 230                 235                 240
Ser Ile Ala His Ser Arg Met Leu Ala Gln Ser Ala Leu Ala Pro Tyr
                245                 250                 255
Leu Pro Ser Pro Val Ser Ser Tyr Gln Gly Ser Val Leu Thr Pro Gly
            260                 265                 270
Met Asp His Pro Leu Ser Leu Gln Pro Ala Ser Met Met Gly Pro Leu
        275                 280                 285
Thr Gln Gln Leu Gly His Leu Ser Leu Asn Ser Leu Gly Thr Phe Met
    290                 295                 300
Pro Ala Ala Ala Ala Met His Gly Ala Tyr Ile Ser Gln Tyr Pro Ala
305                 310                 315                 320
Val Pro Ser Ser Ser Val Ser Ala Glu Glu Ser Asn Gly Gln Gln Asn
                325                 330                 335
Gln Leu Ala Val Glu Pro Pro Ser Asp His Gly Val Tyr Pro Phe Gln
            340                 345                 350
Phe Ser Lys
        355
```

<210> SEQ ID NO 6
<211> LENGTH: 5390
<212> TYPE: DNA
<213> ORGANISM: Mus musculus

<400> SEQUENCE: 6
acttcctgtc ctgttggaaa tgaaagttag gaattggggg tggtagccgt gcacgtattt    60

-continued

```
attctgcagc atgccggcac tgtctgtttc gttatcacag caaagcagcc gcaggaaaaa    120
cagagagcag agctttgttt tagagagagt ctgggcttga ggtctgttgt gacaaagacg    180
gagttaattt acttctggag aatgtgtgtg gcagcagtgg gaggcctgag gaggggctct    240
gaaggcattc agtctccctc cctgttctag gtggatggat aggcttcttt ggtatcactt    300
gtaagttttc ttttcctgtt ccaactcctc cttggagggc atattggagc tcagagagga    360
ctctgtgaac gtcatttggc ttggccataa attccacacc tgctatatgt ggctcagcaa    420
atggcacctc caagtccaag gaatagcacc cccaacagca gcggcggagg cggcggcggg    480
agtggtggga acgaccagct gagcaaaacc aacctgtata tccgaggact gcagccaggc    540
accactgacc aggaccttgt caagctctgt cagccgtatg gcaagattgt ctccactaag    600
gccatcctgg acaagaccac aaacaagtgc aaaggctatg ctttgtggac ttcgacagt    660 ccgtcatcag cacagaaagc tgtaactgca ctgaaagcca gtggtgtgca ggcacaaatg    720
gcaaagcaac aggagcaaga ccctacaaac ttatacatct caaacctccc tctgtcaatg    780
gacgagcagg aactggaggg gatgctgaag ccctttggcc aggtcatctc tactcggatc    840
cttcgagaca ctagtggggc cagcagaggg gtcggctttg caaggatgga gtcaacagag    900
aagtgtgaag ccatcatcac ccactttaat ggaaagtata taaagacacc ccctggagta    960
gcagcacctt ctgacccttt gcttttgcaaa tttgctgacg gtgggccaaa gaaacgacag   1020
agccaaggaa gatacgtgca aaatggacgg gcctggccaa ggaacggaga catgggcggt   1080
atggccttga cctatgaccc cactgctgcc cttcagaatg ggttctacgc agctccttac   1140
agtatcgccc acagcaggat gcttgctcaa tctgcgctag ccccgtatct tccatctcct   1200
gtgtcttcct atcagggctc agttctgaca ccagggatgg accaccccct ctctctccag   1260
cctgcctcca tgatgggacc tcttacccag caactgggtc acctgtcact caacagtctg   1320
ggcacgttca tgccggcagc tgctgctatg catgggctt acatctccca gtacccagct   1380
gtgccttctt ccagtgtttc tgctgaggag agcaatggcc agcagaatca actggcagtg   1440
gagcccccct cagaccacgg ggtctatcct ttccagttca gcaaataatg aggtccagac   1500
ctggggagag aagcctatgc agtcctcctt gggctccttc ctgtggctga tggaacctga   1560
ggaatcacgt tggtttttt ttttgaatgt gctacattca agatcaaaaa gactttttt    1620 tcttttgcaa aagaagtttc ttgctttgta tttaattgca gcgaaccttt ctcctacccc   1680
aaagacacca gttgaggtgc ttctcatctt cgagaggttt gggtatgttg gcttttaaa    1740 atggtttaag aacaatcgca gtgctgtgaa gtcagtgaag gggcgctgct tgccaggttc   1800
agttagggac tattttcaat gtgtgtttta gatatgcagg cttaaaactt tgttttgca    1860 aagctctcaa cacacacttt gcacacaccc cccacctcc ctcccacgca ctgtttaagg   1920
cagggtctca cagtgcagtc ctggctggct gacaatgtag accaggctgg ctttgaactc   1980
agcgatcctt cccactctgt ctgagtgcac cgccatgcct agctagttgt ttttttttt    2040 ttggtttttt ttttttcaag acagggtttc tctgtgtagc cctggctgtc ctggcgctca   2100
ctttgtagac caagctagcc tcgaacttag aaatccacct gcctctgcct cccaagtgct   2160
gggattaaag gcgtgcgcca ccaccgcccg gctagttgtt ttaaaact tctccacaat    2220 ggtcttttt tcttttccat ttagcttagc ctgcctactt tgcctttta caatttttaa    2280 ttttatgaat ttgatttaaa tttcatgtgg aattggggga agggagagca acgcacaggt   2340
agagaagtgt ggcagtagag gttgctttcc ctctgccctc ctggcctagg aggggttaga   2400
ctttgacttc aggaagcaga catgtgacaa ccatgcagcc tttggaaacc accttcaacc   2460
```

```
aactctggtg gcaagtgcca ctgagaagtg gcatccagct tcagcatcct ggatacctgc    2520
tctgcctcct ggagggtctt gggtcttcat cctgccccag gtctcacagc ccctgccct     2580 gctgagcaag ttctgccttc cactttacca ggaggttgtt ttgtccccga gaggctgctg    2640
tcttgtccat catcatcctt gattaccaag cctggggagt atcatgtgtg ctggtcctga    2700
acacctgaca gaacctggcc ccactcctcc acccttatt ccctggcagt tatttggtgt     2760
agactaaacc ccagtccagc cttggacatg gagcctgtta gttcatgtac ttggccagca    2820
gtgacatctg tgactttgcc tcctggagga tcttttctgc ctgggttctc acagcctctc    2880
atcccagctg cacatggctg tactcaagtg gtacttggct gaatcactta attcagcagg    2940
agccatctta tttagcaggg ctcacccttg gttgtatgta catgccaagt gcacacagtt    3000
tgaagggatg aaagcaagaa ctgttgtgta tactgtgcat gcttgagaat ggactgagct    3060
ttctctatgc agcatacccca gcccagccct ggtgtttgga ccccttcccc agggaaccag   3120
accaccagaa ataattttcc ttcttgtgga aggacgacgg ggtgctagga tagaaaaagg    3180
caagactcac agctccctgg ccactcaaag gtcaggaggg acttgtaaac atgcctgccg    3240
ttaactattc ccttctgcaa gactttcagc acaaaatgtg acttgttaca tcacatccct    3300
tcacgtcata agtacacctc cagtagacaa agcaatggag atggggaagt gtgtccagag    3360
gtcagtgtga aagaggaagg gcagggcatg gtgatggtga gaaactggct cagcagctgt    3420
gcacactaca gaattgggaa tcctggcctg actgtgctgc tgtgcgttct agactgagga    3480
aggggctgag gacaatggac agcataaagt acaaaatgac cagttttctc attggtgctt    3540
ccaacatcag gaaggtcata cccagttatc gacctctagc cctctagcac tcagtgacag    3600
actcagagct ctgtcctgtg gaaaccctgc tgacagtctt gctgccactg ctgctccttc    3660 actgccatt aaaaattgtt ccttttctg tagttctaaa gcaatttgaa taactgacag      3720
ttttaaaatt tgaaattacc ttttaggtt tttcttttga gtatactggt tagggttcta    3780
gtgtttctgg ttgaacaggt gtgagcatgg gaaatgaggg caacctgtaa ttttgttttt    3840
atagtggtta atggcactca ctgtgtaatt tctgcttagt gatttccatc cactctttc    3900 ctcattagct cattactcag aaaggtagcg actgaagaca ggaagtagta tgcaagccat    3960
gagggatgag ttgtaagcct cctctccatc atcctgccca aggctcctaa cagtctcctg    4020
agtcctgttt gcatggaggc cagatagatg gctctgcact ctatatctca cctgtactca    4080
ttttagtaca ttgtggtttt gcttccaatc aatcagagtg gactagagct cacacctgac    4140
ctcgtgtgac tcttcactag gctccaggcc tatcccatct cattgggtca gactgtagat    4200
ggactggact tttggagaca ggtcctgcta ttacttagga atatgtggga acaatgatag    4260
ggaccaagct tgtgaagcaa aacggctttg gaaagggcaa gtgctcaata ataaaaaatg    4320
gggtggaagt gaagcgttat ttgctgaggg tttcggaagg actagtttgt ttttgtccct    4380
ggcccttccg gtcaagtggg cacctcccat tttgtcgcca agagcaatac agttgagtag    4440
gtggtagacc caaactcacc cagccatttc tagacctgaa ttcagaggat aaggtgagtc    4500
tagaggtata tacaaccaat gcttgttaga ccaattctta ccaattcgga gcaagccggt    4560
ggctctactt ctgggtaacc tgcctcttaa aagtgccttt gatcccagta gtagattcag    4620
ggtctacagg agccttccct cagcagctaa aaccaatttg tctcctctac tctttgctgc    4680
acctcccgga ggtggtctcc atgtggcagt gatgccctca tcacccttgt gaccaccgct    4740
ctgaatgttc aaaataagca tttcctgtcc aagcaaatcc ctaaactccc tcgtcctcat    4800
```

-continued

| | | |
|---|---|---|
| tactcaacta cctcagtctg acaactcaag gcacacaagc acctacttgc ctcccaccat | 4860 | |
| cctttactgc ccttgtcttt gtggggttgg aacaaatgca aactcctcag ttccacaacc | 4920 | |
| caaaactgct ctttctggat cgtcttctcc agtgacgttg gctccctaca agagcgaact | 4980 | |
| ctccatatgg gtcagtccct gtaggacaag ccagggacta tgctgtgcag tcaaatgcca | 5040 | |
| ggtttggagc atagcttaag accgcagaga gtaaggactt gagtggtggt ggtgtgcagt | 5100 | |
| ttgagagagc tggaatggac gtctctgctc ctgccctctg ggcgggtcgg gtgatgactt | 5160 | |
| ctagatgcac tccttaccct ggagggaagt taatttatac ttaagatgca ttttgtacat | 5220 | |
| ttccccttta cccagaaacc tgtagtttca tactcccatg tctatgccaa cactacctat | 5280 | |
| cgctcactct ccgtggctga cttctggttc catttccttc ctgtgacttg aagagctttt | 5340 | |
| acttttgctc acgtgaacct ttcttttta aataaaacac aaaagcctcc | 5390 | |

<210> SEQ ID NO 7
<211> LENGTH: 4305
<212> TYPE: DNA
<213> ORGANISM: Homo sapiens

<400> SEQUENCE: 7

| | | |
|---|---|---|
| agatgccgcc tggcaccaag cgcagccgcc gctgccgcac tttccacttg tattgatcac | 60 | |
| ctctcagccc cgcgcagccg gctcgcccga gcggaccgcg ccagcgcgc cagcccttgg | 120 | |
| cagccccgga gcagtcgggc tccgggagga aactccttgg gagcgccctg tccggggtgc | 180 | |
| cctctgcgct ctgcagtgtc tttctttctg cctgggagga ggaggaggag gaggaagagg | 240 | |
| aggaggagga ggaggaggag gaggaagagg aggaggagga ggaggacgtc tggtcccggc | 300 | |
| tgggaggtgg agcagcggca gcagcagcag ccgccgccgc cgccgccgct gccgccgccg | 360 | |
| ccggaaaggg agaggcagga gagcccgaga cttggaaacc ccaaagtgtc cgcgaccctg | 420 | |
| cacggcaggc tcccttccag cttcatgggc aaagtgtgga acagcagat gtaccctcag | 480 | |
| tacgccacct actattaccc ccagtatctg caagccaagc agtctctggt cccagcccac | 540 | |
| cccatggccc ctcccagtcc cagcaccacc agcagtaata caacagtag cagcagtagc | 600 | |
| aactcaggat gggatcagct cagcaaaacg aacctctata tccgaggact gcctccccac | 660 | |
| accaccgacc aggacctggt gaagctctgt caaccatatg ggaaaatagt ctccacaaag | 720 | |
| gcaattttgg ataagacaac gaacaaatgc aaaggttatg gttttgtcga ctttgacagc | 780 | |
| cctgcagcag ctcaaaaagc tgtgtctgcc ctgaaggcca gtgggggttca agctcaaatg | 840 | |
| gcaaagcaac aggaacaaga tcctaccaac ctctacattt ctaatttgcc actctccatg | 900 | |
| gatgagcaag aactagaaaa tatgctcaaa ccatttggac aagttatttc tacaaggata | 960 | |
| ctacgtgatt ccagtggtac aagtcgtggt gttggctttg ctaggatgga atcaacagaa | 1020 | |
| aaatgtgaag ctgttattgg tcatttaat ggaaaattta ttaagacacc accaggagtt | 1080 | |
| tctgccccca cagaaccttt attgtgtaag tttgctgatg gaggacagaa aaagagacag | 1140 | |
| aacccaaaca aatacatccc taatggaaga ccatggcata gagaaggaga ggtgagactt | 1200 | |
| gctggaatga cacttactta cgacccaact acagctgcta tacagaacgg attttatcct | 1260 | |
| tcaccataca gtattgctac aaaccgaatg atcactcaaa cttctattac acctatatt | 1320 | |
| gcatctcctg tatctgccta ccaggtgcaa agtccttcgt ggatgcaacc tcaaccatat | 1380 | |
| attctacagc accctggtgc cgtgttaact ccctcaatgg agcacaccat gtcactacag | 1440 | |
| cccgcatcaa tgatcagccc tctggcccag cagatgagtc atctgtcact aggcagcacc | 1500 | |
| ggaacataca tgcctgcaac gtcagctatg caaggagcct acttgccaca gtatgcacat | 1560 | |

```
atgcagacga cagcggttcc tgttgaggag gcaagtggtc aacagcaggt ggctgtcgag   1620
acgtctaatg accattctcc atataccttt caacctaata agtaactgtg agatgtacag   1680
aaaggtgttc ttacatgaag aagggtgtga aggctgaaca atcatggatt tttctgatca   1740
attgtgcttt aggaaattat tgacagtttt gcacaggttc ttgaaaacgt tatttataat   1800
gaaatcaact aaaactattt ttgctataag ttctataagg tgcataaaac ccttaaattc   1860
atctagtagc tgttcccccg aacaggttta ttttagtaaa aaaaaaaaaa caaaaaacaa   1920
aaacaaaaga ttttttatcaa atgttatgat gcaaaaaaag aaaagaaaaa aaaaaaagaa   1980 aagaaaacatt caattttctg ggtatgcaca aagaccatga agactatcc aagtgcatga    2040 ccggattttt gtggttttgt tcattttgtg tttaatttgt gttttttttt tccagctgta   2100
tgaaatgggc tttctgaagt ttaaatagtc cgacttcacc catggtgttc tgtgcttgca   2160
gtgcgagtgt tgctgtaatt cagtgttgcc gtcagtgtct cttttcttag ctttctgtct   2220
ttctttcaac gtagtgtgaa gtgtcttatc cttttctatg aattccaatt tgccttaact   2280
cttttgatgc tgtagctgtt tcagtaaaag ttagttcaaa ctaatgatgt agaatgcttt   2340
gaccaaatga gctggtctat tatgccttgt aaaacagcag catagggctt ttaaaaggta   2400
gtcaataaaa gttgctgaaa ttttggcttt tttaaatatg tagtaggtgt ttttaatgat   2460
ttttcacata atgtgtaagg tagtgaaatg caagaaggga aaaatgtttt gtgtgaaaca   2520
cattttctga ctggggaact tttattaggg taaattgttt gtaaggctgt acgccaacag   2580
tttcctctga tagtttgact gatttaggat atctgctgta tgatgcaatg taaagtcttt   2640
tttgcctttt ttcaggaaaa aaaaaaagct aacttgatgt actagattta gtgtaggtag   2700 tgttgggggtt ggggatgggg gtggggggagg ggagtcactg aatgttttgt ccttcccttta   2760 tactaatgat agtgctttag aatgagaatt atgcctgaaa tctggcaaac cgaaaaatgt   2820
tgctattgca acaaagtggc aaaagctaaa agtaaggatt tatcttcaaa cataagctga   2880
gataacgaat agaagcaaaa cgattggcta ctagctctct ctctctctct ctattaggta   2940
aatttgaaaa ataaaaatga cttggcactt ttaaaggtaa cttcaccaaa gaccgaagag   3000
ccagtaacca gtagctccaa cttgtctcag catcacatct tctgtgctct ttattttgc   3060 cggaccagtt tgcggttagg agaatgtgcc ttttttgtac ctttgcattt aggttttata   3120
attttaattg atgtatggac acacacaaac aaaaaagcat gaaggaagat ttggatccaa   3180
gcagtgccac actttacatc atcactacaa gtgttcaagt gtaaagaaaa ccaattttga   3240
aactatgaaa ttcctgattc ataaatacac agttatttct actttagtac atataagata   3300
attcactgtt attaaagctc ttttattaag gcaattgcat atgtttttaaa agcaatggta   3360 aattaagttg tcttccaaaa ctgtgtactt gtctggtcag ctgtgtatga tcagttatct   3420
acctcagagt ctattttctt ttgtgctggg acaggttgct ggccctccct gtttccacag   3480
accaaatcct cctagctcag gagctagggc taagcagtta tttctttcaa gtattttta   3540 gttcttaaat tttatgcttg tatttgatga tagatgtcag tgacatttca tagtttcaaa   3600
agtccttgct gctctgagaa gtgtagattc tagtgaaaat tacatagtca taagagaaat   3660
gtgtttttgt ttttgttttt gtttcatttt tttaaagttg tggtattatt ggttctatgc   3720
tccctggaat attactgctt tgtgaaagtc cagactgaac gcagcaccct ctgtgtacct   3780
agtacagtta taaacctggg tctctcacta cttgatattt ttgcattagt taagacagaa   3840
atttgatagc tcggttagag gggagggaa atctgctgct agaaatgtct gaactaagtg   3900
```

```
ccatactcgt ctgggtaaga tttgggaaac ataacctctg tacataaaaa aaaaaaaatc    3960
agttaaacat cacatagtag acagccatta aattataaaa aaattaattt atgaagaaag    4020 acctttgta cagattgaaa aaaaaagatt ttcatagaga tatctatatg atcaagagag    4080
ttaatttttt attttgttt tactagtgcc acagacttgc cagtggtaac ttatttgtcc    4140
ggttcaagat aactctgtag ttttctttcc taggacttgt tgttaaacgc caaaagacat    4200
ttttgaactg tacatttgat cagattgtta gcttttctgt tttatttctt ttgagaacct    4260
ttgaataaaa aacatctgaa attttaaaaa aaaaaaaaa aaaaa                     4305

<210> SEQ ID NO 8
<211> LENGTH: 2543
<212> TYPE: DNA
<213> ORGANISM: Mus musculus

<400> SEQUENCE: 8
gggaggtggg gacgcggcgg cgctgctcgt ccgctgccgc cggcaccgcg cgcgaactcc     60
ggtccatggc acgcagggcg gcggcccccg gagctgctcg agagtcgccg gccgcgcgcg    120
tcgcgccgca cttttagggc gggagccgcg agccagtccc cggccgcatc ctccctccgc    180
ctgcccggac aggcgagaga gggagttccc ggagcgccgc ggccccggtt gcctcagctc    240
cccgcgcccg agatgatctt ccccagcggc agcggccacc ccggcgctgc cggcggctgc    300
aggacgccct accgcaagca gcagtctctg gtcccagcac accccatggc cccacccagt    360
cccagcacca ccagcagtaa taacaacagt agcagcagta gcaactcagg atgggatcag    420
ctgagcaaga caaacctcta catccgaggc ctgccccca ataccactga tcaagacctg    480
gtgaagctct gccaaccata tgggaagatc gtgtccacaa aggcgatttt ggataaggcc    540
accaacaagt gcaaaggtta tggttttgtt gactttgaca gtcctgcagc agcccagaaa    600
gctgtctccg ccctgaaggc gaatggagtc caggctcaga tggcaaagca acaggaacaa    660
gatcctacca acctgtacat ttctaacctg ccgctgtcca tggatgagca ggaacttgaa    720
aatatgctca acccctttgg acaagttatt tctacaaggg tcctacgtga ttccagtggt    780
gccagccgtg tgttggctt tgccaggatg gaatcaacgg aaaaatgcga agctgtaatt    840 ggtcattta atggaaaatt catcaagacc ccaccaggag tttctgctcc tacagaacct    900
ttactgtgca gtttgcgga tggaggacag aaaaagagac agaacccaaa caagtacatc    960
cctaacgggc ggccatggcc cagagatgga gaggctggaa tgacactcac ttatgacccg    1020 actcagctg ctctacacaa cggatttta ccttcaccat acagtattgc cacaaaccga    1080
atgatcactc aaacttctct tacaccctat attgcatctc ctgtatctgc ctaccaggtg    1140
gcaaaggaaa ccagagagaa caagtatcgg ggctctgcta tcaaggtgca gagcccctct    1200
tggatgcagc ctcagccgta cattctgcag catcctggtg ccgtgttaac tccctcaatg    1260
gaacatacca tgtcactaca acctgcttcc atgatcagcc ctctggctca gcagatgagt    1320
catctgtcac tgggcagcac cggaacatac atgcctgcaa catcagccat gcaaggagcc    1380
tacttgccac agtatacaca catgcagacc gcggcggtgc ccgttgagga agcaagtggc    1440
cagcagcagg tggctgtgga gacgtctaat gaccattctc catataccctt tccacccaat    1500 aagtaactgt gagatgtacc gaagggagtt cttacctgaa gaagggtgtg aaggctgaac    1560
aatcatggat ttttctgatc aattgtgctt taggaaatta ttgacagttt tgcacaggtt    1620
cttgaaaacg ttatttataa tgaaatcaac taaaactatt tttgctataa gttctataag    1680
gtgcataaaa cccttaaatt catctagtag ctgttcccct gaacaggttt attttagtaa    1740
```

-continued

```
aaaacaaaaa caaaacgaaa aaaaaaaaaa aaaacggaaa aaaaatcaaa gatttttatc    1800
aaatataatg atgcaaaaaa agaaaaagaa aaaaaaagag aaaagaaaaa cttcaatttt    1860
ctgggtatgc acaaagacca cgaagactta tccaagtgca tgaccggatt tttgtggttt    1920
tgttcatttt gtgtttaatt tgtctttttt ttttcagctg tatgaaatgg ctttctgaa     1980 gtttcaattg tccgacttca cccatggtgt cccgtgcttg cgagtgtcgc agtaactcag    2040
tgttggcctc actgtctttg cttagctctc cgttttttc tttcgacgta gtgtgaagtg     2100
tcttatcctt ttctatgaat tccaatttgc cttaactctt ttgatgctgt agctgtttca    2160
gtaaagttag ttcaacctaa tgatgtagaa tgctttgacc aaatgggctg tctagtgca     2220 ccttgtaagc agcagcctag ggcttttaaa aggtagtcaa taaaagttgc tgaaattttg    2280 gctttttaa atatgtagta ggtgttttta atgattttc acatagcgtg taaggtagtg      2340
aagtgcaagg agggaaaact gttttgtgtg aaacacattt tctgactggg gggactttta   2400 ataggtaaa ttgtttataa ggctgtacac taacagtttc ccctaatagt gtgactgatt    2460
taggatatct gctgtatgat gcaatgtaaa gtctttttg ccttttttc aggaagaaaa      2520 aaaaataaaa cttaacgatg ttc                                            2543
```

<210> SEQ ID NO 9
<211> LENGTH: 406
<212> TYPE: PRT
<213> ORGANISM: Homo sapiens
<400> SEQUENCE: 9

```
Met Gly Lys Val Trp Lys Gln Gln Met Tyr Pro Gln Tyr Ala Thr Tyr
1               5                   10                  15

Tyr Tyr Pro Gln Tyr Leu Gln Ala Lys Gln Ser Leu Val Pro Ala His
            20                  25                  30

Pro Met Ala Pro Pro Ser Pro Thr Thr Ser Ser Asn Asn Asn Ser
        35                  40                  45

Ser Ser Ser Asn Ser Gly Trp Asp Gln Leu Ser Lys Thr Asn Leu
    50                  55                  60

Tyr Ile Arg Gly Leu Pro Pro His Thr Thr Asp Gln Asp Leu Val Lys
65                  70                  75                  80

Leu Cys Gln Pro Tyr Gly Lys Ile Val Ser Thr Lys Ala Ile Leu Asp
                85                  90                  95

Lys Thr Thr Asn Lys Cys Lys Gly Tyr Gly Phe Val Asp Phe Asp Ser
            100                 105                 110

Pro Ala Ala Ala Gln Lys Ala Val Ser Ala Leu Lys Ala Ser Gly Val
        115                 120                 125

Gln Ala Gln Met Ala Lys Gln Gln Glu Gln Asp Pro Thr Asn Leu Tyr
    130                 135                 140

Ile Ser Asn Leu Pro Leu Ser Met Asp Glu Gln Glu Leu Glu Asn Met
145                 150                 155                 160

Leu Lys Pro Phe Gly Gln Val Ile Ser Thr Arg Ile Leu Arg Asp Ser
                165                 170                 175

Ser Gly Thr Ser Arg Gly Val Gly Phe Ala Arg Met Glu Ser Thr Glu
            180                 185                 190

Lys Cys Glu Ala Val Ile Gly His Phe Asn Gly Lys Phe Ile Lys Thr
        195                 200                 205

Pro Pro Gly Val Ser Ala Pro Thr Glu Pro Leu Leu Cys Lys Phe Ala
    210                 215                 220
```

```
Asp Gly Gly Gln Lys Lys Arg Gln Asn Pro Asn Lys Tyr Ile Pro Asn
225                 230                 235                 240

Gly Arg Pro Trp His Arg Glu Gly Glu Val Arg Leu Ala Gly Met Thr
            245                 250                 255

Leu Thr Tyr Asp Pro Thr Thr Ala Ala Ile Gln Asn Gly Phe Tyr Pro
            260                 265                 270

Ser Pro Tyr Ser Ile Ala Thr Asn Arg Met Ile Thr Gln Thr Ser Ile
        275                 280                 285

Thr Pro Tyr Ile Ala Ser Pro Val Ser Ala Tyr Gln Val Gln Ser Pro
        290                 295                 300

Ser Trp Met Gln Pro Gln Pro Tyr Ile Leu Gln His Pro Gly Ala Val
305                 310                 315                 320

Leu Thr Pro Ser Met Glu His Thr Met Ser Leu Gln Pro Ala Ser Met
            325                 330                 335

Ile Ser Pro Leu Ala Gln Gln Met Ser His Leu Ser Leu Gly Ser Thr
            340                 345                 350

Gly Thr Tyr Met Pro Ala Thr Ser Ala Met Gln Gly Ala Tyr Leu Pro
        355                 360                 365

Gln Tyr Ala His Met Gln Thr Thr Ala Val Pro Val Glu Glu Ala Ser
370                 375                 380

Gly Gln Gln Gln Val Ala Val Glu Thr Ser Asn Asp His Ser Pro Tyr
385                 390                 395                 400

Thr Phe Gln Pro Asn Lys
                405

<210> SEQ ID NO 10
<211> LENGTH: 417
<212> TYPE: PRT
<213> ORGANISM: Mus musculus

<400> SEQUENCE: 10

Met Ile Phe Pro Ser Gly Ser Gly His Pro Gly Ala Ala Gly Gly Cys
1               5                   10                  15

Arg Thr Pro Tyr Arg Lys Gln Gln Ser Leu Val Pro Ala His Pro Met
            20                  25                  30

Ala Pro Pro Ser Pro Ser Thr Thr Ser Ser Asn Asn Ser Ser Ser Ser
        35                  40                  45

Ser Ser Asn Ser Gly Trp Asp Gln Leu Ser Lys Thr Asn Leu Tyr Ile
    50                  55                  60

Arg Gly Leu Pro Pro Asn Thr Thr Asp Gln Asp Leu Val Lys Leu Cys
65                  70                  75                  80

Gln Pro Tyr Gly Lys Ile Val Ser Thr Lys Ala Ile Leu Asp Lys Ala
                85                  90                  95

Thr Asn Lys Cys Lys Gly Tyr Gly Phe Val Asp Phe Asp Ser Pro Ala
            100                 105                 110

Ala Ala Gln Lys Ala Val Ser Ala Leu Lys Ala Asn Gly Val Gln Ala
        115                 120                 125

Gln Met Ala Lys Gln Gln Glu Gln Asp Pro Thr Asn Leu Tyr Ile Ser
    130                 135                 140

Asn Leu Pro Leu Ser Met Asp Glu Gln Glu Leu Glu Asn Met Leu Lys
145                 150                 155                 160

Pro Phe Gly Gln Val Ile Ser Thr Arg Val Leu Arg Asp Ser Ser Gly
                165                 170                 175

Ala Ser Arg Gly Val Gly Phe Ala Arg Met Glu Ser Thr Glu Lys Cys
            180                 185                 190
```

Glu Ala Val Ile Gly His Phe Asn Gly Lys Phe Ile Lys Thr Pro Pro
            195                 200                 205

Gly Val Ser Ala Pro Thr Glu Pro Leu Leu Cys Lys Phe Ala Asp Gly
            210                 215                 220

Gly Gln Lys Lys Arg Gln Asn Pro Asn Lys Tyr Ile Pro Asn Gly Arg
225                 230                 235                 240

Pro Trp Pro Arg Asp Gly Glu Ala Gly Met Thr Leu Thr Tyr Asp Pro
                245                 250                 255

Thr Thr Ala Ala Leu His Asn Gly Phe Tyr Pro Ser Pro Tyr Ser Ile
            260                 265                 270

Ala Thr Asn Arg Met Ile Thr Gln Thr Ser Leu Thr Pro Tyr Ile Ala
            275                 280                 285

Ser Pro Val Ser Ala Tyr Gln Val Ala Lys Glu Thr Arg Glu Asn Lys
            290                 295                 300

Tyr Arg Gly Ser Ala Ile Lys Val Gln Ser Pro Ser Trp Met Gln Pro
305                 310                 315                 320

Gln Pro Tyr Ile Leu Gln His Pro Gly Ala Val Leu Thr Pro Ser Met
                325                 330                 335

Glu His Thr Met Ser Leu Gln Pro Ala Ser Met Ile Ser Pro Leu Ala
            340                 345                 350

Gln Gln Met Ser His Leu Ser Leu Gly Ser Thr Gly Thr Tyr Met Pro
            355                 360                 365

Ala Thr Ser Ala Met Gln Gly Ala Tyr Leu Pro Gln Tyr Thr His Met
            370                 375                 380

Gln Thr Ala Ala Val Pro Val Glu Glu Ala Ser Gly Gln Gln Gln Val
385                 390                 395                 400

Ala Val Glu Thr Ser Asn Asp His Ser Pro Tyr Thr Phe Pro Pro Asn
                405                 410                 415

Lys

<210> SEQ ID NO 11
<211> LENGTH: 8234
<212> TYPE: DNA
<213> ORGANISM: Homo sapiens

<400> SEQUENCE: 11
tttttttccc cctttacgaa cgctggcaat tgacatcact acagacagcc tggttagaga      60
acaaactgcc tcatcccaag tggaccccgg cagctggggg aagccaggca agatctggga     120
aggctgtgtg tgggtgtttt ttctacagat ctcactcctc gccctttttt tttttccttt     180
ggtgtgtgtt ttttgttttg ttttgttttt taaaaaaatt cttgctgtgt tggaactagc     240
gagtggtgga gtctctgaag cctcatcagt caccgggact gtcaggaata gtggtttaag     300
aggaagctcg gcctggggca ctataccctg tcatccagtt ccctgcctcg agataaaga     360 ttccagctac atgggcaaac gcctggatca gccacaaatg tacccccagt acacttacta     420
ctatcctcat tatctccaaa ccaagcagtc ctatgcacca gctccccacc ccatggctcc     480
tcccagcccc agcacaaaca gcagcagcaa caacagcagc aacaacagca gcggggaaca     540
gttgagtaaa accaacctgt acattcgagg cctcccacca ggcaccactg accaggacct     600
aatcaagctg tgccaaccgt atggaaaaat tgtatctaca aaggcaattc ttgacaaaaa     660
cacaaatcag tgcaaaggtt atggttttgt agattttgac agtcctgcag ccgcacagaa     720
agcggtagca tctctcaagg caatggcgt gcaggcacag atggctaagc aacaagagca     780

```
agacccaaca aacctataca tctcaaatct ccccatttct atggatgagc aggagcttga    840
gaatatgctg aaacccttg gacatgtcat ttccacaaga atactaagag acgctaatgg     900
agtcagcaga ggtgttggct tgccagaat ggagtctact gaaaaatgtg aagtggtaat     960
tcaacatttt aatggaaaat atctgaaaac accaccaggc atcccagccc ccagtgagcc    1020
tttgctgtgc aaattcgctg atggaggaca aaagaagcga cagaatcaaa gcaaatatac    1080
ccagaatggg aggccttggc ccagggaagg agaggctggc atggctttga cctatgaccc    1140
cacagctgcc atacagaatg gattttattc ttcaccgtac agtattgcaa ccaaccgcat    1200
gattccacag acatctatca cgccattcat tgctgcttcc cctgtctcca cataccaggt    1260
ccagagtact tcatggatgc ctcatccgcc atacgttatg caaccaacag gtgctgtgat    1320
tacaccaacc atggaccatc ccatgtcaat gcagccagcc aacatgatgg gcccactgac    1380
acagcagatg aatcaccttt cgttgggcac aacaggaacg attcaatccc aagacaggat    1440
tatgatactc caccagctgt tgtgtcagta tatgactgct gctgctccta tgcaagggac    1500
ctacattcct cagtacacgc ctgtgcctcc gacagctgtt tctattgaag gtgttgttgc    1560
tgatacctct ccccagacag tggcaccttc atcccaggac accagtggtc agcagcaaca    1620
gatagcagtg gacacatcca acgaaatgc acctgcatat tcttaccaac agtctaaacc    1680
ataaacagga ctgaagaatg tctgtctgaa tctttgcctt gaatgaagaa acttcattga    1740
acaagaagtt ggcttccagt ttgcacagac gtcaatggaa tgcattttt tgttgttgtt    1800 gttgtttttt ttttagtgtt ataccttacc caatgaaagc aaagttttta tgtgctgtgc    1860
aaatggtctt catgtggtct gacaatttat ttttgccatc atttttttaa ttaaagaaaa    1920
aatttccaga gaggaaaaa aaaactacaa aaaacaaaac attgaaggtt gatattttat    1980
gtggaagaac atttgaattg aattcagaat ttttctgaag gtgtagatac tttttttttt    2040
tttttaacag aaaacctgat gtcaagaggt gggcaataga aatggaaaca aattgtcttc    2100
ctcaataatt aagctacttt ctcttttcc cttcttgttt taatctagtg gttttttat    2160 tttatttttt cttagaaata tgtaggtaag gtttatcttg aatcttaatt gccttaattt    2220
taaggacgtc aaaggctctc gaggcaagct gtcaacgtct tgttgaaaac aaaaatcaag    2280
aaagaattga aatactgtgc cggctttcac tggcacagaa gtttaagact atgagttttt    2340
agggtgaaga aaaaactgta cagtttaaat gaaaatgttt ttcttcattt gaagaaaatt    2400
tgttgataaa ccatggcaac tgcaagaatt ggaaaaatgc tgggactttt catgaacttt    2460
gtcttaagtg ttgacatgaa tcattctaaa aggctaaaac attttacagt aaagttatta    2520
aggttggttt aaaaacaact gcattagaaa taatgcgtgt ttgggggca gaatgcagat    2580 ttttttaatt tacaaagcgt gatcgctagc aaaagcatta gtgcttttta tctgcagtct    2640
tttttatgag ctttacaaag ttttagtca gctttgcttg tcacattgca aaacctagct    2700
taagagcatt aaaaaaaaaa acttaagtag ataggagctt atggtcaaaa agtgcaaaaa    2760 aaaaacaaa aaaaagcaa tagatagaga aattgttgac aatttctgta gtctttccta    2820
gttgtgatca aattcagcct atggatggcc tattttatac caaagatgaa gtgacaccct    2880
attacagtcc agaagataga ggttgttttc gtttcttttc ttttaaaaa aaaaaaaatt    2940 tatttgaccg acatggccgg accagttctt tctttgttgt ttgtttaaac taccttccac    3000 tggtgttta catagtgcaa aaaaaaaaag agggtggggg gagttgtctc tcttttcttt    3060
aaatgtgtat tcattgatag cagaagcttg tacctgctgt gtttagcagt ttcagcatga    3120
agagttctgg atatgaactg attcatagag ccaagtggct ttaaattctg tgagcttttc    3180
```

```
tggtttctca ctagctgtct tgaatagtga aacctgtatt gatggccact agtaaaccaa    3240
gatgcttatt taacaggtgg aatattcttt atatgaaatt tcagctaaag acactttctg    3300
gacctggtct gaaaggtcat ttgtcaaaaa agcttaggga tattctgtga aatggtgagt    3360
ggtctcctgg aaaggtctca ttgtatttga acaatagtct tccctctaaa ttacaacacc    3420
tctgggtttt gtctttacac ctctgtcttt gtcatcacct accatgaata gtcaccttgg    3480
ttttgcaaat ggggaggggg tatcatcttt ttgcctgttt tcactgtatt tttgtatatt    3540
ggtgttgccg aaagaacttt ttcttcagt ttaattcttt gaggcatgta ggaccaataa     3600
gattgagaat tctattggtg gaatttaggg aagtccttaa aatgctagtt gacaatcaag    3660
gaacagtatg atttatatca ataagaacca aaagaattag gtttgatcaa tcatttaagc    3720
caaggaggaa tacttgcatt tagaacaatg caaaactttg tctaaaatga attaaattga    3780
cccacctgta aaatatatct acatttttaa ttcatgagat gatatgtgtt caacctttac    3840
agttttacct gaaattaagg acaatggaat agaatttgtt aagtgaacca ttcactagat    3900
tgctttctga atgaatcctt tgaatcaaat aggtgaaact cttttcaaaa actaagtcag    3960
tcacaggagc ctgtcttagt ccaaaagaag cagggaaatg tatttaagtg tactataaaa    4020
cagggtaggc ttttaaaaa ctaaaaagtt ttaaaggtaa atcatattcc cattaggtca     4080
acatgagtaa taaggttgac tcatgtgaaa ttgtcaatat tctactatttt ctgtaaactc    4140 tggttctctt atttgcaacc ccatgcactg gaagcccaaa tcagagaatg actccatata    4200
tttatggtca cattggagac aaaagtgtat ccaagaaaat gtagtgtgcg ttatagagaa    4260
attccaactg gtcacactca ccattatggt ttttcatgct ttagagaaaa tgctagattt    4320
atactgtctt tgttccatc cttcagcttc ccatgcatta taaaggtggc acttaagttt      4380
ttatctttga aaagtgggcc ccaaagtttt ttggggtaca aaaagacatg tatgagaacc    4440
atattttctg tttctctttt tcactctcta aactctttt gtataaataa ggattatcct      4500
gggcataatt catttgaata tgaaaccaac atactttctt tcattttgt gaaaaaataa      4560 ccaaaaacat gtattaatgt gatacaaaga aagtctcatt cacacaatca acaatgaggc    4620
taagaggtag ctaccatgtg gctaatgaat gtgcctaggt aacttcctgt ttctattcaa    4680
aactgctgct ttatttgtac attcagaaat attttttttca actatgaaat ttcaatatca    4740
attttttaag ccagtttctg caaaggaaa tgacctgtca tttgatgtgt tcatgtgtgt     4800
tttgtgtttg gatagtttat atcatgccat tctataaaat gtatgttttc aaaccaaaaa    4860
gaaaaaaaat agaaggaaaa caacggcaca tactcaaatt tgccctgctt tgtctgttgt    4920
cttacctaag acttgttttg aagagccaag tctgggagag aaaaaaaagc atcaacaggt    4980
aagcagcatt acattgtgtg gtaataaacc aaaataagtt ttcaatatat acagacaaca    5040
gaattcaaat ttaatcaaca aaatatattg tagtgatttg tttgtttgtt tgtttgagac    5100
ggagtctcgc tctgtcgccc atcctaacta ggactataat cttttttttt ttctttaagt    5160
tgaagttaat tttctgtgca ttctggtcca ccagattttc aagcatttat ttggatgttt    5220 ccattttcc ttttgacttt aatagccaag acttagctta aacatcagga aacaaactaa      5280
agccacaatc caaatgagag aaaacactgtc tcgtctaaac tctagtttca tggtcagtgc    5340
aacagtgagt tttctttaa taatggtatg gtattgtcaa gggaggcaaa gtgttcatgg      5400
taacttggag ctccccaata catggccatg tcttctaaag acaacgtaat gagcccaagt    5460
gaactgaagg tcatactggc aggtgctgat gacagtttgt ccttgaatgc tgacatgtct    5520
```

```
tgaatattgc aaatgtcata atactctttt aaaacagtcc tctacctgac tctagttttg    5580
cgaggattag tttgtttcct tggtagattt caacatttca gaatgttacc tccaaatttc    5640
acttgaatta cttcctcctg tgaccttagc agatctgtca catttgaaag catatgactc    5700
acttccaccc ccttctaatg aaaaactgca tggtgttaaa agcactctca ttagaaatat    5760
aaggctgaga actgaagaag gctgtttaaa gcaggaattt cactttattt tactatgcct    5820
aaaaatacat ctttggaccc cttgcaaagt gctttaaaag tactttcaat ttatgcatga    5880
ctccaaaaaa gtaattttt tttcccaaaa aaacctcttt atttaaataa ttgggatatt    5940
tgctaaatac ctattttttt ttacagtggc ctaaaacccc tattaatgaa aagtgaaatt    6000
tgatttaatt aggactcttg cagtcatctt cacgactgag gagaagtttc aataggctgt    6060
ctagacatta tgatgttaat aggagattaa aatacatttg gcaattcatt tcattctta     6120
atttgagtgc atgaaccact gcagatgagc tgataagcag aaattctcaa gtgggtttca    6180
ctaataaatg ttttttttata tgatttgaaa tcaagtaaag ggacaatgtt tatgtacgtg    6240
tataacaaca ttcagcacat ttgaggaatc acacactata ataaagctta aacctgtcat    6300
agaaccttga tctatattac tttgtcttca gtaaaaagtg aaggatgaga ttttgtcttt    6360
catgttattg tagctggcat gcttcaaaat tttgagctta ctgggactga cagcctctca    6420
cttcaatctg agggattgac agaatttaaa caggctcatt gattctgtac actctaccct    6480
tcctgtggca agtgataatg ggatttcatt aatgaatcaa tttgttttac aaatgacatc    6540
cactgtggca ttggaagaca gttgggtctg actcaagttt aacatttctt accaaacatt    6600
cttaagtatg aaattggtcc tttaatccaa atgctcttgg tcatggctgt cctttgcgga    6660
ttacatagca ttcaggaaag tacaaaaact aaacactaaa tccccaactg gccccaaaga    6720
ccttttatga tgtgagagac aagagttcac cccagattaa tttctttat cattggcttt     6780
atactctaac atatagatac tctctatagc aaaaaaggga tgaatggctt tcaatattca    6840
tttctgttta tttttgtgag ggaaaataat atatcaagaa aatttcttc cacttagaaa     6900
gctttaaagc tgaagtagag gtgcagtcaa gcttggatct gcaggaagaa ccactaggcc    6960
actgagtcat acttgagctt ttcttactac tgccccaatt tctaaattgt gcataaatac    7020
aatcactctc aattttttgaa gggctaatta tctactttgt gggtgtgttt tgttttttct    7080
tttcagcgtg tagggcttgg gctctgtttc cttttattag catgtcacct gagggtggaa    7140
caaacaattg gaaataaaat ttgattattt tatttcttat aaagtattaa tttcttaagg    7200
gggtttgaaa tcattggtaa aattaatatc agtacattat atgtcataaa ttttgattat    7260
ctataatgtc tttctttatc taccacaaat aattgagagt tggctaaatt cttgcagaat    7320
atatgggaaa aaaatcatag caaagaattc agcttccctc aaaagaaagc tattttttgtt   7380
tccttcactc cactaaattt gaaccagtag cacggatcaa cacgacttct gcaatgagag    7440
tataacggta gctcttggta cagtcatatt catatttta aatctttctt tgaccaaaac     7500
tattgcattg ttttcattac attttgactg cgttacttat taaggccgaa tgactttgac    7560
accccgtgg attattttta tgatcacatc aaatttaaac aatgtccaaa gtgtaacttt     7620
aatgttatat tttgtttcaa accctctggt ctaagattat tgagaaagat gttttttcct    7680
cctccctcaa atatgttatc tcttcatata taaaaaaata agttattcca tgcttttcag    7740
gaactgtaaa aattatttca aaagatatt tgaaaaagtt ttctctattc tggacacaaa     7800
tgcttccatt tatttcaaaa gaagaagaag aaaaatggaa tcttaattta aaaaaatata    7860
tgtagtagta tctgctatga gatattcagt ctctataaaa aaaaaaaggg acacagcttc    7920
```

```
ttttaaaacc cttgtttcag tccatattca acttcatgga acttctgaaa catcattcaa    7980
ttttgaactt tatttaagag cattttgta ctgctgtctc tgactgtcat ggaaagttct    8040
gtaattctaa ggtgtttctg gttttatttt taatttcttc atctgtacca cagtcaaatt    8100
agcaaccatc tcccccatcc cttgggcttt ctgtagatca gtggatgtta ggtttaaact    8160
tctgttttct ttgatgaagc tttcaataaa aaatgaaaat aaaatcaatt gaataggaaa    8220
aaaaaaaaaa aaaa                                                      8234

<210> SEQ ID NO 12
<211> LENGTH: 7409
<212> TYPE: DNA
<213> ORGANISM: Mus musculus

<400> SEQUENCE: 12
gtttctactg gaaacaggac atgtcggagc atcctgtctc ccctacacct ccttgtttcc      60
cccatggagg gagggcgact tctcattcgg agcaatgcta atggagtcac tcagtccaac     120
tccacagtga gagcctatca aagcagcaag tcacgagtga ccatgagccc tggtttcagc     180
tcccagtgga gcaacagcca acctgcctgg aacacatact ccttcccaag agcgagctta     240
cactaccagt ctcatgccag ctatacatac tgcactggcc accccgtgtc ctatgcacca     300
gctccccacc ccatggctcc tcccagcccc agcacaaaca gcagcagcaa cagcagcggg     360
gaacagttga gtaagacaaa cctatacatc cgaggacttc caccaggcac cactgaccag     420
gacctcatca gctatgtcac accgtatgga aaaatcgtat ccacaaaggc aattcttgac     480
aagaatacga atcagtgcaa aggttatggt tttgtagatt ttgatagtcc tgcagccgca     540
cagaaagcag tggcgtcctt gaaggcaaat ggcgtgcaag cacagatggc caagcaacaa     600
gagcaagacc ctacgaatct atacatctca aaccttccca tctccatgga tgagcaggag     660
ctggagaaca tgctaaagcc ctttggacac gtgatatcca ccagaatcct gagggatgct     720
aacggagtca gcaggggcgt tggctttgcc agaatggagt ctacggaaaa atgtgaagtg     780
gtgattcaac attttaatgg aaaatatctg aaaacaccac caggcatccc agccccagt      840 gagcctttgc tgtgcaagtt tgctgacgga ggacagaaga agagacaggg tcagagcaag     900
cacacccaga cgggaggcc atggcccaga aaggagagg ctggcatggc tctgacctat     960
gaccccacag ctgccctaca gaacggattt tattcttcac cgtacagtct cgcaaccaac    1020
cgcatgatcc cacagacatc tatcacgccc ttcattgccg cttcccctgt ctccacatac    1080
cagggtgctg tgatcacacc cgccgtggac caccccatgt caatgcagcc aactaacatc    1140
gtgggtcccc tgacgcagca gatgaaccat cttttccctgg ggacagcagg aacgattcaa    1200
tcccaagaca gaattatggt acttcaccag ctgttatgtc agtatatgac tgctgctcct    1260
atgcaaggga cctacattcc ccagtacacg cctgtgcctc cgacagctgt ttctattgaa    1320
ggtgttgttg ctgatacctc tcccagacg gtgcccccct catcccagga cagcagtggt    1380
cagcagcaac agttagcagt ggacacaccc agtgaacacg caccggcata ctccttccaa    1440
cagtccaaac catagacaga agtgaggatg tctgcctgaa cctttacctt caatgaagaa    1500
acgtcactga gcaagaagtt agttggcctc cggtttgcac aggcgccaag ggaaagcttt    1560
cttcttcttt tatttttatt atttttttta ttatttata ttttactcaa agaaaacaaa    1620 attttatgt gctgtgcgaa tggttcctcc gtgtggtcta acacttattt ttgtctttt    1680 tttttaatta acgggaaaaa acaaatccca gaaaggggtg ggggatggca aacatcacaa    1740
```

```
gttgatgctg tctttggaaa acagaatttt gcctgaaggt ataagtagat ttgtttttta   1800
aaaagtagaa acaccaatgt caagagttgg gcaaccagat gtttaagaaa attattttcc   1860
tcagtaatta agctattttt ttcctcttct tttcttttct tgtttgaacc tcctgggttt   1920
tttatatata tataaatatt ttatgttttc ttagaaatat ttaggtaagg tttatcttga   1980
atcttaattg ccttaatttt taaggacgtc aaaggctcca gaggcatgct ttcagcgtct   2040
tgttaaaaaa aaaaaatcaa gaaagaattg agttttgtg ccagccttca ctgacataga    2100
agatggagac tgagttttta gggtggaaaa gaaaagaaa aaaaaaaaa caaaactgta     2160 cagtttgaag gaaaatgtgt tttcttcatt tgaagaaaat ttgttgataa agaaaccaa    2220 ggcaaccgca agagtttgga aacgctggga cttctcatga actttgacac aatcactcta   2280
aaaggctaaa agacattttta tggtaaagtt attcacgttg gttttaaaaa caactgcatt  2340
agaaataatg caagtttggg gggcagaatg cagatttttt tttttttaat ttacaagagc   2400
gtggttgcta gcgaaagcgt cagtgctttt tatctgcagt tttttctatg agctttgtca   2460
ggttttagtc agctttgctt gtcacattgc aaaacctagc ataagagcac tcaaaacaaa   2520
acttaagtag atagacgctt atggtcaaaa agtgcaaaaa aataaaaaat aaaacaaaaa   2580
cacacacaca aaaaaacaaa caaaacaaaa caaaacaaa aaaaagcaat agatagagaa    2640
attgttgaca atttctgtag tcttttcttag ttgtggtcaa ttgcagccta tggatggcct  2700
attttatacc aaagatgaag tgagaccctg ttacaggcgt gatggtagac actgcttttc   2760
tttctttgaa gttttgtttg acctacatgg ccggaccagt tctaacttca tttaaactac   2820
cttccactag tgtgttacat accacaaaaa agaaaaaag aaaaaaaaa acattgtttt     2880 ttctaaaaat gtgtatttgt caatagttga gtttgttcc tacctgctc agcagtttaa     2940 gcatgaagaa tctgagaccc agtggatgaa tggatgcagg cggctttaag tcctgtgagc   3000
tttgctatct cttgaccagc gctctcagca gtggatcgac ggccaccaat acacccgtc    3060 agttgttcaa gagattgaaa tgccctcatc tgaacttcag gctaaggatg cttcctgaag   3120
gatgcttctg atgtctgaaa ggccatttgt cagaaaggct gtgatgttcg gagctgtggg   3180
ttgtggtccc cagagaagtt ctcacgaatt ggtaacaatg tttctttcaa acactgacag   3240 taaccaatttt ttgtcttctc accttggttt agttatcagc cctcctcaca caggcgcttt  3300
gattctgtgt ttggggaggg agtgttttttc ttttacctcc tctgcctgct gtgttctcat  3360
atcttgatac tgacaggaga gacaacacag ccctctttaa attttggttt aattctccaa   3420
gataagtggg gccgttaaga tctaagactc ctttgagtgc agtaggggca agctcttaac   3480
accttagttg acaatcaata aattttttc aacaagaacc acaagaacta ggggttgatc    3540
cagcaccgaa accaaaggag atatttgcac ttagaataat gcaaaacttg gcttaaaatg   3600
atctaaattg gcttagtgag agagtcctaa ctgttctgac tcatcagatc tgggatcaac   3660
ggatcttgtt ttcctggaag ttagaagcag tagcttggaa ctccgttcat gggaccattc   3720
ccaagaactg cttttgaatg aaactttgaa tcaagtaggc aaagctcttt tctgcaggtt   3780
actccatctg agtgcatagg gaggacacaa aaccgagccg ctggagagga aaagagagta   3840
ggctttcaga aacaaagtaa cttgtaaggc aaatcacagt cccattaggc cccacaacta   3900
atgagtctgc aggtccatat tctgctgtct cactagaccc tccttctctt ctttgcaacc   3960
ctgtgaactg agagctcaaa cccagaaagt catcttgtat gttggtcatc aaactaatta   4020
cagaacagta tccaaggaga cagcatcaca ctgcagagac cttgtgggct tcgcctttat   4080
cctaatgtct ttccctgctt tggagggaac ctgagatgcc tacatccttc tgtcacacca   4140
```

```
gtcagctccc tgtgtgttgg aagggtggac ttgaacatgt ctatggaaag caagccctca    4200
agttccaggg gctctcagaa aactcactga gacccaactt tctctttctc cttcggcttc    4260
tctcaattct ctgtgtaagt gaggattatc ctgggcatca ttcatttgaa tatgaaacca    4320
acatactttc ttgtcctttc tgtaaaagaa caaaatgcct gtattcacgt gatacaaaga    4380
gagtctcatt tgcattaccg ataatgaggc ttcaaggtag ctaccatgtg gcagctgaag    4440
gtgcctaggg aacttcatgc tcaaaactcc tgtcttacat atgtagtcat tctgaaacat    4500
ttctttcaac tctaaaattt tcatgatctc ttttcttttta agccatctca ggccaaagga    4560
aatcattatg tcatcttcta tgttcctgtg tgttttatgt ttgggctgtc ttgataatgc    4620
cattccgtaa aatcttttga gaaaagaaa aagtgtgtat tcaaattggc tctctcttct    4680
tctgtcattt ttacctaaga attgtttttt caatagccca atataaaaac aacacccca    4740 ccccccaaa ccttatacgc aatgtgtgca gtgcagatac ctgaatctca acctagtcac    4800
cactacacat ggtagtcctc atgacttagt actacagtca ttttttaaaac taaagtaaaa    4860 ttctaattct tgagattgcc aaaatatttt gattttattc tctttcatta ccacatactg    4920
gatttaggaa accaacaata ggtacaatcc aaacaagata aattccgagt catccaaatg    4980
ctacctattt tgtcagaaca gtgttctctt tgaataatga ccaagatacc aggagaagca    5040
gaatgtgtgg agactgctag ctgtttttcac ctaaggaccc caggatagaa ccttcatgag    5100
ctaatggtaa tgtcagcagg tgctgaagat tagaaataat tacttagttt ttttatattt    5160
taaatctttg tttaatggtt gaaatatcta tgaaaaaacc tacacatctt ttctattgac    5220
ttaaaaatcc tcttcaccga ggagtgggat ttggtctcaa cagggtcctc acgttcttca    5280
tgatggaggt gttttgggtgg gacatctgtg tagactatga tgttaatagg ctaaaactac    5340
tcctgacaat ctaagctcat ctgcatgagt atgcgcacaa ctccaggaga gctgaagact    5400
gaggagtaag cctttctgtgg gcctcaatgg aaaacctgtg atttcaactt ggtgagacag    5460
caggattgaa agtcccctgt aacagctttc agcaagacaa gcaatcacac agcagaatat    5520
tatagaacca tctcacagaa ccttgatctg gttttgtttt ttttttttct ttcttgacca    5580
cagtgtggag caaagaaaaa gatttctttc ttccttcctt tctttctttt cagttttcc    5640 cttttgtgcc cttgagacta gtatgctgaa catttatttt gagcccactg gccttgatag    5700
attctctgga accccaggaa tagctggatt ggcagactcc ttgattccat ttccttcttg    5760
tggggtttct ttcacccatg catcgactca ttttacaact gcggtgttgt aaagtagttg    5820
agcctacctt aagattaaga tttcttaccc atacataagt ggtctgtcct ggccaacctt    5880
tgtgatgact tggagtttag aaaagaacaa aggccgaagc tccaagtgac tccataattt    5940
aagaaactgg gttcagcgca gatttctgat ttctattgtc tttgggtaaa tacccccaact    6000 tataacatgc agtcatagtc actgtcacag gaagggctgg gtgtcttctc gacagtaaca    6060
gtcatgaggt tctgggcaag aaaacaatgt tctggggat ttgcttcaga actgaacagg    6120
gggagaggct agatggagct tgggggttca gggggaaaat gcaagcccaa agtcaactgg    6180
gagattttct taacactact ccatttgaaa gaaacacaat cactgtcaat gttcaaaggg    6240
ctagctaact agtttgtggg gggtgtttca tcttttcttc tctatgactg atcctgttaa    6300
tcttagcatc tcactgcaag ggaggacaga agaaacccct gaaaatagca atgcacacca    6360
gtctgttttg ctttccaagt actgatgaat caagggagct ttaatcatta ttgaaattaa    6420
tgttcacaca tcatacacta tgaaattcaa cagtccatac atgtccatac atgtcatttt    6480
```

```
cctatccatc acacataatc gagagttggc tgcattcttg taaaacacaa atggaaatat    6540
tgtaagaaca aacctggctc cccttagaag aaggctactt tggctccatt ctcttggctg    6600
aaactcaaac caggaaaaaa agatacacac attctctatc aggagaaaat aaggtcattt    6660
cgactaaata cacagtttta atccccttct tttgactaca aaaaaattta ttttttgttgt    6720
```

```
tatttctatt tgaacctgtt ttactgtttt aagactgaaa gttacttgta tcctgaggca    6780 taatttatg gccattatgt acctaaataa aaagtgtaac attagtgtta cactttggac     6840
tttgaaactt ctagttcaac attgtagata aggatgctct ctcctcctcc ccaaatgtgt    6900
tatgctatgt cctcacatgt aaaaagaagt gagctgttcc atccctctta ggaagagtaa    6960
aattgtttca agagacatt aggtatctga aattatattg ttttccagtc tggaaacaat     7020
tgtccccatt aacttaaaaa aaaaaatgga atctttaatt tttcagctct gggtggaaat    7080
acttcagttt caaggaaaac tgtgacaggg cttcctcttt aaaagccttg gtttatgtcg    7140
tcttcaactt catggacctc ctggaatacc cttttgagat tttatttaag ggcatctttg    7200
tattgctgtc tctgactgtc atggagaatt ctgtaatcct atggtgtttc tggttttatc    7260
tctaagttct ttcatgtgta tcatggtcaa gttagatacc atttcccctg tttcctgggc    7320
tctctgtaga tcagtggata ttaggtttca atttctgttt tctttgatga agctttcaat    7380
aaaaaatgga aataaaatca acaaaaaaa                                      7409
```

<210> SEQ ID NO 13
<211> LENGTH: 437
<212> TYPE: PRT
<213> ORGANISM: Homo sapiens

<400> SEQUENCE: 13

Met Gly Lys Arg Leu Asp Gln Pro Gln Met Tyr Pro Gln Tyr Thr Tyr
1               5                   10                  15

Tyr Tyr Pro His Tyr Leu Gln Thr Lys Gln Ser Tyr Ala Pro Ala Pro
            20                  25                  30

His Pro Met Ala Pro Ser Pro Ser Thr Asn Ser Ser Asn Asn
        35                  40                  45

Ser Ser Asn Asn Ser Ser Gly Glu Gln Leu Ser Lys Thr Asn Leu Tyr
    50                  55                  60

Ile Arg Gly Leu Pro Pro Gly Thr Thr Asp Gln Asp Leu Ile Lys Leu
65                  70                  75                  80

Cys Gln Pro Tyr Gly Lys Ile Val Ser Thr Lys Ala Ile Leu Asp Lys
                85                  90                  95

Asn Thr Asn Gln Cys Lys Gly Tyr Gly Phe Val Asp Phe Asp Ser Pro
            100                 105                 110

Ala Ala Ala Gln Lys Ala Val Ala Ser Leu Lys Ala Asn Gly Val Gln
        115                 120                 125

Ala Gln Met Ala Lys Gln Gln Glu Gln Asp Pro Thr Asn Leu Tyr Ile
    130                 135                 140

Ser Asn Leu Pro Ile Ser Met Asp Glu Gln Glu Leu Glu Asn Met Leu
145                 150                 155                 160

Lys Pro Phe Gly His Val Ile Ser Thr Arg Ile Leu Arg Asp Ala Asn
                165                 170                 175

Gly Val Ser Arg Gly Val Gly Phe Ala Arg Met Glu Ser Thr Glu Lys
            180                 185                 190

Cys Glu Val Val Ile Gln His Phe Asn Gly Lys Tyr Leu Lys Thr Pro
        195                 200                 205

-continued

```
Pro Gly Ile Pro Ala Pro Ser Glu Pro Leu Leu Cys Lys Phe Ala Asp
    210                 215                 220

Gly Gly Gln Lys Lys Arg Gln Asn Gln Ser Lys Tyr Thr Gln Asn Gly
225                 230                 235                 240

Arg Pro Trp Pro Arg Glu Gly Glu Ala Gly Met Ala Leu Thr Tyr Asp
                245                 250                 255

Pro Thr Ala Ala Ile Gln Asn Gly Phe Tyr Ser Ser Pro Tyr Ser Ile
            260                 265                 270

Ala Thr Asn Arg Met Ile Pro Gln Thr Ser Ile Thr Pro Phe Ile Ala
        275                 280                 285

Ala Ser Pro Val Ser Thr Tyr Gln Val Gln Ser Thr Ser Trp Met Pro
    290                 295                 300

His Pro Pro Tyr Val Met Gln Pro Thr Gly Ala Val Ile Thr Pro Thr
305                 310                 315                 320

Met Asp His Pro Met Ser Met Gln Pro Ala Asn Met Met Gly Pro Leu
                325                 330                 335

Thr Gln Gln Met Asn His Leu Ser Leu Gly Thr Thr Gly Thr Ile Gln
            340                 345                 350

Ser Gln Asp Arg Ile Met Ile Leu His Gln Leu Leu Cys Gln Tyr Met
        355                 360                 365

Thr Ala Ala Ala Pro Met Gln Gly Thr Tyr Ile Pro Gln Tyr Thr Pro
    370                 375                 380

Val Pro Pro Thr Ala Val Ser Ile Glu Gly Val Val Ala Asp Thr Ser
385                 390                 395                 400

Pro Gln Thr Val Ala Pro Ser Ser Gln Asp Thr Ser Gly Gln Gln Gln
                405                 410                 415

Gln Ile Ala Val Asp Thr Ser Asn Glu His Ala Pro Ala Tyr Ser Tyr
            420                 425                 430

Gln Gln Ser Lys Pro
            435

<210> SEQ ID NO 14
<211> LENGTH: 463
<212> TYPE: PRT
<213> ORGANISM: Mus musculus

<400> SEQUENCE: 14

Met Glu Gly Gly Arg Leu Leu Ile Arg Ser Asn Ala Asn Gly Val Thr
1               5                   10                  15

Gln Ser Asn Ser Thr Val Arg Ala Tyr Gln Ser Ser Lys Ser Arg Val
            20                  25                  30

Thr Met Ser Pro Gly Phe Ser Ser Gln Trp Ser Asn Ser Gln Pro Ala
        35                  40                  45

Trp Asn Thr Tyr Ser Phe Pro Arg Ala Ser Leu His Tyr Gln Ser His
    50                  55                  60

Ala Ser Tyr Thr Tyr Cys Thr Gly His Pro Val Ser Tyr Ala Pro Ala
65                  70                  75                  80

Pro His Pro Met Ala Pro Pro Ser Pro Ser Thr Asn Ser Ser Ser Asn
                85                  90                  95

Ser Ser Gly Glu Gln Leu Ser Lys Thr Asn Leu Tyr Ile Arg Gly Leu
            100                 105                 110

Pro Pro Gly Thr Thr Asp Gln Asp Leu Ile Lys Leu Cys Gln Pro Tyr
        115                 120                 125

Gly Lys Ile Val Ser Thr Lys Ala Ile Leu Asp Lys Asn Thr Asn Gln
    130                 135                 140
```

Cys Lys Gly Tyr Gly Phe Val Asp Phe Asp Ser Pro Ala Ala Ala Gln
145                 150                 155                 160

Lys Ala Val Ala Ser Leu Lys Ala Asn Gly Val Gln Ala Gln Met Ala
            165                 170                 175

Lys Gln Gln Glu Gln Asp Pro Thr Asn Leu Tyr Ile Ser Asn Leu Pro
        180                 185                 190

Ile Ser Met Asp Glu Gln Glu Leu Glu Asn Met Leu Lys Pro Phe Gly
        195                 200                 205

His Val Ile Ser Thr Arg Ile Leu Arg Asp Ala Asn Gly Val Ser Arg
        210                 215                 220

Gly Val Gly Phe Ala Arg Met Glu Ser Thr Glu Lys Cys Glu Val Val
225                 230                 235                 240

Ile Gln His Phe Asn Gly Lys Tyr Leu Lys Thr Pro Pro Gly Ile Pro
            245                 250                 255

Ala Pro Ser Glu Pro Leu Leu Cys Lys Phe Ala Asp Gly Gly Gln Lys
        260                 265                 270

Lys Arg Gln Gly Gln Ser Lys His Thr Gln Asn Gly Arg Pro Trp Pro
        275                 280                 285

Arg Glu Gly Glu Ala Gly Met Ala Leu Thr Tyr Asp Pro Thr Ala Ala
290                 295                 300

Leu Gln Asn Gly Phe Tyr Ser Ser Pro Tyr Ser Leu Ala Thr Asn Arg
305                 310                 315                 320

Met Ile Pro Gln Thr Ser Ile Thr Pro Phe Ile Ala Ala Ser Pro Val
            325                 330                 335

Ser Thr Tyr Gln Gly Ala Val Ile Thr Pro Ala Val Asp His Pro Met
        340                 345                 350

Ser Met Gln Pro Thr Asn Ile Val Gly Pro Leu Thr Gln Gln Met Asn
        355                 360                 365

His Leu Ser Leu Gly Thr Ala Gly Thr Ile Gln Ser Gln Asp Arg Ile
        370                 375                 380

Met Val Leu His Gln Leu Leu Cys Gln Tyr Met Thr Ala Ala Pro Met
385                 390                 395                 400

Gln Gly Thr Tyr Ile Pro Gln Tyr Thr Pro Val Pro Pro Thr Ala Val
            405                 410                 415

Ser Ile Glu Gly Val Val Ala Asp Thr Ser Pro Gln Thr Val Ala Pro
        420                 425                 430

Ser Ser Gln Asp Ser Ser Gly Gln Gln Gln Leu Ala Val Asp Thr
        435                 440                 445

Pro Ser Glu His Ala Pro Ala Tyr Ser Phe Gln Gln Ser Lys Pro
    450                 455                 460

<210> SEQ ID NO 15
<211> LENGTH: 446
<212> TYPE: DNA
<213> ORGANISM: Homo sapiens

<400> SEQUENCE: 15
catgggcacc tcagattgtt gttgttaatg ggcattcctt cttctggtca gaaacctgtc      60
cactgggcac agaacttatg ttgttctcta tggagaacta aaagtatgag cgttaggaca     120 ctatttaat tatttttaat ttattaatat ttaaatatgt gaagctgagt taatttatgt     180
aagtcatatt tatattttta agaagtacca cttgaaacat tttatgtatt agttttgaaa    240
taataatgga agtggctat gcagtttgaa tatcctttgt ttcagagcca gatcatttct    300

```
tggaaagtgt aggcttacct caaataaatg gctaacttat acatattttt aaagaaatat      360
ttatattgta tttatataat gtataaatgg tttttatacc aataaatggc attttaaaaa      420
attcagcaaa aaaaaaaaaa aaaaaa                                           446

<210> SEQ ID NO 16
<211> LENGTH: 171
<212> TYPE: DNA
<213> ORGANISM: Artificial Sequence
<220> FEATURE:
<223> OTHER INFORMATION: IL-6 3'UTR 97-267

<400> SEQUENCE: 16
ctaaaagtat gagcgttagg acactatttt aattattttt aatttattaa tatttaaata       60
tgtgaagctg agttaattta tgtaagtcat atttatattt ttaagaagta ccacttgaaa      120
cattttatgt attagttttg aaataataat ggaaagtggc tatgcagttt g              171

<210> SEQ ID NO 17
<211> LENGTH: 72
<212> TYPE: DNA
<213> ORGANISM: Artificial Sequence
<220> FEATURE:
<223> OTHER INFORMATION: IL-6 3'UTR 122-193

<400> SEQUENCE: 17
tattttaatt attttaatt tattaatatt taaatatgtg aagctgagtt aatttatgta       60 agtcatatttt at                                                         72

<210> SEQ ID NO 18
<211> LENGTH: 39
<212> TYPE: DNA
<213> ORGANISM: Artificial Sequence
<220> FEATURE:
<223> OTHER INFORMATION: IL-6 3'UTR delta ARE1

<400> SEQUENCE: 18
tattttaatt attttaatt tattaatatt taaatatgt                              39

<210> SEQ ID NO 19
<211> LENGTH: 101
<212> TYPE: DNA
<213> ORGANISM: Artificial Sequence
<220> FEATURE:
<223> OTHER INFORMATION: IL-6 3'UTR delta ARE2

<400> SEQUENCE: 19
agttaattta tgtaagtcat atttatattt ttaagaagta ccacttgaaa cattttatgt       60
attagttttg aaataataat ggaaagtggc tatgcagttt g                          101

<210> SEQ ID NO 20
<211> LENGTH: 71
<212> TYPE: DNA
<213> ORGANISM: Artificial Sequence
<220> FEATURE:
<223> OTHER INFORMATION: IL-6 3'UTR ARE mutant

<400> SEQUENCE: 20
tattttaatt attttaagg gattaatagg gaaatatgtg aagctgagtt aagggatgta       60 agtcatagg a                                                            71

<210> SEQ ID NO 21
<211> LENGTH: 1285
```

```
<212> TYPE: DNA
<213> ORGANISM: Homo sapiens

<400> SEQUENCE: 21
atgtttcata aaggaagcac tgttggagct actgcaaatg ctatattgca ctgtgaccga      60 gaactttta gaggatagaa tacatggaaa cgcaaatgag tatttcggag catgaagacc      120
ctggagttca aaaaactctt gatatgacct gttattacca ttagcattct ggttttgaca     180
tcagcattag tcactttgaa atgtaacgaa tggtactaca accaattcca agtttaattt     240
tttaacacca tggcaccttt tgcacataac atgctttaga ttatatattc cgcactcaag     300
gagtaaccag tcgtccaag caaaaacaaa tgggaaaatg tcttaaaaaa tcctgggtgg      360
acttttgaaa agcttttttt tttttttttt tttttttgag acggagtctt gctctgttgc     420
ccaggctgga gtgcagtagc acgatctcgg ctcactgcac cctccgtctc tcgggttcaa     480
gcaattgtct gcctcagcct cccgagtagc tgggattaca ggtgcgcact accacgccaa     540
gctaattttt gtattttta gtagagatgg ggtttcacca tcttggccag ctggtcttg      600 aattcctgac ctcaggtgat ccacccacct tggcctccca aagtgctagt attatgggcg     660
tgaaccacca tgcccagccg aaaagctttt gaggggctga cttcaatcca tgtaggaaag     720
taaaatggaa ggaaattggg tgcatttcta ggacttttct aacatatgtc tataatatag     780
tgtttaggtt ctttttttt tcaggaatac atttggaaat tcaaacaat tggcaaactt       840 tgtattaatg tgttaagtgc aggagacatt ggtattctgg gcaccttcct aatatgcttt     900
acaatctgca ctttaactga cttaagtggc attaaacatt tgagagctaa ctatattttt     960
ataagactac tatacaaact acagagttta tgatttaagg tacttaaagc ttctatggtt    1020
gacattgtat atataattt ttaaaaaggt tttctatatg gggatttttct atttatgtag    1080 gtaatattgt tctatttgta tatatgaga taatttattt aatatacttt aaataaaggt    1140
gactgggaat tgttactgtt gtacttattc tatcttccat ttattattta tgtacaattt    1200
ggtgtttgta ttagctctac tacagtaaat gactgtaaaa ttgtcagtgg cttacaacaa    1260
cgtatctttt tcgcttataa tacat                                           1285

<210> SEQ ID NO 22
<211> LENGTH: 894
<212> TYPE: DNA
<213> ORGANISM: Homo sapiens

<400> SEQUENCE: 22
ggtccccagg gaggaaacgg gcaccacccg cttctttgct ggttgtcatt tttgcagtag      60
agtcatctcc atcagctgta agaagagact gggaagatag gctctgcaca gatggatttg     120
cctgtgccac ccaccagggc gaacgacaat agctttaccc tcaggcatag gcctgggtgc     180
tggctgccca gacccctctg gccaggatgg aggggtggtc ctgactcaac atgttactga     240
ccagcaactt gtcttttct ggactgaagc ctgcaggagt taaaaagggc agggcatctc      300
ctgtgcatgg gtgaagggag agccagctcc cccgacggtg ggcatttgtg aggcccatgg     360
ttgagaaatg aataatttcc caattaggaa gtgtaacagc tgaggtctct tgagggagct     420
tagccaatgt gggagcagcg gtttggggag cagagacact aacgacttca gggcagggct     480
ctgatattcc atgaatgtat caggaaatat atatgtgtgt gtatgtttgc acacttgtgt     540
gtgggctgtg agtgtaagtg tgagtaagag ctggtgtctg attgttaagt ctaaatattt     600
ccttaaactg tgtggactgt gatgccacac agagtggtct ttctggagag gttataggtc     660
```

| | | |
|---|---|---|
| actcctgggg cctcttgggt cccccacgtg acagtgcctg ggaatgtatt attctgcagc | 720 | |
| atgacctgtg accagcactg tctcagtttc actttcacat agatgtccct ttcttggcca | 780 | |
| gttatccctt cctttagcc tagttcatcc aatcctcact gggtggggtg aggaccactc | 840 | |
| ctgtacactg aatatttata tttcactatt tttatttata tttttgtaat ttta | 894 | |

<210> SEQ ID NO 23
<211> LENGTH: 1455
<212> TYPE: DNA
<213> ORGANISM: Homo sapiens

<400> SEQUENCE: 23

| | | |
|---|---|---|
| gagagacttg tgctcaagga atcggctggg gactgctacc tctgagaaga cacaaggtga | 60 | |
| tttcagactg cagaggggaa agacttccat ctagtcacaa agactccttc gtccccagtt | 120 | |
| gccgtctagg attgggcctc ccataattgc tttgccaaaa taccagagcc ttcaagtgcc | 180 | |
| aaacagagta tgtccgatgg tatctgggta agaagaaagc aaaagcaagg gaccttcatg | 240 | |
| cccttctgat tcccctccac caaacccac ttccctcat aagtttgttt aaacacttat | 300 | |
| cttctggatt agaatgccgg ttaaattcca tatgctccag gatctttgac tgaaaaaaaa | 360 | |
| aaagaagaag aagaaggaga gcaagaagga aagatttgtg aactggaaga aagcaacaaa | 420 | |
| gattgagaag ccatgtactc aagtaccacc aagggatctg ccattgggac cctccagtgc | 480 | |
| tggatttgat gagttaactg tgaaatacca caagcctgag aactgaattt tgggacttct | 540 | |
| acccagatgg aaaaataaca actattttg ttgttgttgt ttgtaaatgc ctcttaaatt | 600 | |
| atatatttat tttattctat gtatgttaat ttatttagtt tttaacaatc taacaataat | 660 | |
| atttcaagtg cctagactgt tactttggca atttcctggc cctccactcc tcatccccac | 720 | |
| aatctggctt agtgccaccc acctttgcca caaagctagg atggttctgt gacccatctg | 780 | |
| tagtaattta ttgtctgtct acatttctgc agatcttccg tggtcagagt gccactgcgg | 840 | |
| gagctctgta tggtcaggat gtaggggtta acttggtcag agccactcta tgagttggac | 900 | |
| ttcagtcttg cctaggcgat tttgtctacc atttgtgttt tgaaagccca aggtgctgat | 960 | |
| gtcaaagtgt aacagatatc agtgtctccc cgtgtcctct ccctgccaag tctcagaaga | 1020 | |
| ggttgggctt ccatgcctgt agctttcctg gtccctcacc cccatggccc caggcccaca | 1080 | |
| gcgtgggaac tcactttccc ttgtgtcaag acatttctct aactcctgcc attcttctgg | 1140 | |
| tgctactcca tgcaggggtc agtgcagcag aggacagtct ggagaaggta ttagcaaagc | 1200 | |
| aaaaggctga gaaggaacag ggaacattgg agctgactgt tcttggtaac tgattacctg | 1260 | |
| ccaattgcta ccgagaaggt tggaggtggg gaaggctttg tataatccca cccacctcac | 1320 | |
| caaaacgatg aagttatgct gtcatggtcc tttctggaag tttctggtgc catttctgaa | 1380 | |
| ctgttacaac ttgtatttcc aaacctggtt catatttata ctttgcaatc caaataaaga | 1440 | |
| taacccttat tccat | 1455 | |

<210> SEQ ID NO 24
<211> LENGTH: 3544
<212> TYPE: DNA
<213> ORGANISM: Homo sapiens

<400> SEQUENCE: 24

| | | |
|---|---|---|
| tcatcaaatt gttgattgaa agactgatca taaaccaatg ctggtattgc accttctgga | 60 | |
| actatgggct tgagaaaacc cccaggatca cttctccttg gcttccttct tttctgtgct | 120 | |
| tgcatcagtg tggactccta gaacgtgcga cctgcctcaa gaaaatgcag ttttcaaaaa | 180 | |

```
cagactcagc attcagcctc caatgaataa gacatcttcc aagcatataa acaattgctt    240
tggtttcctt ttgaaaaagc atctacttgc ttcagttggg aaggtgccca ttccactctg    300
cctttgtcac agagcagggt gctattgtga ggccatctct gagcagtgga ctcaaaagca    360
ttttcaggca tgtcagagaa gggaggactc actagaatta gcaaacaaaa ccaccctgac    420
atcctccttc aggaacacgg ggagcagagg ccaaagcact aaggggaggg cgcatacccg    480
agacgattgt atgaagaaaa tatggaggaa ctgttacatg ttcggtacta agtcattttc    540
aggggattga aagactattg ctggatttca tgatgctgac tggcgttagc tgattaaccc    600
atgtaaatag gcacttaaat agaagcagga aagggagaca aagactggct tctggacttc    660
ctccctgatc cccacccta ctcatcacct gcagtggcca gaattaggga atcagaatca    720
aaccagtgta aggcagtgct ggctgccatt gcctggtcac attgaaattg gtggcttcat    780
tctagatgta gcttgtgcag atgtagcagg aaaataggaa aacctaccat ctcagtgagc    840
accagctgcc tcccaaagga ggggcagccg tgcttatatt tttatggtta caatggcaca    900
aaattattat caacctaact aaaacattcc ttttctcttt tttcctgaat tatcatggag    960
ttttctaatt ctctcttttg gaatgtagat ttttttttaaa tgctttacga tgtaaaatat   1020
ttatttttta cttattctgg aagatctggc tgaaggatta ttcatggaac aggaagaagc   1080
gtaaagacta tccatgtcat ctttgttgag agtcttcgtg actgtaagat tgtaaataca   1140
gattatttat taactctgtt ctgcctggaa atttaggctt catacggaaa gtgtttgaga   1200
gcaagtagtt gacatttatc agcaaatctc ttgcaagaac agcacaagga aaatcagtct   1260
aataagctgc tctgcccctt gtgctcagag tggatgttat gggattcttt ttttctctgt   1320
tttatctttt caagtggaat tagttggtta tccatttgca aatgttttaa attgcaaaga   1380
aagccatgag gtcttcaata ctgttttacc ccatcccttg tgcatatttc cagggagaag   1440
gaaagcatat acacttttttt ctttcatttt tccaaaagag aaaaaaatga caaaaggtga   1500
aacttacata caaatattac ctcatttgtt gtgtgactga gtaaagaatt tttggatcaa   1560
gcggaaagag tttaagtgtc taacaaactt aaagctactg tagtacctaa aaagtcagtg   1620
ttgtacatag cataaaaact ctgcagagaa gtattcccaa taaggaaata gcattgaaat   1680
gttaaataca atttctgaaa gttatgtttt tttctatca tctggtatac cattgcttta   1740 ttttatata ttatttttctc attgccattg gaatagatat ctcagattgt gtagatatgc   1800
tatttaaata atttatcagg aaatactgcc tgtagagtta gtatttctat ttttatataa   1860
tgtttgcaca ctgaattgaa gaattgttgg ttttttcttt tttttgtttt gtttttttt   1920 ttttttttt ttgcttttga cctcccattt ttactatttg ccaataccctt tttctaggaa   1980 tgtgcttttt tttgtacaca ttttatcca ttttacattc taaagcagtg taagttgtat   2040
attactgttt cttatgtaca aggaacaaca ataaatcata tggaaattta tatttatact   2100
tactgtatcc atgcttattt gttctctact ggctttatgt catgaagtat atgcgtaaat   2160
accattcata aatcaatata gcatatacaa aaataaatta cagtaagtca tagcaacatt   2220
cacagtttgt atgtgattga gaaagactga gttgctcagg cctaggctta gaatttgctg   2280
cgtttgtgga ataaaagaac aaaatgatac attagcctgc catatcaaaa acatataaaa   2340
gagaaattat ccctaagtca agggcccca taagaataaa atttcttatt aaggtcatta   2400
gatgtcattg aatccttttc aaagtgcagt atgaaaacaa agggaaaaac actgaagcac   2460
acgcaactct cacagcgaca ttttctgacc cacgaatgat gccttgggtg ggcaacacga   2520
```

```
ttgcatgttg tggagacact tcggaagtaa atgtggatga ggaggagct gtccttgcaa      2580 tgttgagcca agcattacag atacctcctc ttgaagaagg aataataagt ttaatcaaaa     2640
aagaagacta aaaatgtaa aatttggaag gaatccataa atgcgtgtgt gtctaaatac     2700
aaattatcat gtgaagaaaa ggcccaagtg taccaataag cagaccttga tttttggatg     2760
ggctaattat gaatgtggaa tactgaccag ttaatttcca gttttaatga aaacagatca     2820
aagaagaaat tttatgagta ggttaaaggt ctggctttga ggtctattaa acactagaaa     2880
ggactggctg ggtgagataa aatcttcctt gttgattttc actctcattc tataaatact     2940
catctttctg agtagccatg atcacataca aatgtaaatt gccaaatcat tttatagtac     3000
caaggtgaag aagcaggaac tagaaagtgt tgataatagc tgtggagtta ggaaaactga     3060
tgtgaaggaa ataattcttt gaaatggcaa agaattaaat accatcattc attatcagaa     3120
gagttcaacg tttgaagtgc tgggagataa ttctaattca ttcttggata gtgaagcaaa     3180
actgattgaa ataccaaga taagacagaa aaagtgactg gaaagaggag cttttcttcc     3240
aggcatgttc cagtttcacc ctaagactga ccttcaaata atcaggttgt actgaaataa     3300
aggacttgtt aaaaattaaa attatgtcat cgagatgata gcttttttcc tcctccaaca     3360
gtttattgtc atgtgttgtg ggagagctcg agtgaagagc aataaactcc aggtcttata     3420
agaatgtaca tacaataaag gtggtgccag cagttttttt ttttctaaag agtcacatgt     3480
agaaaagcct ccagtattaa gctcctgaat tcattcctta aataaattgg ctctctctct     3540
cttc                                                                 3544
```

<210> SEQ ID NO 25
<211> LENGTH: 918
<212> TYPE: DNA
<213> ORGANISM: Homo sapiens

<400> SEQUENCE: 25

```
atgctacctg ggtttccagg gcacacctag acaaacaagg gagaagagtg tcagaatcag      60
aatcatggag aaaatgggcg ggggtggtgt gggtgatggg actcattgta gaaaggaagc     120
cttgctcatt cttgaggagc attaaggtat ttcgaaactg ccaagggtgc tggtgcggat     180
ggacactaat gcagccacga ttggagaata ctttgcttca tagtattgga gcacatgtta     240
ctgcttcatt ttggagcttg tggagttgat gactttctgt tttctgtttg taaattattt     300
gctaagcata ttttctctag cttttttcc ttttgggtt ctacagtcgt aaaagagata     360
ataagattag ttggacagtt taaagctttt attcgtcctt tgacaaaagt aaatgggagg     420
gcattccatc ccttcctgaa ggggacact ccatgagtgt ctgtgagagg cagctatctg     480
cactctaaac tgcaaacaga atcaggtgt tttaagactg aatgttttat ttatcaaaat     540
gtagcttttg gggagggagg ggaaatgtaa tactggaata atttgtaaat gattttaatt     600
ttatattcag tgaaaagatt ttatttatgg aattaaccat ttaataaaga aatatttacc     660
taatatctga gtgtatgcca ttcggtattt ttagaggtgc tccaaagtca ttaggaacaa     720
cctagctcac gtactcaatt attcaaacag gacttattgg gatacagcag tgaattaagc     780
tattaaaata agataatgat tgcttttata cccttcagtag agaaagtct ttgcatataa     840 agtaatgttt aaaaacatg tattgaacac gacattgtat gaagcacaat aaagattctg     900
aagctaaatt tgtgattt                                                  918
```

<210> SEQ ID NO 26
<211> LENGTH: 2386

<212> TYPE: DNA
<213> ORGANISM: Homo sapiens

<400> SEQUENCE: 26

```
tattgatcta cttctgtaat tgtgtggatt ctttaaacgc tctaggtacg atgacagtgt      60
tccccgatac catgctgtaa ggatccggaa agaagagcga gagatcaaag atgaaaagta     120
tattgataac cttgaaaaaa aacagtggat cacaaagtgg aacgaaaatg aaagctactc     180
atagcggggg cctaaaaaaa aaaagcttca cagtacccaa actgcttttt ccaactcaga     240
aattcaattt ggatttaaaa gcctgctcaa tccctgagga ctgatttcag agtgactaca     300
cacagtacga acctcagtt ttaactgtgg atattgttac gtagcctaag gctcctgttt     360
tgcacagcca aatttaaaac tgttggaatg gatttttctt taactgccgt aatttaactt     420
tctgggttgc ctttattttt ggcgtggctg acttacatca tgtgttgggg aagggcctgc     480
ccagttgcac tcaggtgaca tcctccagat agtgtagctg aggaggcacc tacactcacc     540
tgcactaaca gagtggccgt cctaacctcg ggcctgctgc gcagacgtcc atcacgttag     600
ctgtcccaca tcacaagact atgccattgg ggtagttgtg tttcaacgga aagtgctgtc     660
ttaaactaaa tgtgcaatag aaggtgatgt tgccatccta ccgtcttttc ctgtttccta     720
gctgtgtgaa tacctgctca cgtcaaatgc atacaagttt cattctccct ttcactaaaa     780
cacacaggtg caacagactt gaatgctagt tatacttatt tgtatatggt atttatttt     840
tcttttcttt acaaaccatt tgttattga ctaacaggcc aaagagtctc cagtttaccc     900
ttcaggttgg tttaatcaat cagaattaga gcatgggagg tcatcacttt gacctaaatt     960
atttactgca aaagaaaat ctttataaat gtaccagaga gagttgtttt aataacttat    1020
ctataaacta taacctctcc ttcatgacag cctccacccc acaacccaaa aggtttaaga    1080
aatagaatta taactgtaaa gatgtttatt tcaggcattg gatattttt actttagaag    1140
cctgcataat gtttctggat ttcatactgt aacattcagg aattcttgga gaaaatgggt    1200
ttattcactg aactctagtg cggtttactc actgctgcaa atactgtata ttcaggactt    1260
gaaagaaatg gtgaatgcct atggtggatc caaactgatc cagtataaga ctactgaatc    1320
tgctaccaaa acagttaatc agtgagtcga tgttctattt tttgttttgt ttcctcccct    1380
atctgtattc ccaaaaatta ctttgggct aatttaacaa gaactttaaa ttgtgtttta    1440
attgtaaaaa tggcaggggg tggaattatt actctataca ttcaacgag actgaataga    1500
tatgaaagct gattttttt aattaccatg cttcacaatg ttaagttata tggggagcaa    1560
cagcaaacag gtgctaattt gttttggata tagtataagc agtgtctgtg ttttgaaaga    1620
atagaacaca gtttgtagtg ccactgttgt tttgggggg cttttttctt ttcggaaatc    1680
ttaaaccta agatactaag gacgttgttt tggttgtact ttggaattct tagtcacaaa    1740
atatattttg tttacaaaaa tttctgtaaa acaggttata acagtgttta aagtctcagt    1800
ttcttgcttg gggaacttgt gtccctaatg tgtttagatt gctagattgc taaggagctg    1860
atactttgac agtgttttta gacctgtgtt actaaaaaaa agatgaatgt cctgaaaagg    1920
gtgttgggag ggtggttcaa caaagaaaca aagatgttat ggtgtttaga tttatggttg    1980
ttaaaaatgt catctcaagt caagtcactg gtctgtttgc atttgataca tttttgtact    2040
aactagcatt gtaaaattat ttcatgatta gaaattacct gtggatattt gtataaaagt    2100
gtgaaataaa tttttataa aagtgttcat tgtttcgtaa cacagcattg tatatgtgaa    2160
gcaaactcta aaattataaa tgacaacctg aattatctat ttcatcaaac caaagttcag    2220
```

```
tgtttttatt tttggtgtct catgtaatct cagatcagcc aaagatacta gtgccaaagc    2280
aatgggattc ggggttttt tctgttttcg ctctatgtag gtgatcctca agtctttcat    2340
tttccttctt tatgattaaa agaaacctac aggtatttaa caacct                  2386

<210> SEQ ID NO 27
<211> LENGTH: 1744
<212> TYPE: DNA
<213> ORGANISM: Homo sapiens

<400> SEQUENCE: 27
acactgatct gctagtgctg taatattgta aatactggac tcaggaactt ttgttaggaa      60
aaaattgaaa gaacttaagt ctcgaatgta attggaatct tcacctcaga gtggagttga    120
aactgctata gcctaagcgg ctgtttactg cttttcatta gcagttgctc acatgtcttt    180
gggtgggggg gagaagaaga attggccatc ttaaaaagcg ggtaaaaaac ctgggttagg    240
gtgtgtgttc accttcaaaa tgttctattt aacaactggg tcatgtgcat ctggtgtagg    300 aagtttttc taccataagt gacaccaata aatgtttgtt atttacactg gtctaatgtt    360
tgtgagaagc ttctaattag atcaattact tattttagga aatttaagac tagatactcg    420
tgtgtggggt gaggggaggg agtatttggt atgttgggat aaggaaacac ttctatttaa    480
tgcttccagg gattttttt ttttttttta accctcctgg gcccaagtga tccttccacc    540
tcagtctccc agctaattga gaccacaggc ttgttaccac catgctcggc ttttgcatta    600
atctaagaaa aggggagaga agttaatcca catctttact caggcaaggg gcatttcaca    660
gtgcccaaga gtgggttt cttgaacata cttggtttcc tatttcccct tatctttcta    720
aaactgcctt tctggtggct tttttaaaa ttattactaa tgatgctttt atagctgctt    780
ggattctctg agaaatgatg gggagtgagt gatcactggt attaacttta tacacttgga    840
tttcatttgt aactttagga tgtaaaggta tattgtgaac cctagctgtg tcagaatctc    900
catccctgaa atttctcatt agtggtactg ggtgggatc ttggatggtg acattgaaac    960
tacactaaat cccctcacta tgaatgggtt gttaaaggca atggtttgtg tcaaaactgg   1020
tttaggatta cttagattgt gttcctgaag aaaagagtcc aggtaaatgg tatgatcaat   1080
aaaggacagg ctggtgctaa cataaaatcc aatattgtaa tcctagcact ttgggaggcc   1140
aaggcgggtg gatcacaagg tcaagagata gagaccatct tgccaacat ggtgaaactc   1200 catctctact gaaaatacaa aaattagctg gcgtggtag tgcaagctga aggctgaggc   1260
aggagaatca ctcgaacccg ggaggcagag gttgcagtga gccgagatca ccactgta    1320 ctccagcccg gcactccagc ctggcgacaa gagtgagact ccacctcaaa aaaaaaaaa   1380 agaatccaat actgcccaag gataggtatt ttatagatgg gcaactggct gaaaggttaa   1440
ttctctaggg ctagtagaac tggatcccaa caccaaactc ttaattagac ctaggcctca   1500
gctgcactgc ccgaaaagca tttgggcaga ccctgagcag aatactggtc tcaggccaag   1560
cccaatacag ccattaaaga tgacctacag tgctgtgtac cctggggcaa tagggttaaa   1620
tggtagttag caactagggc tagtcttccc ttaccctcaaa ggctctcact accgtggacc   1680
acctagtctg taactctttc tgaggagctg ttactgaata ttaaaaagat agacttcaac   1740
tatg                                                              1744

<210> SEQ ID NO 28
<211> LENGTH: 2835
<212> TYPE: DNA
<213> ORGANISM: Homo sapiens
```

<400> SEQUENCE: 28

```
ggggaggcta catttcacaa ccctcttccc tatttcccta aaagtatctc catggaatga    60
actgtgcaaa atctgtagga aactgaatgg tttttttttt ttttcatga aaaagtgctc    120
aaattatggt aggcaactaa cggtgttttt aagggggtct aagcctgcct tttcaatgat    180
ttaatttgat tttattttat ccgtcaaatc tcttaagtaa caacacatta agtgtgaatt    240
acttttctct cattgtttcc tgaattattc gcattggtag aaatatatta gggaaagaaa    300
gtagccttct ttttatagca agagtaaaaa agtctcaaag tcatcaaata agagcaagag    360
ttgatagagc ttttacaatc aatactcacc taattctgat aaaaggaata ctgcaatgtt    420
agcaataagt ttttttcttc tgtaatgact ctacgttatc ctgtttccct gtgcctacca    480
aacactgtca atgtttatta caaaatttta aagaagaata tgtaacatgc agtactgata    540
ttataattct catttttactt tcattatttc taataagaga ttatgtgact tcttttttctt    600
ttagttctat tctacattct taatattgta tattacctga ataattcaat ttttttctaa    660
ttgaatttcc tattagttga ctaaaagaag tgtcatgttt actcatatat gtagaacatg    720
actgcctatc agtagattga tctgtattta atattcgtta attaaatctg cagttttatt    780
tttgaaggaa gccataacta tttaatttcc aaataattgc ttcataaaga atcccatact    840
ctcagtttgc acaaaagaac aaaaaatata tatgtctctt taaatttaaa tcttcattta    900
gatggtaatt acatatcctt atatttactt taaaaaatcg gcttatttgt ttattttata    960
aaaaatttag caaagaaata ttaatatagt gctgcatagt ttggccaagc atactcatca   1020
tttctttgtt cagctccaca tttcctgtga aactaacatc ttattgagat ttgaaactgg   1080
tggtagtttc ccaggaaggc acaggtggag ttatttgtga aagcaaagt gtttactaat   1140
gacaaagtag taaaccattt tcaagatgaa aactgatttc tatttatttt gcttcaaagg   1200
tcctgaaaaa ataagcaatt atcataacaa tttgttattg atactggagg tttcattgac   1260
atgtctctca aattaaagct cacactgcct ccataaaagt cttcaacatc taatttataa   1320
gctttacaag tatttatttt ataaggctta gacagaatta ttggagtttt aaattaagtg   1380
tattggaaaa gaaaggatgg tatgtgtatg aaatgttaag atcctacgca acactgctat   1440
ttttttcctt taatatttgt gctgcataac aaaagccact agactgttac tgtcttgtct   1500
gtccatgtgt taacagcatt tcttaatgat gtatatatgt agtggtcttc aatcatagtg   1560
aagaatttaa agagaaagtc aattgtattg gcattttttaa taagaacaaa attagttcgt   1620
ctaaggggac tggctggcca catatttgtt ccttgcccat atgctttcta cttcttgttc   1680
ttattatgaa attatgaatt tgaagcctct gaaatggtga tcagttttca acatctttca   1740
aaaacaaaat tactatttcc tccatattgc cttttttaga taactttaaa gttaggattt   1800
taaaatattt gtaactggct aaattttaaa gtcgtgacaa ataattactt aggttcagaa   1860
atatacacac acttactctt tagccagttt cttcaaggt ttactgtccc atcagatatc   1920
tagccatttt cctttgcaaa ttacataccct tcttaagagt gtatttttaa gattattact   1980
tacgctttat gatgatatag ttttcaaaa ttatttatag cttcatatga tgttttgtaa   2040
ttttttctat tgatacctgt tttaaaaata ttttccaagg aagttgatta aaattatatt   2100
tgttaccttt tagaaaaagc attgaaatga gtttctcttg cttttcatt ttccctctgc   2160
tttatatgct cttcgcaata catcatgtcc aacgggatac ctattgttct catgacaccc   2220
aaaattgatg agagcaaagg ggtcgcacca tatggaaatg ttgaaaacta ttgtaaagta   2280
```

-continued

| | |
|---|---|
| gtattatgaa gtagcttttg tgtcattcat gtcgatgaca tgaaagtgaa gtaaatttat | 2340 |
| tctatgtaaa ttcacactaa aaccagtaca gtaccataag tagaatacat gtaagaatca | 2400 |
| cctagtcttc actatattga gtaaatataa catgctaatt ttacaattaa tgaaactaaa | 2460 |
| cttttaaaca tctccattat atctacatcc ttttgaaggt atttatcata gttgccaatt | 2520 |
| ttaattttag gattgactt ctctttctga atgacttcat aaagtttggt gtgaattttg | 2580 |
| aagacttggg ttactaatga ttgtatcttt gctagtcaac aacttatgaa atatactcaa | 2640 |
| tgcgtctgat gtgtcattaa gtgcagaaat aactaagaca caaataacct ttgcaaacct | 2700 |
| tcaagctgtg taatattcca atgttgtttt tttctttgta tatatactta tatcacgtag | 2760 |
| gatgtaaaac cagtatgacc ttgtctagtc tccaaactta aaataaactt ttgaaaagct | 2820 |
| gggaaaaaaa aaaaa | 2835 |

<210> SEQ ID NO 29
<211> LENGTH: 2171
<212> TYPE: DNA
<213> ORGANISM: Homo sapiens

<400> SEQUENCE: 29

| | |
|---|---|
| agggaattct aagctggacg cacagaacag tctctccgtg ggaggagaca ttatggggcg | 60 |
| tccaccacca ccctccctg gccatcctcc tggaatgtgg tctgccctcc accagagctc | 120 |
| ctgcctgcca ggactggacc agagcagcca ggctggggcc cctctgtctc aacccgcaga | 180 |
| cccttgactg aatgagagag gccagaggat gctccccatg ctgccactat ttattgtgag | 240 |
| ccctggaggc tccatgtgc ttgaggaagg ctggtgagcc cggctcagga ccctcttccc | 300 |
| tcagggctg caccctcctc tcactccctt ccatgccgga acccaggcca gggacccacc | 360 |
| ggcctgtggt ttgtgggaaa gcagggtgga cgctgaggag tgaaagaacc ctgcacccag | 420 |
| agggcctgcc tggtgccaag gtatcccagc ctggacaggc atggacctgt ctccagagag | 480 |
| aggagcctga agttcgtggg gcgggacagc gtcggcctga tttcccgtaa aggtgtgcag | 540 |
| cctgagagac gggaagagga ggcctctgga cctgctggtc tgcactgaca gcctgaaggg | 600 |
| tctacaccct cggctcacct aagtgccctg tgctggttgc caggcgcaga ggggaggcca | 660 |
| gccctgccct caggacctgc ctgacctgcc agtgatgcca agaggggat caagcactgg | 720 |
| cctctgccc tcctccttcc agcacctgcc agagcttctc caggaggcca agcagaggct | 780 |
| cccctcatga aggaagccat tgcactgtga acactgtacc tgcctgctga acagcctgcc | 840 |
| cccgtccatc catgagccag catccgtccg tcctccactc tccagcctct ccccagcctc | 900 |
| ctgcactgag ctggcctcac cagtcgactg agggagcccc tcagccctga ccttctcctg | 960 |
| acctggcctt tgactccccg gagtggagtg gggtgggaga acctcctggg ccgccagcca | 1020 |
| gagccggtct ttaggctgtg ttgttcgccc aggtttctgc atcttgcact ttgacattcc | 1080 |
| caagagggaa gggactagtg ggagagagca agggaggga gggcacagac agagaggcta | 1140 |
| cagggcgagc tctgactgaa gatgggcctt tgaaatatag gtatgcacct gaggttgggg | 1200 |
| gagggtctgc actcccaaac cccagcgcag tgtccttttcc ctgctgccga caggaacctg | 1260 |
| gggctgaaca ggttatccct gtcaggagcc tggactggg ctgcatctca gccccacctg | 1320 |
| catggtatcc agctcccatc cacttctcac ccttctttcc tcctgacctt ggtcagcagt | 1380 |
| gatgacctcc aactctcacc cacccctct accatcacct ctaaccaggc aagccagggt | 1440 |
| gggagagcaa tcaggagagc caggcctcag cttccaatgc ctggagggcc tccactttgt | 1500 |
| ggccagcctg tggtggtggc tctgaggcct aggcaacgag cgacagggct gccagttgcc | 1560 |

-continued

```
cctgggttcc tttgtgctgc tgtgtgcctc ctctcctgcc gcccttttgtc ctccgctaag    1620 agaccctgcc ctacctggcc gctgggcccc gtgactttcc cttcctgccc aggaaagtga    1680
gggtcggctg gccccacctt ccctgtcctg atgccgacag cttagggaag ggcagtgaac    1740
ttgcatatgg ggcttagcct tctagtcaca gcctctatat ttgatgctag aaaacacata    1800 ttttttaaatg gaagaaaaat aaaaaggcat tccccctttca tccccctacc ttaaacatat   1860 aatatttttaa aggtcaaaaa agcaatccaa cccactgcag aagctctttt tgagcacttg   1920
gtggcatcag agcaggagga gccccagagc cacctctggt gtcccccccag gctacctgct   1980 caggaacccc ttctgttctc tgagaagtca agagaggaca ttggctcacg cactgtgaga    2040
ttttgttttt atacttggaa gtggtgaatt attttatata aagtcattta aatatctatt    2100
taaaagatag gaagctgctt atatatttaa taataaaaga agtgcacaag ctgccaaaaa    2160
aaaaaaaaaa a                                                         2171

<210> SEQ ID NO 30
<211> LENGTH: 1261
<212> TYPE: DNA
<213> ORGANISM: Homo sapiens

<400> SEQUENCE: 30
gtactgcccg tgcaaatccc acaacactga atgcaaagta gcaatttcca tagtcacagt      60
taggtagctt tagggcaata ttgccatggt tttactcatg tgcaggtttt gaaaatgtac     120
aatatgtata atttttaaaa tgttttatta ttttgaaaat aatgttgtaa ttcatgccag     180
ggactgacaa aagacttgag acaggatggt tactcttgtc agctaaggtc acattgtgcc     240
tttttgacct tttcttcctg gactattgaa atcaagctta ttggattaag tgatatttct     300
atagcgattg aaagggcaat agttaaagta atgagcatga tgagagtttc tgttaatcat     360
gtattaaaac tgattttttag ctttacaaat atgtcagttt gcagttatgc agaatccaaa    420
gtaaatgtcc tgctagctag ttaaggattg ttttaaatct gttattttgc tatttgcctg     480
ttagacatga ctgatgacat atctgaaaga caagtatgtt gagagttgct ggtgtaaaat     540
acgtttgaaa tagttgatct acaaaggcca tgggaaaaat tcagagagtt aggaaggaaa     600
aaccaatagc tttaaaacct gtgtgccatt ttaagagtta cttaatgttt ggtaactttt     660
atgccttcac tttacaaatt caagccttag ataaagaaac cgagcaattt tctgctaaaa     720
agtccttgat ttagcactat ttacatacag gccatacttt acaaagtatt tgctgaatgg     780 ggacctttttg agttgaattt attttattat ttttattttg ttaatgtct ggtgctttct     840 gtcacctctt ctaatctttt aatgtatttg tttgcaattt tggggtaaga cttttttttat    900 gagtactttt tcttttgaagt tttagcggtc aatttgcctt tttaatgaac atgtgaagtt    960
atactgtggc tatgcaacag ctctcaccta cgcgagtctt actttgagtt agtgccataa    1020
cagaccactg tatgtttact tctcaccatt tgagttgccc atcttgtttc acactagtca   1080
cattcttgtt ttaagtgcct ttagttttaa cagttcactt tttacagtgc tatttactga   1140
agttatttat taaatatgcc taaaatactt aaatcggatg tcttgactct gatgtatttt   1200
atcaggttgt gtgcatgaaa ttttttataga ttaaagaagt tgaggaaaag caaaaaaaaa  1260
a                                                                   1261

<210> SEQ ID NO 31
<211> LENGTH: 528
<212> TYPE: DNA
```

<213> ORGANISM: Homo sapiens

<400> SEQUENCE: 31

| | | | | | |
|---|---|---|---|---|---|
| acattactaa | tttgaatgga | aaacacatgg | tgtgagtcca | agaaggtgt | tttcctgaag | 60 |
| aactgtctat | tttctcagtc | attttttaacc | tctagagtca | ctgatacaca | gaatataatc | 120 |
| ttatttatac | ctcagtttgc | atattttttt | actatttaga | atgtagccct | ttttgtactg | 180 |
| atataattta | gttccacaaa | tggtgggtac | aaaaagtcaa | gtttgtggct | tatggattca | 240 |
| tataggccag | agttgcaaag | atcttttcca | gagtatgcaa | ctctgacgtt | gatcccagag | 300 |
| agcagcttca | gtgacaaaca | tatcctttca | agacagaaag | agacaggaga | catgagtctt | 360 |
| tgccggagga | aaagcagctc | aagaacacat | gtgcagtcac | tggtgtcacc | ctggataggc | 420 |
| aagggataac | tcttctaaca | caaaataagt | gtttttatgtt | tggaataaag | tcaaccttgt | 480 |
| ttctactgtt | ttatacactt | tcaaaaaaaa | aaaaaaaaaa | aaaaaaaa | | 528 |

<210> SEQ ID NO 32
<211> LENGTH: 20
<212> TYPE: DNA
<213> ORGANISM: Artificial Sequence
<220> FEATURE:
<223> OTHER INFORMATION: hHPRT-f

<400> SEQUENCE: 32
cctggcgtcg tgattagtga                      20

<210> SEQ ID NO 33
<211> LENGTH: 20
<212> TYPE: DNA
<213> ORGANISM: Artificial Sequence
<220> FEATURE:
<223> OTHER INFORMATION: hHPRT-r

<400> SEQUENCE: 33
cgagcaagac gttcagtcct                      20

<210> SEQ ID NO 34
<211> LENGTH: 20
<212> TYPE: DNA
<213> ORGANISM: Artificial Sequence
<220> FEATURE:
<223> OTHER INFORMATION: hRBMS1-f

<400> SEQUENCE: 34
caccaccagg agtttctgcc                      20

<210> SEQ ID NO 35
<211> LENGTH: 21
<212> TYPE: DNA
<213> ORGANISM: Artificial Sequence
<220> FEATURE:
<223> OTHER INFORMATION: hRBMS1-r

<400> SEQUENCE: 35
cagcaagtct cacctctcct t                    21

<210> SEQ ID NO 36
<211> LENGTH: 20
<212> TYPE: DNA
<213> ORGANISM: Artificial Sequence
<220> FEATURE:
<223> OTHER INFORMATION: hRBMS2-f

<400> SEQUENCE: 36

```
catctctccc tcagcagcac                                               20

<210> SEQ ID NO 37
<211> LENGTH: 20
<212> TYPE: DNA
<213> ORGANISM: Artificial Sequence
<220> FEATURE:
<223> OTHER INFORMATION: hRBMS2-r

<400> SEQUENCE: 37
gctgctctcc tcgactgaaa                                               20

<210> SEQ ID NO 38
<211> LENGTH: 20
<212> TYPE: DNA
<213> ORGANISM: Artificial Sequence
<220> FEATURE:
<223> OTHER INFORMATION: hRBMS3-f

<400> SEQUENCE: 38
tctccaaacc aagcagtcct                                               20

<210> SEQ ID NO 39
<211> LENGTH: 20
<212> TYPE: DNA
<213> ORGANISM: Artificial Sequence
<220> FEATURE:
<223> OTHER INFORMATION: hRBMS3-r

<400> SEQUENCE: 39
ggaggcctcg aatgtacagg                                               20

<210> SEQ ID NO 40
<211> LENGTH: 20
<212> TYPE: DNA
<213> ORGANISM: Artificial Sequence
<220> FEATURE:
<223> OTHER INFORMATION: mHPRT-f

<400> SEQUENCE: 40
cttcctcctc agaccgcttt                                               20

<210> SEQ ID NO 41
<211> LENGTH: 21
<212> TYPE: DNA
<213> ORGANISM: Artificial Sequence
<220> FEATURE:
<223> OTHER INFORMATION: mHPRT-r

<400> SEQUENCE: 41
catcatcgct aatcacgacg c                                             21

<210> SEQ ID NO 42
<211> LENGTH: 20
<212> TYPE: DNA
<213> ORGANISM: Artificial Sequence
<220> FEATURE:
<223> OTHER INFORMATION: mRBMS1-f

<400> SEQUENCE: 42
gagatgatct tccccagcgg                                               20

<210> SEQ ID NO 43
<211> LENGTH: 20
<212> TYPE: DNA
```

```
<213> ORGANISM: Artificial Sequence
<220> FEATURE:
<223> OTHER INFORMATION: mRBMS1-r

<400> SEQUENCE: 43
ggaccagaga ctgctgcttg                                                  20

<210> SEQ ID NO 44
<211> LENGTH: 20
<212> TYPE: DNA
<213> ORGANISM: Artificial Sequence
<220> FEATURE:
<223> OTHER INFORMATION: mRBMS2-f

<400> SEQUENCE: 44
tggcctagga ggggttagac                                                  20

<210> SEQ ID NO 45
<211> LENGTH: 20
<212> TYPE: DNA
<213> ORGANISM: Artificial Sequence
<220> FEATURE:
<223> OTHER INFORMATION: mRBMS2-r

<400> SEQUENCE: 45
gctggatgcc acttctcagt                                                  20

<210> SEQ ID NO 46
<211> LENGTH: 20
<212> TYPE: DNA
<213> ORGANISM: Artificial Sequence
<220> FEATURE:
<223> OTHER INFORMATION: mRBMS3-f

<400> SEQUENCE: 46
tggaccaccc catgtcaatg                                                  20

<210> SEQ ID NO 47
<211> LENGTH: 20
<212> TYPE: DNA
<213> ORGANISM: Artificial Sequence
<220> FEATURE:
<223> OTHER INFORMATION: mRBMS3-r

<400> SEQUENCE: 47
tgaatcgttc ctgctgtccc                                                  20

<210> SEQ ID NO 48
<211> LENGTH: 268
<212> TYPE: DNA
<213> ORGANISM: Homo sapiens

<400> SEQUENCE: 48
catgggcacc tcagattgtt gttgttaatg ggcattcctt cttctggtca gaaacctgtc      60
cactgggcac agaacttatg ttgttctcta tggagaacta aaagtatgag cgttaggaca     120 ctatttttaat tattttttaat ttattaatat ttaaatatgt gaagctgagt taatttatgt   180
aagtcatatt tatattttta agaagtacca cttgaaacat tttatgtatt agttttgaaa     240
taataatgga aagtggctat gcagtttg                                        268

<210> SEQ ID NO 49
<211> LENGTH: 357
<212> TYPE: DNA
<213> ORGANISM: Homo sapiens
```

<400> SEQUENCE: 49

```
ggatccacaa gtccttgttc cactgtgcct tggtttctcc tttatttcta agtggaaaaa      60
gtattagcca ccatcttacc tcacagtgat gttgtgagga catgtggaag cactttaagt     120
ttttcatca taacataaat tattttcaag tgtaacttat taacctattt attatttatg     180
tatttattta agcatcaaat atttgtgcaa gaatttggaa aaatagaaga tgaatcattg     240
attgaatagt tataaagatg ttatagtaaa tttattttat tttagatatt aaatgatgtt     300
ttattagata aatttcaatc agggttttta gattaaacaa acaaacaatt gggtacc        357
```

<210> SEQ ID NO 50
<211> LENGTH: 20
<212> TYPE: DNA
<213> ORGANISM: Artificial Sequence
<220> FEATURE:
<223> OTHER INFORMATION: control shRNA

<400> SEQUENCE: 50

```
gctacacaaa tcagcgattt                                                   20
```

<210> SEQ ID NO 51
<211> LENGTH: 21
<212> TYPE: DNA
<213> ORGANISM: Artificial Sequence
<220> FEATURE:
<223> OTHER INFORMATION: RBMS2 shRNA

<400> SEQUENCE: 51

```
ggaaaccacc ttcaaccaac t                                                 21
```

<210> SEQ ID NO 52
<211> LENGTH: 21
<212> TYPE: DNA
<213> ORGANISM: Artificial Sequence
<220> FEATURE:
<223> OTHER INFORMATION: Linker 1

<400> SEQUENCE: 52

```
uggaauucuc gggugccaag g                                                 21
```

<210> SEQ ID NO 53
<211> LENGTH: 26
<212> TYPE: DNA
<213> ORGANISM: Artificial Sequence
<220> FEATURE:
<223> OTHER INFORMATION: Linker 2

<400> SEQUENCE: 53

```
guucagaguu cuacaguccg acgauc                                            26
```

<210> SEQ ID NO 54
<211> LENGTH: 21
<212> TYPE: DNA
<213> ORGANISM: Artificial Sequence
<220> FEATURE:
<223> OTHER INFORMATION: Primer A

<400> SEQUENCE: 54

```
ccttggcacc cgagaattcc a                                                 21
```

<210> SEQ ID NO 55
<211> LENGTH: 21
<212> TYPE: DNA

```
<213> ORGANISM: Artificial Sequence
<220> FEATURE:
<223> OTHER INFORMATION: RNA PCR Primer 1st

<400> SEQUENCE: 55
gttcagagtt ctacagtccg a                                              21

<210> SEQ ID NO 56
<211> LENGTH: 21
<212> TYPE: DNA
<213> ORGANISM: Artificial Sequence
<220> FEATURE:
<223> OTHER INFORMATION: RNA PCR Primer, Index1 1st

<400> SEQUENCE: 56
ccttggcacc cgagaattcc a                                              21

<210> SEQ ID NO 57
<211> LENGTH: 50
<212> TYPE: DNA
<213> ORGANISM: Artificial Sequence
<220> FEATURE:
<223> OTHER INFORMATION: RNA PCR Primer

<400> SEQUENCE: 57
aatgatacgg cgaccaccga gatctacacg ttcagagttc tacagtccga               50

<210> SEQ ID NO 58
<211> LENGTH: 63
<212> TYPE: DNA
<213> ORGANISM: Artificial Sequence
<220> FEATURE:
<223> OTHER INFORMATION: RNA PCR Primer, Index1

<400> SEQUENCE: 58
caagcagaag acggcatacg agatcgtgat gtgactggag ttccttggca cccgagaatt    60
cca                                                                  63

<210> SEQ ID NO 59
<211> LENGTH: 20
<212> TYPE: DNA
<213> ORGANISM: Artificial Sequence
<220> FEATURE:
<223> OTHER INFORMATION: hKRAS-Fw

<400> SEQUENCE: 59
tggtgaggga gatccgacaa                                                20

<210> SEQ ID NO 60
<211> LENGTH: 20
<212> TYPE: DNA
<213> ORGANISM: Artificial Sequence
<220> FEATURE:
<223> OTHER INFORMATION: hKRAS-Rv

<400> SEQUENCE: 60
aggcatcatc aacacccaga                                                20

<210> SEQ ID NO 61
<211> LENGTH: 20
<212> TYPE: DNA
<213> ORGANISM: Artificial Sequence
<220> FEATURE:
<223> OTHER INFORMATION: hIL6-Fw

<400> SEQUENCE: 61
```
ctccaggagc ccagctatga    20

<210> SEQ ID NO 62
<211> LENGTH: 20
<212> TYPE: DNA
<213> ORGANISM: Artificial Sequence
<220> FEATURE:
<223> OTHER INFORMATION: hIL6-Rv

<400> SEQUENCE: 62
gaggtgagtg gctgtctgtg    20

<210> SEQ ID NO 63
<211> LENGTH: 20
<212> TYPE: DNA
<213> ORGANISM: Artificial Sequence
<220> FEATURE:
<223> OTHER INFORMATION: hHPRT-Fw

<400> SEQUENCE: 63
gctggcgtcg tgattagtga    20

<210> SEQ ID NO 64
<211> LENGTH: 20
<212> TYPE: DNA
<213> ORGANISM: Artificial Sequence
<220> FEATURE:
<223> OTHER INFORMATION: hHPRT-Rv

<400> SEQUENCE: 64
cgagcaagac gttcagtcct    20

<210> SEQ ID NO 65
<211> LENGTH: 20
<212> TYPE: DNA
<213> ORGANISM: Artificial Sequence
<220> FEATURE:
<223> OTHER INFORMATION: hCXCL1-Fw

<400> SEQUENCE: 65
tcacagtgtg tggtcaacat    20

<210> SEQ ID NO 66
<211> LENGTH: 20
<212> TYPE: DNA
<213> ORGANISM: Artificial Sequence
<220> FEATURE:
<223> OTHER INFORMATION: hCXCL1-Rv

<400> SEQUENCE: 66
agcccctttg ttctaagcca    20

<210> SEQ ID NO 67
<211> LENGTH: 20
<212> TYPE: DNA
<213> ORGANISM: Artificial Sequence
<220> FEATURE:
<223> OTHER INFORMATION: hRBMS2-Fw

<400> SEQUENCE: 67
gtgataggcc agggagtag    20

<210> SEQ ID NO 68
<211> LENGTH: 20
<212> TYPE: DNA

```
<213> ORGANISM: Artificial Sequence
<220> FEATURE:
<223> OTHER INFORMATION: hRBMS2-Rv

<400> SEQUENCE: 68
actctgctcc tatgctggtg                                               20

<210> SEQ ID NO 69
<211> LENGTH: 21
<212> TYPE: DNA
<213> ORGANISM: Artificial Sequence
<220> FEATURE:
<223> OTHER INFORMATION: Human RBMS2-1

<400> SEQUENCE: 69
uuugcacaaa uuuuccuugg t                                             21

<210> SEQ ID NO 70
<211> LENGTH: 20
<212> TYPE: DNA
<213> ORGANISM: Artificial Sequence
<220> FEATURE:
<223> OTHER INFORMATION: hIL8-Fw

<400> SEQUENCE: 70
accggaagga accatctcac                                               20

<210> SEQ ID NO 71
<211> LENGTH: 21
<212> TYPE: DNA
<213> ORGANISM: Artificial Sequence
<220> FEATURE:
<223> OTHER INFORMATION: hIL8-Rv

<400> SEQUENCE: 71
ggcaaaactg caccttcaca c                                             21

<210> SEQ ID NO 72
<211> LENGTH: 22
<212> TYPE: DNA
<213> ORGANISM: Artificial Sequence
<220> FEATURE:
<223> OTHER INFORMATION: hRBMS1-Fw

<400> SEQUENCE: 72
ccatggcata gagaaggaga gg                                            22

<210> SEQ ID NO 73
<211> LENGTH: 20
<212> TYPE: DNA
<213> ORGANISM: Artificial Sequence
<220> FEATURE:
<223> OTHER INFORMATION: hRBMS1-Rv

<400> SEQUENCE: 73
tagcagctgt agttgggtcg                                               20

<210> SEQ ID NO 74
<211> LENGTH: 4000
<212> TYPE: DNA
<213> ORGANISM: Artificial Sequence
<220> FEATURE:
<223> OTHER INFORMATION: RBMS2_4k

<400> SEQUENCE: 74
gctagcatca gagcctcaca cgcaaaactga cctgtctcat tgctttcaac cacatatacc   60
```

```
acaccagcct gtctccattg gaatgtctgg ctagggtcca gcacatctac aggtaataca    120
ttcttctgaa ttctccactc tgatatggag gggccaatag aggcatgcaa acatttttct    180
ttatttttct ttttctttta ttttgagaca ggatctcact ttggttgcct gggctggagt    240
acagtggcgc catctcagct cactgcagcc tcgacctccc aggctcagat ggctctccca    300
actcagcctc ctgaggagtt gggactacag atatgcacta ccatgcctgg ctagtttttt    360 gtattttag cagaaatggg gttttgccat gttgcccaca ttggtcttga actcctggac    420
tgaagcaatc tgcccacctc agcctcccaa agtgctggga cattttcag ctacattttg     480 gggttgacct agcccctact ccttcacctt ggacacttgt ttaaaagagt tgtttttctg    540
gagaaatcac aaacaagcct atattgaatc aggtacaaat gtctcttccc caagaagtt    600 acagataact ctcattttgc ttttttccct tcaaaacaat tcctgagtgc tgggttcatg    660
agaaccaaga attagagagg cattgactaa atctggaaaa atgtgggcaa tgtaatgggc    720
aaagcagaag ggcgtcaaag taaatacact ggaggaagta ggattcttcc tcctcccgta    780
tacttcctga atctaaccac agaacaccat taccttcccc atcatttcca cagaattcca    840
taactccttt acaaatatac tcacctgtaa tgccagcagt tttggagact gaggtgggca    900
aattgcttga gctgaggaat tcaagaccag cctgggcaac atgatgaaac cccgtctcta    960
ccaaaaaaaa aaaattaca aaagttagcc aggtgtggtg gtgcatgcct gtagtcccag   1020
ctacagggtg gggaggggtg ggatgggtgt gaggatcacc tgaacctggg gaagtcaaag   1080
ctgcctgttg tgagccgtga ttgtgctact gcactccagc ctaggtgaca gagtgagacc   1140
ctgtcataaa aaaaaatata tgtttataat acatatactc accagaatga aggatttagt   1200 ttccagttt gttggtgctc tttaacataa tacacctttg gcatcagttt gcatatccgg    1260 gtcatttac ttctgtggtc ctaatttacc agattataaa aatttagatt tttcggtcgg    1320
gtgccgtggt tcacacctgt aatcccagca ctttgggagg ccaaggcggg tggattgcct   1380
gaggtcagga gttcgagacc agactggcca acatggtgaa accccgtctc cactaaaaat   1440
acaaaaatta ctgggcgtc gtggcacatg cctgtagtac cagctactca ggaggctaag    1500
gcgggagaat cgtttgaacc cgggaggcag aggtttcagt gagccaagat tgcaccactg   1560
cactccagcc tggcgacaga gtgagactct gtctcagggg gaaaaaaaaa aagtagaaag   1620
aaaaattaga cttaaaaaaa aagttaaatt ggggttgattg cctttatgaa tcaggccttc   1680
aagagaaagg tttctgtacc acattgttag ggtaaaggag aagatatcat ccaagggcct   1740
aaacagcaag gataaattgg ttaatgagag tctctgagag cagaaaaagg acttaaaaaa   1800
atatatatat atatatatat gggccgggcg cggtggctca ctcctgtaat cccagcactt   1860
tgggaggcca aggcgggcag atcacctgag gtcgggagtt tgagaccagt ctggccaaca   1920
agactactaa aaatacaaaa aaattagccg ggcatggtgg cgcatgccta tagtctcagc   1980
tactcgggag gctgaggcag gagaatcgct tgaacccggg acgcagaggt tgcggtgagc   2040
caagatagca ccactgcact ctagcctggg caacagagca agactctgtc tcagaaaaaa   2100
aaaaagatat cactgagtga tgccttcatt tatttattta ctgcatttgg ctgctgtgtt   2160
tccagtctca gttgcaattc ccacactgag gctctcccac ccttcctgtg tccctgagc    2220 tgagcaggca cttcctgtcc tattggaaat gaaagttaga gattgggggt agggtatgta   2280
tatttactct gcagaatact aatactgtct gttccattat catagcaaaa aagtgacacg   2340
gaaactagaa tagagaccag aacttcattt gagggagggt ttgggcttaa tatttgttgt   2400
```

| | | | | |
|---|---|---|---|---|
| cacaaaacag | acagggttaa | tttatatctc | aagaaactac | ttaggatggc | agcaaggtgg | 2460 |
| ccttatgaag | ggatttgaag | gctttcattt | aacatcccta | ttgcacttgg | attggtaggg | 2520 |
| gttactggat | atcattctta | agttttgg | ttcctttctt | gttaaggtta | cgcctacaaa | 2580 |
| gacattcttt | ggaaactagt | agaggtaagt | gttgcaactc | tattaggttc | ttgactctga | 2640 |
| aatttgtatt | ccttcctaag | aattttgtgt | ttttattctg | ttgaagcata | tgcttcttaa | 2700 |
| gtatttttt | ttttaaaca | gctcaaagac | aactcaaagc | agacatccca | actgtagact | 2760 |
| tcaatttaga | cataaactcc | aggtttggtg | agttactgta | attgtttcag | tttcatggat | 2820 |
| cttaaagatg | aggaaatagc | agggtaaagt | gttaaataag | atagcctgca | attgttagag | 2880 |
| aaataacaag | gcaccaagtt | tcatgatata | gtccagtctg | ataattcctt | cttaagtatg | 2940 |
| aactcattcc | tcggagaatc | tgaaatagga | gtgaggggca | tcagcccatt | ggtatgaccc | 3000 |
| aagagaaaca | catctaagga | tctgaaacta | gttataccc | atactctgtt | ttgcttagct | 3060 |
| ctgctctttg | gtgtgttcct | ctgtttgttc | ctttgtacat | taagatcact | ataaatgggc | 3120 |
| caggggtggt | ggctcatgcc | tgtaatccca | gcactttggg | aggttgagtg | ggtggatcac | 3180 |
| ttgaggtcag | gagttcgaga | ccagcctggc | caagatggcg | aaaccccgtc | cctactaaaa | 3240 |
| aatacaaaaa | tcagctgggt | gtggtggtgg | tcacctgtaa | tcccagctac | tcgagaggct | 3300 |
| gaggcaggag | aattgcggaa | ggtggaggtt | gcagtgagcc | ggatccggga | ttgcaccact | 3360 |
| gcacttcagc | ctgggtgaca | gactaaaact | ctgtctcaaa | aaaaaaaaa | aaaatcact | 3420 |
| gtaagtgtaa | agtaggggaa | gccctgagct | tatctcacac | actctaactc | tgttttttt | 3480 |
| ttttttttt | tttgcgtgtt | ctccaaggca | atgtctcagg | agccccttta | aaatcaagct | 3540 |
| tgaaatctta | tagctgagat | ctaagggtgg | aaataaagcc | ctcattgtct | ttatatgaga | 3600 |
| atcggaactt | gttcatagag | gaaaggggat | aaatttgaaa | ggggttagac | ctaagaactc | 3660 |
| ttctttctag | ctttaactcc | tgagactatg | aaaacaaac | aaaaaaaaac | atcttgggca | 3720 |
| ttaggaccca | gtggaagtgc | ctctgcctca | ttcagactct | gttaacttct | ctcagtgacg | 3780 |
| taaaggagca | gcccgagctc | attctctgcc | cgcagccccc | cttcatctct | ctcctcctgc | 3840 |
| tccttttctc | ctcctttctc | ctccccctcc | cttttttcct | ccctccctct | ccccctttcc | 3900 |
| ctcgctcccc | tcctccctcc | ctccccgtct | ttcttacccc | ctcccttct | ctctctctct | 3960 |
| ctctctcgct | cgttccctaa | cattaaagag | aaaagctagc | | | 4000 |

<210> SEQ ID NO 75
<211> LENGTH: 2953
<212> TYPE: DNA
<213> ORGANISM: Artificial Sequence
<220> FEATURE:
<223> OTHER INFORMATION: RBMS2_3k

<400> SEQUENCE: 75

| | | | | |
|---|---|---|---|---|
| tagctcatta | acatttcttg | cctaaggaaa | ctggtatgtt | caataaactg | tttttgtttg | 60 |
| tttgtttgtt | ttgttttgtt | tttactttt | ccctaagaca | taatctcatc | ttttttacca | 120 |
| ggaaataaac | tcagcttttt | tttttttga | cacagagtct | cactctgttg | cccaggctgg | 180 |
| agtgcagtgg | catgatctca | gctcactgca | acctctgcct | cccaggttca | agcgattctc | 240 |
| ctgcctcagt | ctcccaagta | gctgggatta | caggcgtgtg | ccaccacgcc | tggctaattt | 300 |
| ttgtattttt | agtagagaca | gggtttcact | atgttgacta | ggctggtctc | gaactcctca | 360 |
| cctcaagtga | tccgcccacc | tcggcctccc | aaagtgccag | gattacaggc | atgagccacc | 420 |
| gcacctggcc | aataaactca | acttttttgga | ctatttccat | tacatagcct | tttggacaca | 480 |

```
aaagttaatc agtggaatga aagataatc cacagggagt atttatacct agggaaaaat    540
gtttctttgg ctctaatata ccttgttcag gtctcttagc cacaatcaga gcctcacacg    600
caaactgacc tgtctcattg ctttcaacca catataccac accagcctgt ctccattgga    660
atgtctggct agggtccagc acatctacag gtaatacatt cttctgaatt ctccactctg    720
atatggaggg gccaatagag gcatgcaaac attttttcttt attttttcttt ttcttttatt    780 ttgagacagg atctcacttt ggttgcctgg gctggagtac agtggcgcca tctcagctca    840
ctgcagcctc gacctcccag gctcagatgg ctctcccaac tcagcctcct gaggagttgg    900
gactacagat atgcactacc atgcctggct agttttttgt attttttagca gaaatggggt    960 tttgccatgt tgcccacatt ggtcttgaac tcctggactg aagcaatctg cccacctcag   1020
cctcccaaag tgctgggaca ttttttcagct acatttttggg gttgacctag cccctactcc   1080
ttcaccttgg acacttgttt aaaagagttg ttttttctgga gaaatcacaa acaagcctat   1140
attgaatcag gtacaaatgt ctcttcccca aagaagttac agataactct cattttgctt   1200 ttttccttc aaaacaattc ctgagtgctg ggttcatgag aaccaagaat tagagaggca   1260
ttgactaaat ctggaaaaat gtgggcaatg taatgggcaa agcagaaggg cgtcaaagta   1320
aatacactgg aggaagtagg attcttcctc ctcccgtata cttcctgaat ctaaccacag   1380
aacaccatta ccttccccat catttccaca gaattccata actcctttac aaatatactc   1440
acctgtaatg ccagcagttt tggagactga ggtgggcaaa ttgcttgagc tgaggaattc   1500
aagaccagcc tggcaacat gatgaaaccc cgtctctacc aaaaaaaaaa aaattacaaa   1560
agttagccag gtgtggtggt gcatgcctgt agtcccagct acagggtggg gaggggtggg   1620
atgggtgtga ggatcacctg aacctgggga agtcaaagct gcctgttgtg agccgtgatt   1680
gtgctactgc actccagcct aggtgacaga gtgagaccct gtcataaaaa aaaatatatg   1740
tttataatac atatactcac cagaatgaag gatttagttt ccagttttgt tggtgctctt   1800
taacataata caccttttggc atcagtttgc atatccgggt catttttactt ctgtggtcct   1860 aatttaccag attataaaaa tttagatttt tcggtcgggt gccgtggttc acacctgtaa   1920
tcccagcact ttgggaggcc aaggcgggtg gattgcctga ggtcaggagt cgagaccag   1980 actggccaac atggtgaaac cccgtctcca ctaaaaatac aaaaattagc tgggcgtcgt   2040
ggcacatgcc tgtagtacca gctactcagg aggctaaggc gggagaatcg tttgaacccg   2100
ggaggcagag gtttcagtga gccaagattg caccactgca ctccagcctg gcgacagagt   2160
gagactctgt ctcagggga aaaaaaaaa gtagaaagaa aaattagact taaaaaaaaa   2220
gttaaattgg gttgattgcc tttatgaatc aggccttcaa gagaaaggtt tctgtaccac   2280
attgttaggg taaggagaa gatatcatcc aagggcctaa acagcaagga taaattggtt   2340
aatgagagtc tctgagagca gaaaaaggac ttaaaaaaat atatatatat atatatatgg   2400
gccgggcgcg gtggctcact cctgtaatcc cagcactttg ggaggccaag gcgggcagat   2460
cacctgaggt cgggagtttg agaccagtct ggccaacaag actactaaaa atacaaaaaa   2520
attagccggg catggtggcg catgcctata gtctcagcta ctcgggaggc tgaggcagga   2580
gaatcgcttg aacccgggac gcagaggttg cggtgagcca agatagcacc actgcactct   2640
agcctgggca acagagcaag actctgtctc agaaaaaaaa aaagatatca ctgagtgatg   2700
ccttcattta tttatttact gcatttggct gctgtgtttc cagtctcagt tgcaattccc   2760
acactgaggc tctcccaccc ttcctgtgtc ccctgagctg agcaggcact tcctgtccta   2820
```

| | |
|---|---:|
| ttggaaatga aagttagaga ttgggggtag ggtatgtata tttactctgc agaatactaa | 2880 |
| tactgtctgt tccattatca tagcaaaaaa gtgacacgga aactagaata gagaccagaa | 2940 |
| cttcatttga ggg | 2953 |

<210> SEQ ID NO 76
<211> LENGTH: 2879
<212> TYPE: DNA
<213> ORGANISM: Artificial Sequence
<220> FEATURE:
<223> OTHER INFORMATION: RBMS2_2,5k

<400> SEQUENCE: 76

| | |
|---|---:|
| ccagcctagg tgacagagtg agaccctgtc ataaaaaaaa atatatgttt ataatacata | 60 |
| tactcaccag aatgaaggat ttagtttcca gttttgttgg tgctctttaa cataatacac | 120 |
| ctttggcatc agtttgcata tccgggtcat tttacttctg tggtcctaat ttaccagatt | 180 |
| ataaaatttt agattttcg gtcggtgcc gtggttcaca cctgtaatcc cagcactttg | 240 |
| ggaggccaag gcgggtggat tgcctgaggt caggagttcg agaccagact ggccaacatg | 300 |
| gtgaaacccc gtctccacta aaaatacaaa aattagctgg gcgtcgtggc acatgcctgt | 360 |
| agtaccagct actcaggagg ctaaggcggg agaatcgttt gaacccggga ggcagaggtt | 420 |
| tcagtgagcc aagattgcac cactgcactc cagcctggcg acagagtgag actctgtctc | 480 |
| aggggggaaaa aaaaaagta gaaagaaaaa ttagacttaa aaaaaaagtt aaattggggtt | 540 |
| gattgccttt atgaatcagg ccttcaagag aaaggtttct gtaccacatt gttagggtaa | 600 |
| aggagaagat atcatccaag ggcctaaaca gcaaggataa attggttaat gagagtctct | 660 |
| gagagcagaa aaaggactta aaaaaatata tatatatata tatatgggcc gggcgcggtg | 720 |
| gctcactcct gtaatcccag cactttggga ggccaaggcg gcagatcac ctgaggtcgg | 780 |
| gagtttgaga ccagtctggc caacaagact actaaaaata caaaaaaatt agccgggcat | 840 |
| ggtggcgcat gcctatagtc tcagctactc gggaggctga ggcaggagaa tcgcttgaac | 900 |
| ccgggacgca gaggttgcgg tgagccaaga tagcaccact gcactctagc ctgggcaaca | 960 |
| gagcaagact ctgtctcaga aaaaaaaaaa gatatcactg agtgatgcct tcatttattt | 1020 |
| atttactgca tttggctgct gtgtttccag tctcagttgc aattcccaca ctgaggctct | 1080 |
| cccacccttc ctgtgtcccc tgagctgagc aggcacttcc tgtcctattg gaaatgaaag | 1140 |
| ttagagattg ggggtagggt atgtatattt actctgcaga atactaatac tgtctgttcc | 1200 |
| attatcatag caaaaagtg acacggaaac tagaatagag accagaactt catttgaggg | 1260 |
| agggtttggg cttaatattt gttgtcacaa acagacagg gttaatttat atctcaagaa | 1320 |
| actacttagg atggcagcaa ggtggcctta tgaagggatt tgaaggcttt catttaacat | 1380 |
| ccctattgca cttggattgg tagggttac tggatatcat tcttaagttt ttggtttcct | 1440 |
| ttcttgttaa ggttacgcct acaaagacat tctttggaaa ctagtagagg taagtgttgc | 1500 |
| aactctatta ggttcttgac tctgaaattt gtattccttc ctaagaattt tgtgttttta | 1560 |
| ttctgttgaa gcatatgctt cttaagtatt tttttttttt aaacagctca agacaactc | 1620 |
| aaagcagaca tcccaactgt agacttcaat ttagacataa actccaggtt tggtgagtta | 1680 |
| ctgtaattgt ttcagtttca tggatcttaa agatgaggaa atagcagggt aaagtgttaa | 1740 |
| ataagatagc ctgcaattgt tagagaaata acaaggcacc aagtttcatg atatagtcca | 1800 |
| gtctgataat tccttcttaa gtatgaactc attcctcgga gaatctgaaa taggagtgag | 1860 |
| gggcatcagc ccattggtat gacccaagag aaacacatct aaggatctga aactagttat | 1920 |

```
acccatact ctgttttgct tagctctgct ctttggtgtg ttcctctgtt tgttcctttg    1980
tacattaaga tcactataaa tgggccaggg gtggtggctc atgcctgtaa tcccagcact   2040
ttgggaggtt gagtgggtgg atcacttgag gtcaggagtt cgagaccagc ctggccaaga   2100
tggcgaaacc ccgtccctac taaaaaatac aaaaatcagc tgggtgtggt ggtggtcacc   2160
tgtaatccca gctactcgag aggctgaggc aggagaattg cggaaggtgg aggttgcagt   2220
gagccggatc cgggattgca ccactgcact tcagcctggg tgacagacta aaactctgtc   2280
tcaaaaaaaa aaaaaaaaaa tcactgtaag tgtaaagtag gggaagccct gagcttatct   2340
cacacactct aactctgttt tttttttttt ttttttttgc gtgttctcca aggcaatgtc   2400
tcaggagccc ctttaaaatc aagcttgaaa tcttatagct gagatctaag ggtggaaata   2460
aagccctcat tgtctttata tgagaatcgg aacttgttca tagaggaaag gggataaatt   2520
tgaaaggggt tagacctaag aactcttctt tctagcttta actcctgaga ctatgaaaaa   2580
caaacaaaaa aaaacatctt gggcattagg acccagtgga agtgcctctg cctcattcag   2640
actctgttaa cttctctcag tgacgtaaag gagcagcccg agctcattct ctgcccgcag   2700
ccccccttca tctctctcct cctgctcctt ttctcctcct ttctcctccc cctccctttt   2760
ttcctccctc cctctccccc tttccctcgc tcccctcctc cctccctccc cgtctttctt   2820
accccctccc tttctctctc tctctctctc tcgctcgttc cctaacatta aagagaaaa    2879

<210> SEQ ID NO 77
<211> LENGTH: 1009
<212> TYPE: DNA
<213> ORGANISM: Artificial Sequence
<220> FEATURE:
<223> OTHER INFORMATION: RBMS2_1k

<400> SEQUENCE: 77
cgggtggatt gcctgaggtc aggagttcga gaccagactg gccaacatgg tgaaaccccg    60
tctccactaa aaatacaaaa attagctggg cgtcgtggca catgcctgta gtaccagcta   120
ctcaggaggc taaggcggga gaatcgtttg aacccgggag gcagaggttt cagtgagcca   180
agattgcacc actgcactcc agcctggcga cagagtgaga ctctgtctca gggggaaaaa   240 aaaaagtag aaagaaaaat tagacttaaa aaaaagtta aattgggttg attgccttta   300
tgaatcaggc cttcaagaga aaggtttctg taccacattg ttagggtaaa ggagaagata   360
tcatccaagg gcctaaacag caaggataaa ttggttaatg agagtctctg agagcagaaa   420
aaggacttaa aaaatatat atatatatat atatgggccg ggcgcggtgg ctcactcctg   480
taatcccagc actttgggag gccaaggcgg gcagatcacc tgaggtcggg agtttgagac   540
cagtctggcc aacaagacta ctaaaaatac aaaaaaatta gccgggcatg gtggcgcatg   600
cctatagtct cagctactcg ggaggctgag gcaggagaat cgcttgaacc cgggacgcag   660
aggttgcggt gagccaagat agcaccactg cactctagcc tgggcaacag agcaagactc   720
tgtctcagaa aaaaaaaaag atatcactga gtgatgcctt catttattta tttactgcat   780
ttggctgctg tgtttccagt ctcagttgca attcccacac tgaggctctc ccacccttcc   840
tgtgtcccct gagctgagca ggcacttcct gtcctattgg aaatgaaagt tagagattgg   900
gggtagggta tgtatattta ctctgcagaa tactaatact gtctgttcca ttatcatagc   960
aaaaaagtga cacggaaact agaatagaga ccagaacttc atttgaggg              1009
```

METHOD FOR INHIBITING THE EXPRESSION OF CANCER-PROMOTING FACTORS

This application is the national phase entry pursuant to 35 U.S.C. § 371 of International Application No. PCT/JP2018/041758, filed Nov. 9, 2018, which claims the benefit of priority to Japanese Patent Application No. 2017-216747, filed Nov. 9, 2017, both of which are incorporated herein by reference in their entirety.

TECHNICAL FIELD

The present invention relates to an inhibitor of the expression of a cancer promoting factor; a method for screening for an active ingredient of the inhibitor; an expression cassette useful for the method; a diagnostic agent and a diagnosis method both for immune diseases, inflammatory diseases, painful diseases and the like; and others.

In recent years, it has been revealed that an inflammatory cytokine produced by a cancer cell or an immune cell infiltrated into a tumor microenvironment plays an important role in the development and progression of cancer. It is known that an inflammatory cytokine, such as TNFα and IL-6, produced by a lymphocyte such as a tumor-infiltrating macrophage, a fibroblast and a T cell acts on a tumor cell, and acts in a paracrine manner through the production of reactive oxygen species (ROS) or the production of prostaglandin as the result of the increase in expression of cyclooxygenase; in this manner, the inflammatory cytokine contributes to the progression or expansion of cancer associated with the damage of DNA (Nat Rev Cancer, 2013, 13(11), 759-771). On the other hand, it is also known that an inflammatory cytokine (e.g., IL-6 and TNFα), a chemokine (e.g., IL-8 and CXCL1) or a growth factor (e.g., HBEGF and PDGF) produced by a cancer cell acts in an autocrine manner to activate a STAT pathway, a PI3K-Akt pathway and a NF-κB pathway; in this manner, the inflammatory cytokine helps the survival or growth of cancer cells and contributes to the acquisition of an infiltration ability (Cancer Res, 2013, 73(11), 3470-3480; Oncogene, 2014, 33(29), 3784-3793; and Cancer Res, 2007, 67(2), 585-592). It is known that IL-6 contributes to the growth or metastasis of cancer cells through the regulation of a migratory factor such as S100A8/9, an apoptosis-resistant gene such as Bcl2 and Myc and a Jagged-1 that is a Notch ligand in breast cancer, lung cancer and liver cancer (Cancer Cell, 2008, 13(1), 7-9, J Clin Invest, 2007, 117(12), 3988-4002, J Clin Invest, 2007, 117(12), 3846-3856, Cell, 2013, 155(2), 384-396, Neoplasia, 2013, 15(7), 848-862, Oncogene, 2006, 25(31), 4300-4309, and Genes Dev, 2015, 29(15), 1631-1648).

RNA-binding motif, single-stranded-interacting protein 2 (RBMS2) is a protein that is believed to have two RNA-binding domains on the N-terminal side. However, it is not reported yet that the functions of the protein are actually analyzed, and the functions of the protein are not elucidated yet.

The present invention addresses the problem of: discovering a novel factor that can affect the expression amount/level of a cancer promoting factor; providing an inhibitor of the expression of a cancer promoting factor and a tool for developing the inhibitor on the basis of the discovering the factor; and providing a diagnostic agent and a diagnosis method both for immune diseases, inflammatory diseases, painful diseases and other diseases.

Means for Solving the Problems mRNA molecules encoding many inflammatory cytokines including IL-6 are very unstable, and are degraded rapidly after transcription. On the other hand, it is believed that the stabilization of the mRNA at a post-transcriptional level induces the increase in the expression amount/level of the mRNA and the prolongation of an inflammation and, as a result, leads to the chronicity of the inflammation and finally the development of cancer. In these situations, it is attempted to identify a novel factor that can regulate IL-6 at a post-transcriptional level.

The present inventors have made extensive and intensive studies. As a result, it is found that RBMS is involved in the post-transcriptional regulation of mRNA molecules of various cancer promoting factors such as IL-6. It is also found that RBMS is involved in the growth of cells, the migration of cells, the infiltration of cells and the metastasis of cells. On the basis of these findings, it is also found that a cancer promoting factor can be inhibited and cancer can be prevented or treated by inhibiting the expression or function of RBMS, and that cancer can be diagnosed by employing the expression amount/level of RBMS as an index. The studies are further pursued on the basis of these findings. As a result, the present invention has been accomplished.

That is, the present invention includes the following aspects.

1. A reagent for screening for an active ingredient for an inhibitor of the expression of a cancer promoting factor, comprising at least one component selected from the group consisting of an expression cassette containing a RBMS gene expression regulation region and a gene arranged in such a manner that the expression thereof can be regulated by the region, a vector carrying the expression cassette and a cell harboring the vector.
2. The screening reagent according to item 1, wherein the expression cassette is at least one expression cassette selected from the group consisting of an expression cassette containing a RBMS1 gene expression regulation region, an expression cassette containing a RBMS2 gene expression regulation region and an expression cassette containing a RBMS3 gene expression regulation region.
3. A method for screening for an active ingredient for an inhibitor of the expression of a cancer promoting factor by employing at least one item selected from the group consisting of items (i) to (iii) as an index in the presence of a test substance:
   (i) the expression amount/level of a gene of which the expression can be regulated by a RBMS gene expression regulation region;
   (ii) the binding amount/level of RBMS to RNA containing an AU-rich element; and
   (iii) the amount/level of mRNA containing an AU-rich element in a 3'-UTR thereof or the amount/level of a protein derived from the mRNA in a RBMS-over-expressing cell.
4. The screening method according to item 3, wherein the expression amount/level of a gene in the index (i) is at least one item selected from the group consisting of the expression amount/level of a gene of which the expression can be regulated by a RBMS1 gene expression regulation region, the expression amount/level of a gene of which the expression can be regulated by a RBMS2 gene expression regulation region and the expression amount/level of a gene of which the expression can be regulated by a RBMS3 gene expression regulation region, and the RBMS in each of the indices (ii) and (iii) is at least one component selected from the group consisting of RBMS1, RBMS2 and RBMS3.

5. The screening method according to item 3 or 4, wherein, when the value of the index in the presence of a test substance is smaller than the value of the index in the absence of the test substance, the test substance is selected as an active ingredient for an inhibitor of the expression of a cancer promoting factor.

6. The screening method according to any one of items 3 to 5, wherein the AU-rich element is an AU-rich element derived from mRNA for at least one component selected from the group consisting of CSF2, IL-6, ADAM10, ADM, CTGF, HBEGF, HILPDA, IL-24, THBS1, MYC, TGFB2, ADAM10, ITGA6, F3, PTP4A1, HBEGF, HSPA5, THBS1, PLAU, CYR61, ITGA6, EDIL3, CSF1, ITGB1 and MMP1.

7. The screening method according to any one of items 3 to 6, wherein the method includes steps (a1) to (c1):
    (a1) bringing an expression system which contains an expression cassette containing a RBMS gene expression regulation region and a gene arranged in such a manner that the expression thereof can be regulated by the region into contact with a test substance;
    (b1) measuring, as an expression amount/level of interest, the expression amount/level of the gene in the expression system that has been contacted with the test substance and then comparing the expression amount/level of interest with a control expression amount/level that is the expression amount/level of the gene in an expression system that has not been contacted with the test substance; and
    (c1) selecting the test substance as an active ingredient for an inhibitor of the expression of a cancer promoting factor when the expression amount/level of interest is smaller than the control expression amount/level.

8. The screening method according to item 7, wherein the expression cassette is at least one expression cassette selected from the group consisting of an expression cassette containing a RBMS1 gene expression regulation region, an expression cassette containing a RBMS2 gene expression regulation region and an expression cassette containing a RBMS3 gene expression regulation region.

9. The screening method according to item 7 or 8, wherein the expression system is a cell.

10. The screening method according to any one of items 7 to 9, wherein the gene is a reporter gene.

11. The screening method according to any one of items 3 to 6, wherein the method includes steps (a2) to (c2):
    (a2) bringing RNA containing an AU-rich element into contact with RBMS in the presence of a test substance;
    (b2) measuring the binding amount/level between the RNA and the RBMS which are contacted with each other in the presence of the test substance as a binding amount/level of interest, and then comparing the binding amount/level of interest with a control binding amount/level that is the binding amount/level between the RNA and the RBMS which are contacted with each other in the absence of the test substance; and
    (c2) selecting the test substance as an active ingredient for an inhibitor of the expression of a cancer promoting factor when the binding amount/level of interest is smaller than the control binding amount/level.

12. The screening method according to item 11, wherein the RBMS is at least one component selected from the group consisting of RBMS1, RBMS2 and RBMS3.

13. The screening method according to any one of items 3 to 6, wherein the method includes steps (a3) to (c3):
    (a3) bringing a cell which contains mRNA containing an AU-rich element in a 3'-UTR thereof and in which RBMS is overexpressed into contact with a test substance;
    (b3) measuring the amount/level of the mRNA or a protein derived from the mRNA in the cell that has been contacted with the test substance as an amount/level of interest, and then comparing the amount/level of interest with a control amount/level that is the amount/level of the mRNA or a protein derived from the mRNA in a cell that is not contacted with the test substance; and
    (c3) selecting the test substance as an active ingredient for an inhibitor of the expression of a cancer promoting factor when the amount/level of interest is smaller than the control amount/level.

14. The screening method according to item 13, wherein the RBMS is at least one component selected from the group consisting of RBMS1, RBMS2 and RBMS3.

15. The screening method according to item 13 or 14, wherein the mRNA contains an ORF of a reporter protein.

16. An inhibitor of the expression of a cancer promoting factor, comprising at least one component selected from the group consisting of a RBMS expression inhibitor and a RBMS function inhibitor.

17. The inhibitor of the expression of a cancer promoting factor according to item 16, wherein the RBMS expression inhibitor is at least one component selected from the group consisting of a RBMS1 expression inhibitor, a RBMS2 expression inhibitor and a RBMS3 expression inhibitor; and
    the RBMS function inhibitor is at least one component selected from the group consisting of a RBMS1 function inhibitor, a RBMS2 function inhibitor and a RBMS3 function inhibitor.

18. The inhibitor of the expression of a cancer promoting factor according to item 16 or 17, wherein the RBMS expression inhibitor contains at least one RBMS expression inhibitor selected from the group consisting of RBMS-specific siRNA, RBMS-specific miRNA, a RBMS-specific antisense nucleic acid, expression vectors for these components and IL-10.

19. The inhibitor of the expression of a cancer promoting factor according to any one of items 16 to 18, wherein the cancer promoting factor of which the expression is to be inhibited is at least one component selected from the group consisting of CSF2, IL-6, ADAM10, ADM, CTGF, HBEGF, HILPDA, IL-24, THBS1, MYC, TGFB2, ADAM10, ITGA6, F3, PTP4A1, HBEGF, HSPA5, THBS1, PLAU, CYR61, ITGA6, EDIL3, CSF1, ITGB1 and MMP1.

20. The inhibitor of the expression of a cancer promoting factor according to any one of items 16 to 19, wherein the inhibitor is used as a preventing or treating agent for cancer.

21. The inhibitor of the expression of a cancer promoting factor according to item 20, wherein the cancer to be prevented or treated is at least one type of cancer selected from the group consisting of (X) to (Z):
    (X) at least one type of cancer selected from the group consisting of pancreatic cancer, colorectal cancer, lung cancer, bile duct cancer and breast cancer;
    (Y) the cancer is cancer of a type of RAS gene mutation; and
    (Z) the cancer is highly malignant cancer.
22. The inhibitor of the expression of a cancer promoting factor according to item 21, wherein the RAS gene mutation is a KRAS gene mutation.
23. A diagnostic agent for cancer, comprising a RBMS gene expression product detecting agent.
24. The diagnostic agent for cancer according to item 23, wherein the RBMS gene expression product detecting agent is at least one component selected from the group consisting of a RBMS1 gene expression product detecting agent, a RBMS2 gene expression product detecting agent and a RBMS3 gene expression product detecting agent.
25. The diagnostic agent according to item 23 or 24, wherein a cancer promoting factor is at least one component selected from the group consisting of CSF2, IL-6, ADAM10, ADM, CTGF, HBEGF, HILPDA, IL-24, THBS1, MYC, TGFB2, ADAM10, ITGA6, F3, PTP4A1, HBEGF, HSPA5, THBS1, PLAU, CYR61, ITGA6, EDIL3, CSF1, ITGB1 and MMP1.
26. The diagnostic agent for cancer according to any one of items 23 to 25, wherein the cancer to be diagnosed is at least one type of cancer selected from the group consisting of (X) to (Z):
    (X) at least one type of cancer selected from the group consisting of pancreatic cancer, colorectal cancer, lung cancer, bile duct cancer and breast cancer;
    (Y) the cancer is cancer of a type of RAS gene mutation; and
    (Z) the cancer is highly malignant cancer.
27. The diagnostic agent according to item 26, wherein the RAS gene mutation is a KRAS gene mutation.
28. A method for detecting cancer, comprising the steps of:
    (a1) measuring the expression amount/level of interest of a RBMS gene expression product in a sample collected from a subject; and
    (b1) comparing the expression amount/level of interest measured in step (a1) with a control expression amount/level of the RBMS gene expression product in a sample collected from a control subject which does not suffer from cancer, wherein
    (c1) the matter that the expression amount/level of interest is larger than the control expression amount/level is employed as an index for the determination that the subject has the cancer.
29. A method for determining the degree of progression of cancer, comprising the steps of:
    (a2) measuring the expression amount/level of interest of a RBMS gene expression product in a sample collected from a subject suffering from the cancer; and
    (b2) comparing the expression amount/level of interest measured in step (a2) with a control expression amount/level of a RBMS gene expression product in a sample collected from a control subject suffering from the cancer, wherein
    (c2) the matter that the expression amount/level of interest is larger than the control expression amount/level is employed as an index for the determination that the subject has a higher degree of progression of the cancer than that of the control subject.
30. The method according to item 28 or 29, wherein the RBMS gene expression product is at least one component selected from the group consisting of a RBMS1 gene expression product, a RBMS2 gene expression product and a RBMS3 gene expression product.
31. The method according to any one of items 28 to 30, wherein the cancer can be developed or worsened by at least one component selected from the group consisting of CSF2, IL-6, ADAM10, ADM, CTGF, HBEGF, HILPDA, IL-24, THBS1, MYC, TGFB2, ADAM10, ITGA6, F3, PTP4A1, HBEGF, HSPA5, THBS1, PLAU, CYR61, ITGA6, EDIL3, CSF1, ITGB1 and MMP1.

Advantages of the Invention

According to the present invention, it becomes possible to provide a novel inhibitor of the expression of a cancer promoting factor, a novel preventing or treating agent for an immune disease, an inflammatory disease, a painful disease or the like, and a tool for developing the inhibitor or the preventing or treating agent (e.g., a method for screening for an active ingredient, an expression cassette useful for the method), all of which utilize a novel target factor that affects the expression amount/level of a cancer promoting factor. According to the present invention, it also becomes possible to provide a diagnostic agent and a diagnosis method for an immune disease, an inflammatory disease, a painful disease or the like, which rely on a novel mechanism.

BRIEF DESCRIPTION OF DRAWINGS

FIG. 1A illustrates a schema of screening of Example 1A.
FIG. 1B illustrates the results of Example 1B. In the left side of the graph, an upper schematic diagram illustrates a partial structure of a control reporter vector (without an IL-6 3'UTR) used, and a lower schematic diagram illustrates a partial structure of a reporter vector (with an IL-6 3'UTR) used. A white column represents a case where an empty vector (pcDNA3.1) is introduced, and a black column represents a case where a RBMS2 expression vector (pcDNA3.1 FLAG-RBMS2) is introduced. The transverse axis represents a relative value of a measured luciferase activity.
FIG. 2 shows the results of Example 2. The schematic diagram on the left side of the graph shows a partial structure of the mutant 3'UTR reporter vector used. The horizontal axis indicates a relative value of luciferase activity. The white column indicates the case where an empty vector is introduced, and the black column indicates a case where the RBMS2 expression vector is introduced. As a result of t-test, * indicates that the p value was 0.05 or less.
FIG. 3A illustrates the results of Example 5A. The vertical axis represents a luciferase activity that reflects the number of surviving cells. In the transverse axes, "siNega" represents a case where control siRNA is introduced, and "siRBMS2" represents a case where siRNA for RBMS2 is introduced.
FIG. 3B illustrates the results of Example 5B. The vertical axis represents an absorbance that reflects the number of cells, and the transverse axis represents a time lapsed after the transfection of siRNA. "siNega" represents a case where control siRNA is introduced, and "siRBMS2" represents a case where siRNA for RBMS2 is introduced.

FIG. 3C illustrates the results of Example 5C. In the upper part in the photograph, "siNega" represents a case where control siRNA is introduced, "siRBMS2" represents a case where siRNA for RBMS2 is transfected, and each of numerical values represents a time lapsed after the start of stimulation with IL-1β. On the left side in the photograph, substances to be detected by western blotting are shown.

FIG. 4 illustrates the results of Example 6. "siNega" represents a case where control siRNA is introduced, and "siRBMS2" represents a case where siRNA for RBMS2 is introduced.

FIG. 5 illustrates the results of Example 7. "siNega" represents a case where control siRNA is introduced, and "siRBMS2" represents a case where siRNA for RBMS2 is introduced.

FIG. 6 illustrates the results of Example 8A. The transverse axis represents a value relative to a luciferase activity (e.g., (an activity obtained when a RBMS2 expression vector is introduced)/(an activity obtained when an empty vector is introduced)). In the vertical axis, 3'UTR-derived genes each arranged downstream from a luciferase gene in a reporter vector are shown. In the vertical axis, "Empty" represents a case where a 3'UTR derived from other gene is not arranged downstream from the luciferase gene in the reporter vector.

FIG. 7 illustrates the results of Example 8B. The vertical axis represents a relative value of an amount/level of luciferase mRNA in an immunoprecipitation product, wherein the amount/level of luciferase mRNA in a cell lysate before immunoprecipitation is 100%. In the transverse axis, "AUUUA" represents a case where a reporter vector in which a F3 gene wild-type 3'UTR is linked to the downstream of luciferase gene (Examples 8A) is introduced, and "AGGGA" represents a case where a reporter vector in which a F3 gene mutant 3'UTR (a mutant of an AU-rich element) is linked to the downstream of luciferase gene is introduced. A black column represents a case where immunoprecipitation is performed with an anti-FLAG antibody, and a white column represents a case where immunoprecipitation is performed by a non-specific IgG.

FIG. 8 illustrates the results of Example 9. Amino acid residues are represented by single letter codes. Each of the numerical values above and on the right side of the amino acid sequence represents an amino acid number counted from the N-terminal side. The sequence of RBMS1 corresponds to amino acids at positions 39 to 238 of SEQ ID NO: 9. The sequence of RBMS2 corresponds to the amino acids at positions 36 to 232 of SEQ ID NO: 3. The sequence of RBMS3 corresponds to the amino acids at positions 40 to 237 of SEQ ID NO: 13.

FIG. 9 illustrates the results of Example 10. The vertical axis represents a relative value of an expression amount/level of RBMS gene relative to an expression amount/level of HPRT gene. In the transverse axis, the names of cell strains are shown.

FIG. 10 illustrates the results of Example 11. The vertical axis represents a luciferase activity. In the vertical axis, 3'UTR-derived genes each arranged downstream from a luciferase gene in a reporter vector are shown.

FIG. 11 illustrates the results of Example 12. The vertical axis represents an absorbance that reflects the number of cells, and the transverse axis represents a time lapsed after the transfection of siRNA. "siNega" represents a case where control siRNA is introduced, "siRBMS1" represents a case where siRNA for RBMS1 is introduced, and "siRBMS2" represents a case where siRNA for RBMS2 is introduced.

FIG. 12 illustrates the results of Example 13.

FIG. 13 illustrates the results of Example 14. The vertical axis represents a relative value of an expression amount/level of RBMS2 mRNA relative to an expression amount/level of HPRT mRNA. The transverse axis represents a time lapsed after the addition of IL-10 protein or TGFβ protein. A white column represents a case where IL-10 protein is added, and a black column represents a case where TGFβ protein is added.

FIG. 14 illustrates the schematic illustration of PAR-CLIP in Example 15.

FIG. 15 illustrates the results of Example 15. Each bar represents a gene shown in above (from the left side, 5'→3'), each black box in a bar represents an exon. In a black box, a thin part represents an UTR (a non-code region) and a thick part represents a CDS (a code region). A dot below a bar represents a position of an AU-rich element. A graph above a bar is a graph in which the vertical axis represents the binding amount/level of RBMS2 (=the number of sequence reads).

FIG. 16A illustrates the results of Example 16 (data of expression of RBMS2). The vertical axis represents an expression amount/level, and the transverse axis represents cell species.

FIG. 16B illustrates the results of Example 16 (data of expression of RBMS1). The vertical axis represents an expression amount/level, and the transverse axis represents cell species.

FIG. 17A illustrates the results of Example 17 (quantitative PCR 1). The vertical axis represents the expression amount/level of RBMS2 which is corrected by the expression amount/level of HPRT, and the transverse axis represents cell species.

FIG. 17B illustrates the results of Example 17 (western blotting). In the upper part in the photograph, cell species are shown. "siRBMS2" represents a case where siRNA for RBMS2 is introduced.

FIG. 17C illustrates the results of Example 17 (quantitative PCR 2). A photograph in the upper part is an observation image of MCF-7 cells (Control) and cells (KRAS$^{G13D}$) produced by introducing a KRAS G13D mutant into the cells. A graph in the lower part shows the expression amount/level of RBMS2 or IL-6 which is corrected by the expression amount/level of HPRT. In the transverse axis of each of the graphs, cell species used (MCF-7 cells (Control), and cells produced by introducing a KRAS G13D mutant into the cells are shown.

FIG. 17D illustrates the results of Example 17 (quantitative PCR 3). In each of graphs, the vertical axis represents the expression amount/level of a gene shown in the upper part of the graph which is corrected by the expression amount/level of HPRT. In the transverse axes, "siNega" represents a case where negative control siRNA is introduced, and "siKRAS" represents a case where siRNA for KRAS is introduced.

FIG. 17E illustrates the mechanism of regulating the expression of RBMS2 and the mechanism of regulating the expression of a cancer promoting factor, which is suggested from the results of Example 17.

FIG. 18 illustrates the results of Example 18. In each of graphs, the vertical axis represents a survival rate, and the transverse axis represents a time (unit: year).

FIG. 19 illustrates the results of Example 19. In each of graphs, the vertical axis represents the expression amount/ level of RBMS2 which is corrected by the expression amount/level of HPRT, and the transverse axis represents cell species.

FIG. 20A represents the results of Example 20 (RBMS2). The vertical axis represents the expression amount/level of RBMS2 which is corrected by the expression amount/level of HPRT. In the transverse axis, "empty" represents a case where an empty vector is introduced, and "KRAS" represents a case where an expression vector for wild-type KRAS (WT) or each of various KRAS mutants (G12D, G12S, G12V and G13D) is introduced. A white column represents a case where culture is carried out in a culture medium containing 100 ng/ml of doxycycline, and a black column represents a case where culture is carried out in a culture medium containing 1000 ng/ml of doxycycline.

FIG. 20B represents the results of Example 20 (RBMS1). The vertical axis represents the expression amount/level of RBMS1 which is corrected by the expression amount/level of HPRT. Other statements are the same as those mentioned with respect to FIG. 20A.

FIG. 20C illustrates the results of Example 20 (IL-6). The vertical axis represents the expression amount/level of IL-6 which is corrected by the expression amount/level of HPRT. Other statements are the same as those mentioned with respect to FIG. 20A.

FIG. 20D illustrates the results of Example 20 (IL-8). The vertical axis represents the expression amount/level of IL-8 which is corrected by the expression amount/level of HPRT. Other statements are the same as those mentioned with respect to FIG. 20A.

FIG. 21A illustrates the results of Example 21 (a case where MCF-7 cells and MDA-MB-231 cells are used). The vertical axis represents the amount/level of remaining RNA wherein the expression amount/level in a sample without actinomycin D is defined as 100%, and the transverse axis represents the time lapsed after the addition of actinomycin D.

FIG. 21B illustrates the results of Example 21 (a case where HepG2 cells, LoVo cells and HPAF-II cells are used). Other statements are the same as those mentioned with respect to FIG. 21A.

FIG. 21C illustrates the results of Example 21 (a case where siRNA for KRAS is introduced). Other statements are the same as those mentioned with respect to FIG. 21A.

FIG. 21D illustrates the results of Example 21 (a case where siRNA for RBMS2 is introduced). Other statements are the same as those mentioned with respect to FIG. 21A.

FIG. 22 illustrates the results of Example 22. Beside the graph, schematic illustrations of promoters used are shown. Each of boxes represents an exon of RBMS2 (exon-1 and exon-2 from the left). The transverse axis in the graph represents a corrected value of a luciferase activity.

MODE FOR CARRYING OUT THE INVENTION

1. Definitions

The wordings "contain" and "comprise" as used herein include all of the concepts of "contain", "comprise", "substantially consisting of" and "consisting only of".

The amino acid sequence "identity" refers to the degree of amino acid sequence agreement between at least two amino acid sequences that can be compared with each other. Therefore, the identity or similarity of two amino acid sequences becomes higher with the increase in the degree of amino acid sequence agreement between the amino acid sequences. The level of amino acid sequence identity can be determined using FASTA as a sequence analysis tool and employing a default parameter. Alternatively, the level of amino acid sequence identity can also be determined using an algorithm BLAST established by Karlin and Altschul (Karlin S, Altschul S F." Methods for assessing the statistical significance of molecular sequence features by using general scoringschemes" Proc Natl Acad Sci USA. 87:2264-2268 (1990), Karlin S, Altschul S F." Applications and statistics for multiple high-scoring segments in molecular sequences." Proc Natl Acad Sci USA. 90:5873-7 (1993)). Aprogram called "BLASTX" which relies on the algorithm BLAST has been developed. Specific techniques for these analysis methods are known, and see a web site of National Center of Biotechnology Information (NCBI) (http://www.ncbi.nlm-.nih.gov/). The nucleotide sequence "identity" can also be defined accordingly as mentioned above.

The term "conservative substitution" as used herein refers to the matter that an amino acid residue is substituted by an amino acid residue having a similar side chain. For example, the substitution between amino acid residues each having a basic side chain, e.g., lysine, arginine, histidine, is included within the scope of the conservative substitution. In addition, the substitution between amino acid residues each having an acidic side chain, e.g., aspartic acid, glutamic acid, the substitution between amino acid residues each having an uncharged polar side chain, e.g., glycine, asparagine, glutamine, serine, threonine, tyrosine and cysteine, the substitution between amino acid residues each having a non-polar side chain, e.g., alanine, valine, leucine, isoleucine, proline, phenylalanine, methionine and tryptophan, the substitution between amino acid residues each having a β-branched side chain, e.g., threonine, valine and isoleucine, and the substitution between amino acid residues each having an aromatic side chain, e.g., tyrosine, phenylalanine, tryptophan and histidine, are included within the scope of the conservative substitution.

The term "RBMS" as used herein includes a RBMS family, specifically at least one member selected from the group consisting of RBMS1, RBMS2 and RBMS3. Among these members, RBMS1 and RBMS2 are preferred, and RBMS2 is more preferred. RBMS may comprise a single member, or may comprise a combination of two or more members. An example of the preferred combination is a combination of RBMS2 and RBMS1 and/or RBMS3.

In the description, the expression "RBMS", "RBMS1", "RBMS2" or "RBMS3" means a protein.

In the description, each of "a nucleotide", "an oligonucleotide" and "a polynucleotide" has the same meaning as "a nucleic acid", and both of DNA and RNA are included. Each of these substances may be in a double-stranded form or a single-stranded form. The term a "nucleotide" (or an "oligonucleotide" or a "polynucleotide") having a given sequence also includes a "nucleotide" (or an "oligonucleotide" or a "polynucleotide") having a sequence complementary to the sequence therefor comprehensively, unless otherwise stated. In addition, in the case where the "nucleotide" (or an "oligonucleotide" or a "polynucleotide") is RNA, the nucleotide symbol "T" shown in a sequence for the nucleotide is to be read "U".

The term "cancer" as used herein includes various types of cancer. Examples of the cancer include pancreatic cancer, kidney cancer, leukemia, esophagus cancer, stomach cancer, colorectal cancer, liver cancer, lung cancer, bile duct cancer, prostate cancer, skin cancer, breast cancer and cervical cancer.

The cancer is preferably at least one type of cancer selected from the group consisting of (X) to (Z):

(X) at least one type of cancer selected from the group consisting of pancreatic cancer, colorectal cancer, lung cancer, bile duct cancer and breast cancer;
(Y) the cancer is cancer of a type of RAS gene mutation; and
(Z) the cancer is highly malignant cancer.

Among pancreatic cancer, colorectal cancer, lung cancer, bile duct cancer and breast cancer, those cancer which is of a type of RAS gene mutation, and highly malignant cancer are preferred.

The term "RAS" includes various types of RAS, and the type of RAS is not particularly limited as long as the RAS is RAS that can cause cancer when mutated and/or RAS that can progress cancer when mutated. Examples of the type of RAS include KRAS, NRAS and HRAS, and KRAS is preferred.

The RAS gene mutation is not particularly limited, as long as the mutation is a mutation that can cause cancer and/or a mutation that can progress cancer. In the case of human KRAS, examples of the mutation include a mutation of an amino acid residue located at 12th position from the N-terminal (G) and a mutation of an amino acid residue located at 13th position from the N-terminal (G), and more specific examples include G12S, G12C, G12R, G12D, G12V, G12A, G13S, G13C, G13R, G13D, G13V and G13A. In the case of RAS other than human KRAS, a mutation corresponding to each of the above-mentioned mutations in human KRAS can be identified easily by comparing the amino acid sequences, domain arrangements and the like.

The highly malignant cancer (including a cancer stem cell) is not particularly limited, as long as the cancer has a high growing ability, a high infiltration ability, a high metastasis ability, a high undifferentiation degree and the like. The degree of malignancy can be determined using, as an index, a malignancy degree marker (including a cancer stem cell marker). For example, when the cancer has a RAS gene mutation, it is determined that the cancer is highly malignant cancer. In addition, in the case of acute myeloid leukemia, the cancer is determined as highly malignant cancer when $CD34^+CD38^-$ is detected; in the case of breast cancer, the cancer is determined as highly malignant when $CD44^+CD24^{-/low}$ is detected; in the case of brain tumor, the tumor is detected as highly malignant cancer when $CD133^+$ is detected; in the case of prostate cancer, the cancer is determined as highly malignant cancer when $CD133^+$ or $Sca-1^+$ is detected; in the case of colorectal cancer, the cancer is determined as highly malignant cancer when $CD133^+$ is detected; in the case of head and neck squamous cell carcinoma, the cancer is determined as highly malignant cancer when $CD44^+$ is detected; in the case of pancreatic cancer, the cancer is determined as highly malignant cancer when $CD133^+CXCR4^+$ is detected; and in the case of ovarian cancer, the cancer is determined as highly malignant cancer when $CD44^+CD24^+ESA$ (epithelial specific antigen)$^+$ is detected. In addition, in the case of breast cancer, an estrogen receptor-negative property, a progesterone receptor-negative property, a HER2-negative property and the like can be employed as an index for high malignancy. In addition to the above-mentioned indices, various known markers associated with a growing ability, an inflation ability, a metastasis ability and the like can also be employed as the indices for high malignancy. The malignancy degree may be determined employing a single marker or a combination of two or more markers.

2. Screening Reagent

The present invention relates to a reagent for screening for an active ingredient for an inhibitor of the expression of a cancer promoting factor (wherein the reagent is also referred to as a "screening reagent of the present invention", hereinafter), which comprises at least one component selected from the group consisting of an expression cassette containing a RBMS gene expression regulation region and a gene arranged in such a manner that the expression thereof can be regulated by the region (wherein the expression cassette is also referred to as an "expression cassette of the present invention, hereinafter), a vector carrying the expression cassette and a cell harboring the vector. Hereinbelow, the screening reagent will be described.

In the present application, the term an "expression cassette" refers to a polynucleotide having such a function that a gene contained in the expression cassette can be expressed in a cell (e.g., a eukaryotic cell, preferably an animal cell, more preferably a mammalian cell).

In the present application, the "RBMS gene expression regulation region" is not particularly limited, as long as the region is a DNA region capable of regulating the expression of endogenous RBMS gene in a cell or a DNA region having the same regulation ability as that of the aforementioned DNA region. An example of the region is a promoter that contains a transcription initiation site for RBMS gene, a sequence located upstream (5' side) from the transcription initiation site, and optionally a sequence located downstream (3' side) from the transcription initiation site. A specific example of the promoter is a DNA region lying between −10000 to +2000, preferably −5000 to +1000, more preferably −2000 to +500, further preferably −1000 to +200, still further preferably −500 to +100, especially preferably −200 to +50, wherein a nucleotide corresponding to the transcription initiation site for RBMS gene is expressed as "+1", a nucleotide located downstream (3' side) from the aforementioned nucleotide is expressed by a positive value, and a nucleotide located upstream from the aforementioned nucleotide is expressed by 0 or a negative value. In RBMS2, a region that is important for a transcriptional activity is contained between about 4 kbp and 2.5 kbp upstream of exon-2 and between exon-1 and exon-2. Therefore, a promoter containing at least one of the two regions is preferred. The promoter may have a mutation, as long as the promoter has the same level of expression regulation ability as that of a promoter capable of regulating the expression of endogenous RBMS gene in a cell. In this case, the nucleotide sequence for the promoter having a mutation has, for example, a 70% or more, preferably 80% or more, more preferably 90% or more, further preferably 95% or more, still further preferably 97% or more, especially preferably 99% or more identity to a nucleotide sequence for a promoter capable of regulating the expression of endogenous RBMS gene in a cell. It is desirable that the position of the mutation is a position other than the position of a known expression regulation element (e.g., a basic transcription factor binding region, any one of various activator binding regions). The consensus sequence for the expression regulation element is already known, and can be searched easily on various data base.

In the present application, "RBMS gene" is not particularly limited, and examples of the gene include those from animals including various mammals such as human, monkey, mouse, rat, dog, cat, rabbit, pig, horse, cow, sheep, goat and deer.

RBMS genes derived from various animals are known. RBMS mRNA and RBMS protein which are expression products of the RBMS genes can be exemplified as follows.

A specific example of human RBMS2 mRNA such as mRNA consisting of the nucleotide sequence represented by SEQ ID NO: 1 (NCBI Reference Sequence: NM_002898.3); murine RBMS2 mRNA such as mRNA consisting of the nucleotide sequence represented by SEQ ID NO: 2 (NCBI Reference Sequence: NM_019711.2); human RBMS2 protein such as a protein consisting of the amino acid sequence represented by SEQ ID NO: 3 (NCBI Reference Sequence: NP_002889.1); and murine RBMS2 protein such as a protein consisting of the amino acid sequence represented by SEQ ID NO: 4 (NCBI Reference Sequence: NP_062685.2). The RBMS2 protein includes, within the scope thereof, a type in which the N-terminal is deleted. Specific examples of the RBMS2 protein of this type include a mouse-derived protein, which is consisting of the amino acid sequence represented by SEQ ID NO: 5 (NCBI Reference Sequence: NP_001034169.1) (whose mRNA is consisting of the nucleotide sequence represented by SEQ ID NO: 6 (NCBI Reference Sequence: NM_001039080.1)).

(RBMS1)

A specific example of human RBMS1 mRNA is mRNA comprising the nucleotide sequence represented by SEQ ID No: 7 (NCBI Reference Sequence: NM_016836.3), and a specific example of murine RBMS1 mRNA is mRNA comprising the nucleotide sequence represented by SEQ ID NO: 8 (NCBI Reference Sequence: NM_001141932.1). An example of human RBMS1 protein is a protein comprising the amino acid sequence represented by SEQ ID NO: 9 (NCBI Reference Sequence: NP_058520.1), and an example of murine RBMS1 protein is a protein comprising the amino acid sequence represented by SEQ ID NO: 10 (NCBI Reference Sequence: NP_001135404.1). The RBMS1 protein includes, within the scope thereof, a type in which the N-terminal is deleted.

(RBMS3)

A specific example of human RBMS3 mRNA is mRNA comprising the nucleotide sequence represented by SEQ ID No: 11 (NCBI Reference Sequence: NM_001003793.2), and a specific example of murine RBMS3 mRNA is mRNA comprising the nucleotide sequence represented by SEQ ID NO: 12 (NCBI Reference Sequence: NM_001172121.1). An example of human RBMS3 protein is a protein comprising the amino acid sequence represented by SEQ ID NO: 13 (NCBI Reference Sequence: NP_001003793.1), and an example of murine RBMS3 protein is a protein comprising the amino acid sequence represented by SEQ ID NO: 14 (NCBI Reference Sequence: NP_001165592.1). The RBMS3 protein includes, within the scope thereof, a type in which the N-terminal is deleted.

RBMS protein, which is an expression product of RBMS gene, may have an amino acid mutation such as substitution, deletion, addition and insertion, as long as the RBMS protein can have an activity to promote the expression of mRNA having a 3'UTR derived from cancer promoting factor mRNA (e.g., CSF2 mRNA, IL-6 mRNA, ADAM10 mRNA, ADM mRNA, CTGF mRNA, HBEGF mRNA, HILPDA mRNA, IL-24 mRNA, THBS1 mRNA, MYC mRNA, TGFB2 mRNA, ADAM10 mRNA, ITGA6 mRNA, F3 mRNA, PTP4A1 mRNA, HBEGF mRNA, HSPA5 mRNA, THBS1 mRNA, PLAU mRNA, CYR61 mRNA, ITGA6 mRNA, EDIL3 mRNA, CSF1 mRNA, ITGB1 mRNA and MP1mRNA) or a protein translated from the mRNA (wherein the activity is also referred to as an "cancer promoting factor expression promoting activity", hereinafter). From the viewpoint that the cancer promoting factor expression promoting activity is less likely to be deteriorated, the type of the mutation is preferably substitution, more preferably conservative substitution.

RBMS mRNA, which is a transcription product of RBMS gene, may have a nucleotide mutation, such as substitution, deletion, addition and insertion, as long as a protein translated from the mRNA can have an inflammation promoting factor expression promoting activity. The type of the mutation is preferably a mutation by which an amino acid substitution does not occur in a protein translated from the mRNA or a mutation by which a conservative substitution of an amino acid residue can occur.

The presence or absence of an inflammation promoting factor expression promoting activity can be determined by or in accordance with a known method. For example, this presence or absence can be determined by or in accordance with the methods described in the section "Examples". A specific example is as follows: in Example 1B, when an expression vector for a test protein is used as the expression vector, it is determined that the test protein has an inflammation promoting factor expression promoting activity when the luciferase activity is higher than that achieved when an empty vector is used as the expression vector.

A preferred specific example of RBMS protein which is an expression product of RBMS gene is at least one protein selected from the group consisting of a protein mentioned in (a) and a protein mentioned in (b):
  (a) a protein which is consisting of an amino acid sequence represented by SEQ ID NO: 2, 5 or 6; and
  (b) a protein which has 85% or more identity to an amino acid sequence represented by SEQ ID NO: 2, 5 or 6 and has an inflammation promoting factor expression promoting activity.

In (b), the degree of identity is more preferably 90% or more, further preferably 95% or more, still further preferably 98% or more.

An example of the protein mentioned in (b) is:
  (b') a protein which is consisting of an amino acid sequence having the substitution, deletion, addition or insertion of one or several amino acid residues in an amino acid sequence represented by SEQ ID NO: 2, 5 or 6 and has an inflammation promoting factor expression promoting activity.

In (b'), the wording "several amino acid residues" refers to, for example, 2 to 30 amino acid residues, preferably 2 to 10 amino acid residues, more preferably 2 to 5 amino acid residues, still further preferably 2 or 3 amino acid residues.

A preferred specific example of RBMS mRNA which is a transcription product of RBMS gene is at least one component selected from the group consisting of mRNA mentioned in (c) and mRNA mentioned in (d):
  (c) mRNA consisting of a nucleotide sequence represented by SEQ ID NO: 3, 4 or 7; and
  (d) mRNA which has 85% or more identity to a nucleotide sequence represented by SEQ ID NO: 3, 4 or 7 and encodes a protein having an inflammation promoting factor expression promoting activity.

In (d), the degree of identity is more preferably 90% or more, further preferably 95% or more, still further preferably 98% or more.

An example of the mRNA mentioned in (d) is:
  (d') mRNA encoding a protein which is consisting of a nucleotide sequence having the substitution, deletion, addition or insertion of one or several nucleotides in a nucleotide sequence represented by SEQ ID NO: 3, 4 or 7 and has an inflammation promoting factor expression promoting activity.

In (d'), the wording "several nucleotides" refers to, for example, 2 to 500 nucleotides, preferably 2 to 100 nucleotides, more preferably 2 to 50 nucleotides, still further preferably 2 to 10 nucleotides.

In the present application, the term "gene" which is arranged so that the expression of the gene can be regulated by a RBMS gene expression regulation region is not particularly limited, as long as an expression product of the gene can be detected. In this regard, the term "gene" has a concept that a sequence encoding a protein that is an expression product of the gene is included, other sequence in the gene (e.g., an intron sequence) may be included, but a promoter is not contained. Examples of the gene include a reporter gene, a drug-resistant gene, an enzyme gene, a structural gene, a transport gene, a storage gene, a contractile gene, a defense gene, a regulatory gene, and modified genes thereof. Examples of the modified gene include a gene produced by mutating a nucleotide so that an amino acid mutation, e.g., substitution, deletion, addition and insertion, can occur in a part of a protein that is an expression product of the above-mentioned gene; and a gene which can express a protein that is a fusion of expression products of some of the above-mentioned genes. Among these genes, a reporter gene, a drug-resistant gene or the like is preferred, and a reporter gene is more preferred.

In the present application, the "reporter gene" is not particularly limited, as long as the gene is, for example, a gene encoding a light-emitting (color-developing) protein capable of reacting with a specific substrate to emit light (develop a color) or a fluorescent protein capable of emitting fluorescence by the action of excited light. Examples of the light-emitting (color-developing) protein include luciferase, β-galactosidase, chloramphenicol acetyltransferase and β-glucuronidase. Examples of the fluorescent protein include GFP, Azami-Green, ZsGreen, GFP2, HyPer, Sirius, BFP, CFP, Turquoise, Cyan, TFP1, YFP, Venus, ZsYellow, Banana, KusabiraOrange, RFP, DsRed, AsRed, Strawberry, Jred, KillerRed, Cherry, HcRed and mPlum.

In the present application, the "drug-resistant gene" is not particularly limited, as long as the gene is a gene capable of imparting resistance to a drug, e.g., an antibacterial drug, to a cell in which the gene is expressed. Specific examples of the drug-resistant gene include a chloramphenicol-resistant gene, a tetracycline-resistant gene, a neomycin-resistant gene, an erythromycin-resistant gene, a spectinomycin-resistant gene, a kanamycin-resistant gene, a hygromycin-resistant gene and a puromycin-resistant gene.

With respect to the above-mentioned "gene", the wording "(being) arranged so that the expression of the gene can be regulated" means that the gene is arranged so that a protein encoded by the gene can be expressed. A specific example of the arrangement is an aspect in which the gene expression regulating region and the gene are arranged in this order as observed from the 5'-side.

If necessary, the expression cassette of the present invention may contain other element (e.g., a multi-cloning site (MCS)). For example, in the case where a RBMS gene expression regulation region and the above-mentioned "gene" are arranged in this order as observed from the 5'-side, an aspect can be mentioned in which a MCS is arranged on the 5'-side of the RBMS gene expression regulation region (preferably adjacent to the region), or between the RBMS gene expression regulation region and the above-mentioned "gene" (preferably adjacent to one or both of the region and the gene), or on the 3'-side of the above-mentioned "gene" (preferably adjacent to the gene). The MCS is not particularly limited, as long as multiple (e.g., 2 to 50, preferably 2 to 20, more preferably 2 to 10) restriction enzyme sites are contained.

In the present invention, a single of the expression cassette may be used, or a combination of two or more of the expression cassettes may be used.

The expression cassette of the present invention may constitute a vector by itself or in conjunction with other sequence. The vector (also referred to as a "vector of the present invention", hereinafter) is also included within the scope of the present invention. The "other sequence" is not particularly limited, and any one of various known sequences that can be contained in an expression vector can be used. Examples of the sequence include a replication origin and a drug-resistant gene. With respect to the type of the drug-resistant gene, the above-mentioned types can be mentioned. The type of the vector is not particularly limited, and examples of the vector include a plasmid vector such as an animal cell expressing plasmid; and a virus vector such as a retrovirus, a lentivirus, an adenovirus, an adeno-associated virus, a herpesvirus and a Sendai virus.

The vector according to the present invention may be contained in a cell. The cell (also referred to as "a cell of the present invention", hereinafter) is also included within the scope of the present invention. In the cell of the present invention, the vector of the present invention may be present outside of the genome or may be present in such a form that the vector is integrated in the genome. The organism species from which the cell is derived is not particularly limited, and examples of the species include various mammals such as human, monkey, mouse, rat, dog, cat, rabbit, pig, horse, cow, sheep, goat and deer. The type of the cell is not particularly limited, and cells derived from various tissues or having various properties can be mentioned, such as a blood cell, a hematopoietic stem cell/progenitor cell, a gamete (a sperm, an ovum), a fibroblast, an epithelial cell, a vascular endothelial cell, a nerve cell, a liver cell, a keratin generating cell, a muscle cell, an epidermal cell, an endocrine cell, an ES cell, an iPS cell, a tissue stem cell and a cancer cell.

From this viewpoint, in the present invention, at least one component selected from the group consisting of the expression cassette of the present invention, the vector of the present invention and the cell of the present invention can be used as a reagent for screening for an active ingredient for an inhibitor of the expression of a cancer promoting factor.

The screening reagent of the present invention is not particularly limited, as long as at least one component selected from the group consisting of the expression cassette of the present invention, the vector of the present invention and the cell of the present invention is contained. In addition, the screening reagent may also contain, for example, a component necessary for the detection of an expression product from the expression cassette of the present invention. Specific examples of the component include a hybridization reagent, a label for a probe, a detecting agent for a labeled material, a buffer solution and a tool. The reagent of the present invention may be in the form of a screening kit including these components.

3. A Screening Method

The present invention relates to a method for screening for a substance capable of inhibiting the expression or function of RBMS by employing at least one item selected from the group consisting of items (i) to (iii) as an index in the presence of a test substance:

(i) the expression amount/level of a gene of which the expression can be regulated by a RBMS gene expression regulation region;

(ii) the binding amount/level of RBMS to RNA containing an AU-rich element; and
(iii) the amount/level of mRNA containing an AU-rich element in a 3'-UTR thereof or the amount/level of a protein derived from the mRNA in a RBMS-overexpressing cell. Hereinbelow, the expression cassette will be described (wherein the reagent is also referred to as a "screening method of the present invention", hereinafter).

As the "test substance (i.e., substance to be tested)" to be used in the present application, any one of wide varieties of compounds can be used, regardless of the fact that the compound is a naturally occurring compound or an artificially produced compound. Alternatively, a purified compound, a composition prepared by mixing many types of compounds together, or an extract of an animal or plant origin may also be used. The compound includes a low-molecular-weight compound as well as a high-molecular-weight compound such as a protein, a nucleic acid and a polysaccharide.

More specifically, according to the screening method of the present invention, when the value of the index in the presence of a test substance is smaller than the value of the index in the absence of the test substance, the test substance is selected as an active ingredient for an inhibitor of the expression of a cancer promoting factor or a candidate substance for the active ingredient.

Herein below, specific screening methods for the aspects which utilize the indices (i) to (iii), respectively, will be described.

3-1. Screening Method Utilizing Index (i)

The screening method utilizing index (i) includes steps (a1) to (c1):
(a1) bringing an expression system which contains an expression cassette containing a RBMS gene expression regulation region and a gene arranged in such a manner that the expression thereof can be regulated by the region into contact with a test substance;
(b1) measuring, as an expression amount/level of interest, the expression amount/level of the gene in the expression system that has been contacted with the test substance, and then comparing the expression amount/level of interest with a control expression amount/level that is the expression amount/level of the gene in an expression system that has not been contacted with the test substance; and
(c1) selecting the test substance as an active ingredient for an inhibitor of the expression of a cancer promoting factor when the expression amount/level of interest is smaller than the control expression amount/level.

In step (a1), the "expression cassette containing a RBMS gene expression regulation region and a gene arranged in such a manner that the expression thereof can be regulated by the region" is as mentioned in the section "2. Expression cassette". However, the expression cassette in step (a1) is different from the expression cassette in the section "2. Expression cassette" in that the expression cassette in step (a1) includes an expression cassette containing an endogenous RBMS gene expression regulation region in the genome of a cell and RBMS gene located downstream from the region.

In step (a1), the "expression system" is not particularly limited, as long as a component necessary for the expression of a gene from the expression cassette is contained. Examples of the expression system include a cell-free protein expression system and a cell. The cell-free protein expression system is generally consisting of a solution (e.g., a liquid extract from cells) containing a factor necessary for transcription and translation (e.g., an RNA polymerase, a ribosome, any one of various ribonucleotides), and a commercially available product may be used. The cell is not particularly limited, as long as a gene can be expressed from the expression cassette in the cell. Examples of the cell include a cell derived from any one of various tissues or a cell having any one of various properties, such as a blood cell, a hematopoietic stem cell/progenitor cell, a gamete (a sperm, an ovum), a fibroblast, an epithelial cell, a vascular endothelial cell, a nerve cell, a liver cell, a keratin generating cell, a muscle cell, an epidermal cell, an endocrine cell, an ES cell, an iPS cell, a tissue stem cell and a cancer cell. From the viewpoint that the screening can be performed more easily, the expression system is preferably a cell.

In step (a1), in the case where the expression system containing the expression cassette is a cell-free protein expression system, it is preferred that the expression cassette is contained in the solution in the system. In the case where the expression system is a cell, there are an aspect where the expression cassette is integrated into the genome of the cell, an aspect where the expression cassette is present outside of the genome of the cell (e.g., in the form of a plasmid), and the like.

In step (a1), the aspect of bringing the test substance into contact is not particularly limited. In the case where the expression system is a cell-free protein expression system, it is preferred to add the test substance to the solution in the system, for example. In the case where the expression system is a cell, it is preferred to add the test substance to a cell culture medium, for example.

In step (a1), the contacting time of the test substance is not particularly limited, and can be set appropriately depending on the type of the test substance, the type of the expression system and others. The time is, for example, 5 minutes to 72 hours.

In step (b1), the measurement of the expression amount/level of interest and the control expression amount/level can be carried out in accordance with or based on a known method. It is preferred to carry out the measurement using the diagnostic agent of the present invention mentioned above. In the case where the substance to be measured is a nucleic acid (RBMS mRNA or a nucleic acid derived therefrom (e.g., cDNA)), the measurement can be carried out by a northern blotting method, a RT-PCR method, a DNA chip analysis method, an in situ hybridization analysis method or the like using the nucleic acid as a probe or a primer, for example. In the case where the substance to be measured is a protein, the measurement can be carried out by a western blotting method, an ELISA method or the like using a specific antibody. In the case where the substance to be measured is a reporter protein, the measurement can be carried out by a method capable of detecting a reporter signal (e.g., a fluorescence, a developed color, emitted light) coming from the reporter protein (e.g., the microscopic observation of fluorescence, a luciferase assay). In the case where the substance to be measured is a drug-resistant protein, the measurement can be carried out indirectly by counting the number of cells surviving in the presence of the drug.

In the case where a northern blotting method is employed, concretely, a method can be exemplified, in which a probe is labeled with a radioactive isotope (e.g., $^{32}P$ $^{33}P$: RI), a fluorescent substance or the like, then the labeled probe is hybridized with mRNA derived from the expression system and transferred onto a nylon membrane or the like in the conventional manner, and then a double strand formed by the diagnostic agent and mRNA derived from the sample from the subject is subjected to the detection and measurement of a signal coming from a labeled probe (a labeling substance such as an RI or a fluorescent substance) using a radioactive ray detector BAS-180011 (manufactured by Fujifilm Corporation), a fluorescence detector or the like. Alternatively, a method may also be employed, in which the diagnostic agent is labeled using AlkPhos Direct Labelling and Detection System (manufactured by Amersham Pharmacia Biotech) in accordance with the protocol, then the labeled diagnostic agent is hybridized with mRNA derived from the expression system, and then a signal coming from a labeled product of the diagnostic agent is detected and measured using a multibioimager STORM860 (manufactured by Amersham Pharmacia Biotech).

In the case where a RT-PCR method is employed, concretely, a method can be exemplified, in which cDNA is prepared from RNA derived from the expression system in the conventional manner, then a pair of primers prepared from the diagnostic agent of the present invention (i.e., a positive strand capable of binding to the cDNA (− strand), a negative strand capable of binding to + strand) are hybridized with the cDNA to perform a PCR method so that a target region can be amplified using the cDNA as a template, and then amplified double-stranded DNA thus produced is detected. For the detection of the amplified double-stranded DNA, a method in which the above-mentioned PCR is carried out using a primer that is labeled with an RI or a fluorescent substance in advance to detect labeled double-stranded DNA produced; a method in which double-stranded DNA thus produced is transferred onto a nylon membrane or the like in the conventional manner, then the labeled probe is used as a probe and is hybridized with the double-stranded DNA, and then a hybridized product is detected; and other method can be employed. In this regard, a labeled double-stranded DNA product thus produced can be measured using an arrangement 2100 bioanalyzer (manufactured by Yokogawa Analytical Systems, Inc.) or the like. Alternatively, it is also possible to prepare a RT-PCR reaction solution using SYBR Green RT-PCR Reagents (manufactured by Applied Biosystems) in accordance with the protocol, then react the reaction solution using ABI PRISM 7700 Sequence Detection System (manufactured by Applied Biosystems), and then detect a reaction product.

In the case where DNA chip analysis is utilized, a method can be mentioned, in which a DNA chip to which a (single-stranded or double-stranded) DNA probe is attached is provided, then the DNA chip is hybridized with cRNA prepared from RNA derived from the expression system in the conventional manner to produce a double-stranded product formed from the DNA and the cRNA, then the double-stranded product is bonded to a labeling probe prepared from the diagnostic agent of the present invention, and then the bonded product is detected.

As the western blotting method, a method can be exemplified, in which a primary antibody is used, then a labeled antibody (an antibody capable of binding to the primary antibody) that is labeled with a radioactive isotope such as $^{125}$I, a fluorescent substance, an enzyme such as horseradish peroxidase (HRP) or the like is used as a secondary antibody, and a signal coming from the labeling substance, e.g., the radioactive isotope, the fluorescent substance or the like, in the labeled compound is detected using a radioactive ray measurement device BAS-180011 (manufactured by Fujifilm Corporation), a fluorescence detector or the like. Alternatively, it is also possible to use a primary antibody, then the signal is detected using ECL Plus Western Blotting Detection System (manufactured by Amersham Pharmacia Biotech) in accordance with the protocol and is then measured using multibioimager STORM860 (manufactured by Amersham Pharmacia Biotech).

In step (c1), for example, in the case where the expression amount/level of interest is smaller than the control expression amount/level, for example when the expression amount/level of interest is smaller by ½, ⅕, 1/10, 1/20, 1/50 or 1/100 than that of the control expression amount/level, the test substance can be selected as an active ingredient for an inhibitor of the expression of a cancer promoting factor or a candidate substance for the active ingredient.

3-2. Screening Method Utilizing Index (ii)

The screening method utilizing index (ii) includes steps (a2) to (c2):

(a2) bringing RNA containing an AU-rich element into contact with RBMS in the presence of a test substance;

(b2) measuring the binding amount/level between the RNA and the RBMS which are contacted with each other in the presence of the test substance as a binding amount/level of interest, and then comparing the binding amount/level of interest with a control binding amount/level that is the binding amount/level between the RNA and the RBMS which are contacted with each other in the absence of the test substance; and (c2) selecting the test substance as an active ingredient for an inhibitor of the expression of a cancer promoting factor when the binding amount/level of interest is smaller than the control binding amount/level.

In step (a2), the "AU-rich element" refers to an element in which a nucleotide sequence represented by general formula: $(U)_n W^1 (U)_m W^2 (U)_o$ [wherein U represents an uracil; $W^1$ and $W^2$ may be the same as or different from each other and independently represent an adenine or uracil (provided that a case where each of $W^1$ and $W^2$ represents an uracil is excluded); n represents an integer of 0 to 3; o represents an integer of 0 to 3; and m represents an integer of 3 to 5 (preferably 3)] typified by a sequence AUUUA is a consensus sequence. The AU-rich element is preferably an AU-rich element derived from mRNA of an inflammation promoting factor (e.g., at least one type of mRNA selected from the group consisting of IL-6 mRNA, COX-2 mRNA, IL-8 mRNA, IL-1βmRNA, TNF-α mRNA, MMP1 mRNA, IL-24 mRNA and c-Myc mRNA). In other words, the term "an AU-rich element derived from . . . " refers to an AU-rich element contained in each of these mRNA.

In step (a2), the RNA containing an AU-rich element is not particularly limited, as long as the RNA contains the AU-rich element. The number of the AU-rich elements in the RNA is, for example, 1 to 20, preferably 2 to 15, more preferably 3 to 12, further preferably 4 to 10, still further preferably 6 to 9. When the number of the AU-rich elements in the RNA is multiple, it is desirable that the AU-rich elements are present in a relatively narrow region (e.g., 20 to 400 bp, preferably 40 to 200 bp, more preferably 60 to 150 bp, further preferably 80 to 120 bp). It is preferred that the region is U-rich. The degree of U-richness is as follows: the rate of the number of U residues relative to the total number of nucleotides in the region is, for example, 20% or more, preferably 30% or more, more preferably 50% or more. The upper limit of the ratio is not particularly limited, and examples of the upper limit include 90%, 80%, 70% and the like.

In step (a2), the RBMS is the same as that in the RBMS protein mentioned in the section "2. Expression cassette".

In step (a2), the aspect of bringing the test substance into contact is not particularly limited, as long as the three components, i.e., the RNA containing an AU-rich element, RBMS and the test substance, can be contacted with one another. For example, an aspect where the three components are mixed together in a proper solvent, an aspect where the three components are allowed to co-exist in a cell, and the like can be mentioned.

In step (a2), the contacting time of the test substance is not particularly limited, and can be set appropriately depending on the type of the test substance, whether the contact is achieved in a test tube or in a cell, or the like. The time is, for example, 5 minutes to 72 hours.

In step (b2), the measurement of the binding amount/level of interest and the control binding amount/level can be carried out by or in accordance with a known method. For example, the measurement can be carried out by an immunoprecipitation method, a gel shift method or the like.

The immunoprecipitation method can be carried out typically in the following manner. A cell lysate each containing RNA containing an AU-rich element and RBMS (and being in contact with the test substance or being not in contact with the test substance) is prepared, then the lysate is immunoprecipitated with an antibody directed against RBMS or an antibody directed against a tag in the case where the tag is attached to the RBMS, and then the amount/level of "RNA containing an AU-rich element" contained in a precipitate is measured by a PCR. It is demonstrated that the binding amount/level of interest or the control binding amount/level becomes larger with the increase in the measured amount/level.

A gel shift method can be carried out typically in the following manner. A solution containing the RNA containing an AU-rich element and RBMS (and further containing the test substance or not containing the test substance) is electrophoresed using a proper gel (e.g., an acrylamide gel), and then a signal of a band that indicates a complex of the RNA containing an AU-rich element and RBMS which are bonded together is measured. It is demonstrated that the binding amount/level of interest or the control binding amount/level becomes larger with the increase in the measured amount/level.

In step (c2), for example, in the case where the binding amount/level of interest is smaller than the control binding amount/level, the test substance can be selected as a substance capable of inhibiting the expression of RBMS when the binding amount/level of interest is smaller by $1/2$, $1/5$, $1/10$, $1/20$, $1/50$ $1/100$ than the control binding amount/level.

3-3. Screening Method Utilizing Index (iii)

The screening method utilizing index (iii) includes steps (a3) to (c3):
  (a3) bringing a cell which contains mRNA containing an AU-rich element in a 3'-UTR thereof and in which RBMS is overexpressed into contact with a test substance;
  (b3) measuring the amount/level of the mRNA or a protein derived from the mRNA in the cell that has been contacted with the test substance as an amount/level of interest, and then comparing the amount/level of interest with a control amount/level that is the amount/level of the mRNA or a protein derived from the mRNA in a cell that is not contacted with the test substance; and
  (c3) selecting the test substance as a substance capable of inhibiting the function of RBMS when the amount/level of interest is smaller than the control amount/level.

In step (a3), the AU-rich element is the same as that mentioned in the section "3-2. Screening method utilizing index (ii)".

In step (a3), the mRNA containing an AU-rich element in a 3'-UTR thereof is not particularly limited, as long as the mRNA contains an AU-rich element in a 3'-UTR thereof. The number of AU-rich elements in the 3'-UTR of the mRNA is, for example, 1 to 20, preferably 2 to 15, more preferably 3 to 12, further preferably 4 to 10, and still further preferably 6 to 9. In the case where the number if AU-rich elements in the mRNA is multiple, it is desirable that the AU-rich elements are present in a relatively narrow region (e.g., 20 to 400, preferably 40 to 200, more preferably 60 to 150, further preferably 80 to 120).

In step (a3), the mRNA containing an AU-rich element in the 3'-UTR thereof is preferably mRNA for an inflammation promoting factor, more preferably IL-6 mRNA, COX-2 mRNA, IL-8 mRNA, IL-1β mRNA, TNF-α mRNA, MMP1 mRNA, IL-24 mRNA, c-Myc mRNA or the like, or a variant of any one of these mRNA molecules. As the variant, mRNA in which one or several (e.g., 2 to 50, preferably 2 to 20, more preferably 2 to 10, further preferably 2 to 5, still further preferably 2 or 3) nucleotides are substituted, deleted, added or inserted preferably in a sequence other than the AU-rich element or a part of the AU-rich element can be mentioned.

In step (a3), the RBMS is the same as the RBMS protein in the section "2. Expression cassette".

In step (a3), the cell is the same as the cell in the section "3-1. Screening method utilizing index (i)".

In step (a3), the aspect of bringing the test substance into contact is not particularly limited. For example, an aspect where the test substance is added to the cell culture medium can be mentioned.

In step (a3), the contacting time of the test substance is not particularly limited, and can be set appropriately depending on the type of the test substance and the like. The time is, for example, 5 minutes to 72 hours.

In step (b3), the measurement of the amount/level of interest and the control amount/level is carried out in the same manner as in the measurement of the expression amount/level of interest and the control expression amount/level in the section "3-1. Screening method utilizing index (i)".

In step (c3), in the case where the amount/level of interest is smaller than the control amount/level, the test substance can be selected as a substance capable of inhibiting the expression of RBMS when the amount/level of interest is smaller by $1/2$, $1/5$, $1/10$, $1/20$, $1/50$ or $1/100$ than the control amount/level.

4. Inhibitor of Expression of Inflammation Promoting Factor

The present invention relates to an inhibitor of the expression of an inflammation promoting factor (wherein the inhibitor is also referred to as "the agent of the present invention" in the description) which contains at least one component selected from the group consisting of a RBMS expression inhibitor and a RBMS function inhibitor. Hereinbelow, the inhibitor will be described.

The RBMS of which the expression and function are to be inhibited is the same as the RBMS protein in the section "2. Expression cassette" above.

The RBMS expression inhibitor is not particularly limited, as long as the inhibitor can reduce the expression amount/level of RBMS protein. Specific examples of the inhibitor include RBMS-specific small interfering RNA (siRNA), RBMS-specific microRNA (miRNA), a RBMS-specific antisense nucleic acid, and expression vectors therefore. In addition, it is mentioned in the section "Examples" that IL-10 protein can act as a RBMS expression inhibitor.

The RBMS-specific siRNA is not particularly limited, as long as the siRNA is a double-stranded RNA molecule capable of specifically inhibiting the expression of a gene encoding RBMS. In one embodiment, the siRNA preferably has a length of 18 nucleotides or more, 19 nucleotides or more, 20 nucleotides or more, or 21 nucleotides or more. The siRNA preferably has a length of, for example, 25 nucleotides or less, 24 nucleotides or less, 23 nucleotides or less, or 22 nucleotides or less. It is conceived that the value of the upper limit and the value of the lower limit of the length of the siRNA which are mentioned herein can be combined arbitrarily. For example, the following combinations of the length can be conceived: a length in which the lower limit is 18 nucleotides and the upper limit is 25 nucleotides, 24 nucleotides, 23 nucleotides, or 22 nucleotides; a length in which the lower limit is 19 nucleotides and the upper limit is 25 nucleotides, 24 nucleotides, 23 nucleotides, or 22 nucleotides; a length in which the lower limit is 20 nucleotides and the upper limit is 25 nucleotides, 24 nucleotides, 23 nucleotides, or 22 nucleotides; and a length in which the lower limit is 21 nucleotides and the upper limit is 25 nucleotides, 24 nucleotides, 23 nucleotides, or 22 nucleotides.

The siRNA may be shRNA (small hairpin RNA). The shRNA can be designed so that a part thereof forms a stem loop structure. For example, when a sequence lying in a specific region is named "sequence a" and a complementary strand to the sequence a is named "sequence b", the shRNA can be designed in such a manner that the sequence a, a spacer and the sequence b are arranged in this order on a single RNA strand and the whole length becomes 45 to 60 nucleotides. The sequence a is a sequence for a partial region of the nucleotide sequence encoding the target RBMS, and the target region is not limited particularly, and an arbitrary region can be employed as a candidate. The length of the sequence a is 19 to 25 nucleotides, preferably 19 to 21 nucleotides.

The RBMS-specific siRNA may have additional nucleotides at the 5'- or 3'-terminal thereof. The length of the additional nucleotides is generally about 2 to 4 nucleotides. The additional nucleotides may be in the form of DNA or RNA. When additional nucleotides are in the form of DNA, the stability of the nucleic acid may be improved. Examples of the sequence for the additional nucleotides include, but are not limited to, ug-3', uu-3', tg-3', tt-3', ggg-3', guuu-3', gttt-3', ttttt-3' and uuuuu-3'.

The siRNA may have an overhang at the 3'-terminal thereof, and a specific example of the overhang is dTdT (wherein dT represents a deoxythymidine). Alternatively, the siRNA may have a blunt end without the addition of a terminal. In the siRNA, the number of nucleotides in a sense strand may be different from that in an antisense strand. For example, the siRNA may be "asymmetrical interfering RNA (aiRNA)" in which the antisense strand has an overhang at each of the 3'-terminal and the 5'-terminal. Typical aiRNA is one in which the antisense strand is consisting of 21 nucleotides, the sense strand is consisting of 15 nucleotides, and an overhang structure consisting of 3 nucleotides is formed at each terminal of the antisense strand.

The position of the target sequence in the RBMS-specific siRNA is not particularly limited. In one embodiment, it is desirable to select the target sequence from a 5'-UTR and a sequence lying between the initiation codon and about 50th nucleotide from the initiation codon and not to select the target sequence from a 3'-UTR. It is preferred that candidates for the selected target sequence are determined with respect to the matter that there is no homology in a sequence consisting of contiguous 16 to 17 nucleotides in mRNA other than the target sequence using a homology search software such as BLAST (http://www.nebi.nlm.nih.ov/BLAST/), and the specificity of the selected target sequence is confirmed. With respect to a target sequence of which the specificity has been confirmed, double-stranded RNA which is consisting of a sense strand having a 3'-terminal TT or UU overhang in a sequence lying between 19st nucleotide and 21st nucleotide following AA (or NA) and an antisense strand which is consisting of a sequence complementary to the sequence lying between 19st nucleotide and 21st nucleotide and a 3'-terminal TT or UU overhang may be designed as the siRNA. shRNA, which is a precursor of the siRNA, can be designed by appropriately selecting an arbitrary linker sequence (e.g., about 5 to 25 nucleotides) that can form a loop structure and then connecting the sense strand to the antisense strand with the linker sequence interposed therebetween.

The sequence for the siRNA and/or the shRNA can be searched using various search software which is provided for free on web sites. Examples of the sites are as follows.

siRNATarget Finder (http://www.ambion.com/jp/techlib/misc/siRNA_finder.html) provided by Ambion, pSilencer (registered trademark) Insert design tool for Expression Vectors (http://www.amibion.com/jp/techlib/misc/psilencer_converter.html)

GeneSeer (http://codex.cshl.edu/scripts/newsearchhairpin.cgi) provided by RNAi Codex.

The siRNA can be prepared by separately synthesizing an sense strand and an antisense strand in the target sequenced on mRNA using a DNA/RNA automatic synthesizer, then denaturing these strands in a proper annealing buffer solution at about 90 to 95° C. for about 1 minute and then annealing the resultant product at about 30 to about 70° C. for about 1 to about 8 hours. Alternatively, the siRNA may also be prepared by synthesizing shRNA that is a precursor of the siRNA and then cutting the shRNA with a RNA cutting protein dicer.

The RBMS-specific miRNA may be any one, as long as the miRNA can inhibit the translation of a gene encoding RBMS. For example, the miRNA may inhibit the translation of target mRNA by forming a pair with a 3'-untranslated region (UTR) in the target rather than by cutting the target mRNA like siRNA. The miRNA may be any one of pri-miRNA (primary miRNA), pre-miRNA (precursor miRNA) and mature miRNA. The length of the miRNA is not particularly limited, and the length of the pri-miRNA is generally several hundreds to several thousands of nucleotides, the length of the pre-miRNA is generally 50 to 80 nucleotides, and the length of the mature miRNA is generally 18 to 30 nucleotides. In one embodiment, the RBMS-specific miRNA is preferably pre-miRNA or mature miRNA, more preferably mature miRNA. The RBMS-specific miRNA may be synthesized by a known procedure, or may be purchased from a synthetic RNA supplier company.

The RBMS-specific antisense nucleic acid contains a nucleotide sequence complementary or substantially complementary to the nucleotide sequence for mRNA of a gene encoding RBMS or a part of the nucleotide sequence, and has a function to form a specific and stable double strand with the mRNA and bind to the mRNA so as to inhibit the synthesis of RBMS protein. The antisense nucleic acid may be any one selected from DNA, RNA and DNA/RNA chimera. In the case where the antisense nucleic acid is DNA, an RNA:DNA hybrid formed from a target RNA and the antisense DNA can be recognized by endogenous ribonuclease H (RNase H) to cause the selective degradation of the target RNA. Therefore, in the case of antisense DNA that directs the degradation with RNase H, the target sequence may be contained in mRNA as well as a sequence for an intron region in an RBMS initial translation product. The intron sequence can be determined by comparing the genome sequence with cDNA nucleotide sequence in RBMS gene using a homology search program such as BLAST and FASTA.

The length of the target region in the RBMS-specific antisense nucleic acid is not particularly limited, as long as the antisense nucleic acid can hybridize with the target region so as to inhibit the translation into RBMS protein. The RBMS-specific antisense nucleic acid may be the full length or a partial sequence of mRNA encoding RBMS. From the viewpoint of easiness of the synthesis and the problems of antigenicity and intracellular migration and the like, an oligonucleotide having a length of about 10 to about 40 nucleotides, particularly about 15 to about 30 nucleotides, is preferred, but the oligonucleotide is not limited thereto. More concretely, a preferred target region for the antisense nucleic acid can be selected from a 5'-terminal hairpin loop, a 5'-terminal untranslated region, a translation initiation codon, a protein coding region, an ORF translation stop codon, a 3'-terminal untranslated region, a 3'-terminal palindrome region and a 3'-terminal hairpin loop of RBMS gene, but is not limited thereto.

The RBMS-specific antisense nucleic acid may also be one which can hybridize with mRNA for RBMS gene or an initial transcription product of the mRNA to inhibit the translation into a protein and can also bind to these genes, each of which is double-stranded DNA, to form a triplex so as to inhibit the transcription into RNA (i.e., an antigene).

Each of nucleotide molecules that constitute the RBMS-specific siRNA, the RBMS-specific miRNA and the RBMS-specific antisense nucleic acid may contain various chemical modification for the purpose of improving (chemical and/or enzymatical) stability or specific activity (affinity for RNA). For example, in order to prevent the degradation caused by a hydrolysis enzyme such as a nuclease, a phosphate residue (phosphate) in each of the nucleotides constituting the antisense nucleic acid may be substituted by, for example, a chemically modified phosphate residue such as phosphorothioate (PS), methylphosphonate and phosphorodithioate. Alternatively, the hydroxyl group at 2'-position in a ribose in each nucleotide may be substituted by —OR (R=$CH_3$(2'-O-Me), $CH_2CH_2OCH_3$(2'-O-MOE), $CH_2CH_2NHC(NH)NH_2$, $CH_2CONHCH_3$, or $CH_2CH_2CN$, etc.). In addition, the base moiety (pyrimidine, purine) may be chemically modified. For example, the introduction of a methyl group or a cationic functional group to the 5'-position in a pyrimidine base, the substitution of a carbonyl group at 2'-position by a thiocarbonyl group, or the like may be applied. In addition, a part of each of the nucleotide molecules that constitute siRNA and miRNA may be substituted by naturally occurring DNA.

The RBMS-specific siRNA, the RBMS-specific miRNA, the RBMS-specific antisense nucleic acid and the like can be prepared by determining mRNA or a target sequence for an initial transcription product on the basis of the cDNA sequence or the genomic DNA sequence for RBMS gene and then synthesizing a sequence complementary to the sequence using a commercially available DNA/RNA automatic synthesizer. The antisense nucleic acid containing the above-mentioned modifications can also be chemically synthesized by a known technique.

The expression vector for the RBMS-specific siRNA, the RBMS-specific miRNA or the RBMS-specific antisense nucleic acid is not particularly limited, as long as the RBMS-specific siRNA, the RBMS-specific miRNA or the RBMS-specific antisense nucleic acid is integrated in an expressible state. Typically, the expression vector contains a promoter sequence, a polynucleotide containing a sequence encoding the RBMS-specific siRNA, the RBMS-specific miRNA or the RBMS-specific antisense nucleic acid (optionally also containing a transcription stop signal sequence) and optionally other sequence. The promoter is not particularly limited, and examples of the promoter include an RNA polymerase II (polII)-type promoter, such as a CMV promoter, an EF1 promoter, an SV40 promoter, a MSCV promoter, a hTERT promoter, a β-actin promoter and a CAG promoter; and a RNA polymerase III (polIII)-type promoter, such as a mouse or human U6-snRNA promoter, a human H1-RNase P RNA promoter and a human valine-tRNA promoter. Among these promoters, a polIII-type promoter is preferred from the viewpoint of the correct transcription ability of short RNA. The "other sequence" is not particularly limited, and any one of various known sequences which can be contained in expression vectors can be employed. Examples of the sequence include a replication origin and a drug-resistant gene. As the types of the drug-resistant gene and the vector, those mentioned above can be exemplified.

Another example of the RBMS expression inhibitor is a RBMS-specific ribozyme. The term "ribozyme" refers to RNA having an enzymatic activity to cleave a nucleic acid in the narrow sense. In the present application, however, DNA can also be included, as long as the DNA has a sequence-specific nucleic acid cleavage activity. The ribozyme having the broadest utility as a ribozyme nucleic acid is self-splicing RNA that is found in infectious RNA such as a viroid and a virusoid, and a hammerhead-type, hairpin-type and the like are known. A hammerhead-type ribozyme nucleic acid can exhibit the enzymatic activity thereof when the length is about 40 nucleotides, and can cleave only target mRNA specifically by converting several nucleotides located in both ends adjacent to a hammerhead structure-forming part (about 10 nucleotides in total) into sequences complementary to a desired cleavage site in mRNA. The ribozyme nucleic acid of this type can utilize only RNA as the substrate thereof, and therefore has such an advantage that the ribozyme nucleic acid never attacks genomic DNA. In the case where the mRNA for the RBMS gene forms a double-stranded structure by itself, the target sequence can be made into a single strand by using a hybrid ribozyme to which an RNA motif derived from a viral nucleic acid and capable of binding specifically to an RNA helicase is linked [Proc. Natl. Acad. Sci. USA, 98(10): 5572-5577 (2001)]. In the case where it is intended to use the ribozyme in the form of an expression vector containing DNA encoding the ribozyme, the ribozyme may be used in the form of a hybrid ribozyme to which a tRNA-modified sequence is linked in order to accelerate the migration of a transcript into a cell cytoplasm [Nucleic Acids Res., 29(13): 2780-2788 (2001)].

The RBMS function inhibitor is not limited particularly, as long as the inhibitor can inhibit the function of RBMS protein. The wording "inhibition of the function of RBMS protein" refers to (x) the matter that the binding amount/level between RBMS and RNA containing an AU-rich element is reduced and/or (y) the matter that the amount/level of mRNA containing an AU-rich element in the 3'-UTR thereof or the amount/level of a protein derived from the mRNA in an RBMS-overexpressing cell is reduced. Whether or not the function of RBMS protein is inhibited can be determined by, for example, the methods mentioned in the sections "3-2. Screening method utilizing index (ii)" and "3-3. Screening method utilizing index (iii)" below.

The cancer promoting factor of which the expression is to be inhibited by the agent of the present invention is not particularly limited, as long as the cancer promoting factor is a factor capable of contributing to the improvement of a cell growth inhibiting ability, a cell migration inhibiting ability, a cell infiltration inhibiting ability, a cancer cell metastasis inhibiting ability and the like. Examples of the factor include CSF2, IL-6, ADAM10, ADM, CTGF, HBEGF, HILPDA, IL-24, THBS1, MYC, TGFB2, ADAM10, ITGA6, F3, PTP4A1, HBEGF, HSPA5, THBS1, PLAU, CYR61, ITGA6, EDIL3, CSF1, ITGB1 and MMP1.

The inhibitor of the present invention can be used as a preventing or treating agent for cancer. The inhibitor of the present invention can also be used as a cell growth inhibitor, a cell migration inhibitor, a cell infiltration inhibitor, a cancer cell metastasis inhibitor and the like.

The agent of the present invention is not particularly limited, as long as the agent contains at least one component selected from the group consisting of a RBMS expression inhibitor and a RBMS function inhibitor (wherein the component is also simply referred to as an "active ingredient" in the description). The agent may additionally contain other component, if necessary. The "other component" is not particularly limited, as long as the component is a pharmaceutically acceptable component. Examples of the "other component" include a base material, a carrier, a solvent, a dispersant, an emulsifying agent, a buffering agent, a stabilizer, an excipient, a binder, a disintegrating agent, a lubricant, a thickening agent, a moisturizing agent, a coloring agent, a fragrance and a chelating agent.

The mode of the usage of the agent of the present invention is not particularly limited, and a proper usage mode can be selected depending on the type of the agent. The agent of the present invention may be used in vitro (e.g., may be added to a culture medium for cultured cells) or may be used in vivo (e.g., may be administered to an animal).

The subject to which the agent of the present invention is to be applied is not particularly limited, and examples of the subject include various mammals such as human, monkey, mouse, rat, dog, cat, rabbit, pig, horse, cow, sheep, goat and deer; and animal cells. The type of the cell is not particularly limited, either. For example, a blood cell, a hematopoietic stem cell/progenitor cell, a gamete (a sperm, an ovum), a fibroblast, an epithelial cell, a vascular endothelial cell, a nerve cell, a liver cell, a keratin generating cell, a muscle cell, an epidermal cell, an endocrine cell, an ES cell, an iPS cell, a tissue stem cell, a cancer cell and the like can be mentioned.

The dosage form of the agent of the present invention is not particularly limited, and a proper dosage form may be selected depending on the mode of the usage of the agent. For example, in the case where it is intended to administer the agent to an animal, examples of the dosage form include an oral preparation such as a tablet, a capsule, a granule, a powder, a fine granule, a syrup, an enteric preparation, a sustained release capsule, a chewable tablet, a drop, a pill, a liquid or solution for oral application, a lozenge, a sustained-release preparation and sustained-release granule; and a preparation for cutaneous application such as a nasal preparation, an inhalation, a suppository for rectal application, a pessary, an enema and a jelly. The agent of the present invention may have any dosage form selected from a solid dosage form, a semi-solid dosage form and a liquid dosage form.

The content of the active ingredient in the agent of the present invention is not limited and varies depending on the intended use of the agent, a subject of the application of the agent, the condition of a subject of the application of the agent, and the like. The content is, for example, 0.0001 to 100% by weight, preferably 0.001 to 50% by weight.

In the case where it is intended to administer the agent to an animal, the dose of the agent to be administered is not particularly limited, as long as the dose is a dose effective for developing the pharmacological activity of the agent. The dose is generally 0.1 to 1000 mg/kg body weight per day, preferably 0.5 to 500 mg/kg body weight per day, in terms of the weight of the active ingredient for oral administration, and is generally 0.01 to 100 mg/kg body weight, preferably 0.05 to 50 mg/kg body weight per day, in terms of the weight of the active ingredient for parenteral administration. The dose is preferably administered in 1, 2 or 3 divided doses, per day, and may be increased or decreased appropriately depending on the age, clinical condition and disease conditions of a subject.

5. Diagnostic Agent

The present invention relates to a diagnostic agent for a disease in an animal, which contains a RBMS gene expression product detecting agent (wherein the diagnostic agent is also referred to as a "diagnostic agent of the present invention" in the present description). Hereinbelow, the diagnostic agent will be described.

The RBMS gene expression product which is to be detected with the RBMS gene expression product detecting agent is not particularly limited, as long as the RBMS gene expression product is one which is expressed in a living body of an organism to be diagnosed. Examples of the RBMS gene expression product include RBMS mRNA or a nucleic acid (e.g., cDNA) derived from the RBMS mRNA, RBMS protein and the like.

The animal to be diagnosed is not particularly limited, as long as the animal can express RBMS gene in vivo. Examples of the animal include various mammals such as human, monkey, mouse, rat, dog, cat and rabbit.

With respect to the RBMS gene expression product that is a substance to be detected, the same statements can apply to the statements mentioned with respect to the RBMS protein and the RBMS mRNA in the section "2. Screening reagent" above.

The RBMS gene expression product detecting agent is not particularly limited, as long as the detection and the quantification of the RBMS gene expression product as mentioned above can be achieved. In the case where the RBMS gene expression product is a nucleic acid (e.g., RBMS mRNA, a nucleic acid derived therefrom (e.g., cDNA)), examples of the RBMS gene expression product detecting agent include a primer and a probe. In the case where the RBMS gene expression product is a protein, an example of the RBMS gene expression product detecting agent is an antibody.

The primer, the probe or the like is not particularly limited, as long as RBMS mRNA, a nucleic acid derived therefrom or the like can be recognized selectively (specifically). The wording "recognize (recognizing) selectively (specifically)" as used herein refers to, but is not limited to, the matter that RBMS mRNA can be detected specifically in a northern blotting method, the matter that RBMS mRNA or a nucleic acid derived therefrom (e.g., cDNA) can be amplified specifically in a RT-PCR method, for example. The primer, the probe or the like may be any one, as long as a person skilled in the art can determine that the above-mentioned detected substance or amplified product is derived from RBMS mRNA.

Specific examples of the primer or the probe include at least one substance selected from the group consisting of a polynucleotide mentioned in item (e) and a polynucleotide mentioned in item (f):

(e) a polynucleotide having at least 15 contiguous nucleotides in the nucleotide sequence for RBMS mRNA and/or a polynucleotide complementary to the polynucleotide; and (f) a polynucleotide which can hybridize with the nucleotide sequence for RBMS mRNA or a nucleotide sequence complementary to the nucleotide sequence for RBMS mRNA under stringent conditions and has at least 15 nucleotides.

The term "a complementary polynucleotide" or "a complementary nucleotide sequence (a complementary strand, a negative strand) refers to a polynucleotide or a nucleotide sequence which is complementary to the full length sequence of a polynucleotide consisting of the nucleotide sequence for RBMS mRNA or a partial sequence of the full length sequence which has a nucleotide sequence consisting of at least 15 contiguous nucleotides in the above-mentioned nucleotide sequence (wherein each of the full length sequence and the partial sequence is referred to as a "positive strand" for convenience) on the basis of the nucleotide base pair relationship of A:T and G:C. In this regard, the complementary strand is not limited to one that can form a completely complementary sequence with the nucleotide sequence for the positive strand, and may also be one which has a complementary relationship with the positive strand of interest to such an extent that the complementary strand can hybridize with the positive strand under stringent conditions. The stringent conditions can be determined on the basis of the melting temperature (Tm) of a nucleic acid to which a complex or a probe is to be bonded, as taught by Berger and Kimmel (1987, Guide to Molecular Cloning Techniques Methods in Enzymology, Vol. 152, Academic Press, San Diego CA). For example, as the washing conditions after hybridization, the conditions around "1×SSC, 0.1% SDS, 37° C." can be mentioned. It is preferred that the complementary strand can be maintained in such a state that the complementary strand is hybridized with the positive strand of interest even when the complementary strand is washed under these conditions. Examples of the washing conditions include, but are not limited to around "0.5×SSC, 0.1% SDS, 42° C." as more stringent hybridization conditions, around "0.1×SSC, 0.1% SDS, 65° C." as still more stringent conditions. Concrete examples of the complementary strand include a strand consisting of a nucleotide sequence completely complementary to the nucleotide sequence for the positive strand of interest, and a strand consisting of a nucleotide sequence having at least 90%, preferably 95%, more preferably 98% or more, further preferably 99% or more identity to the strand.

The primer, the probe or the like can be designed by utilizing a vector NTI (manufactured by Infomax) on the basis of the nucleotide sequence for RBMS mRNA, such as a nucleotide sequence represented by SEQ ID NO: 3, 4, or 7. Concretely, the probe or the like can be obtained by applying the nucleotide sequence for RBMS mRNA to software of vector NTI. It is also possible to use a candidate sequence for the primer or probe or a sequence containing at least the sequence as a part thereof, as the primer or probe.

The nucleotide length of the primer, probe or the like is not particularly limited, as long as the primer, probe or the like has a length consisting of at least contiguous 15 nucleotides as mentioned above. The length of the primer, probe or the like can be set appropriately depending on the intended use. For example, in the case where it is intended to use as a primer, the nucleotide length is, for example, 15 to 100 nucleotides, preferably 15 to 50 nucleotides, more preferably 15 to 35 nucleotides. In the case where it is intended to use as a probe, the nucleotide length is, for example, 15 nucleotides to total number of nucleotides in the entire sequence, preferably 15 to 1000 nucleotides, more preferably 100 to 1000 nucleotides.

The primer, probe or the like may be modified, as long as the function thereof cannot be impaired significantly. Examples of the modification include the addition of a labeling substance, such as a fluorescent dye, an enzyme, a protein, a radioactive isotope, a chemiluminescent substance and biotin.

As the fluorescent dye to be used in the present invention, one which can label a nucleotide and can be used for the detection or quantification of a nucleic acid can be generally used. Specific examples of the fluorescent dye include, but are not limited to HEX (4,7,2',4',5',7'-hexachloro-6-carboxylfluorescein, a green fluorescent dye), fluorescein, NED (product name, manufactured by Applied Biosystems, a yellow fluorescent dye), 6-FAM (product name, manufactured by Applied Biosystems, a greenish yellow fluorescent dye), and rhodamine and a derivative thereof [e.g., tetramethyl rhodamine (TMR)]. As the method for labeling the nucleotide with a fluorescent dye, a proper method among known labeling methods can be employed [see Nature Biotechnology, 14, 303-308 (1996)]. Alternatively, a commercially available fluorescent labeling kit may also be used (e.g., an oligonucleotide ECL 3'-oligolabeling system, manufactured by Amersham Pharmacia).

The primer may also be immobilized onto an arbitrary solid phase upon use. Therefore, in the diagnostic agent of the present invention, the probe (an oligo- or polynucleotide) can be provided in the form of an immobilized probe (e.g., a DNA chip, a cDNA microarray, an oligo DNA array, a membrane filter or the like, on each of which the probe is immobilized; which are collectively named "a DNA chip or the like", hereinafter).

The solid phase to be used for the immobilization is not particularly limited, as long as an oligo- or polynucleotide can be immobilized thereon. Specific examples of the solid phase include a glass plate, a nylon membrane, microbeads, a silicon chip, a capillary and other substrates. The immobilization of the oligo- or polynucleotide onto the solid phase may be performed by a method in which a previously synthesized oligo- or polynucleotide is applied on a solid phase or by a method in which a desired oligo- or polynucleotide is synthesized on a solid phase. The immobilization method to be employed is well known in the art depending on the type of the probe to be immobilized, such as a method in which a commercially available spotter (manufactured by Amersham) is used in a DNA microarray technique [e.g., in situ synthesis of an oligonucleotide by a photolithographic technique (Affymetrix) or an inkjet technique (Rosetta Inpharmatics)].

The antibody or the like is not particularly limited, as long as the antibody or the like can recognize RBMS protein selectively (specifically). The wording "recognize selectively (specifically)" refers to the matter that RBMS protein can be detected specifically in, for example, a western blotting method or an ELISA method. The antibody or the like is not limited to the above-mentioned one, and may be any one as long as a person skilled in the art can determine that the substance to be detected is derived from RBMS protein.

The antibody includes a polyclonal antibody, a monoclonal antibody, a chimeric antibody, a single-stranded antibody, or a part of the antibody which has an antigen-binding property, such as a Fab fragment and a fragment produced by a Fab expression library. An antibody having an antigen-binding property to a polypeptide generally consisting of at least contiguous 8 amino acid residues, preferably 15 amino acid residues, more preferably 20 amino acid residues, contained in the amino acid sequence for RBMS protein can also be included within the scope of the antibody of the present invention.

The method for producing these antibodies is already known, and the antibody of the present invention can be produced by this conventional method (Current protocols in Molecular Biology, Chapter 11.12 to 11.13(2000)). Concretely, in the case where the antibody of the present invention is a polyclonal antibody, the antibody can be obtained by using RBMS protein that is expressed in *Escherichia coli* or the like and then purified in the conventional manner, or by synthesizing an oligopeptide having a partial amino acid sequence of the RBMS protein in the conventional manner, then immunizing a non-human animal, e.g., a domestic rabbit, with the RBMS protein or the oligopeptide and then collecting the antibody from serum from the immunized animal in the conventional manner. On the other hand, in the case where the antibody is a monoclonal antibody, the antibody can be obtained by immunizing a non-human animal, e.g., a mouse, with RBMS protein that is expressed in *Escherichia coli* or the like and then purified in the conventional manner or an oligopeptide having a partial amino acid sequence of the RBMS protein to produce a spleen cell, then performing cell fusion of the spleen cell to a myeloma cell to prepare a hybridoma cell, and then collecting the antibody from the hybridoma cell (Current protocols in Molecular Biology edit. Ausubel et al. (1987) Publish. John Wiley and Sons. Section 11.4 to 11.11).

The RBMS protein to be used as an immunizing antigen in the production of the antibody can be obtained on the basis of known gene sequence information by procedures including the cloning of DNA, the construction of plasmids, the transfection into a host cell, the culture of a transformant and the collection of a protein from a culture. These procedures can be carried out by a method known to a person skilled in the art or a method disclosed in a document (Molecular Cloning, T. Maniatis et al., CSH Laboratory (1983), DNA Cloning, DM. Glover, IRL PRESS (1985)) or the like.

Concretely, a protein that can be used as an immunizing antigen for the production of the antibody of the present invention can be obtained by producing recombinant DNA (expression vector) which enables the expression of a gene encoding RBMS to be expressed in a desired host cell, then introducing the recombinant DNA into a host cell to transform the host cell with the recombinant DNA to produce a transformant, then culturing the transformant to produce a culture, and then collecting the desired protein from the culture. Alternatively, a partial peptide of RBMS protein can also be produced by a conventional chemical synthesis method (peptide synthesis) in accordance with known gene sequence information.

The antibody of the present invention may be prepared by using an oligopeptide having a partial amino acid sequence of RBMS protein. The oligo(poly)peptide to be used for the production of the antibody is not required to have a functional biological activity but desirably has the same immunogenic property as that of RBMS protein. An example of the antibody is an oligo(poly)peptide that preferably has the immunogenic property and is consisting of at least 8 contiguous amino acid residues, preferably 15 amino acid residues, more preferably 20 amino acid residues, in the amino acid sequence for the RBMS protein.

The production of the antibody against the oligo(poly) peptide can be achieved by enhancing an immunological reaction using any one of various adjuvants depending on a host to be used. Examples of the adjuvant include, but are not limited to Freund's adjuvant; a mineral gel such as aluminum hydroxide; a surface-active substance such as lysolecithin, pluronic polyol, a polyanion, a peptide, an oil emulsifying agent, keyhole limpet hemocyanin and dinitrophenol; and a human adjuvant such as BCG (Bacille Calmette-Guerin) and *Corynebacterium parvum*.

The diagnostic agent of the present invention is not particularly limited, as long as the above-mentioned RBMS gene expression product detecting agent is contained. The diagnostic agent may be consisting of only the detection agent, or may additionally contain a substance necessary for the detection of a RBMS gene expression product in addition to the detection agent. Specific examples of the substance include a hybridization reagent, a label for a probe, a detection agent for a labeled substance, a buffer solution and a device. The diagnostic agent of the present invention may be in the form of a diagnostic agent kit including the above-mentioned components.

The diagnostic agent of the present invention can be used for the diagnosis about the occurrence of the cancer (i.e., whether or not a subject is suffering from the cancer) and the diagnosis about the degree of progression of the above-mentioned disease of interest, as mentioned in the sections "6. Method for detection of disease" and "7. Method for determination of degree of progression of disease" below.

6. Method for Detection of Disease

The present invention relates to a method for detecting a cancer (which is also referred to as the "disease detection method of the present invention" in the description), using the expression amount/level of RBMS as an index. Hereinbelow, the method will be described.

As a specific aspect of the disease detection method of the present invention, the following aspect can be mentioned:
(a1) measuring the expression amount/level of interest of a RBMS gene expression product in a sample collected from a subject; and
(b1) comparing the expression amount/level of interest measured in step (a1) with a control expression amount/level of the RBMS gene expression product in a sample collected from a control subject which does not suffer from the cancer, wherein (c1) the matter that the expression amount/level of interest is higher than the control expression amount/level is employed as an index for the determination that the subject has the cancer.

The subject is a target to which the disease detection method of the present invention is to be applied, and the species of the subject is not particularly limited. Examples of the subject include various mammals including human, monkey, mouse, rat, dog, cat, rabbit and the like.

The sample is not particularly limited, as long as a RBMS gene expression product is contained. The sample can be selected appropriately depending on the type of the disease to be detected and the like. Specific examples of the sample include a blood sample, a urine sample, and various tissue grafts. As the sample, a sample collected from a living organism may be used without any modification, and a sample produced by purifying and concentrating a RBMS gene expression product to be detected in the conventional manner is preferred. In the case where the RBMS gene expression product to be detected is a nucleic acid, it is possible to prepare a nucleic acid (e.g., cDNA) that reflects the sequence information of RBMS mRNA from the mRNA and use the resultant product as the sample.

The measurement of the expression amount/level of interest and the control expression amount/level of the RBMS gene expression product can be carried out by or in accordance with a known method. It is preferred to carry out the measurement using the diagnostic agent of the present invention mentioned below. In the case where the substance to be measured is a nucleic acid (RBMS mRNA or a nucleic acid derived therefrom (e.g., cDNA)), the measurement can be carried out by a northern blotting method, a RT-PCR method, a DNA chip analysis method, an in situ hybridization analysis method or the like using the nucleic acid as a probe or a primer, for example. In the case where the substance to be measured is a protein, the measurement can be carried out by a western blotting method, an ELISA method or the like using a specific antibody. The concrete manner of the method is as mentioned in the section "3.1 Screening method utilizing index (i)" above.

The control expression amount/level, which is to be compared with the expression amount/level of interest, may be a control expression amount/level of a single sample. However, it is preferred to employ an average value or a mean value of control expression amount/levels of multiple samples.

The determination whether or not a subject is suffering from a cancer is carried out by employing the matter that an expression amount/level of interest is larger compared with a control expression amount/level as a criterion. Concretely, for example, the determination can be carried out by employing, as an index, the matter that an expression amount/level of interest is increased by 50% or more, preferably 100% or more, more preferably 200% or more, relative to a control expression amount/level.

7. Method for Determination of Degree of Progression of Disease

The present invention relates to a method for determining the degree of progression of a cancer employing the expression amount/level of RBMS as an index (wherein the method also referred to as "the method for determining the degree of progression of the present invention" in the description). Hereinbelow, the method will be described.

As a specific aspect of the method for determining the degree of progression of the present invention, the following aspect can be mentioned:

(a2) measuring the expression amount/level of interest of a RBMS gene expression product in a sample collected from a subject suffering from the cancer; and (b2) comparing the expression amount/level of interest measured in step (a2) with a control expression amount/level of a RBMS gene expression product in a sample collected from a control subject suffer from the cancer, wherein (c3) the matter that the expression amount/level of interest is larger than the control expression amount/level is employed as an index for the determination that the subject has a higher degree of progression of the cancer than that of the control subject.

The subject, the sample, the measurement of the expression amount/level of interest and the control expression amount/level, the control expression amount/level to be compared with the expression amount/level of interest, and the like are as described in the section "6. Method for detection of disease" above.

The degree of progression of a disease can be defined as the severity of a condition associated with the expression of a cancer promoting factor such as CSF2, IL-6, ADAM10, ADM, CTGF, HBEGF, HILPDA, IL-24, THBS1, MYC, TGFB2, ADAM10, ITGA6, F3, PTP4A1, HBEGF, HSPA5, THBS1, PLAU, CYR61, ITGA6, EDIL3, CSF1, ITGB1 and MMP1.

The determination as at whether or not the degree of progression of a cancer in a subject is higher than that in a control subject can be determined by employing, as an index, the matter that the expression amount/level of interest is higher compared with the control expression amount/level. Concretely, the determination can be carried out by employing, as an index, the matter that the expression amount/level of interest is higher compared with the control expression amount/level by 50% or more, preferably 100% or more, more preferably 200% or more.

EXAMPLES

Hereinbelow, the present invention will be described in detail with reference to examples. However, the present invention is not limited to these examples.

Example 1: Identification of RBMS2 as IL-6 Post-Transcriptional Regulatory Factor Example 1A For the purpose of discovering an IL-6 post-transcriptional regulatory factor, screening was carried out. The schema is shown in FIG. 1A. Concretely, the following procedures were carried out. First, a reporter vector in which a luciferase ORF and an IL-6 3'UTR (SEQ ID NO: 1) were arranged downstream from a SV40 promoter in this order as observed from the 5' side was produced. The reporter vector and an expression vector for each of various genes were transfected into a HEK293T cell on a 384-well plate using a transfection reagent (Fugene H D, manufactured by Promega Corporation). 48 hours after the transfection, the luciferase activity in each well was measured. A measurement value thus obtained was compared with a measurement value of a control (i.e., a sample in which an empty vector was introduced as an expression vector), and an expression vector of which the measurement value was changed compared with the control was screened (primary screening). About 100 gene expression vectors which was correlated with RNA was picked up from the selected expression vectors, and the screening was carried out in the same manner as mentioned above (secondary screening).

As a result of the secondary screening, RBMS2 (NP_002889.1, SEQ ID NO: 2) was identified as an IL-6 post-transcriptional regulatory factor.

Example 1B

The reporter vector produced in Example 1A or a control reporter vector which was produced by removing a human TL-6 3'UTR from the reporter vector was introduced into a HEK 293 T cell together with a RBMS2 expression vector or an empty vector. 48 hours after the transfection, a luciferase activity was measured. The results are shown in FIG. 1B.

As shown in FIG. 1B, RBMS2 increased a luciferase activity in an IL-6 3'UTR-dependent manner.

Example 2: Stabilization of IL-6 mRNA by RBMS2 Via ARE

A mutant 3'UTR reporter vector was produced, in which a luciferase ORF and a mutant IL-6 3'UTR (97-267 (nucleotide sequence: SEQ ID NO: 16), 122-193 (nucleotide sequence: SEQ ID NO: 17), ΔARE1 (nucleotide sequence: SEQ ID NO: 18), ΔARE2 (nucleotide sequence: SEQ ID NO: 19) or an ARE mutant (nucleotide sequence: SEQ ID NO: 20)) were arranged downstream from a promoter in this order as observed from the 5' side. The mutant 3'UTR reporter vector was transfected into a HEK293T cell together with a RBMS2 expression vector or an empty vector. 48 hours lapsed after the transfection, a luciferase activity was measured. The results are shown in FIG. 2.

In a 3'UTR in IL-6 mRNA, there are a stem loop structure involved in the stabilization of mRNA and an AU-rich element (ARE) that is rich in AU. The stem loop structure is an element critical for the recognition by Regnase-1 (ZC3H12A) that is an RNase and the subsequent degradation. It is reported that ARID5a contributes to the stabilization of IL-6 mRNA by antagonizing the function of Regnase-1. However, as shown in FIG. 2C, RBMS2 increased the activity of a reporter (97-267 and 122-193) in which the stem loop structure was deleted in a 3'UTR.

In IL-6 mRNA, there are two adjacent AREs that are close to each other. It is known that an ARE binding protein, e.g. TTP, is involved in the degradation of mRNA through this area. As shown in FIG. 2C, when one of the ARE regions is deleted, the increase in the reporter activity caused by RBMS2 was not observed (ΔARE1 and ΔARE2). When the sequence for ARE was mutated (by substituting U by G), the increase in the reporter activity by RBMS2 was not observed, either (ARE mutant). From these results, it was suggested that RBMS2 was involved in the stabilization of mRNA through the ARE regions.

Example 3: Comprehensive Analysis of Factor Regulated by RBMS2 siRNA for RBMS2 (Thermo Fisher Scientific, Silencer® Select s11867) or control siRNA (Thermo Fisher Scientific, Silencer™ Select Negative Control No. 1) was transfected into cells of MDA-MB-231 that was a breast cancer cell strain using Lipofectamine RNAiMax. After 48 hours, RNA was prepared from the cell, and sequencing was carried out with a next generation sequencer (Illumina, Inc., Next-seq). 427 genes were identified as genes each of which was mutated in such a manner the gene expression thereof was increased by two-hold or more or was decreased by two-fold or more by RBMS2 knockdown. 243 genes were extracted as genes in each of which an ARE sequence was contained in 3'UTR.

Example 4: Gene Ontology Analysis

A group of genes in each of which the gene expression was changed by two-fold or more or ½ or less by RBMS2 knockdown and an ARE was contained in 3'UTR was subjected to a gene ontology analysis using DAVID (https://david.ncifcrf.gov/tools.jsp). As a result, "cell growth" and "cell migration" were extracted as biological processes in each of which the p value was 5% or less and the FDR value was 10% or less. From the result, it was suggested that "cell growth" and "cell migration" were regulated by RBMS2. Furthermore, as target genes of RBMS2, 11 genes capable of promoting cell growth (CSF2, IL6, ADAM10, ADM, CTGF, HBEGF, HILPDA, IL24, THBS1, MYC and TGFB2) and 9 types of genes capable of promoting cell migration (ADAM10, ITGA6, F3, PTP4A1, HBEGF, HSPA5, THBS1, PLAU and CYR61) were identified. All of these genes are genes in each of which the gene expression was decreased by half or less by RBMS2 knockdown.

Example 5: Analysis of Influence of RBMS2 on Cell Growth

Example 5A: Analysis on Surviving Cells siRNA for RBMS2 (Thermo Fisher Scientific, Silencer® Select s11867) or control siRNA (Thermo Fisher Scientific, Silencer™ Select Negative Control No. 1) was transfected into MDA-MB-231 cells using Lipofectamine RNAiMax. After 48 hours, the amount of surviving cells was measured using RealTime-Glo™ MT Cell Viability Assay (Promega Corporation). The results are shown in FIG. 3A.

As shown in FIG. 3A, the cell growth was inhibited by RBMS2 knockdown.

Example 5B: Analysis of Number of Cells

MDA-MB-231 cells were seeded onto a 96-well plate and were then cultured overnight (16 hours), and then siRNA for RBMS2 (Thermo Fisher Scientific, Silencer® Select s11867) or control siRNA (Thermo Fisher Scientific, Silencer™ Select Negative Control No. 1) was transfected into the cells using Lipofectamine RNAiMax. The time point immediately after the transfection of siRNA was defined as "time 0", and the number of cells was counted every 24 hours thereafter. For the counting of the number of cells, CellTiter 96® AQueous One Solution Cell Proliferation Assay (Promega Corporation) was used. The results are shown in FIG. 3B.

As shown in FIG. 3B, the cell growth was inhibited by RBMS2 knockdown.

Example 5C: Analysis of Akt Pathway and STAT3 Pathway siRNA for RBMS2 (Thermo Fisher Scientific, Silencer® Select s11867) or control siRNA (Thermo Fisher Scientific, Silencer™ Select Negative Control No. 1) was transfected into MDA-MB-231 cells using Lipofectamine RNAiMax.

After 48 hours, the cells were stimulated with IL-1β (20 ng/ml) for 30 minutes or 60 minutes. The cells were washed with PBS, and were then suspended in a lysis solution (20 mM Tris-HCl, pH 7.5, 150 mM NaCl, 1% NP40, 0.5% Sodium deoxycholate). An extracted protein (10 μg) was separated by SDS-PAGE and was then transferred onto a PVDF membrane, and then western blotting was carried out. As primary antibodies, anti-Phospho-Akt (Ser473) (Cell Signaling Technology, #4060), anti-Akt (total) (Cell Signaling Technology, #4691), anti-Phospho-Stat3 (Tyr705) (Cell Signaling Technology, #9145), anti-STAT3 (total) (Santa Cruz, sc-482) and anti-Tubulin (Cell Signaling Technology, #2148) were used each at a dilution rate of ×1,000. As a secondary antibody, Anti-Rabbit IgG, HRP-Linked F(ab')2 Fragment Donkey (GE Healthcare, NA9340) was used at a dilution rate of ×10,000. Emission of light was caused with an ECL reagent (Thermo Fisher Scientific, Pierce™ ECL Western Blotting Substrate) and was then imaged with ImageQuant LAS4000mini (GE Healthcare). The results are shown in FIG. 3C.

As shown in FIG. 3C, the signaling pathway associated with cell growth was inhibited by RBMS2 knockdown.

Example 6: Analysis of Influence of RBMS2 on Cell Migration Ability siRNA for RBMS2 (Thermo Fisher Scientific, Silencer® Select s11867) or control siRNA (Thermo Fisher Scientific, Silencer™ Select Negative Control No. 1) were transfected into MDA-MB-231 cells using Lipofectamine RNAiMax. After 48 hours, the cells were treated with trypsin to prepare a cell suspension. The cells were washed twice with a culture medium without serum (a serum-free DMEM culture medium). DMEM containing 800 μl of 10% serum was added into a 24-well plate, and then Transwell insert (Corning, #353097) was installed therein. The cells suspended in the serum-free DMEM culture medium were seeded onto the Transwell insert. After 16 hours, the cells were stained with crystal violet. The matter that a larger number of stained cells are detected indicates that cell migration ability is higher. The results are shown in FIG. 4.

As shown in FIG. 4, the cell migration ability was inhibited by RBMS2 knockdown.

Example 7: Analysis of Influence of RBMS2 on Cell Infiltration Ability siRNA for RBMS2 (Thermo Fisher Scientific, Silencer® Select s11867) or control siRNA (Thermo Fisher Scientific, Silencer™ Select Negative Control No. 1) was transfected into MDA-MB-231 cells using Lipofectamine RNAiMax. After 48 hours, the cells were treated with trypsin to prepare a cell suspension. The cells were washed twice with a culture medium without serum (a serum-free DMEM culture medium). DMEM containing 800 μl of 10% serum was added into a 24-well plate, and then a matrigel invasion chamber (Corning, #354480) was installed therein. The cells suspended in the serum-free DMEM culture medium were seeded onto the matrigel invasion chamber. After 16 hours, the cells were stained with crystal violet. The matter that a larger number of stained cells are detected indicates that the cell infiltration ability is higher. The results are shown in FIG. 5.

As shown in FIG. 5, the cell infiltration ability was inhibited by RBMS2 knockdown.

Example 8: Analysis of Metastasis-Associated Factor Regulation Ability of RBMS2

Example 8A

A reporter vector shown below, a *Renilla luciferase* expression vector and a RBMS2 expression vector or a control empty vector were transfected into HEK293T cells. After 48 hours, a luciferase assay was carried out using Dual-Glo Luciferase Assay System (Promega Corporation). The results are shown in FIG. 6.

The reporter vector: a vector in which a 3'UTR (F3: refseqID NM_001178096.1 939 to 2233 (SEQ ID NO: 21), PLAU: refseqID NM_001145031.2 1731 to 2625 (SEQ ID NO: 22), HBEGF: refseqID NM_001945.2 903 to 2358 (SEQ ID NO: 23), THBS1: refseqID NM_003246.3 3693 to 7237 (SEQ ID NO: 24), CYR61: refseqID NM_001554.4 1371 to 2288 (SEQ ID NO: 25), ITGA6: refseqID NM_000210.3 3457 to 5842 (SEQ ID NO: 26), HSPA5: refseqID NM_005347.4 2227 to 3970 (SEQ ID NO: 27)), (EDIL3: refseqID NM_005711.4 1937 to 4772 (SEQ ID NO: 28), (CSF1: refseaID NM_000757.5 2079 to 4250 (SEQ ID NO: 29), (ITGB1: refseqID NM_002211.3 2619 to 3880 (SEQ ID NO: 30) or (MMP1: refseqID NM_002421.3 1554 to 2082 (SEQ ID NO: 31) of a gene showing gene ontology that defines cell motion (i.e., a metastasis-related factor), among genes each showing the decrease in an expression amount/level when RBMS2 was knocked down, was arranged downstream from Firefly luciferase gene that can be expressed under the regulation of SV40 promoter.

As shown in FIG. 6, the expression amount/level of the reporter vector carrying the 3'UTR of the metastasis-related factor was increased by the overexpression of RBMS2. From these results, it was suggested that RBMS2 stabilized mRNA of a metastasis-related factor through a 3'UTR.

Example 8B

A reporter vector carrying a 3'UTR of F3 gene (Example 8A) or a reporter vector prepared by mutating all elements (6 elements) of an Au-rich element (AUUUA) in the 3'UTR in the above-mentioned vector and a FLAG-tagged RBMS2 expression vector were introduced into HEK293T cells. The cells were collected after 48 hours, and were then dissolved in 1 ml of RIP lysis buffer (20 mM Tris-HCl, pH 7.5, 100 mM KCl, 5 mM MgCl$_2$, 0.5% NP-40, 40 U/μl RNase inhibitor (Toyobo Co., Ltd.), Complete mini protease inhibitor cocktail (Roche) and 1 μM PMSF). The resultant solution was allowed to leave on ice for 15 minutes and was then centrifuged at 20,000×g for 5 minutes, and a supernatant was collected. A portion (50 μl) of the supernatant was stored as an input. The remainder of the supernatant was divided into two 450-1 portions, and then 2 μg of a normal mouse IgG and an anti-FLAG antibody (SIGMA, F1804) were added to the portions, respectively. Subsequently, 50 μl of Protein G Dynabeads (Thermo Fisher Scientific) was added to each of the solutions, and the resultant solutions were allowed to react at 4° C. for 2 hours. After the reaction, the beads were washed three times with a RIP lysis buffer. Each of the input and immunoprecipitated RNA was purified with ReliaPrep™ RNA Cell Miniprep System (Promega Corporation), and was then subjected to reverse transcription using a random primer. The contraction efficiency was determined as a value relative to the value of the input by quantitative PCR. The results are shown in FIG. 7.

As shown in FIG. 7, it was found that RBMS2 bound to the 3'UTR of F3 gene and the binding amount/level therebetween was decreased when the AU-rich element was mutated. From these results, it was suggested that RBMS2 was bound to the 3'UTR of F3 gene through the AU-rich element.

Example 9: Analysis of Homology Among RBMS Family Members

The homology among human RBMS1 (RefseqID; NP_058520.1), human RBMS2 (RefseqID; NP_002889.1) and human RBMS3 (RefseqID; NP_001003793.1) was analyzed using CLC sequence viewer. The results of the analysis are shown in FIG. 8.

As shown in FIG. 8, in RBMS2, a RRM1 domain (i.e., a region laying between the 1st position and the 128th position from the N-terminal) that is critical for the binding to target RNA and aromatic amino acid residues (*phenylalanine, RBMS1; F107 and F110, RBMS2; F101 and F104, RBMS3; F106 and F109) in the RPM1 domain were highly conserved.

Example 10: Analysis of Expression of RBMS Family

RNA was prepared from each of a HEK293T cell (a human embryonic kidney cell), a MCF7 cell (breast cancer), a MDA-MB-231 cell (breast cancer), an A549 cell (lung cancer), a HeLa cell (cervical cancer), a HepG2 cell (lung cancer), a U87 cell (brain tumor), a THP1 cell (monocytic leukemia), a U937 cell (monocytic leukemia), a Ramos cell (Burkitt's lymphoma, B-cell neoplasm), a Jurkat cell (acute T-cell leukemia), a RAW264.7 cell (a macrophage), a HH4-13 cell (a T cell), an A20 cell (a B cell, a B16 cell (melanoma), a 3T3 cell (a fibroblast), a 3T3L1 cell (a fibroblast) and a 10T1/2 cell (a mesenchymal stem cell), and was then reverse-transcribed using oligo-dT as a primer. The expression amount/level of human or murine RBMS1, 2 or 3 was measured by quantitative PCR using THUNDER-BIRD (registered trade name) SYBR qPCR Mix (Toyobo Co., Ltd.). The results are shown in FIG. 9. In FIG. 9, the expression amount/level of each of the genes was expressed by an expression amount/level relative to that of HPRT gene.

The sequences for primers used in the PCR are as shown below.

```
Human HPRT
                              (SEQ ID NO: 32)
(5'-CCTGGCGTCGTGATTAGTGA-3'
and
                              (SEQ ID NO: 33))
5'-CGAGCAAGACGTTCAGTCCT-3'
Human RBMS1
                              (SEQ ID NO: 34)
(5'-CACCACCAGGAGTTTCTGCC-3'
and
                              (SEQ ID NO: 35))
5'-CAGCAAGTCTCACCTCTCCTT-3'
Human RBMS2
                              (SEQ ID NO: 36)
(5'-CATCTCTCCCTCAGCAGCAC-3'
and
                              (SEQ ID NO: 37))
5'-GCTGCTCTCCTCGACTGAAA-3'
Human RBMS3
                              (SEQ ID NO: 38)
(5'-TCTCCAAACCAAGCAGTCCT-3'
and
                              (SEQ ID NO: 39))
5'-GGAGGCCTCGAATGTACAGG-3'
Murine HPRT
                              (SEQ ID NO: 40)
(5'-CTTCCTCCTCAGACCGCTTT-3'
and
                              (SEQ ID NO: 41))
5'-CATCATCGCTAATCACGACGC-3'
Murine RBMS1
                              (SEQ ID NO: 42)
(5'-GAGATGATCTTCCCCAGCGG-3'
and
                              (SEQ ID NO: 43))
5'-GGACCAGAGACTGCTGCTTG-3'
Murine RBMS2
                              (SEQ ID NO: 44)
(5'-TGGCCTAGGAGGGGTTAGAC-3'
and
                              (SEQ ID NO: 45))
5'-GCTGGATGCCACTTCTCAGT-3'
Murine RBMS3
                              (SEQ ID NO: 46)
(5'-TGGACCACCCCATGTCAATG-3'
and
                              (SEQ ID NO: 47))
5'-TGAATCGTTCCTGCTGTCCC-3'.
```

Example 11: Post-Transcriptional Regulation by RBMS Family

A reporter vector shown below, a *Renilla luciferase* expression vector and a RBMS1, RBMS2 or RBMS3 expression vector or a control empty vector were transfected into HEK293T cells. After 48 hours, a luciferase assay was carried out using Dual-Glo Luciferase Assay System (Promega Corporation). The results are shown in FIG. 10.

The reporter vector; a vector in which a 3'UTR of human IL-6 (RefseqID:NM_000600.4, nucleotide-755 to nucleotide-1023) (SEQ ID NO: 48) or a 3'UTR of human IL-8 (RefseqID; NM_000584.3, nucleotide-936 to nucleotide-1293 (SEQ ID NO: 49)) was arranged downstream from Firefly luciferase gene that can be expressed under the regulation of SV40 promoter.

As shown in FIG. 10, the expression amount/level of the reporter vector carrying the 3'UTR of IL-6 or IL-8 was increased by the overexpression of RBMS. From these results, it was suggested that RBMS1 and RBMS3 as well as RBMS2 stabilized mRNA through a 3'UTR.

Example 12: Inhibition of Growth of Cancer by RBMS Family

MDA-MB-231 cells were seeded onto a 96-well plate and were then cultured overnight (16 hours), and then siRNA for RBMS1 (Thermo Fisher Scientific, Silencer® Select s11864), siRNA for RBMS2 (Thermo Fisher Scientific, Silencer® Select s11867) or control siRNA (Thermo Fisher Scientific, Silencer™ Select Negative Control No. 1) was transfected into the cells using Lipofectamine RNAiMax. The time point immediately after the transfection of siRNA was defined as "time 0", and the number of cells was counted every 24 hours thereafter. For the counting of the number of cells, CellTiter 96® AQueous One Solution Cell Proliferation Assay (Promega Corporation) was used. The results are shown in FIG. 11.

As shown in FIG. 11, the growth of cancer cells was inhibited by RBMS knockdown.

Example 13: Inhibition of Metastasis of Cancer by RBMS Family

Control or short hairpin RNA (shRNA) for RBMS2 was expressed in cells of murine melanoma cell strain B16 using a retrovirus to establish knockdown cells. Cells that were in a logarithmic growth phase were detached with trypsin/EDTA, were then washed twice with PBS, and were then suspended in a serum-free DMEM culture medium so that the concentration of the cells became $1 \times 10^6$/ml. A liquid cell suspension containing $2 \times 10^5$ cells (200 µl) was administered to a C57BL/6J mouse (8-week-age, female) through a tail vein. After 3 weeks, the lung was excised, and the occurrence of metastasis was evaluated.

The shRNA sequences are as follows.

```
Control shRNA;
                                       (SEQ ID NO: 50)
5'-GCTACACAAATCAGCGATTT-3', RBMS2 shRNA;
                                       (SEQ ID NO: 51)
5'-GGAAACCACCTTCAACCAACT-3'.
```

The results are shown in FIG. 12. When B16 cells in each of which control shRNA was expressed were administered, two metastatic lesions in the lung were observed (one lesion is a black part indicated by an arrow in FIG. 12, and the other is not observed in the view field in FIG. 12 or occurs on the rear surface of the view field). When RBMS2 knockdown B16 cells were administered, the occurrence of metastasis to the lung was not observed.

Example 14: Search for Factor Capable of Regulating Expression of RBMS

IL-10 protein or TGFβ protein was added to a culture medium of a Jurkat cell that was a human T cell strain (final concentration: IL-10 protein→20 ng/mL, TGFβ protein→10 ng/mL). cDNA from the cell before the addition and 8 hours after the addition and 24 hours after the addition was prepared, and the expression amount/levels of RBMS2 mRNA and HPRT (control) mRNA were measured by quantitative PCR. The results are shown in FIG. 13.

As shown in FIG. 3, the expression amount/level of RBMS2 mRNA was decreased by the addition of IL-10 protein. This result demonstrated that IL-10 protein had an effect to inhibit the expression of RBMS2.

Example 15: Analysis of Binding Site of RBMS on RNA

Binding sites of RBMS on RNA were analyzed by PAR-CLIP. The schematic illustration of PAR-CLIP is shown in FIG. 14. Concretely, the following procedures were carried out.

Establishment of Doxycycline-Induced RBMS2-Expressing Cell

Human RBMS2 having a FLAG tag attached thereto was cloned into a pCLT-EFS-Pur vector, and was then transfected into HEK293T cells together with a pCAG-HIVgp vector and a pCMV-VSV-G-RSV-Rev vector to produce lentiviruses. MDA-MB-231 cells were infected with the lentiviruses thus produced for 24 hours, and were then cultured for 5 days in the presence of 1 µg/ml of puromycin.

Immunoprecipitation $2 \times 10^6$ cells were seeded onto six 15-cm dishes and were then cultured overnight, then doxycycline (final concentration: 10 ng/ml) and 4-thiouridine (final concentration: 100 µM) were added to the cells, and the cells were cultured for 16 hours and were then irradiated with UV light having a wavelength of 365 nm at 150 J/cm$^2$ to cause the crosslinking of RNA and the protein. The cells were collected with a cell scraper, and were then suspended in a cell lysing solution to prepare a cell lysate. An anti-FLAG-tagged antibody (SIGMA; M2, 10 µg) and Protein A magnetic beads (Thermo Fisher Scientific K.K.) were added, and then the resultant solution was allowed to react at 4° C. for 2 hours to cause immunoprecipitation.

Extraction of RNA and Addition of Linker

A linker (sequence: 5'-UGGAAUUCUCGGGUGC-CAAGG-3' (SEQ ID NO: 52)) was added to the immunoprecipitate (an RNA-(RBMS2 protein) complex) on the 3' side of the RNA using T4 RNA ligase (NEB), and then the 5' side of the RNA was radioisotope-labeled with [γ-32P] ATP. The resultant product was electrophorased on SDS-PAGE and was then transferred onto a nitrocellulose membrane, then the RNA/(RBMS2 protein) complex (about 55 to 80 kDa) was cleaved out, and then RNA was purified from the cleaved specimen. A linker (sequence: 5'-GUUCAGAGUUCUACAGUCCGACGAUC-3' (SEQ ID NO: 53)) was added to the 5' side of the purified RNA using T4 RNA ligase (NEB), then reverse transcription was carried out using the resultant RNA as a template and using a specific primer (sequence: 5'-CCTTGGCACCCGAGAAT-TCCA-3' (SEQ ID NO: 54)) to synthesize cDNA (Thermo Fisher Scientific K.K., SuperScript III).

PCR

PCR was carried out using the cDNA as a template and using the following primers to perform the addition of an index.

```
RNA PCR Primer 1st
                                       (SEQ ID NO: 55)
5'-GTTCAGAGTTCTACAGTCCGA-3'

RNA PCR Primer, Index1 1st
                                       (SEQ ID NO: 56)
5'-CCTTGGCACCCGAGAATTCCA-3'
```

The addition of an index was carried out using a first-stage PCR product as a template and using the primers shown below, and a PCR product having about 200 bp was cleaved out and was then purified.

```
RNA PCR Primer
                                       (SEQ ID NO: 57)
5'-AATGATACGGCGACCACCGAGATCTACACGTTCAGAGTTCTACAGTC

CGA-3'

RNA PCR Primer, Index1
                                       (SEQ ID NO: 58)
5'-CAAGCAGAAGACGGCATACGAGATCGTGATGTGACTGGAGTTCCTTG

GCACCCGAGAATTCCA-3'.
```

Next Generation Sequencer

The concentration of the PCR product was adjusted to 10 pM, and was then sequenced using MiSeq (Illumina, Inc.). An adapter sequence was trimmed from the sequence information of Fastq film obtained by the next generation sequencing analysis using FaQCs, and was then mapped on human genome sequence (hg38) using Bowtie. The mapped sequence information was visualized using IGV.

Results

As a representative example, the results in genome regions of IL-6, IL-8 (CXCL8) and CXCL1 are shown in FIG. 15. It was found that RBMS2 was bonded to the 3'UTR (particularly an AU-rich element) in each of the genes.

Example 16: Expression of RBMS in Highly Malignant Cancer

Date on GSE6883-GPL96 or GSE6883-GPL97 was obtained from GEO (Gene Expression Omnibus) database (the original literature: Liu et al. N Engl J Med 2007; 356:217-26), and the expression data on RBMS2 (probe ID; 205228_at) and RBMS1 (probe ID; 237860_at) were analyzed.

The expression data of RBMS2 is shown in FIG. 16A, and the expression data of RBMS1 is shown in FIG. 16B. It was found that RBMS was highly expressed in highly malignant cancer (H: CD44$^+$CD24$^-$ cancer cell).

Example 17: Analysis of Mechanism of Regulation of Expression of RBMS

The mechanism of regulation of the expression of RBMS was analyzed. Concretely, the following procedures were carried out.

The quantitative PCR primers used are as follows. In the examples mentioned below, the primers mentioned in this section were also used, unless otherwise stated.

```
KRAS primers
hKRAS-Fw:
                                    (SEQ ID NO: 59)
TGGTGAGGGAGATCCGACAA hKRAS-Rv:
                                    (SEQ ID NO: 60)
AGGCATCATCAACACCCAGA IL-6 primers
hIL6-Fw:
                                    (SEQ ID NO: 61)
CTCCAGGAGCCCAGCTATGA hIL6-Rv:
                                    (SEQ ID NO: 62)
GAGGTGAGTGGCTGTCTGTG HPRT primers
hHPRT-Fw:
                                    (SEQ ID NO: 63)
GCTGGCGTCGTGATTAGTGA hHPRT-Rv:
                                    (SEQ ID NO: 64)
CGAGCAAGACGTTCAGTCCT CXCL1 primers
hCXCL1-Fw:
                                    (SEQ ID NO: 65)
TCACAGTGTGTGGTCAACAT hCXCL1-Rv:
                                    (SEQ ID NO: 66)
AGCCCCTTTGTTCTAAGCCA RBMS2 primers
hRBMS2-Fw:
                                    (SEQ ID NO: 67)
GTGATAGGCCAGGGGAGTAG hRBMS2-Rv:
                                    (SEQ ID NO: 68)
ACTCTGCTCCTATGCTGGTG.
```

The siRNA molecules used are as follows. In the examples mentioned below, the siRNA molecules mentioned in this section were also used, unless otherwise stated.

siRNA for KRAS Knockdown Test (Qiagen K. K.)

siNega: AllStars Negative Control siRNA (SI03650318) Sequence is undisclosed. siKRAS: Hs_KRAS_2 FlexiTube siRNA (Cat. No. SI03106824) Sequence is undisclosed.

siRNA for RBMS2 Knockdown Test (Thermo-Fisher Scientific)

Negative control (Thermo Fisher Scientific (Ambion), Silencer (registered trade name) Select Negative Control No. 1 siRNA, product No.: 4390843) Sequence is undisclosed. Human RBMS2-1 (Thermo Fisher Scientific (Ambion), Silencer (registered trade name) Select, siRNAID No. s11867) Sequence: UUUGCACAAAUUUUCCUUGGT (SEQ ID NO: 69).

Quantitative PCR 1

RNA was purified from MCF-7 or MDA-MB-231 cells (Promega Corporation; ReliaPrep Cell mini prep kit), and was then reverse-transcribed with an oligo-dT primer (Toyobo Co., Ltd.; ReverTra Ace). The expression of RBMS2 was analyzed using qPCR (Toyobo Co., Ltd.; THUNDERBIRD (registered trade name) qPCR Mix). The measured value was corrected by the expression amount/level of HPRT. The results are shown in FIG. 17A.

Western Blotting

MCF-7 or MDA-MB-231 cells were suspended in a lysis buffer (20 mM Tris-HCl, pH7.5, 150 mM NaCl, 0.5 m MEDTA, 1% Triton X-100, 0.5% sodium deoxycholate, Complete mini protease inhibitor cocktail (Roche)), then the resultant suspension was allowed to leave on ice for 15 minutes and was then centrifuged (15,000 rpm, 4° C., 5 minutes), and then a supernatant was collected. A protein sample (20 μg) was electrophoresed with 10% SDS-PAGE and was then transferred onto a PVDF membrane. The membrane was blocked (Nacalai Tesque INC.; Blocking One) at room temperature for 1 hour, and was then reacted with a 2,000-fold-diluted RBMS2 antibody (a rabbit polyclonal, an autologously produced antibody) overnight. The resultant product was washed three times with TBST (20 mM Tris-HCl, pH 7.5, 150 mM NaCl, 0.05% Tween-20) for 10 minutes, and was then reacted with an HRP-labeled anti-rabbit IgG antibody at room temperature for 1 hour. Bands were visualized with an ECL reagent. The results are shown in FIG. 17B.

Quantitative PCR 2

KRAS (a G13D mutant) was cloned into a pCSII-CMV-MCS-Venus vector. A pCSII-CMV-MCS-Venus empty vector or a pCSII-CMV-MCS-Venus-KRAS (G13D) vector was transfected together with a pCAG-HIVgp vector and a pCMV-VSV-G-RSV-Rev vector into HEK293T cells with polyethylenimine, and the resultant product was cultured for 48 hours to produce lentiviruses. MCF-7 cells were infected with a collected supernatant and were then cultured for 5 days, then RNA was purified (Promega Corporation; ReliaPrep Cell mini prep kit) and was then reverse-transcribed with an oligo-dT primer (Toyobo Co., Ltd.; ReverTra Ace).

The expression of RBMS2 and IL-6 was analyzed using qPCR (Toyobo Co., Ltd.; THUNDERBIRD (registered trade name) qPCR Mix). The measured value was corrected by the expression amount/level of HPRT. The results are shown in FIG. 17C.

Quantitative PCR 3 siRNA negative control (siNega) or siRNA for KRAS (siKRAS) (10 pmol) was transfected into MDA-MB-231 cells using Lipofectamine RNAiMAX Transfection Reagent (Thermo Fisher Scientific), and the cells were cultured for 48 hours. RNA was purified (Promega Corporation; ReliaPrep Cell mini prep kit) and was then reverse-transcribed with an oligo-dT primer (Toyobo Co., Ltd.; ReverTra Ace). The expression of RBMS2, KRAS and IL-6 was analyzed using qPCR (Toyobo Co., Ltd.; THUNDERBIRD (registered trade name) qPCR Mix). The measured value was corrected by the expression amount/level of HPRT. The results are shown in FIG. 17D.

Results

It was found that RBMS2 was expressed in a high expression amount/level in highly malignant cancer having a KRAS G13D mutation (MDA-MB-231) (FIGS. 17A and 17B). It was also found that, when a KRAS G13D mutant was transfected into cells each having no KRAS G13D mutation (MCF-7), the expression amount/level of RBMS2 and the expression amount/level of a cancer promoting factor of which the expression can be regulated by RBMS2 (IL-6) were increased (FIG. 17C). It was also found that, when KRAS in cells each having a KRAS G13D mutant (MDA-MB-231) was inhibited, the expression amount/level of RBMS2 and the expression amount/level of a cancer promoting factor of which the expression can be regulated by RBMS2 (IL-6) were decreased (FIG. 17D). From these results, such a mechanism was suggested that the expression of RBMS2 was promoted by a KRAS G13D mutant and, as a result, mRNA for a cancer promoting factor such as IL-6 was stabilized and the expression amount/level of the cancer promoting factor was increased (FIG. 17E).

Example 18: Relationship Between Expression of RBMS and Prognosis

The expression of RBMS2 or RBMS1 in pancreatic cancer, colorectal cancer, lung cancer or breast cancer was analyzed on the basis of Human protein atlas database (http://www.proteinatlas.org).

The results are shown in FIG. 18. It was found that the prognosis of these types of cancer tended to be worsened when RBMS1 and RBMS2 were highly expressed.

Example 19: Correlation Between Expression of RBMS and Mutation of KRAS 1

RNA was purified from MCF-7 (breast cancer, KRAS; WT), MDA-MB-231 (breast cancer, KRAS; G13D), LoVo (colorectal cancer, KRAS; G13D) or Panc1 (pancreatic cancer, KRAS; G12V) (Promega Corporation; ReliaPrep Cell mini prep kit), and was then reverse-transcribed with an oligo-dT primer (Toyobo Co., Ltd.; ReverTra Ace). The expression of RBMS2 was analyzed using qPCR (Toyobo Co., Ltd.; THUNDERBIRD (registered trade name) qPCR Mix). The measured value was corrected by the expression amount/level of HPRT.

The results are shown in FIG. 19. It was found that the expression amount/level of RBMS was increased in various KRAS mutant cells. From this result, it was suggested that the expression of RBMS2 was induced by a KRAS mutant.

Example 20: Correlation Between Expression of RBMS and Mutation of KRAS 2

The quantitative PCR primers used in this example for the first time were as follows. In the examples mentioned below, the primers mentioned in this section were also used, unless otherwise stated.

```
IL-8 primers
hIL8-Fw:
                                  (SEQ ID NO: 70)
ACCGGAAGGAACCATCTCAC hIL8-Rv:
                                  (SEQ ID NO: 71)
GGCAAAACTGCACCTTCACAC RBMS1 primers
hRBMS1-Fw:
                                  (SEQ ID NO: 72)
CCATGGCATAGAGAAGGAGAGG hRBMS1-Rv:
                                  (SEQ ID NO: 73)
TAGCAGCTGTAGTTGGGTCG.
```

Each of KRAS and mutants thereof (G12D, G12S, G12V, G13D) was cloned into a pCLT-EFS-Pur vector. ApCLT-EFS-Pur empty vector, a pCLT-EFS-Pur-KRAS vector or a mutant vector thereof was transfected together with a pCAG-HIVgp vector and a pCMV-VSV-G-RSV-Rev vector into HEK293T cells with polyethylenimine, and the cells were cultured for 48 hours to produce lentiviruses. MCF-7 cells were infected with a collected supernatant, and were then cultured for 5 days in the presence of 1 g/ml of puromycin. The cells were cultured in a culture medium containing 100 ng/ml or 1000 ng/ml of doxycycline for 72 hours, and then RNA was purified (Promega Corporation; ReliaPrep Cell mini prep kit) and was then reverse-transcribed with an oligo-dT primer (Toyobo Co., Ltd.; ReverTra Ace). The expression of RBMS2, RBMS1, IL-8 and IL-6 was analyzed using qPCR (Toyobo Co., Ltd.; THUNDERBIRD (registered trade name) qPCR Mix). The measured value was corrected by the expression amount/level of HPRT.

The results for RBMS2 are shown in FIG. 20A, the results for RBMS1 are shown in FIG. 20B, the results for IL-6 are shown in FIG. 20C, and the results for IL-8 are shown in FIG. 20D. From these results, it was suggested that the expression of RBMS2 and RBMS1 was induced by a KRAS mutant.

Example 21: Stability of mRNA in KRAS Mutant Cells

Stability of mRNA in KRAS mutant cells was analyzed. Concretely, the following procedures were carried out.

MCF-7 cells and MDA-MB-231 cells were stimulated with 20 ng/ml of human IL-1β for 3 hours, then 5 μg/ml of actinomycin D was added to the cells, and RNA each of after 1 hour and 2 hours was purified (Promega Corporation; ReliaPrep Cell mini prep kit) and was then reverse-transcribed with an oligo-dT primer (Toyobo Co., Ltd.; ReverTra Ace). The expression of IL-6 was analyzed using qPCR (Toyobo Co., Ltd.; THUNDERBRD (registered trade name) qPCR Mix). The measured value was corrected by the expression amount/level of HPRT. The amount of remaining RNA was calculated, wherein the expression amount/level in a sample without the addition of actinomycin D was defined as "100%". The results are shown in FIG. 21A.

Actinomycin D (5 μg/ml) was added to MCF-7 cells and MDA-MB-231 cells, and then RNA each of after 1 hour and after 2 hours was purified (Promega Corporation; ReliaPrep Cell mini prep kit), and was then reverse-transcribed with an oligo-dT primer (Toyobo Co., Ltd.; ReverTraAce). The expression of IL-8 and CXCL1 was analyzed using qPCR (Toyobo Co., Ltd.; THUNDERBRD (registered trade name) qPCR Mix). The measured value was corrected by the expression amount/level of HPRT. The amount of remaining RNA was calculated, wherein the expression amount/level in a sample without the addition of actinomycin D was defined as "100%". The results are shown in FIG. 21A.

Actinomycin D (5 μg/ml) was added to HepG2 cells (liver cancer, KRAS; WT), LoVo cells (colorectal cancer, KRAS; G13D) or HPAF-II cells (pancreatic cancer, KRAS; G13D), and then RNA each of after 1 hour and after 2 hours was purified (Promega Corporation; ReliaPrep Cell mini prep kit), and was then reverse-transcribed with an oligo-dT primer (Toyobo Co., Ltd.; ReverTra Ace). The expression of IL-6, IL-8 and CXCL1 was analyzed using qPCR (Toyobo Co., Ltd.; THUNDERBIRD (registered trade name) qPCR Mix). The measured value was corrected by the expression amount/level of HPRT. The amount of remaining RNA was calculated, wherein the expression amount/level in a sample without the addition of actinomycin D was defined as "100%". The results are shown in FIG. 21B.

siRNA negative control (siNega) or siRNA for KRAS (siKRAS) (10 pmol) was transfected into MDA-MB-231 cells using Lipofectamine RNAiMAX Transfection Reagent (Thermo Fisher Scientific), and the cells were cultured for 48 hours. Actinomycin D (5 μg/ml) was added, and then RNA each of after 1 hour and after 2 hours was purified (Promega Corporation; ReliaPrep Cell mini prep kit), and was then reverse-transcribed with an oligo-dT primer (Toyobo Co., Ltd.; ReverTra Ace). The expression of IL-6, IL-8 and CXCL1 was analyzed using qPCR (Toyobo Co., Ltd.; THUNDERBIRD (registered trade name) qPCR Mix). The measured value was corrected by the expression amount/level of HPRT. The amount of remaining RNA was calculated, wherein the expression amount/level in a sample without the addition of actinomycin D was defined as "100%". The results are shown in FIG. 21C.

siRNA negative control (siNega) or siRNA for RBMS2 (siRBMS2) (10 pmol) was transfected into MDA-MB-231 cells using Lipofectamine RNAiMAX Transfection Reagent (Thermo Fisher Scientific), and the cells were cultured for 48 hours. Actinomycin D (5 μg/ml) was added, and then RNA each of after 1 hour and after 2 hours was purified (Promega Corporation; ReliaPrep Cell mini prep kit), and was then reverse-transcribed with an oligo-dT primer (Toyobo Co., Ltd.; ReverTra Ace). The expression of IL-6, IL-8 and CXCL1 was analyzed using qPCR (Toyobo Co., Ltd.; THUNDERBIRD (registered trade name) qPCR Mix). The measured value was corrected by the expression amount/level of HPRT. The amount of remaining RNA was calculated, wherein the expression amount/level in a sample without the addition of actinomycin D was defined as "100%". The results are shown in FIG. 21D.

It was found that the stability of mRNA for each of IL-6, IL-8 and CXCL1 was improved in KRAS mutant cells (FIGS. 21A and 21B). It was also found that the improved state was inhibited by inhibiting the KRAS mutant or RBMS2 (FIGS. 21C and 21D). These results support the fact that there is such a mechanism that the expression of RBMS2 can be promoted by a KRAS G13D mutant and, as a result, mRNA for a cancer promoting factor such as IL-6 can be stabilized and the expression amount/level of the cancer promoting factor can be increased (Example 17, FIG. 17E).

Example 22: RBMS Promoter Analysis

Each of a region lying about 4 kbp upstream from exon-2 (SEQ ID NO: 74), a region lying about 3 kbp upstream from exon-1 (SEQ ID NO: 75), a region lying about 2.5 kbp upstream from exon-2 (SEQ ID NO: 76) and a region lying about 1 kbp upstream from exon-1 in human RBMS2 gene (SEQ ID NO: 77) was cloned into a luciferase vector (pGL4. Promega Corporation). A vector containing an upstream region of RBMS1 gene and a *Renilla luciferase* vector (phRL-TK, Promega Corporation) was transfected into HEK293T cells with polyethyleneimine, and the cells were then cultured for 48 hours. A luciferase activity was measured using Dual-Glo (registered trade name) Luciferase Assay System (Promega Corporation) and was corrected with *Renilla luciferase*.

The results are shown in FIG. 22. It was found that a region critical for a transcriptional activity was contained in a region between about 4 kbp and about 2.5 kbp both upstream from exon-2 and a region between exon-1 and exon-2.

The invention claimed is:

1. A method for inhibiting the expression of at least one cancer promoting factor comprising administering at least one RNA-binding motif, single-stranded-interacting protein 2 (RBMS2) expression inhibitor to a patient having at least one type of cancer in need of inhibition of the expression of at least one cancer promoting factor, wherein the at least one RBMS2 expression inhibitor is selected from the group consisting of a RBMS2-specific siRNA, a miRNA inhibiting the translation of a gene encoding RBMS2, a RBMS2-specific antisense nucleic acid, and expression vectors thereof.

2. The method according to claim 1, wherein the at least one cancer promoting factor is selected from the group consisting of CSF2, IL-6, ADAM10, ADM, CTGF, HBEGF, HILPDA, IL-24, THBS1, MYC, TGFB2, ITGA6, F3, PTP4A1, HSPA5, PLAU, CYR61, ITGA6, EDIL3, CSF1, ITGB1 and MMP1.

3. The method according to claim 1, wherein the at least one type of cancer is:
    (X) selected from the group consisting of pancreatic cancer, colorectal cancer, lung cancer, bile duct cancer and breast cancer;
    (Y) a cancer of a type of RAS gene mutation; and/or
    (Z) a highly malignant cancer.

4. The method according to claim 3, wherein the RAS gene mutation is a KRAS gene mutation.

* * * * *